US008765917B2

(12) United States Patent
Deckert et al.

(10) Patent No.: US 8,765,917 B2
(45) Date of Patent: Jul. 1, 2014

(54) CD37-BINDING MOLECULES AND IMMUNOCONJUGATES THEREOF

(75) Inventors: Jutta Deckert, Lexington, MA (US); Peter Park, Somerville, MA (US); Daniel Tavares, Natick, MA (US); Lingyun Rui, Weston, MA (US)

(73) Assignee: ImmunoGen, Inc., Waltham, MA (US)

( * ) Notice: Subject to any disclaimer, the term of this patent is extended or adjusted under 35 U.S.C. 154(b) by 257 days.

(21) Appl. No.: 13/045,693

(22) Filed: Mar. 11, 2011

(65) Prior Publication Data

US 2011/0256153 A1 Oct. 20, 2011

Related U.S. Application Data

(60) Provisional application No. 61/313,628, filed on Mar. 12, 2010, provisional application No. 61/327,314, filed on Apr. 23, 2010, provisional application No. 61/412,644, filed on Nov. 11, 2010.

(51) Int. Cl.
*C12P 21/08* (2006.01)

(52) U.S. Cl.
USPC .................................... 530/387.3; 530/391.1

(58) Field of Classification Search
None
See application file for complete search history.

(56) References Cited

U.S. PATENT DOCUMENTS

| | | | | |
|---|---|---|---|---|
| 7,303,749 | B1 | 12/2007 | Chari | |
| 7,585,491 | B2 | 9/2009 | Govindan | |
| 7,601,354 | B2 | 10/2009 | Chari | |
| 7,989,598 | B2 | 8/2011 | Steeves et al. | |
| 8,088,387 | B2 | 1/2012 | Steeves et al. | |
| 2005/0136049 | A1 | 6/2005 | Hayden-Ledbetter | |
| 2007/0009519 | A1 | 1/2007 | Hariharan et al. | |
| 2007/0059306 | A1 | 3/2007 | Grosmaire et al. | |
| 2007/0237779 | A1 | 10/2007 | Ledbetter | |
| 2008/0226626 | A1* | 9/2008 | Hariharan et al. | 424/133.1 |
| 2008/0227198 | A1 | 9/2008 | Hariharan et al. | |
| 2009/0274692 | A1 | 11/2009 | Tan et al. | |
| 2009/0274713 | A1 | 11/2009 | Chari et al. | |
| 2010/0135900 | A1 | 6/2010 | Cerveny et al. | |
| 2010/0189722 | A1* | 7/2010 | Heider et al. | 424/172.1 |
| 2012/0276119 | A1 | 11/2012 | Deckert et al. | |

FOREIGN PATENT DOCUMENTS

| | | | |
|---|---|---|---|
| EP | 0 328 147 | B1 | 5/1994 |
| WO | WO 01/24763 | A2 | 4/2001 |
| WO | 2005017148 | A1 | 2/2005 |
| WO | WO 2005/037992 | A2 | 4/2005 |
| WO | 2007014278 | A2 | 2/2007 |
| WO | 2009/019312 | A2 | 2/2009 |
| WO | WO 2009/019312 | A2 | 2/2009 |
| WO | WO 2009/134977 | A1 | 11/2009 |
| WO | 2010008726 | A1 | 1/2010 |
| WO | WO 2010/009124 | A2 | 1/2010 |

OTHER PUBLICATIONS

Kovtun et al (Can Res, 70(6):2528-2537, 2010).*

Angelisová, P., et al., "Association of four antigens of the tetraspans family (CD37, CD53, TAPA-1, and R2/C33) with MHC class II glycoproteins," *Immunogenetics* 39:249-256, Springer-Verlag, Germany (1994).

Bernstein, I.D., et al., "High Dose Radiolabeled Antibody Therapy of Lymphoma," *Cancer Research* (*Suppl.*) 50:1017s-1021s, American Association for Cancer Research, United States (1990).

Braslawsky, G.R., et al., "Antitumor Activity of Adriamycin (Hydrazone-linked) Immunoconjugates Compared with Free Adriamycin and Specificity of Tumor Cell Killing," *Cancer Research* 50:6608-6614, American Association for Cancer Research, United States (1990).

Deckert, J., et al., "IMGN529: A therapeutic maytansinoid conjugate of an anti-CD37 antibody with multiple mechanisms of action for B-cell lymphoma and leukemia," AACR Poster Abstract #2.

Deckert, J., et al., "IMGN529: An Anti-CD37 Antibody-Maytansinoid Conjugate with Multiple Mechanisms of Actions for B-Cell Malignancies," Poster #306, *Keystone Symphosis—B Cells: New Insights into Normal versus Dysregulated Function*, Apr. 12-16, 2011, ImmunoGen, Inc., United States (2011).

Deckert, J., et al., "Potent B-Cell Depletion by IMGN529, a CD37-Targeting Antibody-Maytansinoid Conjugate for the Treatment of B-Cell Malignancies," ASH Poster Abstract #3726:1-2 (2011).

Dijoseph, J.F., et al. "CD-20-specific antibody-targeted chemotherapy of non-Hodgkin's B-cell lymphoma using calicheamicin-conjugated rituximab," *Cancer Immunol Immunother* 56:1107-1117, Springer-Verlag, Germany (2007).

Greenfield, R.S., et al., "Evaluation in Vitro of Adriamycin Immunoconjugates Synthesized Using an Acid-sensitive Hydrazone Linker," *Cancer Research* 50:6600-6607, American Association for Cancer Research, United States (1990).

International Search Report with Written Opinion for International Application No. PCT/US11/28172, International Searching Authority, United States, mailed Jul. 13, 2011.

Kaminski, M.S., et al. "Imaging, Dosimetry, and Radioimmunotherapy With Iodine 131-Labeled Anti-CD37 Antibody in B-Cell Lymphoma," *Journal of Clinical Oncology* 10:(11)1696-1711, American Society of Clinical Oncology, United States (1992).

Knobeloch, K-P., et al., "Targeted Inactivation of the Tetraspanin CD37 Impairs T-Cell-Dependent B-Cell Response under Suboptimal Costimulatory Conditions," *Molecular and Cellular Biology* 20(15):5363-5369, American Society for Microbiology, United States (2000).

Lai, K.C., et al., "The CD37-targeting ADC IMGN529 combines the potent anti-cancer activity of K7153A antibody with efficient maytansinoid delivery," Poster Abstract #B209, *AACR-EORTC-NCI 2011*, ImmunoGen, Inc., United States (2011).

Lai, K.C., et al., "The CD37-targeting ADC IMGN529 combines the potent anti-cancer activity of K7153A antibody with efficient maytansinoid delivery," *Oasis, the Online Abstract Submission System*, Abstract 11-A-226-AACR:1-2, United States (2011).

(Continued)

*Primary Examiner* — Brad Duffy

(74) *Attorney, Agent, or Firm* — Sterne, Kessler, Goldstein & Fox P.L.L.C.

(57) ABSTRACT

Novel anti-cancer agents, including, but not limited to, antibodies and immunoconjugates, that bind to CD37 are provided. Methods of using the agents, antibodies, or immunoconjugates, such as methods of inhibiting tumor growth are further provided.

26 Claims, 32 Drawing Sheets

(56) References Cited

OTHER PUBLICATIONS

Link, M.P., "A Unique Antigen on Mature B Cells Defined by a Monoclonal Antibody," *The Journal of Immunology* 137(9):3013-3018, The American Association of Immunologists, United States (1986).
Maecker, H.T., et al., "The tetraspanin superfamily: molecular facilitators," *FASEB J.* 11:428-442, The Federation, United States (1997).
Meyer-Wentrup, F., et al., "Dectin-1 Interaction with Tetraspanin CD37 Inhibits IL-6 Production," *The Journal of Immunology* 178:154-162, The American Association of Immunologists, Inc., United States (2007).
Moore, K., et al., "Use of the Monoclonal Antibody WR17, Identifying the CD37 gp40-45 Kd Antigen Complex, in the Diagnosis of B-Lymphoid Malignancy," *Journal of Pathology* 152:13-21, John Wiley & Sons, Ltd., England (1987).
Park, P.U., et al., "Antibody and linker selection for the anti-CD37 antibody-maytansinoid conjugate IMGN529 for the treatment of B-cell malignancies," *Experimental and Molecular Therapeutics session*, Abstract #2830:1-24, AACR Annual Meeting 2011, ImmunoGen, Inc. (2011).
Pinkas, J., "Antibody Maytansinoid Conjugates for the Treatment of Cancer," Protein Therapeutics Forum 2012:1-23, ImmunoGen, Inc., United States (2012).
Polson, A.G., et al., "Antibody-Drug Conjugates for the Treatment of Non-Hodgkin's Lymphoma: Target and Linker-Drug Selection," *Cancer Res* 69(6):2358-2364, American Association for Cancer Research, United States (2009).
Press, O.W., et al., "Endocytosis and Degradation of Monoclonal Antibodies Targeting Human B-Cell Malignancies," *Cancer Research* 49:4906-4912, American Association for Cancer Research, United States (1989).
Press, O.W., et al., "Radiolabeled-Antibody Therapy of B-Cell Lymphoma with Autologous Bone Marrow Support," *N Engl J Med* 329(17):1219-1224, Massachusetts Medical Society, United States (1993).
Press, O.W., et al., "Retention of B-Cell-Specific Monoclonal Antibodies by Human Lymphoma Cells," *Blood* 83(5):1390-1397, The American Society of Hematology (1994).
Press, O.W., et al., "Treatment of Refractory Non-Hodgkin's Lymphoma With Radiolabeled MB-1 (Anti-CD37) Antibody," *J Clin Oncol* 7(8):1027-1038, American Society of Clinical Oncology, United States (1989).
Rops, A.L., et al., "The Tetraspanin CD37 Protects Against Glomerular IgA Deposition and Renal Pathology," *Am J Pathol* 176:2188-2197, American Society for Investigative Pathology (2010).
Schwartz-Albiez, R., et al., "The B Cell-Associated CD37 Antigen (gp40-52): Structure and Subcellular Expression of an Extensively Glycosylated Glycoprotein," *The Journal of Immunology* 140(3):905-914, The American Association of Immunologists, United States (1988).
Sheng, K-C., et al., "Tetraspanins CD37 and CD151 differentially regulate Ag presentation and T-cell co-stimulation by DC," *Eur. J. Immunol.* 39:50-55, Wiley-VCH Verlag GmbH & Co. KGaA, Germany (2009).
Van Spriel, A.B., et al., "A Regulatory Role for CD37 in T Cell Proliferation," *The Journal of Immunology* 172:2953-2961, The American Association of Immunologists, United States (2004).
Van Spriel, A.B., et al., "The Tetraspanin Protein CD37 Regulates IgA Responses and Anti-Fungal Immunity," *PLoS Pathogens* 5(3) e1000338:1-11, Public Library of Science, United States (2009).
Tedder, T.F., et al., "Structure of the Gene Encoding the Human B Lymphocyte Diff erentiation Antigen CD20 (B1)," *The Journal of Immunology* 142(7):2560-2568, The American Association of Immunologists, United States (1989).
Zhao, X., et al., "Targeting CD37-positive lymphoid malignancies with a novel engineered small modular immunopharmaceutical," *Blood* 110(7):2569-2577, The American Society of Hematology, United States (2007).
Awan, F., et al., "Phase 1 Study of TRU-016, an Anti-CD37 SMIP Protein in Naïve and Relapsed and/or Refractory CLL Patients," Poster (2011).
Awan, F.T, et al., "Phase 1 Study of TRU-016, an Anti-CD37 SMIP™ Protein in Naïve and Relapsed and/or Refractory CLL Patients," *Blood* (*ASH Annual Meeting Abstracts*) 2011 188:Abstract 1792 (2011).
Barrena, S., et al.,"Aberrant expression of tetraspanin molecules in B-cell chronic lymphoproliferative disorders and its correlation with normal B-Cell maturation," *Leukemia* 19:1376-1383, Nature Publishing Group, England (2005).
Blanc, V., et al., "SAR3419: An Anti-CD19-Maytansinoid Immunoconjugate for the Treatment of B-Cell Malignancies," *Clin Cancer Res* 17(20):6448-6458, American Association for Cancer Research, United States (2011).
Heider, K-H., et al., "A novel Fc-engineered monoclonal antibody to CD37 with enhanced ADCC and high proapoptotic activity for treatment of B-cell malignancies," *Blood* 118(15):4159-4168, The American Society of Hematology, United States (2011).
Lambert, J.M., "Antibody-Maytansinoid Conjugates: A New Strategy for the Treatment of Cancer," *Drugs of the Future* 35(6):471-480, Prous Science, S.A.U., Spain (2010).
Pagel, J.M, et al., "Phase 1 Study of TRU-016, an Anti-CD37 SMIP™ Protein in Relapsed and/or Refractory NHL Patients," *Blood* (*ASH Annual Meeting Abstracts*) 2011 118(21):Abstract 1636 (2011).
Roguska, M.A., et al., "A comparison of two murine monoclonal antibodies humanized by CDR-grafting and variable domain resurfacing," *Protein Engineering* 9(10):895-904, Oxford University Press, England (1996).
Roguska, M.A., et al., "Humanization of murine monoclonal antibodies through variable domain resurfacing," *Proc. Natl. Acad. Sci. USA* 91:969-973, National Academy of Sciences, United States (1994).
Teicher, B.A. and Chari, R.V.J., "Antibody Conjugate Therapeutics: Challenges and Potential," *Clin Cancer Res* 17(20):6389-6397, American Association for Cancer Research, United States (2011).
Dahle, J., et al., "Evaluating Antigen Targeting and Anti-tumor Activity of a New Anti-CD37 Radioimmunoconjugate Against Non-Hodgkin's Lymphoma," *Anticancer Research* 33:85-96, International Institute of Anticancer Research, Greece (2013).
Lapalombella, R., et al., "Tetraspanin CD37 Directly Mediates Transduction of Survival and Apoptotic Signals," *Cancer Cell* 21:694-708, Elsevier Inc., United States (2012).
Xiaobin B Zhaos, "Novel Anti-CD37 Small Modular Immunopharmaceutical (SMIP) Induces B-Cell-Specific, Caspase-Independent Apoptosis in Human CLL Cells," Abstract, 2004, ASH Annual Meeting Abstract 104: Journal for the American Society of Hematology.

* cited by examiner

Figure 4
A
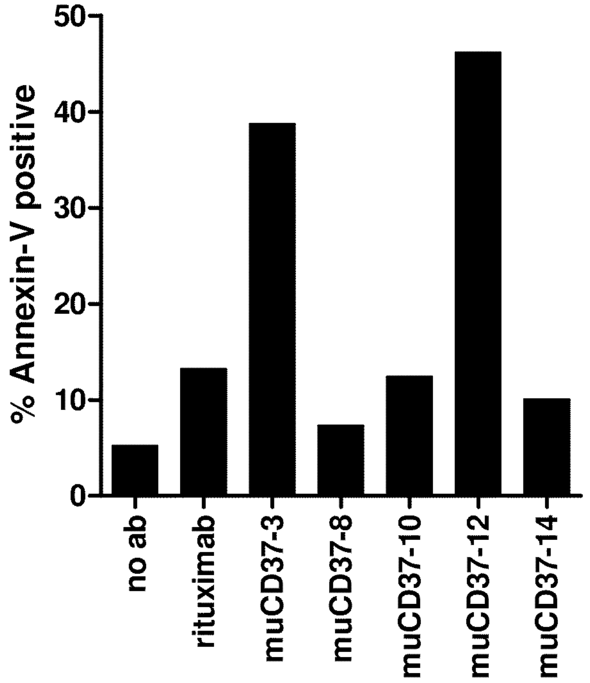
B
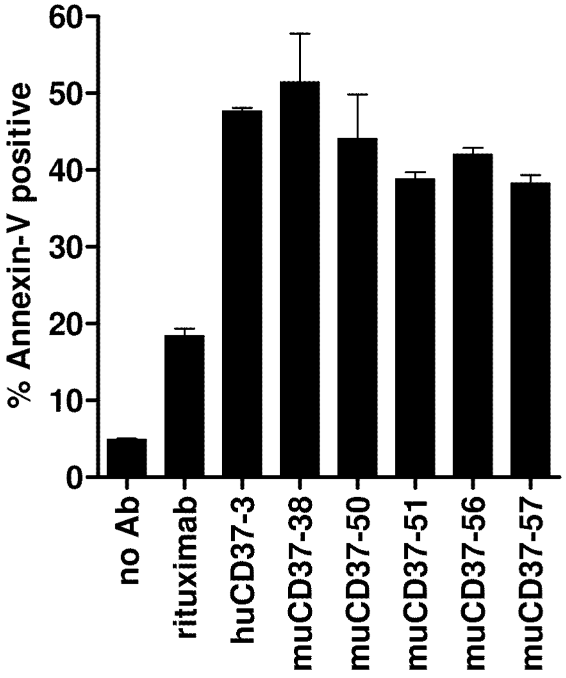

| CD37-3 $V_L$ | | |
|---|---|---|
| Kabat position | Murine residue | Human residue |
| 1 | D | D |
| 3 | Q | Q |
| **9** | **A** | ***S*** |
| 15 | V | V |
| **18** | **T** | ***R*** |
| **40** | **Q** | ***P*** |
| 41 | G | G |
| 42 | K | K |
| **45** | **Q** | ***K*** |
| 57 | G | G |
| 60 | S | S |
| 67 | S | S |
| **70** | **Q** | ***D*** |
| **80** | **S** | ***P*** |
| 81 | E | E |
| **100** | **G** | ***Q*** |
| 103 | K | K |
| 107 | K | K |
| 108 | R | R |

B

| CD37-3 $V_H$ | | | |
|---|---|---|---|
| Kabat position | Murine residue | Human v1.00 residue | Human v1.01 residue |
| 1 | Q | Q | Q |
| 3 | Q | Q | Q |
| **5** | **K** | ***Q*** | ***Q*** |
| 11 | L | L | L |
| 15 | S | S | S |
| 16 | Q | Q | Q |
| **17** | **S** | ***T*** | ***T*** |
| 28 | S | S | S |
| 41 | P | P | P |
| 42 | G | G | G |
| 43 | K | K | K |
| **61** | **S** | ***P*** | **S** |
| **62** | **A** | ***S*** | ***S*** |
| 64 | K | K | K |
| 65 | S | S | S |
| 74 | S | S | S |
| 75 | K | K | K |
| **83** | **Q** | ***T*** | ***T*** |
| **84** | **T** | ***A*** | ***A*** |
| **85** | **D** | ***A*** | ***A*** |
| 105 | Q | Q | Q |
| 108 | L | L | L |
| 112 | S | S | S |

| CD37-50 $V_L$ | | |
|---|---|---|
| Kabat position | Murine residue | Human residue |
| **1** | **D** | ***<u>E</u>*** |
| 3 | V | V |
| 5 | T | T |
| 9 | A | A |
| **10** | **I** | ***<u>T</u>*** |
| 15 | P | P |
| **18** | **K** | ***<u>R</u>*** |
| **40** | **S** | ***<u>P</u>*** |
| 41 | G | G |
| **42** | **T** | ***<u>Q</u>*** |
| 57 | G | G |
| **60** | **G** | ***<u>A</u>*** |
| 67 | S | S |
| 77 | S | S |
| 81 | E | E |
| **100** | **S** | ***<u>Q</u>*** |
| 107 | K | K |
| 108 | R | R |

B

| CD37-50 $V_H$ | | |
|---|---|---|
| Kabat position | Murine residue | Human residue |
| 1 | Q | Q |
| 3 | Q | Q |
| 5 | Q | Q |
| **10** | **D** | ***<u>G</u>*** |
| 11 | L | L |
| 13 | K | K |
| 15 | S | S |
| 16 | Q | Q |
| **25** | **T** | ***<u>S</u>*** |
| 39 | Q | Q |
| **40** | **F** | ***<u>H</u>*** |
| 61 | P | P |
| 62 | S | S |
| 64 | K | K |
| 65 | S | S |
| 74 | S | S |
| 75 | K | K |
| **84** | **T** | ***<u>A</u>*** |
| **85** | **E** | ***<u>A</u>*** |
| 105 | Q | Q |
| 108 | L | L |
| 112 | S | S |

```
                    1                                                          60
    muCD37-3 VL     DIQMTQSPASLSVSVGETVTITCRASENIRSNLAWYQQKQGKSPQLLVNVATNLADGVPS
huCD37-3 VLv1.00     --------S--------R---------------------P----K---------------
                    61                                             108
    muCD37-3 VL     RFSGSGSGTQYSLKINSLQSEDFGTYYCQHYWGTTWTFGGGTKLEIKR
huCD37-3 VLv1.00     ---------D---------P-------------------Q--------
```

B

```
                    1                                                          60
    muCD37-3 VH     QVQVKESGPGLVAPSQSLSITCTVSGFSLTTSGVSWVRQPPGKGLEWLGVIWGDGSTNYH
huCD37-3 VHv1.00     ----Q-----------T-------------------------------------------
huCD37-3 VHv1.01     ----Q-----------T-------------------------------------------
                    61                                                    115
    muCD37-3 VH     SALKSRLSIKKDHSKSQVFLKLNSLQTDDTATYYCAKGGYSLAHWGQGTLVTVSS
huCD37-3 VHv1.00     PS-----------------------TAA---------------------------
huCD37-3 VHv1.01     -S-----------------------TAA---------------------------
```

C

```
                    1                                                          60
muCD37-50 VL        QIVLTQSPAIMSASPGEKVTMTCSATSSVTYMHWYQQKSGTSPKRWIYDTSKLPYGVPGR
huCD37-50 VL        E--------T-------R--------------------P-Q----------N------A-
                    61                                            107
muCD37-50 VL        FSGSGSGTSYSLTISSMEAEDAATYYCQQWSDNPPTFGSGTKLEIKR
huCD37-50 VL        --------------------------------------Q--------
```

D

```
                    1                                                          60
muCD37-50 VH        QVQLQESGPDLLKPSQSLSLTCTVTGYSITSGFAWHWIRQFPGNKLEWMGYILYSGSTVY
huCD37-50 VH        ---------G--------------S---------------H-------------------
                    61                                                        120
muCD37-50 VH        SPSLKSRISITRDTSKNHFFLQLNSVTTEDTATYYCARGYYGYGAWFAYWGQGTLVTVSA
huCD37-50 VH        ---------------------------AA-------------------------------
```

Figure 9
A
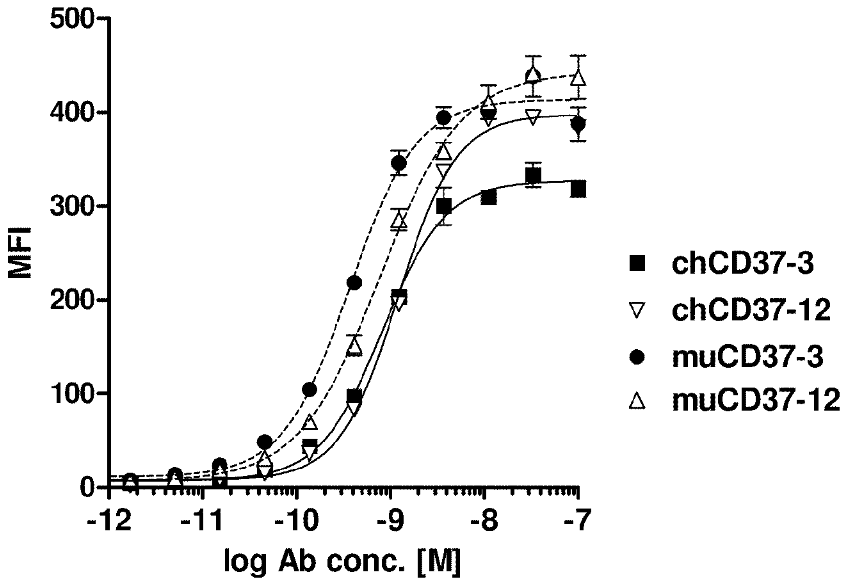
B
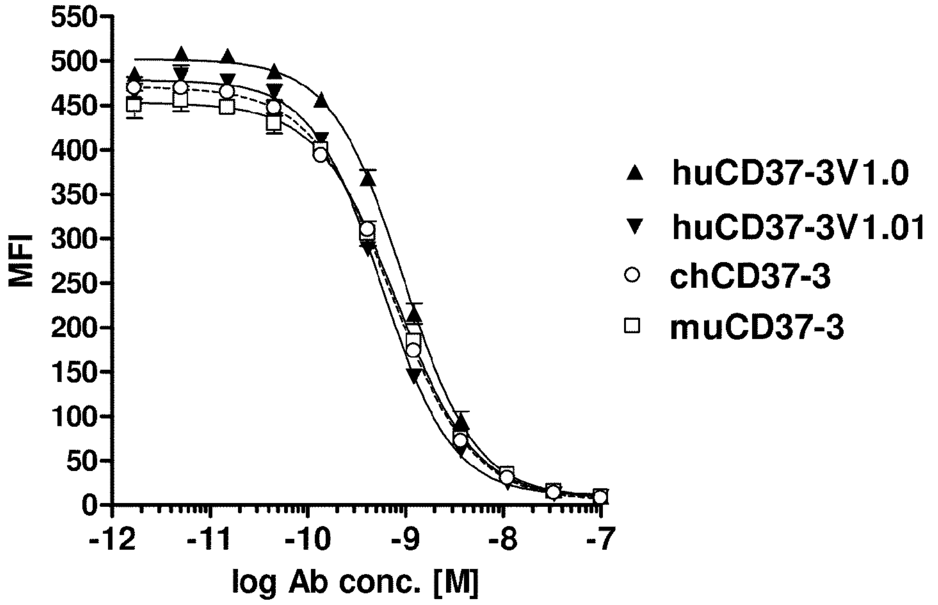

Figure 10
A
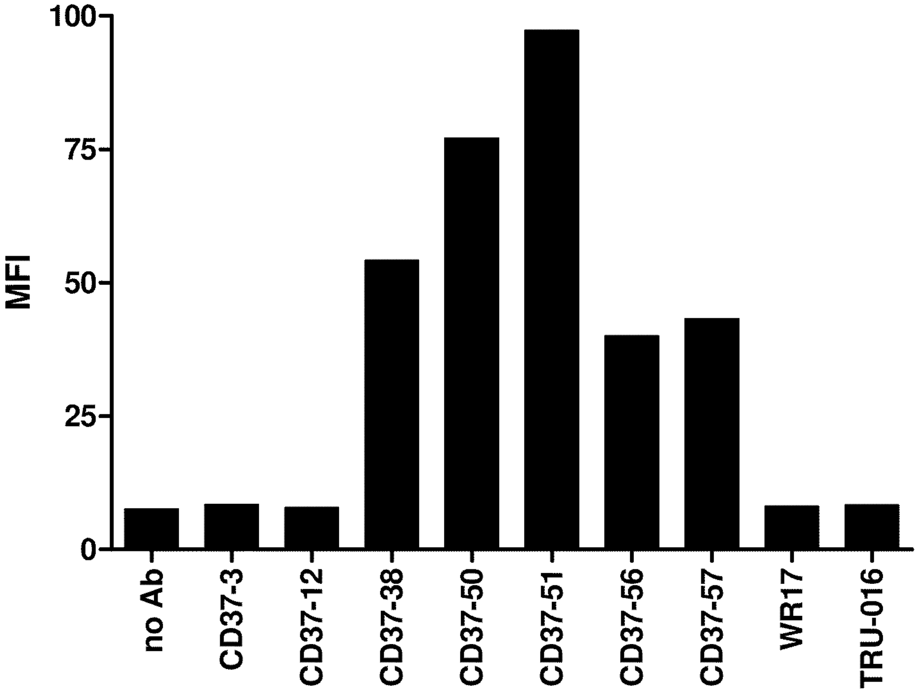
B
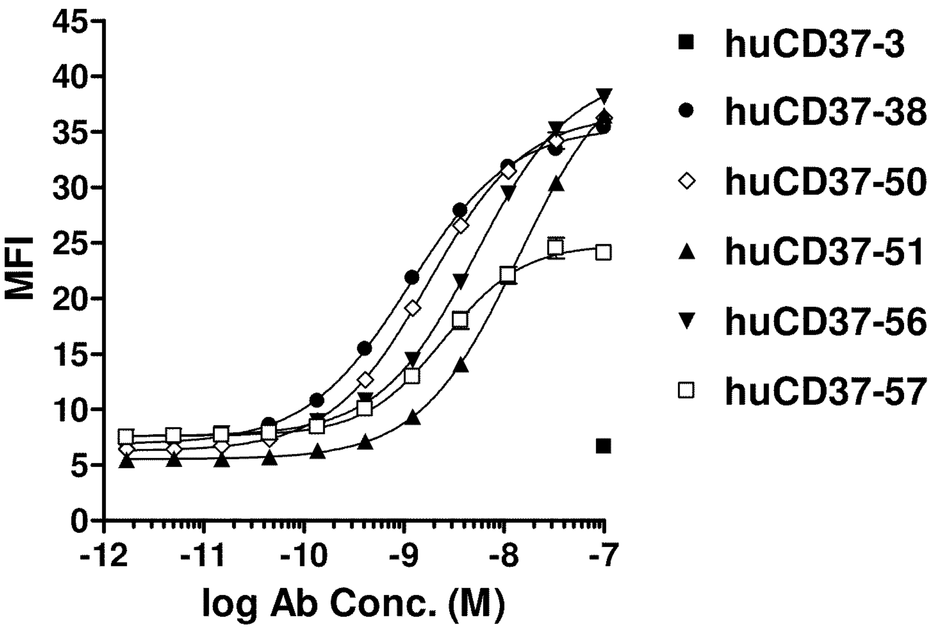

Figure 12
A
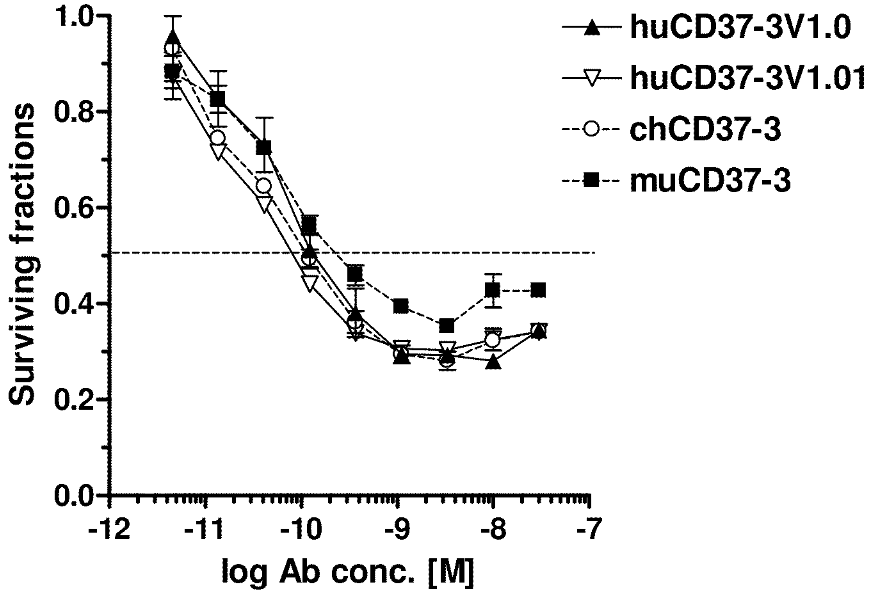
B
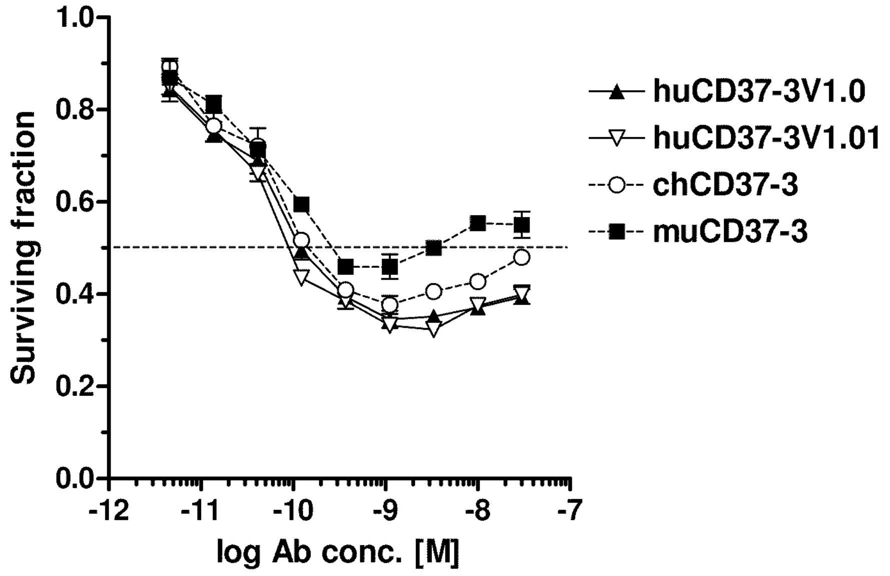

Figure 14
A
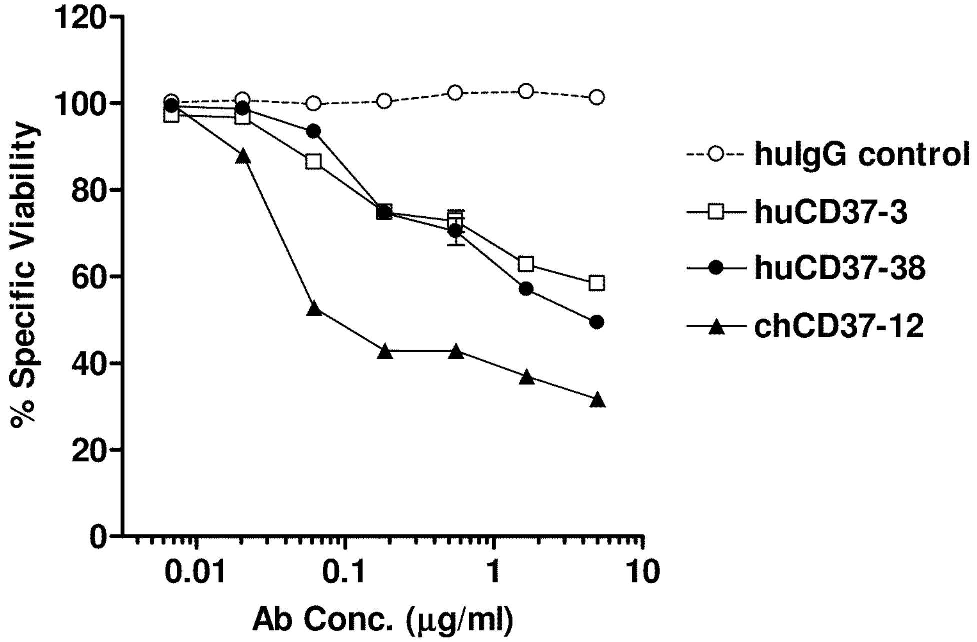
B
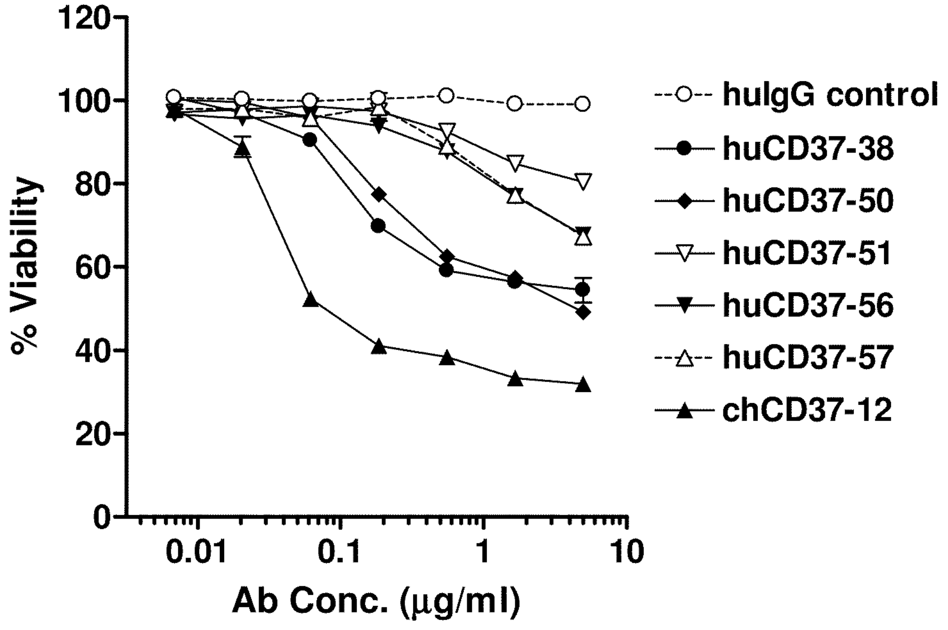

Figure 16

```
         1                                              Small ECD      60
muCD37   MSAQESCLSLIKYFLFVFNLFFFV.LGGLIFCFGTWILIDKTSFVSFVGLSFVPLQTWSK
huCD37   ------------------------.--S------I---------------A-----I---
macCD37  ------------------------I--S------I---------------A-----I---

         61                                                         120
muCD37   VLAVSGVLTMALALLGCVGALKELRCLLGLYFGMLLLLFATQITLGILISTQRVRLERRV
huCD37   ---I--IF--GI-----------------------------------------AQ---SL
macCD37  ---I---F--G------------------------------------------AQ---SL

         121                      Large ECD                         180
muCD37   QELVLRTIQSYRTNPDETAAEESWDYAQFQLRCCGWQSPRDWNKAQMLKANESEEPFVPC
huCD37   RDV-EK---K-G---E----------V---------HY-Q--FQVLI-RG-G--AHR---
macCD37  -DI-EK---R-H---E----------V---------HS-Q--FQVLT-RG-G--AHR---

         181                      Large ECD                         240
muCD37   SCYNSTATNDSTVFDKLFFSQLSRLGPRAKLRQTADICALPAKAHIYREGCAQSLQKWLE
huCD37   ----LS------IL--VILP------HL-RS-HS-----V--ES---------G------
macCD37  ----LS------IL--VILP------QL-RS-HST----V--NS--------R-------

         241                                     282
muCD37   NNIISIVGICLGVGLLELGFMTLSIFLCRNLDHVYDRLARYR
huCD37   --L--------------------------------N------
macCD37  --L--------------------------------N------
```

Figure 17

```
             100    EcoRV                                 SacII       149
     huCD37  TQITLGILISTQRAQLERSLRDVVEKTIQKYGTNPEETAAEESWDYVQFQ
  huCD37-M1  -------------VR---RVQEL-LR---S-R---D--------------
  huCD37-M2  ----------------------------------------------A---
  huCD37-M3  --------------------------------------------------
 huCD37-M45  --------------------------------------------------
muCD37-R176  -------------VR---RVQEL-LR---S-R---D----------A---
     muCD37  -------------VR---RVQEL-LR---S-R---D----------A---

             150                        Kpn1                      199
     huCD37  LRCCGWHYPQDWFQVLILRGNGSEAHRVPCSCYNLSATNDSTILDKVILP
  huCD37-M1  --------------------------------------------------
  huCD37-M2  ------QS-R--NKAQM-KA-E--EP------------------------
  huCD37-M3  ----------------------------------ST------VF--LFFS
 huCD37-M45  --------------------------------------------------
muCD37-R176  ------QS-R--NKAQM-KA-E--EP--------ST------VF--LFFS
     muCD37  ------QS-R--NKAQM-KA-E--EPF-------ST------VF--LFFS

             Blp1           Nde1                Pst1              249
     huCD37  QLSRLGHLARSRHSADICAVPAESHIYREGCAQGLQKWLHNNLISIVGIC
  huCD37-M1  --------------------------------------------------
  huCD37-M2  --------------------------------------------------
  huCD37-M3  --------------------------------------------------
 huCD37-M45  ------PR-KL-QT-----L--KA---------S----------------
muCD37-R176  ------PR-KL-QT-----L--KA---------S----------------
     muCD37  ------PR-KL-QT-----L--KA---------S--------I-------
```

Figure 18
A
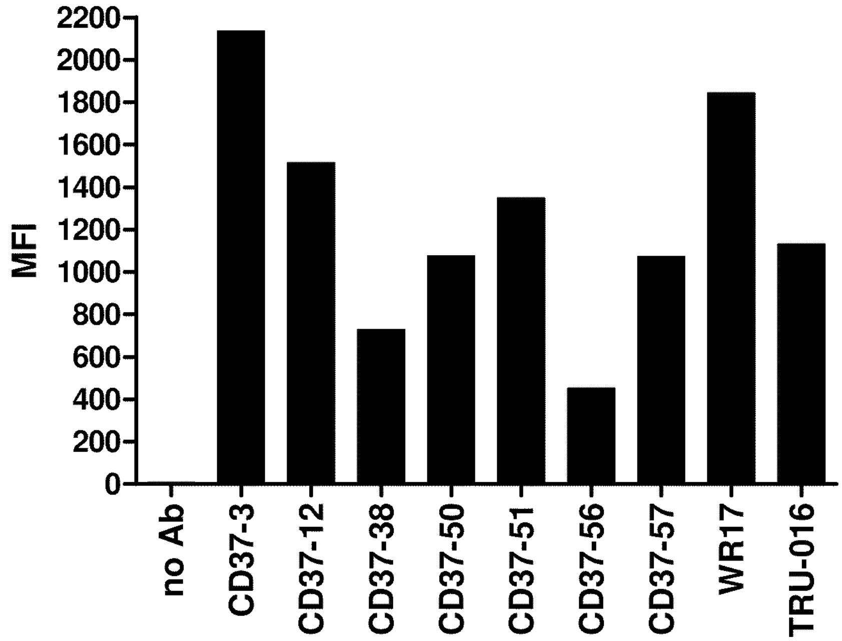
B
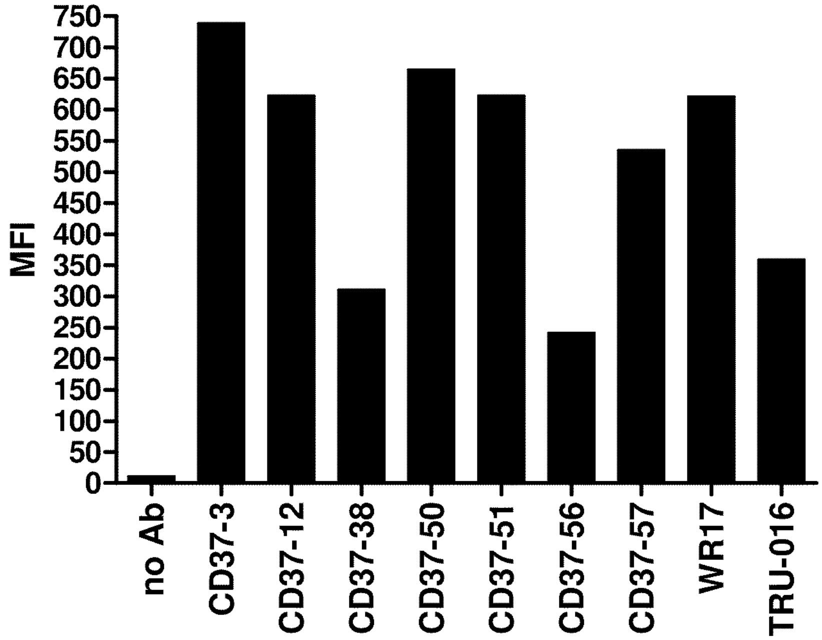

Figure 20
A
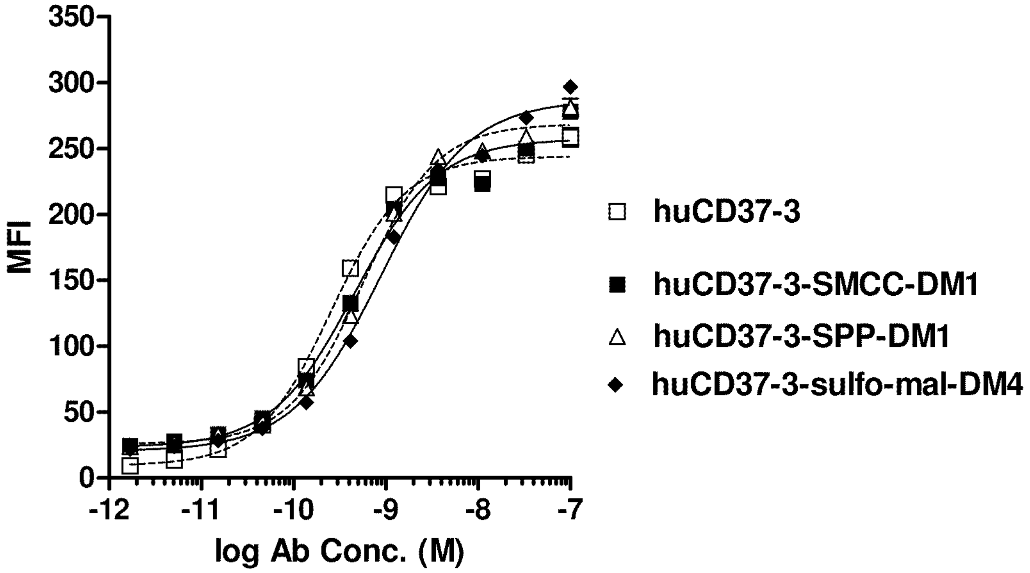
B
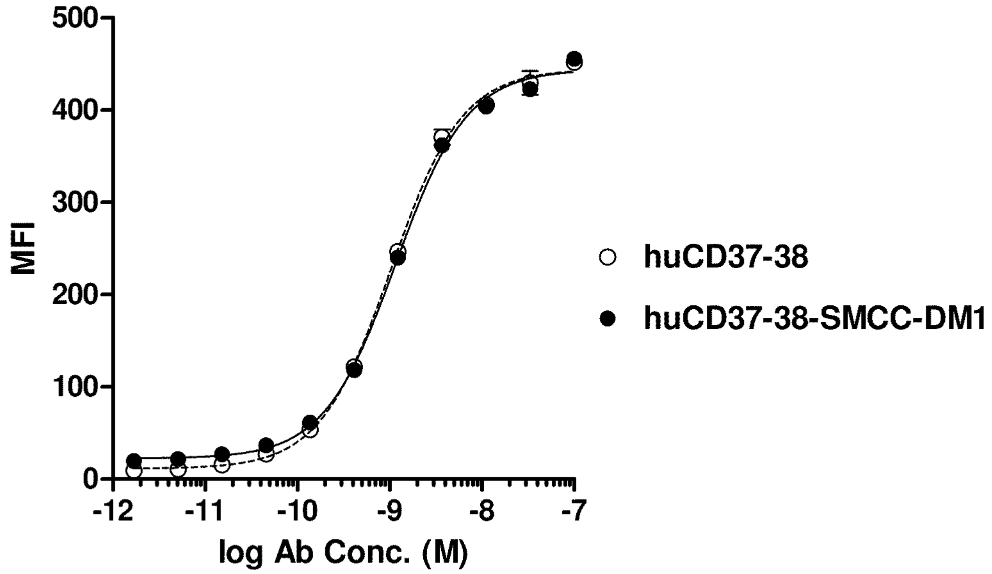

Figure 22
A
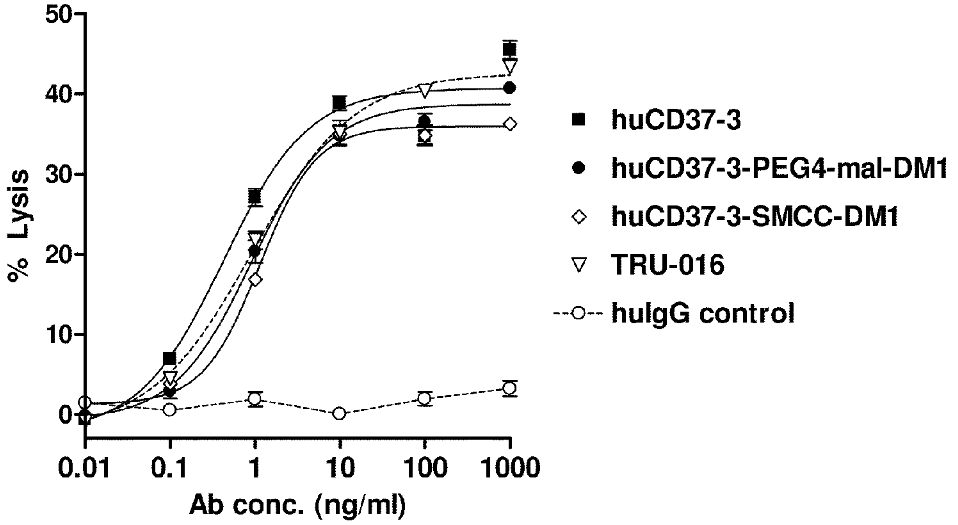
B
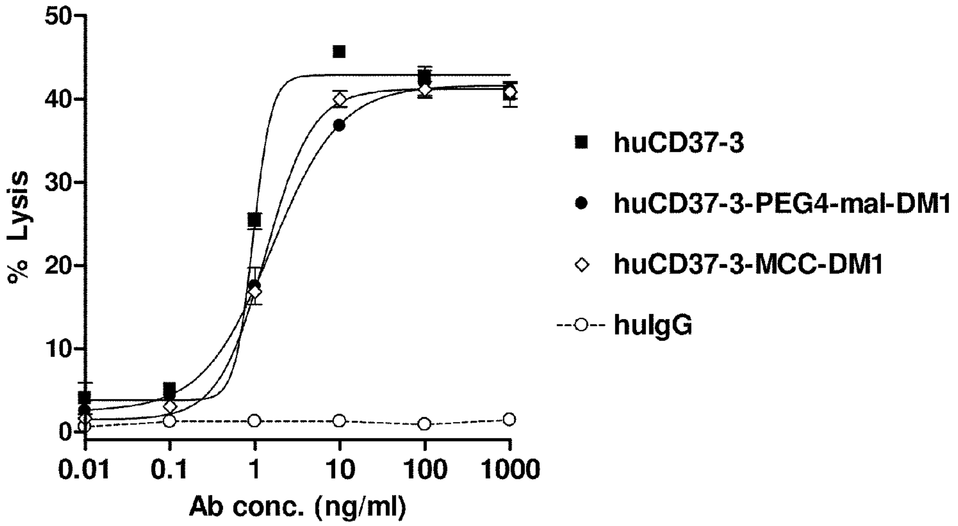

Figure 24
A
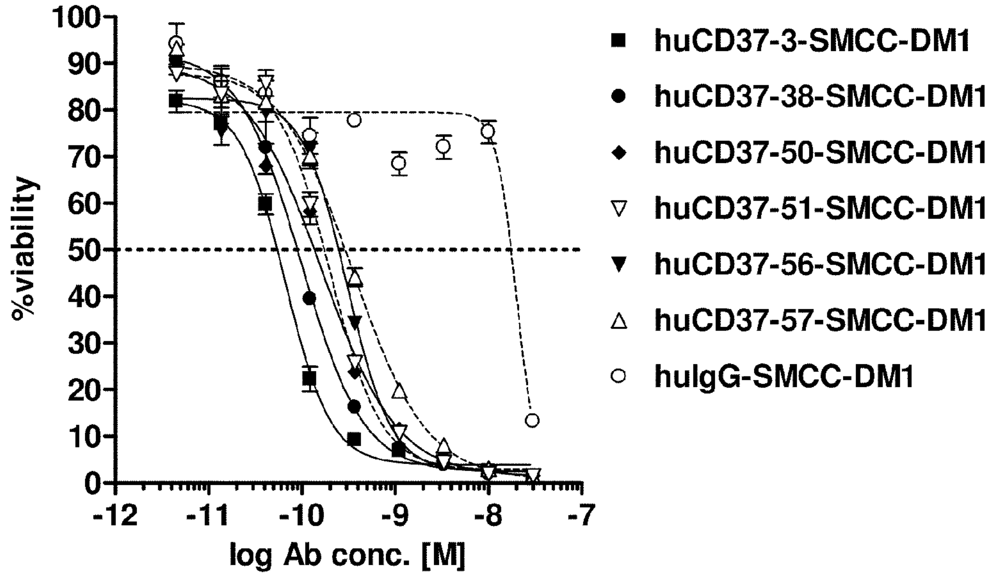
B
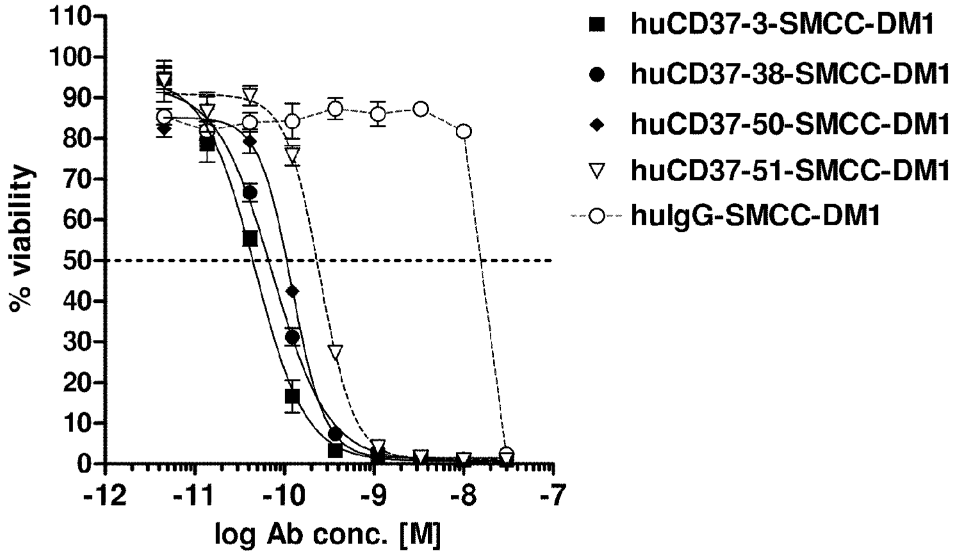

Figure 25
A
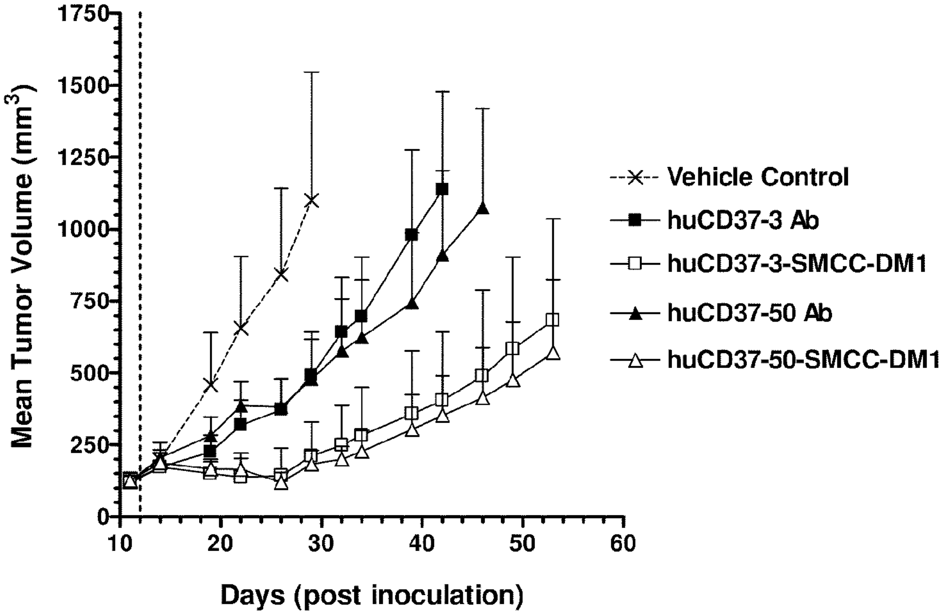
B
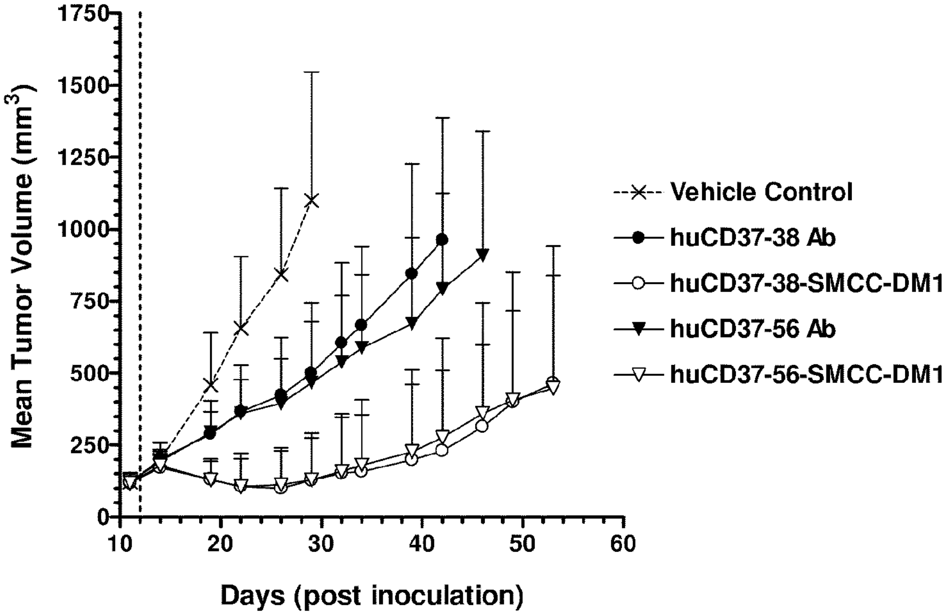

CD37-BINDING MOLECULES AND IMMUNOCONJUGATES THEREOF

CROSS REFERENCE TO RELATED APPLICATIONS

This application claims the priority benefit of U.S. Provisional Application No. 61/313,628, filed Mar. 12, 2010, U.S. Provisional Application No. 61/327,314, filed Apr. 23, 2010, and U.S. Provisional Application No. 61/412,644, filed Nov. 11, 2010, each of which is hereby incorporated by reference herein in its entirety.

REFERENCE TO A SEQUENCE LISTING SUBMITTED ELECTRONICALLY VIA EFS-WEB

The content of the electronically submitted substitute sequence listing (Name: 2921.0030003Revisedsequencelisting.ascii.txt, Size 251,449 bytes; and Date of Creation: Jun. 12, 2013) is herein incorporated by reference in its entirety.

FIELD OF THE INVENTION

The field of the invention generally relates to antibodies, antigen-binding fragments thereof, polypeptides, and immunoconjugates that bind to CD37, as well as to methods of using such CD37-binding molecules for the treatment of diseases, such as B-cell malignancies.

BACKGROUND OF THE INVENTION

Leukocyte antigen CD37 ("CD37"), also known as GP52-40, tetraspanin-26, or TSPAN26, is a transmembrane protein of the tetraspanin superfamily (Maecker et al., 1997 FASEB J. 11:428-442). It is a heavily glycosylated protein with four transmembrane domains that is expressed on B cells during the pre-B to peripheral mature B-cell stages, but is absent on terminal differentiation to plasma cells. (Link et al., 1987, J Pathol. 152:12-21). The CD37 antigen is only weakly expressed on T-cells, myeloid cells and granulocytes (Schwartz-Albiez et al. 1988, J. Immunol., 140(3)905-914). However, CD37 is also expressed on malignant B-cells such as those founding non-Hodgkin's lymphoma (NHL) and chronic lymphoid leukemia (CLL) (Moore et al. 1986, J Immunol. 137(9):3013-8). This expression profile suggests that CD37 represents a promising therapeutic target for B-cell malignancies.

While the exact physiological role of CD37 in unclear, studies suggest a potential role in T-cell proliferation (van Spriel et al. 2004, J Immunol., 172(5):2953-61) As part of the tetraspanin family of cell surface glycoproteins, CD37 may also complex with other surface proteins (Angelisová 1994, Immunogenetics., 39(4):249-56). Mice deficient in CD37 expression were developed and revealed no changes in development and cellular composition of lymphoid organs. Only reduced levels of IgG1 and alterations of responses to T-cell dependent antigens were observed (Knobeloch et al. 2000, Mol Cell Biol., 20(15):5363-9).

Antibodies are emerging as a promising method to treat such cancers. In particular, antibodies that are able to induce apoptosis in target cells are desirable. In addition, antibodies having complement-dependent cytotoxicity (CDC) activity and antibody-dependent cytotoxicity (ADCC) are also desirable.

Currently, an anti-CD20 antibody called rituximab is being used to treat B-cell malignancies (Leget et al., 1998, Curr. Opin. Oncol., 10:548-551). However, only a subset of patients respond to rituximab treatment, and even responding patients taking rituximab eventually relapse and often develop resistance to rituximab treatment. In addition, CD37-binding agents are also being tested as potential therapeutics for B-cell malignancies. Trubion Pharmaceuticals developed the CD37-binding agents SMIP-016 and TRU-016 (Zhao et al., 2007, Blood, 110:2569-2577). SMIP-016 is a single chain polypeptide that includes variable regions from a hybridoma and engineered human constant regions. TRU-016 is a humanized version of the anti-CD37 SMIP protein. See e.g. U.S. Published Application No. 2007/0009519. TRU-016 is being tested clinically for the treatment of chronic lymphocytic leukemia (CLL). Boehringer Ingelheim has also disclosed a CD37 binding agent in International Published Application No. WO 2009/019312. However, no CDC activity has been described for any of these binding agents and no in vitro pro-apoptotic activity has been described in the absence of cross-linking agents.

Radio-immunotherapy (RIT) has been attempted using a radio-labeled anti-CD37 antibody MB-1 in two separate trials. Therapeutic doses of $^{131}$I-MB-1 were administered to six relapsed NHL patients (Press et al. 1989 J Clin Oncol. 7(8): 1027-38, Press at el. 1993, N Engl J Med. 329(17):1219-24). All six patients achieved a complete remission (CR) with a duration of four to thirty-one months. In another trial, $^{131}$I-MB-1 was administered to ten relapsed NHL patients (Kaminski et al. 1992 J Clin Oncol. 10(11):1696-711). A total of four patients had a response ranging in duration from two to six months, although only one CR was reported. However, not all patients could be treated due to an unfavorable biodistribution of the radio-label which raised concern for radiation exposure of vital non-target organs. Indeed, RIT related toxicities were observed in these trials including severe myelosupression and cardiopulmonary toxicity. While these clinical data suggest that anti-CD37 radio-immunoconjugates may be effective, these therapies are cumbersome to administer, and at relapse post-RIT patients cannot be retreated with RIT due to the risks associated with high doses of radiation.

To overcome the limitations of RIT, antibody-cytotoxic agent conjugates (ACC), also called antibody-drug conjugates (ADC), have been developed. These are immunoconjugates that include a cytotoxic agent covalently linked to an antibody through a chemical linker which can allow for specific delivery of cytotoxic drugs to cells expressing a protein recognized by the antibody. However, proteins that are poorly internalized are not considered to be favorable targets for such therapeutics. CD37 is structurally similar to CD20 as both antigens contain four transmembrane domains, although CD20 is not part of the tetraspanin family (Tedder et al. 1989, J. Immun. 142: 2560-2568). Antibodies against several B-cell antigens including CD37 and CD20 have been studied for their ability to undergo endocytosis and degradation (Press et al. 1989, Cancer Res. 49(17):4906-12, and Press et al. 1994, Blood. 83(5):1390-7). The anti-CD37 antibody MB-1 was retained on the cell surface and internalized slowly in Daudi lymphoma cells in vitro. The MB-1 antibody also had a low rate of endocytosis and intracellular metabolism in NHL patient cells in vitro. Similar results were obtained with the anti-CD20 antibody 1F5, which was also retained mainly on the lymphoma cell surface and internalized poorly. ADCs of CD20 antibodies have been studied previously but have not demonstrated significantly strong potency, especially when non-disulfide or acid stable linkers are used (see for example Polson et al., 2009, Cancer Res., 69(6):2358-2364). In light of these observations, CD37 has not been considered a favorable target for antibody-drug conjugates.

Therefore, there exists a need for CD37 binding agents including antibodies, antigen-binding fragments thereof, and antibody-drug conjugates (immunoconjugates) as a means to treat B-cell malignancies. The present invention addresses that need.

BRIEF SUMMARY OF THE INVENTION

Novel antibodies that bind to human CD37, immunoconjugates comprising these antibodies, and methods of their use are described herein. Novel polypeptides, such as antibodies that bind human CD37, fragments of such antibodies, and other polypeptides related to such antibodies are also provided. Polynucleotides comprising nucleic acid sequences encoding the polypeptides are also provided, as are vectors comprising the polynucleotides. Cells comprising the polypeptides and/or polynucleotides of the invention are further provided. Compositions (e.g., pharmaceutical compositions) comprising the novel CD37 antibodies or immunoconjugates are also provided. In addition, methods of making and using the novel CD37 antibodies or immunoconjugates are also provided, such as methods of using the novel CD37 antibodies or immunoconjugates to inhibit tumor growth and/or treat cancer.

Antibodies or antigen binding fragment thereof that specifically bind to CD37, and are capable of inducing complement dependent cytotoxicity (CDC) are provided. In some embodiments, the antibody is also capable of inducing apoptosis and/or antibody dependent cell mediated cytotoxicity (ADCC).

The antibody or antigen binding fragment thereof can be one that specifically binds to the same CD37 epitope as an antibody selected from the group consisting of: (a) an antibody comprising the polypeptide of SEQ ID NO:55 and the polypeptide of SEQ ID NO:72; (b) an antibody comprising the polypeptide of SEQ ID NO:59 and the polypeptide of SEQ ID NO:75; (c) an antibody comprising the polypeptide of SEQ ID NO:61 and the polypeptide of SEQ ID NO:77; (d) an antibody comprising the polypeptide of SEQ ID NO:64 and the polypeptide of SEQ ID NO:80; (e) an antibody comprising the polypeptide of SEQ ID NO:66 and the polypeptide of SEQ ID NO:82; (f) an antibody comprising the polypeptide of SEQ ID NO:68 and the polypeptide of SEQ ID NO:84; and (g) an antibody comprising the polypeptide of SEQ ID NO:70 and the polypeptide of SEQ ID NO:86.

In some embodiments, the antibody or antigen binding fragment thereof specifically binds to CD37 and specifically binds to the polypeptide of SEQ ID NO: 180. In a certain embodiment, the antibody or antigen binding fragment thereof does not bind to the polypeptide of SEQ ID NO: 184.

In some embodiments, the antibody or antigen binding fragment thereof specifically binds to CD37, and the antibody or fragment thereof competitively inhibits an antibody selected from the group consisting of: (a) an antibody comprising the polypeptide of SEQ ID NO:55 and the polypeptide of SEQ ID NO:72; (b) an antibody comprising the polypeptide of SEQ ID NO:59 and the polypeptide of SEQ ID NO:75; (c) an antibody comprising the polypeptide of SEQ ID NO:61 and the polypeptide of SEQ ID NO:77; (d) an antibody comprising the polypeptide of SEQ ID NO:64 and the polypeptide of SEQ ID NO:80; (e) an antibody comprising the polypeptide of SEQ ID NO:66 and the polypeptide of SEQ ID NO:82; (f) an antibody comprising the polypeptide of SEQ ID NO:68 and the polypeptide of SEQ ID NO:84; and (g) an antibody comprising the polypeptide of SEQ ID NO:70 and the polypeptide of SEQ ID NO:86.

In certain embodiments, the antibody or antigen binding fragment thereof is produced by hybridoma selected from the group consisting of ATCC Deposit Designation PTA-10664, deposited with the ATCC on Feb. 18, 2010, ATCC Deposit Designation PTA-10665, deposited with the ATCC on Feb. 18, 2010, ATCC Deposit Designation PTA-10666, deposited with the ATCC on Feb. 18, 2010, ATCC Deposit Designation PTA-10667 deposited with the ATCC on Feb. 18, 2010, ATCC Deposit Designation PTA-10668, deposited with the ATCC on Feb. 18, 2010, ATCC Deposit Designation PTA-10669, deposited with the ATCC on Feb. 18, 2010, and ATCC Deposit Designation PTA-10670, deposited with the ATCC on Feb. 18, 2010.

The ATCC is located at 10801 University Boulevard Manassas Va. 20110.

In some embodiments, the antibody or antigen binding fragment thereof specifically binds to CD37, and the antibody comprises polypeptide sequences selected from the group consisting of: (a) SEQ ID NOs: 4, 5, and 6 and SEQ ID NOs: 28, 29, and 30; (b) SEQ ID NOs: 7, 8, and 9 and SEQ ID NOs: 31, 32, and 33; (c) SEQ ID NOs: 10, 11, and 12 and SEQ ID NOs: 34, 35, and 36; (d) SEQ ID NOs: 13, 14, and 15 and SEQ ID NOs: 37, 38, and 39; (e) SEQ ID NOs: 13, 14, and 15 and SEQ ID NOs: 37, 40, and 39; (f) SEQ ID NOs: 16, 17, and 18 and SEQ ID NOs: 41, 42, and 43; (g) SEQ ID NOs: 19, 20, and 21 and SEQ ID NOs: 44, 45, and 46; (h) SEQ ID NOs: 19, 20, and 21 and SEQ ID NOs: 44, 47, and 46; (i) SEQ ID NOs: 22, 23, and 24 and SEQ ID NOs: 48, 49, and 50; (j) SEQ ID NOs: 22, 23, and 24 and SEQ ID NOs: 48, 51, and 50; (k) SEQ ID NOs: 25, 26, and 27 and SEQ ID NOs: 52, 53, and 54; and (l) variants of (a) to (k) comprising 1, 2, 3, or 4 conservative amino acid substitutions.

In further embodiments, the antibody or antigen binding fragment thereof comprises polypeptide sequences that are at least 90% identical, at least 95% identical, at least 99% identical, or identical to polypeptide sequences selected from the group consisting of: (a) SEQ ID NO:55 and SEQ ID NO:72; (b) SEQ ID NO:56 and SEQ ID NO:73; (c) SEQ ID NO:57 and SEQ ID NO:74; (d) SEQ ID NO:58 and SEQ ID NO:74; (e) SEQ ID NO:59 and SEQ ID NO:75; (f) SEQ ID NO:60 and SEQ ID NO:76; (g) SEQ ID NO:61 and SEQ ID NO:77; (h) SEQ ID NO:62 and SEQ ID NO:78; (i) SEQ ID NO:63 and SEQ ID NO:79; (j) SEQ ID NO:64 and SEQ ID NO:80; (k) SEQ ID NO:65 and SEQ ID NO:81; (l) SEQ ID NO:66 and SEQ ID NO:82; (m) SEQ ID NO:67 and SEQ ID NO:83; (n) SEQ ID NO:68 and SEQ ID NO:84; (o) SEQ ID NO:69 and SEQ ID NO:85; (p) SEQ ID NO:70 and SEQ ID NO:86; and (q) SEQ ID NO:71 and SEQ ID NO:87.

In some embodiments, the antibody or antigen binding fragment thereof is murine, non-human, humanized, chimeric, resurfaced, or human.

In some embodiments, the antibody or antibody fragment is capable of inducing apoptosis of a cell expressing CD37 in vitro in the absence of cross-linking agents. In some embodiments, the antibody or antigen binding fragment is capable of inducing complement dependent cytotoxicity (CDC). In still further embodiments, the antibody or antigen binding fragment is capable of inducing antibody dependent cell mediated cytotoxicity (ADCC).

In other embodiments, the antibody or antigen binding fragment thereof is human or humanized, specifically binds to CD37, and is capable of inducing apoptosis of a cell expressing CD37 in vitro in the absence of cross-linking agents. In further embodiments, the human or humanized antibody or antigen binding fragment thereof is also capable of inducing complement dependent cytotoxicity (CDC) and/or capable of inducing antibody dependent cell mediated cytotoxicity (ADCC).

In still other embodiments, the antibody or antigen binding fragment thereof binds to human CD37 and macaque CD37.

In some embodiments, the antibody or antigen binding fragment thereof is a full length antibody or an antigen binding fragment. The antibody or antigen binding fragment thereof can comprise a Fab, Fab', F(ab')2, Fd, single chain Fv or scFv, disulfide linked Fv, V-NAR domain, IgNar, intrabody, IgGΔCH2, minibody, F(ab')3, tetrabody, triabody, diabody, single-domain antibody, DVD-Ig, Fcab, mAb2, (scFv) 2, or scFv-Fc.

In other embodiments, the CD37-binding agent is a polypeptide that specifically binds CD37, and the polypeptide comprises sequences selected from the group consisting of: (a) SEQ ID NOs: 4, 5, and 6 and SEQ ID NOs: 28, 29, and 30; (b) SEQ ID NOs: 7, 8, and 9 and SEQ ID NOs: 31, 32, and 33; (c) SEQ ID NOs: 10, 11, and 12 and SEQ ID NOs: 34, 35, and 36; (d) SEQ ID NOs: 13, 14, and 15 and SEQ ID NOs: 37, 38, and 39; (e) SEQ ID NOs: 13, 14, and 15 and SEQ ID NOs: 37, 40, and 39; (f) SEQ ID NOs: 16, 17, and 18 and SEQ ID NOs: 41, 42, and 43; (g) SEQ ID NOs: 19, 20, and 21 and SEQ ID NOs: 44, 45, and 46; (h) SEQ ID NOs: 19, 20, and 21 and SEQ ID NOs: 44, 47, and 46; (i) SEQ ID NOs: 22, 23, and 24 and SEQ ID NOs: 48, 49, and 50; (j) SEQ ID NOs: 22, 23, and 24 and SEQ ID NOs: 48, 51, and 50; (k) SEQ ID NOs: 25, 26, and 27 and SEQ ID NOs: 52, 53, and 54; and (l) variants of (a) to (k) comprising 1, 2, 3, or 4 conservative amino acid substitutions.

In other embodiments, the CD37-binding agent is a polypeptide that specifically binds CD37, and the polypeptide comprises sequences that are at least 90% identical, at least 95% identical, at least 99% identical, or identical to sequences selected from the group consisting of: (a) SEQ ID NO:55 and SEQ ID NO:72; (b) SEQ ID NO:56 and SEQ ID NO:73; (c) SEQ ID NO:57 and SEQ ID NO:74; (d) SEQ ID NO:58 and SEQ ID NO:74; (e) SEQ ID NO:59 and SEQ ID NO:75; (f) SEQ ID NO:60 and SEQ ID NO:76; (g) SEQ ID NO:61 and SEQ ID NO:77; (h) SEQ ID NO:62 and SEQ ID NO:78; (i) SEQ ID NO:63 and SEQ ID NO:79; (j) SEQ ID NO:64 and SEQ ID NO:80; (k) SEQ ID NO:65 and SEQ ID NO:81; (l) SEQ ID NO:66 and SEQ ID NO:82; (m) SEQ ID NO:67 and SEQ ID NO:83; (n) SEQ ID NO:68 and SEQ ID NO:84; (o) SEQ ID NO:69 and SEQ ID NO:85; (p) SEQ ID NO:70 and SEQ ID NO:86; and (q) SEQ ID NO:71 and SEQ ID NO:87.

Cells producing the antibody or antigen binding fragment thereof or the polypeptide can also be made and used according to the methods described herein. The methods provide methods of making an antibody or antigen-binding fragment thereof or a polypeptide comprising (a) culturing a cell producing such a CD37-binding agent; and (b) isolating the antibody, antigen-binding fragment thereof, or polypeptide from the cultured cell.

In some embodiments, the CD37-binding agent is an immunoconjugate having the formula (A)-(L)-(C), wherein: (A) is a CD37-binding agent; (L) is a linker; and (C) is a cytotoxic agent; and wherein the linker (L) links (A) to (C).

In some embodiments, the CD37-binding agent is an immunoconjugate having the formula (A)-(L)-(C), wherein: (A) is an antibody or antigen binding fragment that specifically binds to CD37; (L) is a non-cleavable linker; and (C) is a cytotoxic agent; and wherein the linker (L) links (A) to (C).

In some embodiments, the CD37-binding agent is an immunoconjugate having the formula (A)-(L)-(C), wherein: (A) is an antibody or antigen binding fragment that specifically binds to CD37; (L) is a linker; and (C) is a maytansinoid; and wherein the linker (L) links (A) to (C).

The immunoconjugate linker can be a non-cleavable linker. The linker can be selected from a group consisting of a cleavable linker, a non-cleavable linker, a hydrophilic linker, and a dicarboxylic acid based linker The linker can be selected from the group consisting of: N-succinimidyl 4-(2-pyridyldithio) pentanoate (SPP); N-succinimidyl 4-(2-pyridyldithio)butanoate (SPDB) or N-succinimidyl 4-(2-pyridyldithio)-2-sulfobutanoate (sulfo-SPDB); N-succinimidyl 4-(maleimidomethyl)cyclohexanecarboxylate (SMCC); N-sulfosuccinimidyl 4-(maleimidomethyl)cyclohexanecarboxylate (sulfoSMCC); N-succinimidyl-4-(iodoacetyl)-aminobenzoate (SIAB); and N-succinimidyl-[(N-maleimidopropionamido)-tetraethyleneglycol]ester (NHS-PEG4-maleimide). The linker can be N-succinimidyl-[(N-maleimidopropionamido)-tetraethyleneglycol]ester (NHS-PEG4-maleimide).

The cytotoxic agent can be selected from the group consisting of a maytansinoid, maytansinoid analog, doxorubicin, a modified doxorubicin, benzodiazepine, taxoid, CC-1065, CC-1065 analog, duocarmycin, duocarmycin analog, calicheamicin, dolastatin, dolastatin analog, aristatin, tomaymycin derivative, and leptomycin derivative or a prodrug of the agent. The cytotoxic agent can be a maytansinoid. The cytotoxic agent can be N(2)-deacetyl-N(2')-(3-mercapto-1-oxopropyl)-maytansine (DM1) or N(2')-deacetyl-N2-(4-mercapto-4-methyl-1-oxopentyl)-maytansine (DM4).

Also provided herein is a pharmaceutical composition comprising a CD37-binding agent and a pharmaceutically acceptable carrier. The pharmaceutical composition can comprise a second anti-cancer agent.

A diagnostic reagent comprising a CD37-binding agent which is labeled is also provided herein. The label can be selected from the group consisting of a radiolabel, a fluorophore, a chromophore, an imaging agent and a metal ion.

Also provided herein is a kit comprising a CD37-binding agent.

The methods described herein include methods for inhibiting the growth of a cell expressing CD37 comprising contacting the cell with a CD37 binding agent or pharmaceutical composition comprising the same.

The methods also provide methods for treating a patient having cancer comprising administering to the patient a therapeutically effective amount of a CD37 binding agent or pharmaceutical composition comprising the same to the subject.

The methods can comprise administering a second anti-cancer agent to the subject. The second anti-cancer agent can be a chemotherapeutic agent.

The cancer can be a cancer selected from the group consisting of B cell lymphomas, NHL, precursor B cell lymphoblastic leukemia/lymphoma and mature B cell neoplasms, B cell chronic lymphocytic leukemia (CLL)/small lymphocytic lymphoma (SLL), B cell prolymphocytic leukemia, lymphoplasmacytic lymphoma, mantle cell lymphoma (MCL), follicular lymphoma (FL), low grade, intermediate-grade and high-grade (FL), cutaneous follicle center lymphoma, marginal zone B cell lymphoma, MALT type marginal zone B cell lymphoma, nodal marginal zone B cell lymphoma, splenic type marginal zone B cell lymphoma, hairy cell leukemia, diffuse large B cell lymphoma, Burkitt's lymphoma, plasmacytoma, plasma cell myeloma, post-transplant lymphoproliferative disorder, Waldenstrom's macroglobulinemia, and anaplastic large-cell lymphoma (ALCL).

Isolated polynucleotides comprising a sequence that encodes a polypeptide at least 90% identical, at least 95% identical, at least 99% identical, or identical to a sequence selected from the group consisting of SEQ ID NOs: 55-87 are also provided herein. The polynucleotide can comprise a sequence that is at least 90%, at least 95% identical, at least 99% identical, or identical to SEQ ID NOs: 121-151.

Vectors and host cells comprising such polynucleotides and vectors are also provided herein.

BRIEF DESCRIPTION OF THE DRAWINGS/FIGURES

FIG. 1 depicts the histograms for antibody binding to non-transfected 300-19 control cells (left panels) and CD37-expressing 300-19 cells (right panels). Histograms are shown for staining with 10 nM of muCD37-3, muCD37-12, muCD37-38 and the absence of primary antibody.

FIG. 2 depicts the histograms for antibody binding to non-transfected 300-19 control cells (left panels) and CD37-expressing 300-19 cells (right panels). Histograms are shown for staining with 10 nM muCD37-50, muCD37-51, muCD37-56 and muCD37-57.

FIG. 3 depicts the binding of (A) muCD37-3 and muCD37-12 and (B) muCD37-8, muCD37-10 and muCD37-14 to WSU-DLCL-2 cells as assayed by flow cytometry. Mean fluorescence intensity (MFI) is plotted for each antibody concentration used. The binding curves were used to determine the EC50 of antibody binding, which corresponds to the apparent Kd of each antibody.

FIG. 4 depicts results from an Annexin-V assay to measure induction of apoptosis using Ramos lymphoma cells incubated with a 10 nM concentration of (A) rituximab, muCD37-3, muCD37-8, muCD37-10, muCD37-12 or muCD37-14 and (B) rituximab, huCD37-3, muCD37-38, muCD37-50, muCD37-51, muCD37-56 or muCD37-57. Control samples of untreated cells in the absence of antibody (no Ab) are used in comparison.

FIG. 6 depicts a list of CD37-3 surface residues and substitutions in resurfaced versions for (A) CD37-3 VL and (B) CD37-3 VH.

FIG. 7 depicts a list of CD37-50 surface residues and substitutions in the resurfaced version for (A) CD37-50 VL and (B) CD37-50 VH.

FIG. 8 depicts alignments of resurfaced sequences for the CD37-3 and CD37-50 variable region with their murine counterparts: A) CD37-3 light chain variable domain; B) CD37-3 heavy chain variable domain. C) CD37-50 light chain variable domain; D) CD37-50 heavy chain variable domain. Dashes "-" denote identity with the murine sequence.

FIG. 9 depicts (A) direct binding assays of muCD37-3, chCD37-3, muCD37-12 and chCD37-12 to Ramos cells as assayed by flow cytometry and (B) competitive binding assays with muCD37-3, chCD37-3, huCD37-3v1.0 and huCD37-3v1.01 to BJAB cells in the presence of 2 nM concentration of muCD37-3-PE conjugates.

FIG. 10 depicts binding of anti-CD37 antibodies to 300-19 cells expressing the macaque CD37 antigen as assayed by flow cytometry: (A) binding of muCD37-3, muCD37-12, muCD37-38, muCD37-50, muCD37-51, muCD37-56, muCD37-57, WR17 and TRU-016 and (B) binding of huCD37-3, huCD37-38, huCD37-50, huCD37-51, huCD37-56 and huCD37-57. The binding curves were used to determine the EC50 of antibody binding, which corresponds to the apparent Kd of each antibody.

Figure 11:
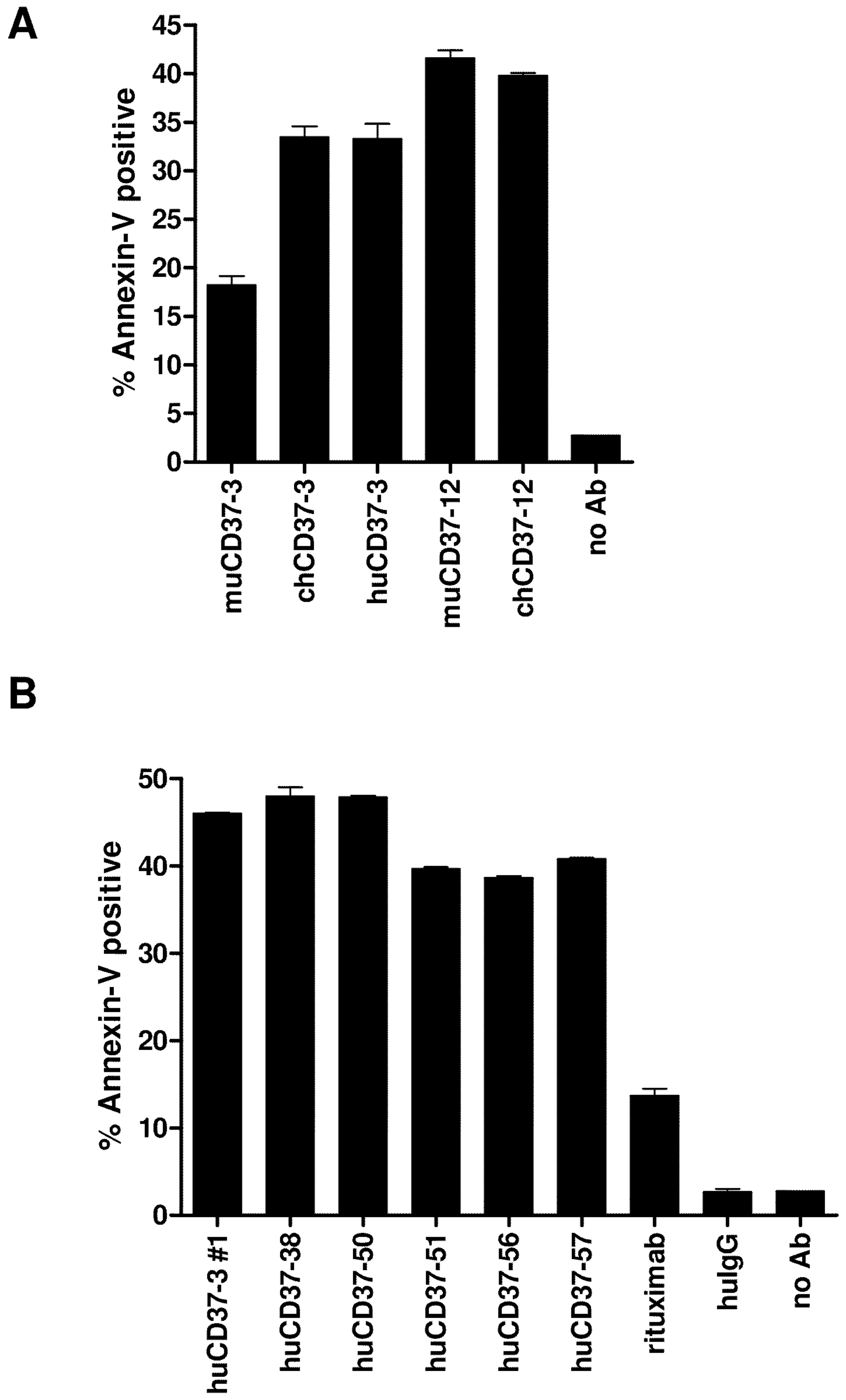

FIG. 11 depicts the results from an Annexin-V assay to measure induction of apoptosis on Ramos lymphoma cells incubated with varying concentration of (A) huCD37-3, huCD37-38, huCD37-50 and (B) huCD37-51, huCD37-56, huCD36-57 and rituximab. Control samples of cells treated with a human IgG1 isotype control antibody (huIgG control) are used in comparison.

FIG. 12 depicts the results from WST-8 proliferation assays on (A) SU-DHL-4 and (B) DOHH-2 lymphoma cells incubated with varying concentrations of muCD37-3, chCD37-3, huCD37-3v1.0 and huCD37-3v1.01 antibodies for 5 days.

Figure 13:
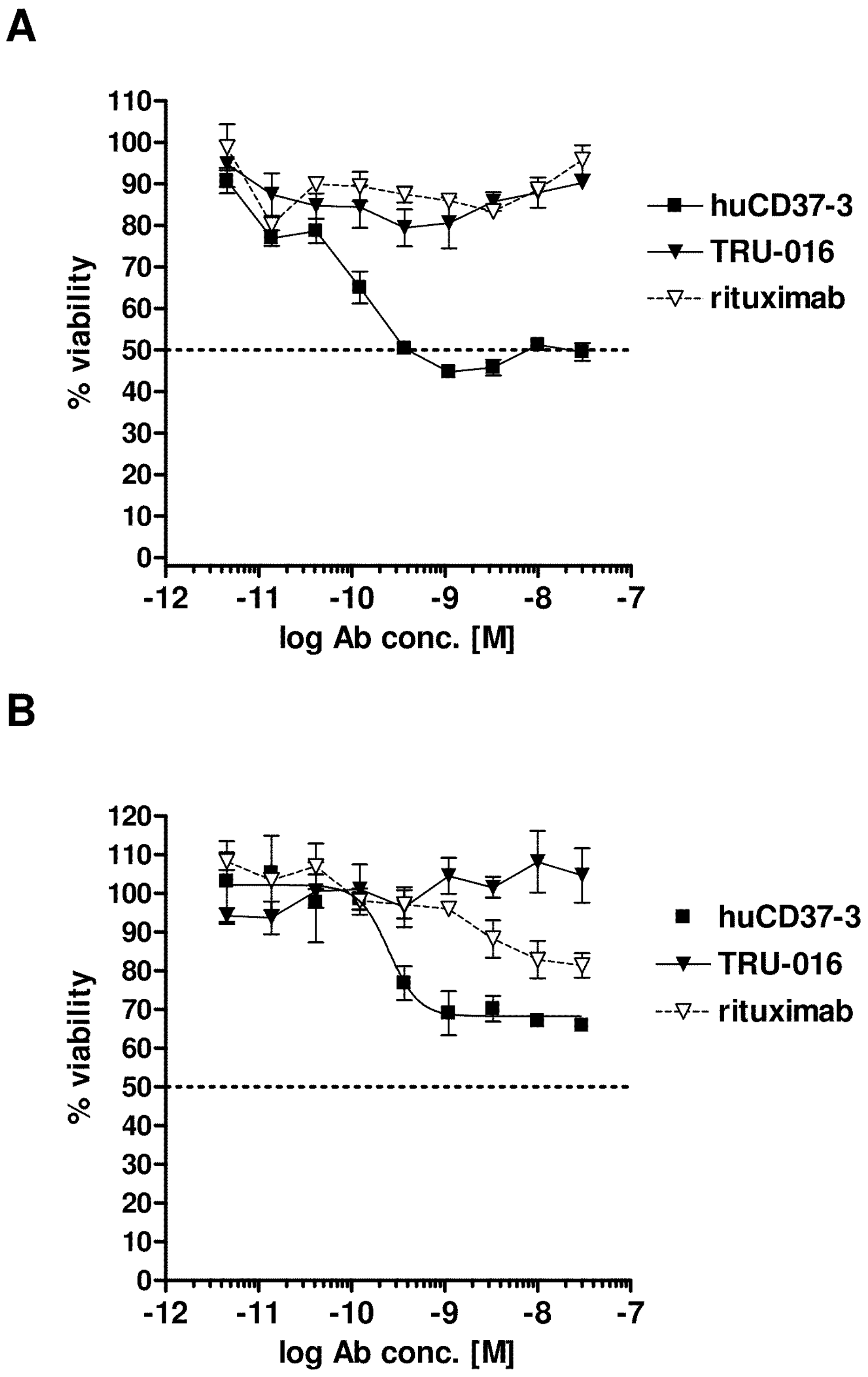

FIG. 13 depicts the results from WST-8 proliferation assays on (A) Granta-519 and (B) SU-DHL-4 lymphoma cells incubated with varying concentrations of huCD37-3, TRU-016 or rituximab antibodies for 5 days.

FIG. 14 depicts the results from CDC assays on Ramos lymphoma cells incubated with (A) huCD37-3, huCD37-38, chCD37-12 or a huIgG1 isotype control antibody and (B) huCD37-38, huCD37-50, huCD37-51, huCD37-56, huCD37-57, chCD37-12 or a huIgG1 isotype control antibody in the presence of 5% human serum as a source of complement.

Figure 15:
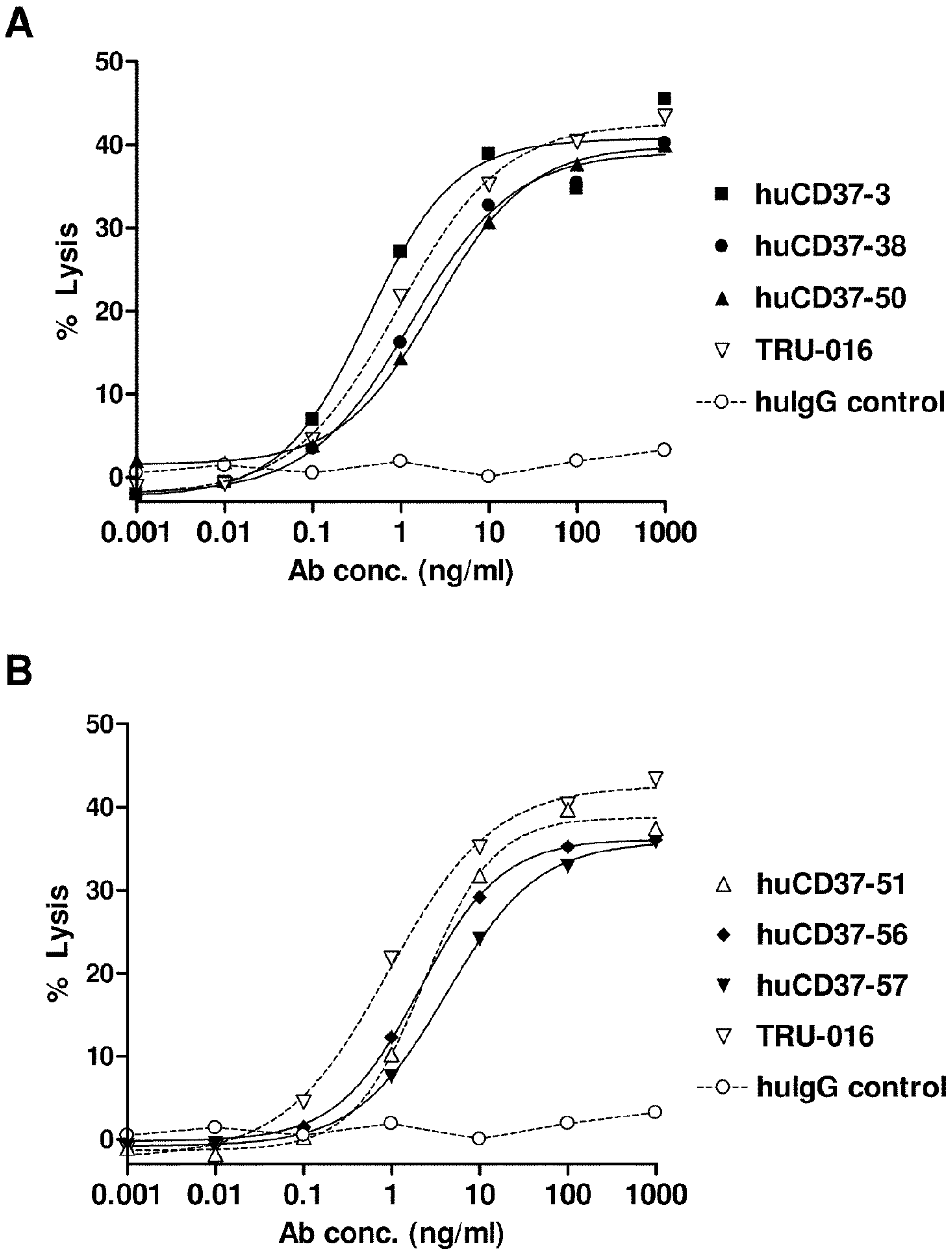

FIG. 15 depicts the results from an ADCC assay on Daudi lymphoma cells incubated with (A) huCD37-3, huCD37-38, huCD37-50, TRU-016 and (B) huCD37-51, huCD37-56, huCD37-57, TRU-016 or a human IgG1 isotype control antibody in the presence of purified human NK cells as effector cells.

FIG. 16 depicts the alignment of the full length murine, human, and macaca CD37 amino acid sequences. Dashes "-" denote identity with the murine sequence. The small and large extracellular domains are marked with underlines.

FIG. 17 depicts the alignment of the large extracellular domain of human, recombinant and wild type murine, macaca and the chimeric CD37 sequences. Dashes "-" denote identity with the human sequence. The positions of the engineered restriction sites are given and the affected residues are underlined.

FIG. 18 depicts binding of a panel of CD37 antibodies to cells transfected with (A) human CD37 wildtype and (B) hCD37-M3 variant as assayed by flow cytometry using 1.5 μg/mL of each antibody.

Figure 19:
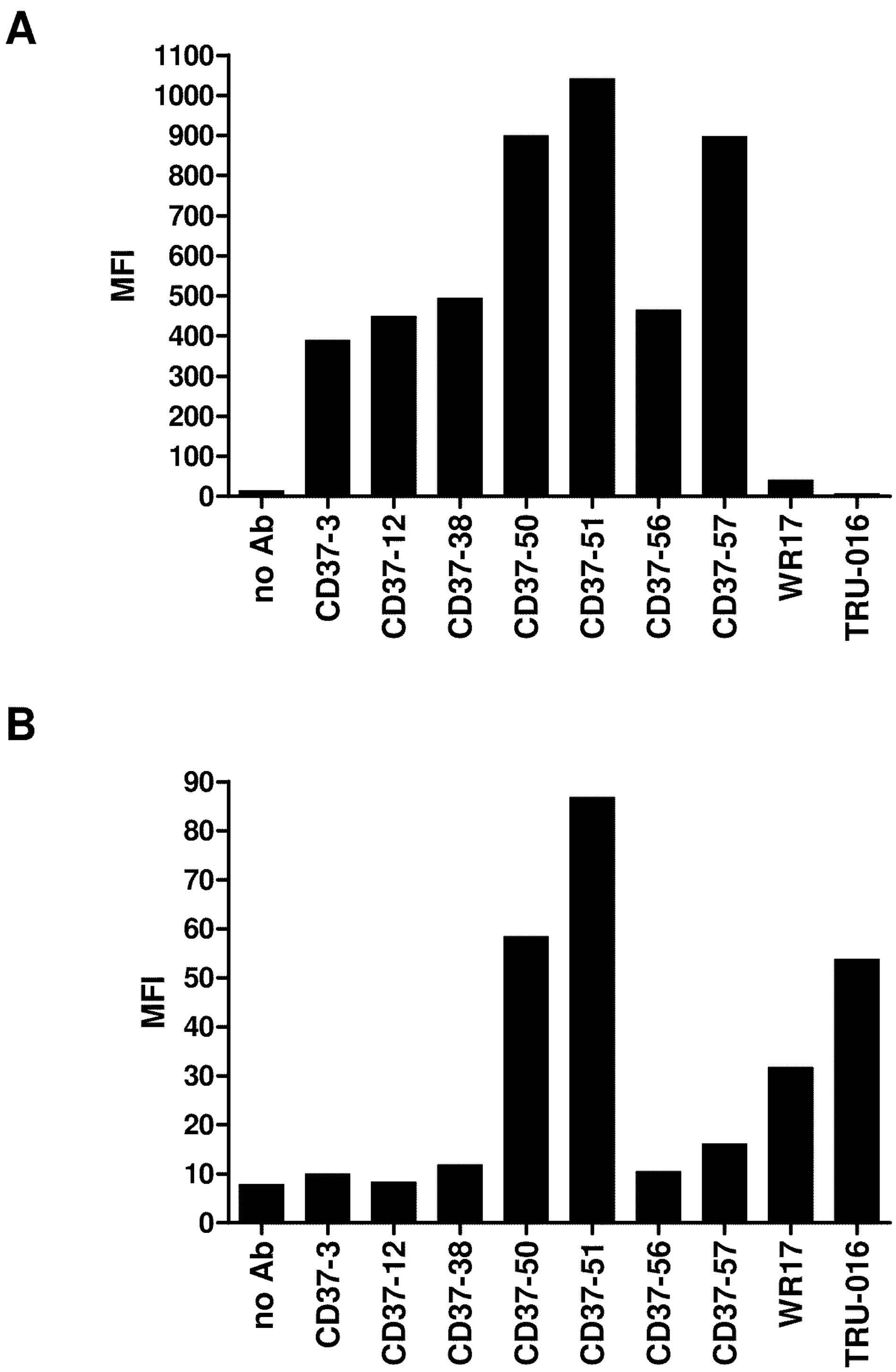

FIG. 19 depicts binding of a panel of CD37 antibodies to cells transfected with (A) the hCD37-M1 variant and (B) the hCD37-M45 variant as assayed by flow cytometry using 1.5 μg/mL of each antibody.

FIG. 20 depicts binding of (A) huCD37-3 in comparison with huCD37-3-SMCC-DM1 huCD37-3-SPP-DM1 and huCD37-3-sulfo-mal-DM4 and (B) huCD37-38 in comparison with huCD37-38-SMCC-DM1 to BJAB cells as assayed by flow cytometry. The binding curves were used to determine the EC50 of antibody or conjugate binding, which corresponds to the apparent Kd of each.

Figure 21:
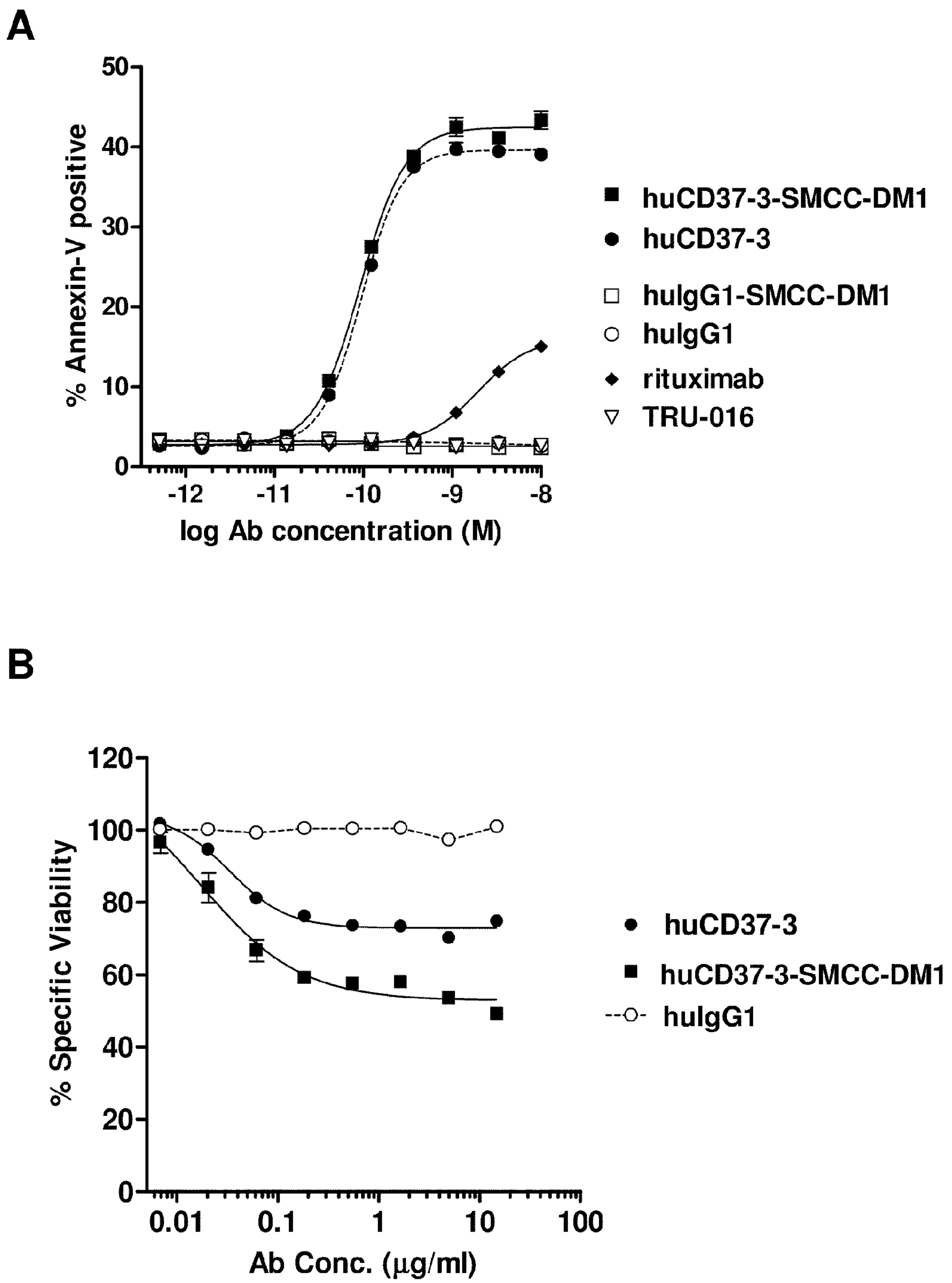

FIG. 21 depicts the results of (A) an Annexin-V assay to measure induction of apoptosis and (B) the results from a CDC assay. Assays were performed on Ramos lymphoma cells incubated with varying concentrations of the huCD37-3, huCD37-3-SMCC-DM1, huIgG1 control antibody, huIgG1-SMCC-DM1 control conjugate, or rituximab. CDC assays were performed in the presence of 5% human serum as a source of complement.

FIG. 22 depicts the results from ADCC assays on (A) Daudi lymphoma cells incubated with huCD37-3, huCD37-3-SMCC-DM1, huCD37-3-PEG4-mal-DM1, TRU-016 or a huIgG1 isotype control antibody and (B) Ramos lymphoma cells incubated with huCD37-3, huCD37-3-SMCC-DM1, huCD37-3-PEG4-mal-DM1 or a huIgG1 isotype control antibody in the presence of purified human NK cells as effector cells.

Figure 23:
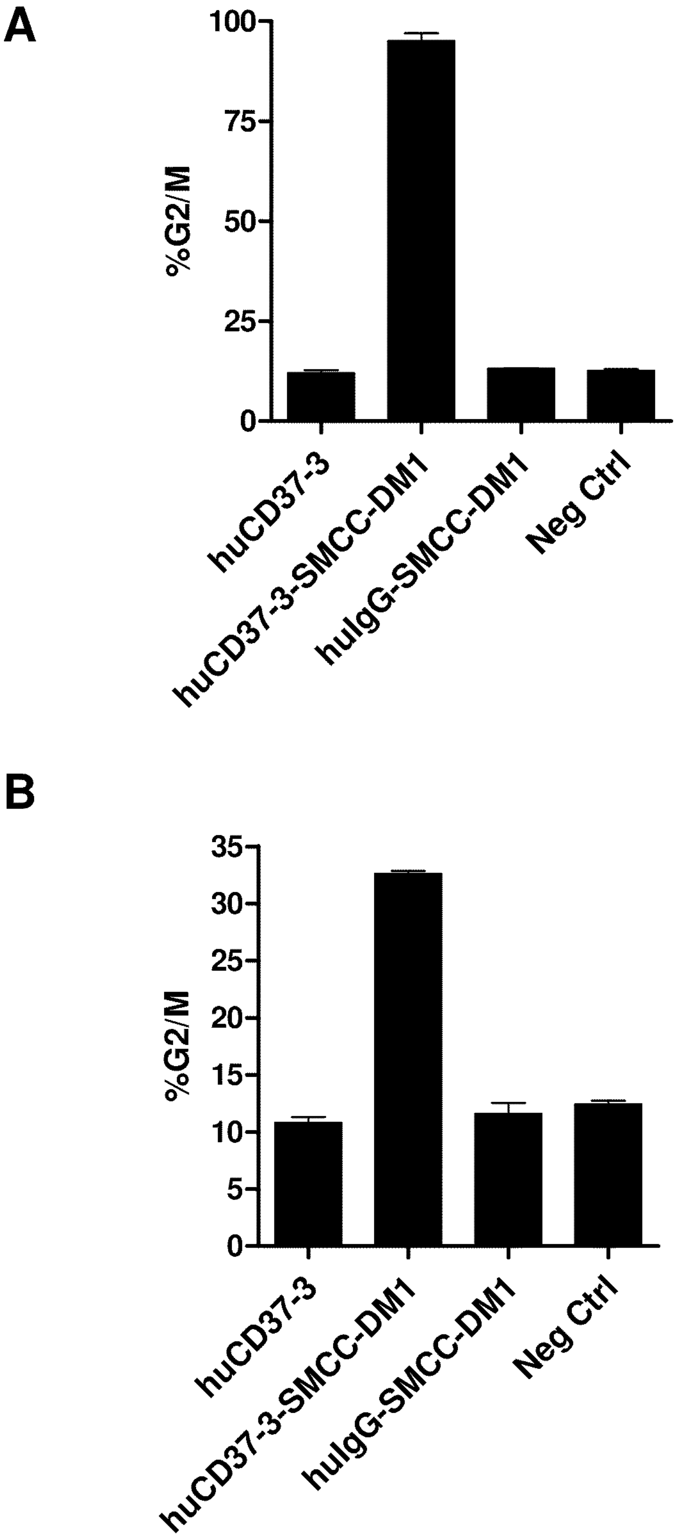

FIG. 23 depicts the results from a cell cycle analysis using propridium iodide staining on (A) BJAB cells and (B) RL cells incubated with huCD37-3, huCD37-3-SMCC-DM1, or a non-binding huIgG1-SMCC-DM1 control conjugate at a 10 nM concentration for 20 hours.

FIG. 24 depicts the results from a WST-8 cytotoxicity assay on (A) Daudi cells incubated with huCD37-3-SMCC-DM1, huCD37-38-SMCC-DM1, huCD37-50-SMCC-DM1, huCD37-51-SMCC-DM1, huCD37-56-SMCC-DM1, huCD37-57-SMCC-DM1, and (B) Granta-519 cells incubated with huCD37-3-SMCC-DM1, huCD37-38-SMCC-DM1, huCD37-50-SMCC-DM1, huCD37-51-SMCC-DM1, or a non-binding huIgG1-SMCC-DM1 control conjugate at concentrations ranging from $3\times10^{-8}$ M to $1\times10^{-11}$ M for 5 days.

FIG. 25 depicts the results of an established xenograft model using BJAB lymphoma cells implanted subcutaneous into SCID mice. Animals were treated once on day 12 post cell inoculation with either 10 mg/kg of (A) huCD37-3 Ab, huCD37-3-SMCC-DM1, huCD37-50 Ab, huCD37-50-SMCC-DM1 or (B) huCD37-38 Ab, huCD37-38-SMCC-DM1, huCD37-56 Ab, huCD37-56-SMCC-DM1. The mean tumor volume of the different treatment groups is plotted against time post tumor cell inoculation.

Figure 26:
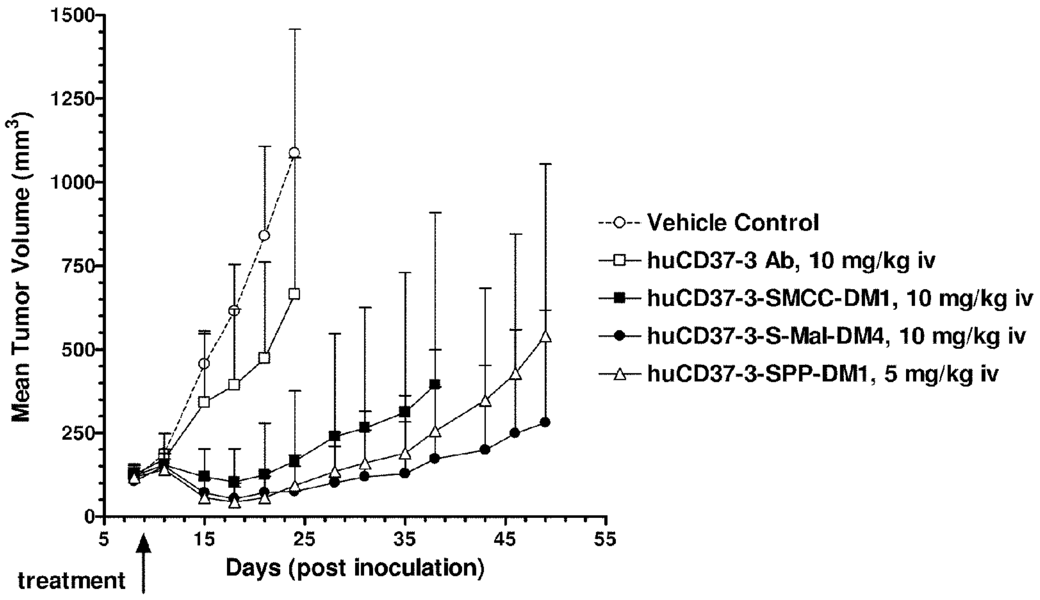

FIG. 26 depicts results from an established xenograft study using BJAB lymphoma cells implanted subcutaneous into SCID mice. Animals were treated once on day 9 post cell inoculation with either 10 mg/kg of huCD37-3 Ab, huCD37-3-SMCC-DM1, huCD37-3-sulfo-mal-DM4 or 5 mg/kg of huCD37-3-SPP-DM1. The mean tumor volume of the different treatment groups is plotted against time post tumor cell inoculation.

Figure 27:
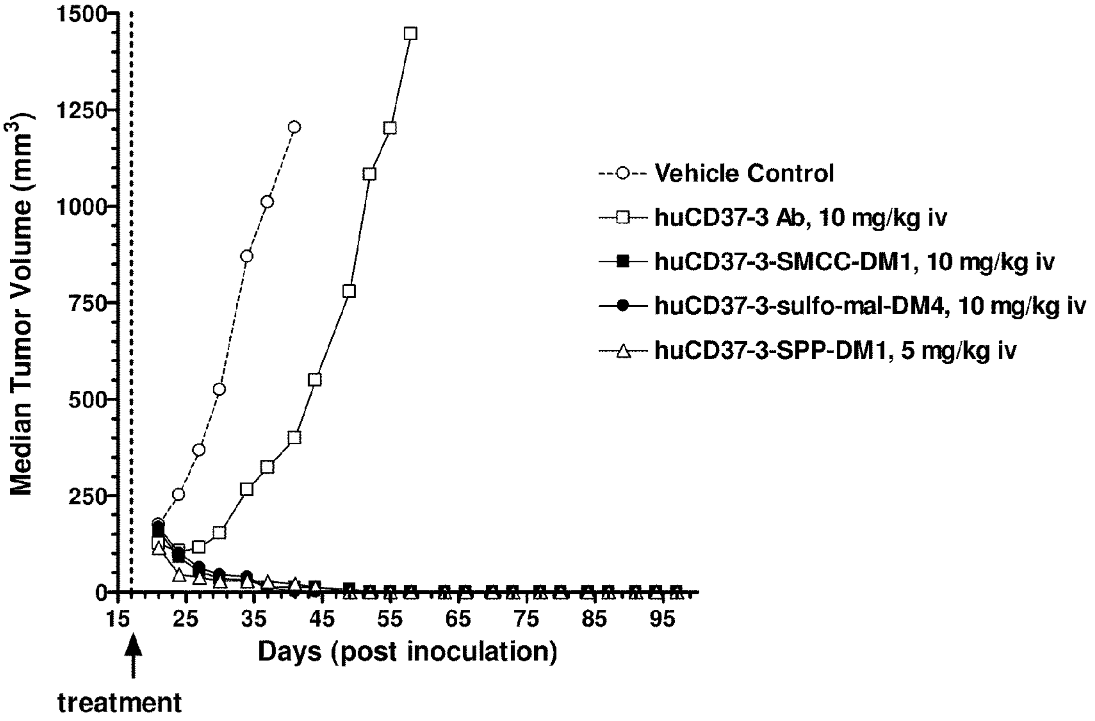

FIG. 27 depicts results from an established xenograft model using SU-DHL-4 diffuse large B-cell lymphoma cells implanted subcutaneous into SCID mice. Animals were treated once on day 17 post cell inoculation with either 10 mg/kg of huCD37-3 Ab, huCD37-3-SMCC-DM1, huCD37-3-sulfo-mal-DM4 or 5 mg/kg of huCD37-3-SPP-DM1. The median tumor volume of the different treatment groups is plotted against time post tumor cell inoculation.

Figure 28:
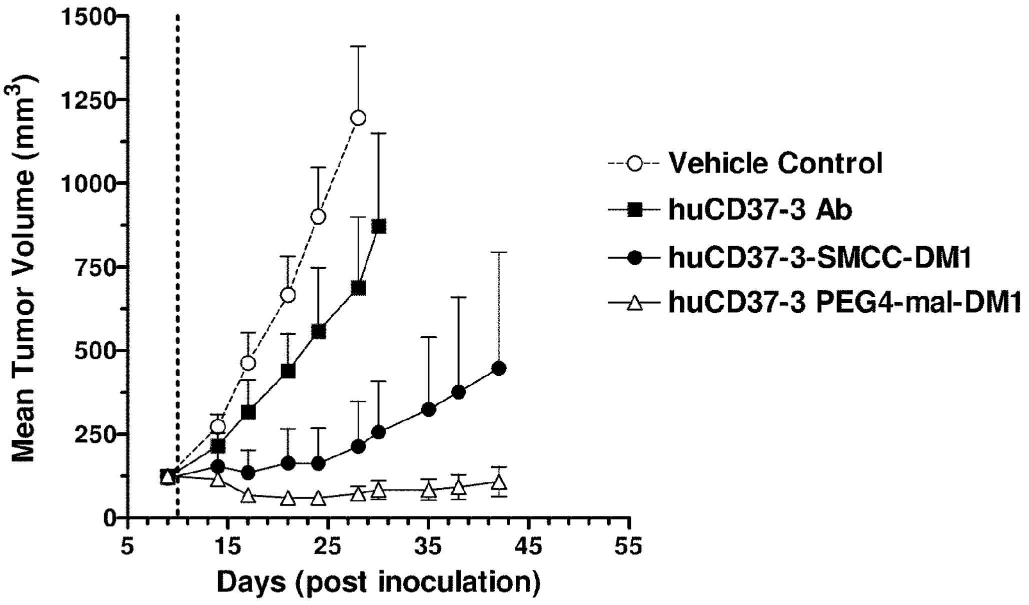

FIG. 28 depicts the results of an established xenograft model using BJAB lymphoma cells implanted subcutaneous into SCID mice. Animals were treated once on day 9 post cell inoculation with either 10 mg/kg of huCD37-3 Ab, huCD37-3-SMCC-DM1 or huCD37-3-PEG4-mal-DM1. The mean tumor volume of the different treatment groups is plotted against time post tumor cell inoculation.

Figure 29:
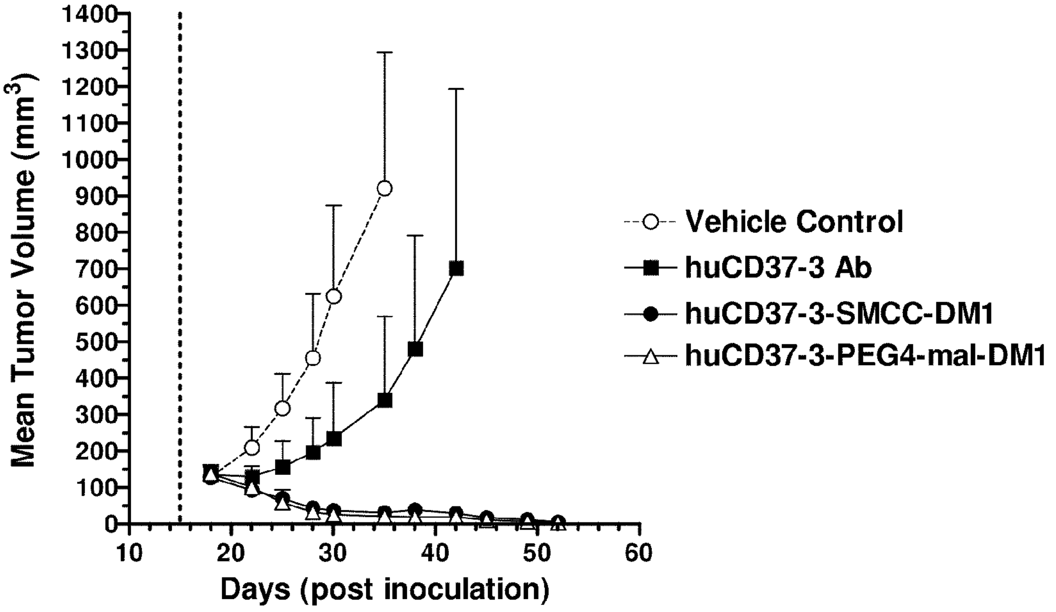

FIG. 29 depicts the results of an established xenograft model using SU-DHL-4 diffuse large B-cell lymphoma cells implanted subcutaneous into SCID mice. Animals were treated once on day 15 post cell inoculation with either 10 mg/kg of huCD37-3 Ab, huCD37-3-SMCC-DM1 or huCD37-3-PEG4-mal-DM1. The mean tumor volume of the different treatment groups is plotted against time post tumor cell inoculation.

Figure 30:
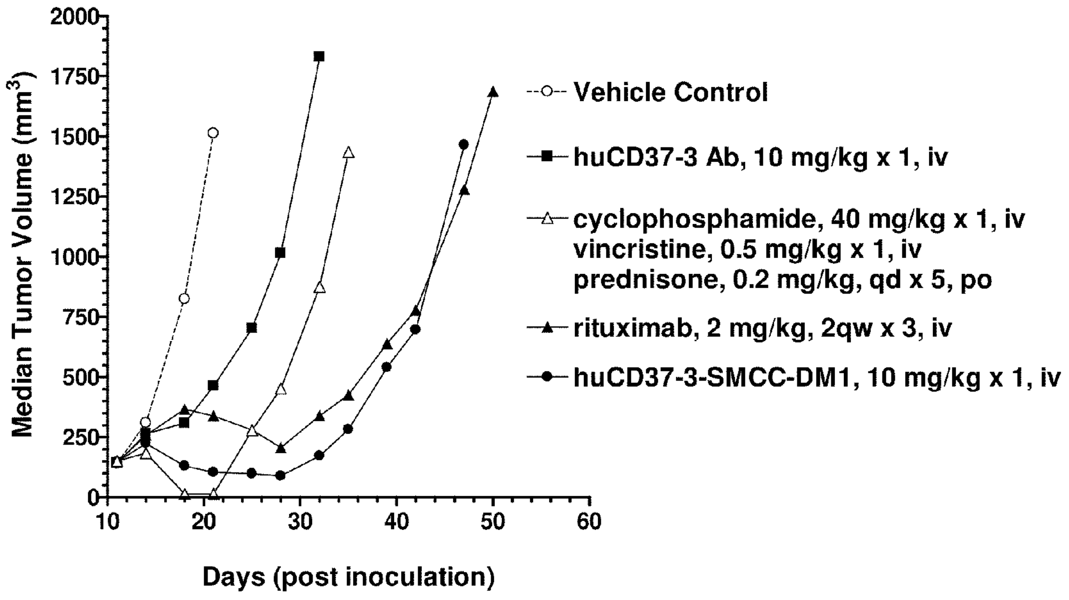

FIG. 30 depicts the results of an assay using an established xenograft model with DoHH2 follicular B-cell lymphoma cells implanted subcutaneously into SCID mice. Animals were treated starting on day 12 post inoculation with (i) a single dose of 10 mg/kg of huCD37-3 antibody, (ii) a single dose of 10 mg/kg of huCD37-3-SMCC-DM1 conjugate, (iii) six doses of 2 mg/kg of Rituximab twice per week for three weeks, (iv) a regimen of a single 40 mg/kg dose of cyclophosphamide and 0.5 mg/kg of vincristine, along with five daily 0.2 mg/kg doses of prednisone (CVP), or (v) a vehicle control. The median tumor volume of the different treatment groups is plotted against time post tumor cell inoculation.

Figure 31:
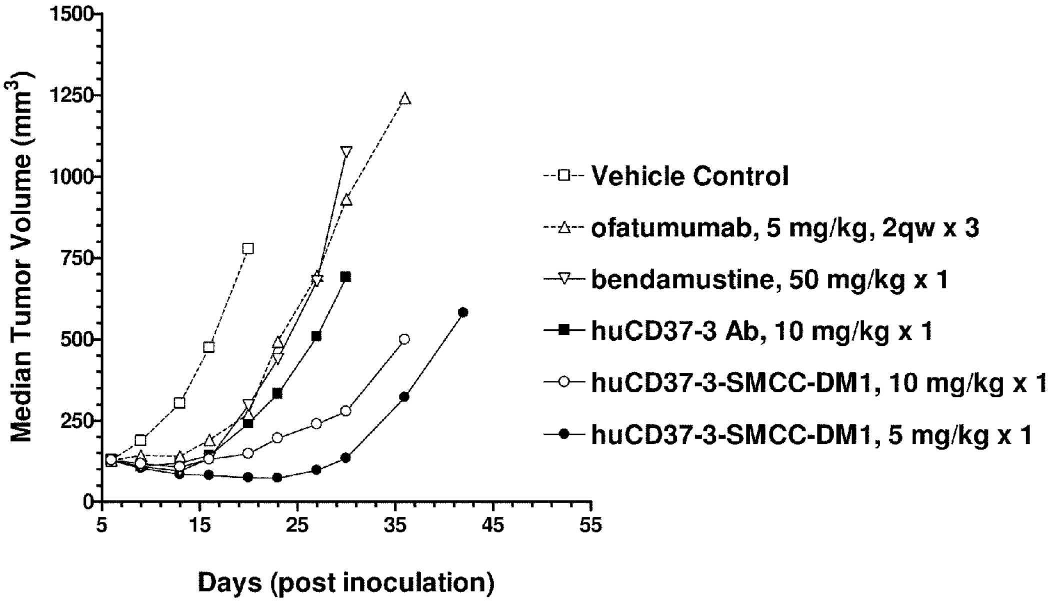

FIG. 31 depicts the results of an assay an using established xenograft model with JVM3 CLL cells implanted subcutaneous into SCID mice. Animals were treated starting on day 7 post inoculation with (i) a single dose of 10 mg/kg of huCD37-3 antibody, (ii) a 5 mg/kg dose of huCD37-3-SMCC-DM1 conjugate, (iii) a 10 mg/kg dose of huCD37-3-SMCC-DM1 conjugate, (iv) six doses of 5 mg/kg of ofatumumab twice per week for three weeks, (v) a single 50 mg/kg dose of bendamustine, or (vi) a vehicle control. The median tumor volume of the different treatment groups is plotted against time post tumor cell inoculation.

Figure 32:
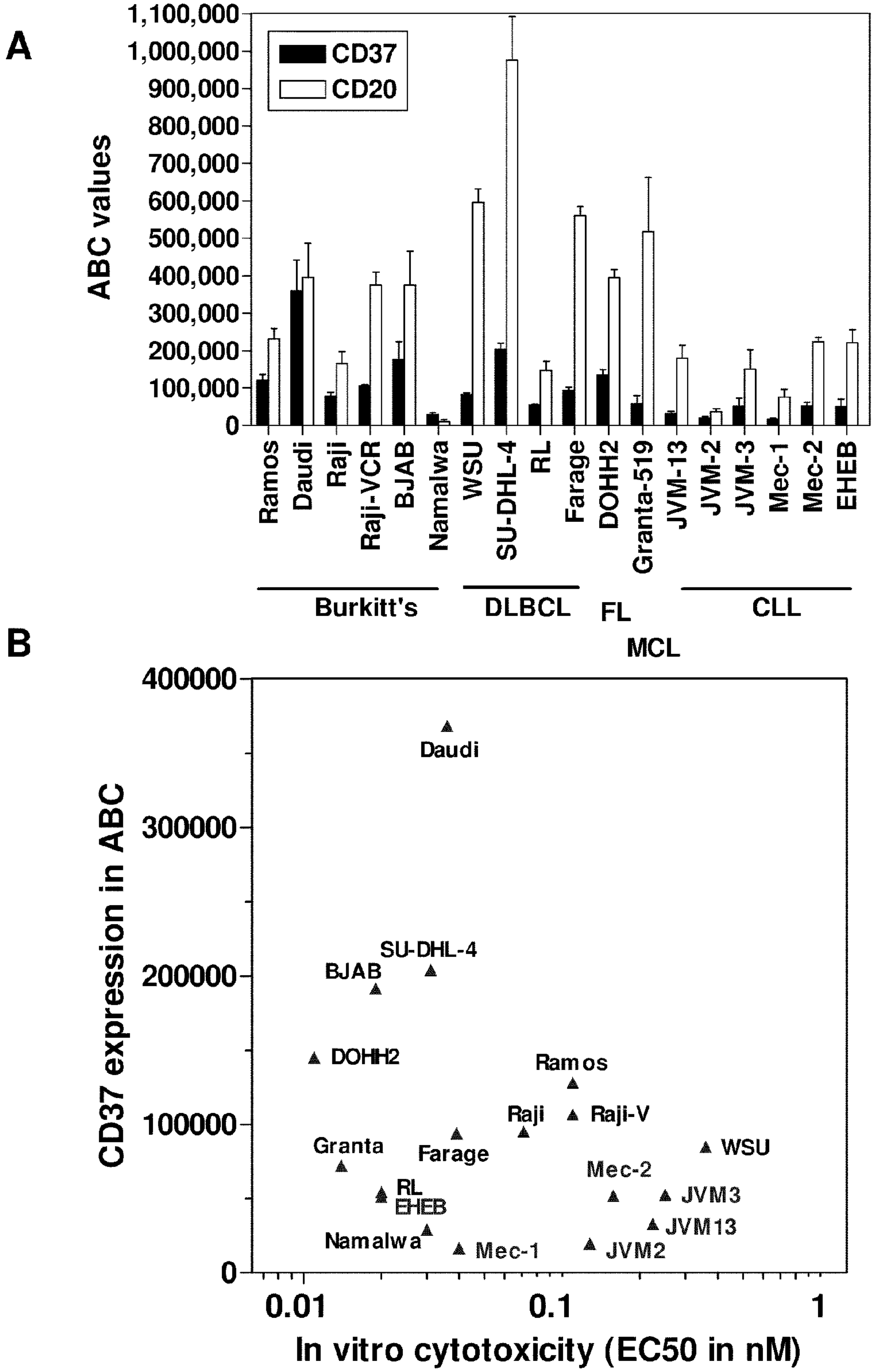

FIG. 32 depicts the CD37 and CD20 expression levels measured in various NHL and CLL tumor cell lines (A) and the in vitro cytotoxicity of huCD37-3-SMCC-DM1 measured in these cell lines (B).

DETAILED DESCRIPTION OF THE INVENTION

The present invention provides a new class of CD37 binding molecules having high potency in the following three cytotoxic activities against CD37 expressing (e.g., positive) cells: induction of apoptosis, ADCC, and CDC. Further, immunoconjugates of anti-CD37 antibodies kill CD37 expressing cells unexpectedly well, as demonstrated using in vivo tumor models.

I. Definitions

To facilitate an understanding of the present invention, a number of terms and phrases are defined below.

The term CD37 as used herein, refers to any native CD37, unless otherwise indicated. CD37 is also referred to as GP52-40, leukocyte antigen CD37, and Tetraspanin-26. The term "CD37" encompasses "full-length," unprocessed CD37 as well as any form of CD37 that results from processing in the cell. The term also encompasses naturally occurring variants of CD37, e.g., splice variants, allelic variants, and isoforms. The CD37 polypeptides described herein can be isolated from a variety of sources, such as from human tissue types or from another source, or prepared by recombinant or synthetic methods.

The term "antibody" means an immunoglobulin molecule that recognizes and specifically binds to a target, such as a protein, polypeptide, peptide, carbohydrate, polynucleotide, lipid, or combinations of the foregoing through at least one antigen recognition site within the variable region of the immunoglobulin molecule. As used herein, the term "antibody" encompasses intact polyclonal antibodies, intact monoclonal antibodies, antibody fragments (such as Fab, Fab', F(ab')2, and Fv fragments), single chain Fv (scFv) mutants, multispecific antibodies such as bispecific antibodies generated from at least two intact antibodies, chimeric antibodies, humanized antibodies, human antibodies, fusion proteins comprising an antigen determination portion of an antibody, and any other modified immunoglobulin molecule comprising an antigen recognition site so long as the antibodies exhibit the desired biological activity. An antibody can be of any the five major classes of immunoglobulins: IgA, IgD, IgE, IgG, and IgM, or subclasses (isotypes) thereof (e.g. IgG1, IgG2, IgG3, IgG4, IgA1 and IgA2), based on the identity of their heavy-chain constant domains referred to as alpha, delta, epsilon, gamma, and mu, respectively. The different classes of immunoglobulins have different and well known subunit structures and three-dimensional configurations. Antibodies can be naked or conjugated to other molecules such as toxins, radioisotopes, etc.

A "blocking" antibody or an "antagonist" antibody is one which inhibits or reduces biological activity of the antigen it binds, such as CD37. In some embodiments, blocking antibodies or antagonist antibodies substantially or completely inhibit the biological activity of the antigen. The biological activity can be reduced by 10%, 20%, 30%, 50%, 70%, 80%, 90%, 95%, or even 100%.

The term "anti-CD37 antibody" or "an antibody that binds to CD37" refers to an antibody that is capable of binding CD37 with sufficient affinity such that the antibody is useful as a diagnostic and/or therapeutic agent in targeting CD37. The extent of binding of an anti-CD37 antibody to an unrelated, non-CD37 protein can be less than about 10% of the binding of the antibody to CD37 as measured, e.g., by a radioimmunoassay (RIA). In certain embodiments, an antibody that binds to CD37 has a dissociation constant (Kd) of ≤1 μM, ≤100 nM, ≤10 nM, ≤1 nM, or ≤0.1 nM.

The term "antibody fragment" refers to a portion of an intact antibody and refers to the antigenic determining variable regions of an intact antibody. Examples of antibody fragments include, but are not limited to Fab, Fab', F(ab')2, and Fv fragments, linear antibodies, single chain antibodies, and multispecific antibodies formed from antibody fragments.

A "monoclonal antibody" refers to a homogeneous antibody population involved in the highly specific recognition and binding of a single antigenic determinant, or epitope. This is in contrast to polyclonal antibodies that typically include different antibodies directed against different antigenic determinants. The term "monoclonal antibody" encompasses both intact and full-length monoclonal antibodies as well as antibody fragments (such as Fab, Fab', F(ab')2, Fv), single chain (scFv) mutants, fusion proteins comprising an antibody portion, and any other modified immunoglobulin molecule comprising an antigen recognition site. Furthermore, "monoclonal antibody" refers to such antibodies made in any number of manners including but not limited to by hybridoma, phage selection, recombinant expression, and transgenic animals.

The term "humanized antibody" refers to forms of non-human (e.g. murine) antibodies that are specific immunoglobulin chains, chimeric immunoglobulins, or fragments thereof that contain minimal non-human (e.g., murine) sequences. Typically, humanized antibodies are human immunoglobulins in which residues from the complementary determining region (CDR) are replaced by residues from the CDR of a non-human species (e.g. mouse, rat, rabbit, hamster) that have the desired specificity, affinity, and capability (Jones et al., 1986, *Nature,* 321:522-525; Riechmann et al., 1988, *Nature,* 332:323-327; Verhoeyen et al., 1988, *Science,* 239:1534-1536). In some instances, the Fv framework region (FR) residues of a human immunoglobulin are replaced with the corresponding residues in an antibody from a non-human species that has the desired specificity, affinity, and capability. The humanized antibody can be further modified by the substitution of additional residues either in the Fv framework region and/or within the replaced non-human residues to refine and optimize antibody specificity, affinity, and/or capability. In general, the humanized antibody will comprise substantially all of at least one, and typically two or three, variable domains containing all or substantially all of the CDR regions that correspond to the non-human immunoglobulin whereas all or substantially all of the FR regions are those of a human immunoglobulin consensus sequence. The humanized antibody can also comprise at least a portion of an immunoglobulin constant region or domain (Fc), typically that of a human immunoglobulin. Examples of methods used to generate humanized antibodies are described in U.S. Pat. No. 5,225,539.

A "variable region" of an antibody refers to the variable region of the antibody light chain or the variable region of the antibody heavy chain, either alone or in combination. The variable regions of the heavy and light chain each consist of four framework regions (FR) connected by three complementarity determining regions (CDRs) also known as hypervariable regions. The CDRs in each chain are held together in close proximity by the FRs and, with the CDRs from the other chain, contribute to the formation of the antigen-binding site of antibodies. There are at least two techniques for determining CDRs: (1) an approach based on cross-species sequence variability (i.e., Kabat et al. Sequences of Proteins of Immunological Interest, (5th ed., 1991, National Institutes of Health, Bethesda Md.)); and (2) an approach based on crystallographic studies of antigen-antibody complexes (Al-lazikani et al (1997) *J. Molec. Biol.* 273:927-948)). In addition, combinations of these two approaches are sometimes used in the art to determine CDRs.

The Kabat numbering system is generally used when referring to a residue in the variable domain (approximately residues 1-107 of the light chain and residues 1-113 of the heavy chain) (e.g, Kabat et al., Sequences of Immunological Interest. 5th Ed. Public Health Service, National Institutes of Health, Bethesda, Md. (1991)).

The amino acid position numbering as in Kabat, refers to the numbering system used for heavy chain variable domains or light chain variable domains of the compilation of antibodies in Kabat et al., Sequences of Proteins of Immunological Interest, 5th Ed. Public Health Service, National Institutes of Health, Bethesda, Md. (1991). Using this numbering system, the actual linear amino acid sequence can contain fewer or additional amino acids corresponding to a shortening of, or insertion into, a FR or CDR of the variable domain. For example, a heavy chain variable domain can include a single amino acid insert (residue 52a according to Kabat) after residue 52 of H2 and inserted residues (e.g. residues 82a, 82b, and 82c, etc according to Kabat) after heavy chain FR residue 82. The Kabat numbering of residues can be determined for a given antibody by alignment at regions of homology of the sequence of the antibody with a "standard" Kabat numbered sequence. Chothia refers instead to the location of the structural loops (Chothia and Lesk J. Mol. Biol. 196:901-917 (1987)). The end of the Chothia CDR-H1 loop when numbered using the Kabat numbering convention varies between H32 and H34 depending on the length of the loop (this is because the Kabat numbering scheme places the insertions at H35A and H35B; if neither 35A nor 35B is present, the loop ends at 32; if only 35A is present, the loop ends at 33; if both 35A and 35B are present, the loop ends at 34). The AbM hypervariable regions represent a compromise between the Kabat CDRs and Chothia structural loops, and are used by Oxford Molecular's AbM antibody modeling software.

| Loop | Kabat | AbM | Chothia |
|---|---|---|---|
| L1 | L24-L34 | L24-L34 | L24-L34 |
| L2 | L50-L56 | L50-L56 | L50-L56 |
| L3 | L89-L97 | L89-L97 | L89-L97 |
| H1 | H31-H35B | H26-H35B | H26-H32 . . . 34 |
| | | (Kabat Numbering) | |
| H1 | H31-H35 | H26-H35 | H26-H32 |

-continued

| Loop | Kabat | AbM | Chothia |
|---|---|---|---|
| (Chothia Numbering) | | | |
| H2 | H50-H65 | H50-H58 | H52-H56 |
| H3 | H95-H102 | H95-H102 | H95-H102 |

The term "human antibody" means an antibody produced by a human or an antibody having an amino acid sequence corresponding to an antibody produced by a human made using any technique known in the art. This definition of a human antibody includes intact or full-length antibodies, fragments thereof, and/or antibodies comprising at least one human heavy and/or light chain polypeptide such as, for example, an antibody comprising murine light chain and human heavy chain polypeptides.

The term "chimeric antibodies" refers to antibodies wherein the amino acid sequence of the immunoglobulin molecule is derived from two or more species. Typically, the variable region of both light and heavy chains corresponds to the variable region of antibodies derived from one species of mammals (e.g. mouse, rat, rabbit, etc) with the desired specificity, affinity, and capability while the constant regions are homologous to the sequences in antibodies derived from another (usually human) to avoid eliciting an immune response in that species.

The term "epitope" or "antigenic determinant" are used interchangeably herein and refer to that portion of an antigen capable of being recognized and specifically bound by a particular antibody. When the antigen is a polypeptide, epitopes can be formed both from contiguous amino acids and noncontiguous amino acids juxtaposed by tertiary folding of a protein. Epitopes formed from contiguous amino acids are typically retained upon protein denaturing, whereas epitopes formed by tertiary folding are typically lost upon protein denaturing. An epitope typically includes at least 3, and more usually, at least 5 or 8-10 amino acids in a unique spatial conformation.

"Binding affinity" generally refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein. Low-affinity antibodies generally bind antigen slowly and tend to dissociate readily, whereas high-affinity antibodies generally bind antigen faster and tend to remain bound longer. A variety of methods of measuring binding affinity are known in the art, any of which can be used for purposes of the present invention. Specific illustrative embodiments are described in the following.

"Or better" when used herein to refer to binding affinity refers to a stronger binding between a molecule and its binding partner. "Or better" when used herein refers to a stronger binding, represented by a smaller numerical Kd value. For example, an antibody which has an affinity for an antigen of "0.6 nM or better", the antibody's affinity for the antigen is <0.6 nM, i.e. 0.59 nM, 0.58 nM, 0.57 nM etc. or any value less than 0.6 nM.

By "specifically binds," it is generally meant that an antibody binds to an epitope via its antigen binding domain, and that the binding entails some complementarity between the antigen binding domain and the epitope. According to this definition, an antibody is said to "specifically bind" to an epitope when it binds to that epitope, via its antigen binding domain more readily than it would bind to a random, unrelated epitope. The term "specificity" is used herein to qualify the relative affinity by which a certain antibody binds to a certain epitope. For example, antibody "A" may be deemed to have a higher specificity for a given epitope than antibody "B," or antibody "A" may be said to bind to epitope "C" with a higher specificity than it has for related epitope "D."

By "preferentially binds," it is meant that the antibody specifically binds to an epitope more readily than it would bind to a related, similar, homologous, or analogous epitope. Thus, an antibody which "preferentially binds" to a given epitope would more likely bind to that epitope than to a related epitope, even though such an antibody may cross-react with the related epitope.

An antibody is said to "competitively inhibit" binding of a reference antibody to a given epitope if it preferentially binds to that epitope to the extent that it blocks, to some degree, binding of the reference antibody to the epitope. Competitive inhibition may be determined by any method known in the art, for example, competition ELISA assays. An antibody may be said to competitively inhibit binding of the reference antibody to a given epitope by at least 90%, at least 80%, at least 70%, at least 60%, or at least 50%.

The phrase "substantially similar," or "substantially the same", as used herein, denotes a sufficiently high degree of similarity between two numeric values (generally one associated with an antibody of the invention and the other associated with a reference/comparator antibody) such that one of skill in the art would consider the difference between the two values to be of little or no biological and/or statistical significance within the context of the biological characteristic measured by said values (e.g., Kd values). The difference between said two values can be less than about 50%, less than about 40%, less than about 30%, less than about 20%, or less than about 10% as a function of the value for the reference/comparator antibody.

A polypeptide, antibody, polynucleotide, vector, cell, or composition which is "isolated" is a polypeptide, antibody, polynucleotide, vector, cell, or composition which is in a form not found in nature. Isolated polypeptides, antibodies, polynucleotides, vectors, cell or compositions include those which have been purified to a degree that they are no longer in a form in which they are found in nature. In some embodiments, an antibody, polynucleotide, vector, cell, or composition which is isolated is substantially pure.

As used herein, "substantially pure" refers to material which is at least 50% pure (i.e., free from contaminants), at least 90% pure, at least 95% pure, at least 98% pure, or at least 99% pure.

The term "immunoconjugate" or "conjugate" as used herein refers to a compound or a derivative thereof that is linked to a cell binding agent (i.e., an anti-CD37 antibody or fragment thereof) and is defined by a generic formula: C-L-A, wherein C=cytotoxin, L=linker, and A=cell binding agent or anti-CD37 antibody or antibody fragment. Immunoconjugates can also be defined by the generic formula in reverse order: A-L-C.

A "linker" is any chemical moiety that is capable of linking a compound, usually a drug, such as a maytansinoid, to a cell-binding agent such as an anti CD37 antibody or a fragment thereof in a stable, covalent manner. Linkers can be susceptible to or be substantially resistant to acid-induced cleavage, light-induced cleavage, peptidase-induced cleavage, esterase-induced cleavage, and disulfide bond cleavage, at conditions under which the compound or the antibody remains active. Suitable linkers are well known in the art and include, for example, disulfide groups, thioether groups, acid labile groups, photolabile groups, peptidase labile groups and esterase labile groups. Linkers also include charged linkers, and hydrophilic forms thereof as described herein and know in the art.

The terms "cancer" and "cancerous" refer to or describe the physiological condition in mammals in which a population of cells are characterized by unregulated cell growth. Examples of cancer include, but are not limited to, carcinoma, lymphoma, blastoma, sarcoma, and leukemia. "Tumor" and "neoplasm" refer to one or more cells that result from excessive cell growth or proliferation, either benign (noncancerous) or malignant (cancerous) including pre-cancerous lesions. Examples of "cancer" or "tumorigenic" diseases which can be treated and/or prevented include B-cell lymphomas including NHL, precursor B-cell lymphoblastic leukemia/lymphoma and mature B-cell neoplasms, such as B-cell chronic lymphocytic leukemia (CLL)/small lymphocytic lymphoma (SLL), B-cell prolymphocytic leukemia, lymphoplasmacytic lymphoma, mantle cell lymphoma (MCL), follicular lymphoma (FL), including low-grade, intermediate-grade and high-grade FL, cutaneous follicle center lymphoma, marginal zone B-cell lymphoma (MALT type, nodal and splenic type), hairy cell leukemia, diffuse large B-cell lymphoma, Burkitt's lymphoma, plasmacytoma, plasma cell myeloma, post-transplant lymphoproliferative disorder, Waldenstrom's macroglobulinemia, and anaplastic large-cell lymphoma (ALCL).

The terms "cancer cell," "tumor cell," and grammatical equivalents refer to the total population of cells derived from a tumor or a pre-cancerous lesion, including both non-tumorigenic cells, which comprise the bulk of the tumor cell population, and tumorigenic stem cells (cancer stem cells). As used herein, the term "tumor cell" will be modified by the term "non-tumorigenic" when referring solely to those tumor cells lacking the capacity to renew and differentiate to distinguish those tumor cells from cancer stem cells.

The term "subject" refers to any animal (e.g., a mammal), including, but not limited to humans, non-human primates, rodents, and the like, which is to be the recipient of a particular treatment. Typically, the terms "subject" and "patient" are used interchangeably herein in reference to a human subject.

Administration "in combination with" one or more further therapeutic agents includes simultaneous (concurrent) and consecutive administration in any order.

The term "pharmaceutical formulation" refers to a preparation which is in such form as to permit the biological activity of the active ingredient to be effective, and which contains no additional components which are unacceptably toxic to a subject to which the formulation would be administered. The formulation can be sterile.

An "effective amount" of an antibody as disclosed herein is an amount sufficient to carry out a specifically stated purpose. An "effective amount" can be determined empirically and in a routine manner, in relation to the stated purpose.

The term "therapeutically effective amount" refers to an amount of an antibody or other drug effective to "treat" a disease or disorder in a subject or mammal. In the case of cancer, the therapeutically effective amount of the drug can reduce the number of cancer cells; reduce the tumor size; inhibit (i.e., slow to some extent or stop) cancer cell infiltration into peripheral organs; inhibit (i.e., slow to some extent or stop) tumor metastasis; inhibit, to some extent, tumor growth; and/or relieve to some extent one or more of the symptoms associated with the cancer. See the definition herein of "treating". To the extent the drug can prevent growth and/or kill existing cancer cells, it can be cytostatic and/or cytotoxic. A "prophylactically effective amount" refers to an amount effective, at dosages and for periods of time necessary, to achieve the desired prophylactic result. Typically but not necessarily, since a prophylactic dose is used in subjects prior to or at an earlier stage of disease, the prophylactically effective amount will be less than the therapeutically effective amount.

The word "label" when used herein refers to a detectable compound or composition which is conjugated directly or indirectly to the antibody so as to generate a "labeled" antibody. The label can be detectable by itself (e.g. radioisotope labels or fluorescent labels) or, in the case of an enzymatic label, can catalyze chemical alteration of a substrate compound or composition which is detectable.

A "chemotherapeutic agent" is a chemical compound useful in the treatment of cancer, regardless of mechanism of action. Chemotherapeutic agents include, for example, antagonists of CD20 such as Rituximab and cyclophosphamide, doxorubicin, vincristine, prednisone, fludarabine, etoposide, methotrexate, lenalidomide, chlorambucil, bentamustine and/or modified versions of such chemotherapeutics.

Terms such as "treating" or "treatment" or "to treat" or "alleviating" or "to alleviate" refer to both 1) therapeutic measures that cure, slow down, lessen symptoms of, and/or halt progression of a diagnosed pathologic condition or disorder and 2) prophylactic or preventative measures that prevent and/or slow the development of a targeted pathologic condition or disorder. Thus, those in need of treatment include those already with the disorder; those prone to have the disorder; and those in whom the disorder is to be prevented. In certain embodiments, a subject is successfully "treated" for cancer according to the methods of the present invention if the patient shows one or more of the following: a reduction in the number of or complete absence of cancer cells; a reduction in the tumor size; inhibition of or an absence of cancer cell infiltration into peripheral organs including, for example, the spread of cancer into soft tissue and bone; inhibition of or an absence of tumor metastasis; inhibition or an absence of tumor growth; relief of one or more symptoms associated with the specific cancer; reduced morbidity and mortality; improvement in quality of life; reduction in tumorigenicity, tumorgenic frequency, or tumorgenic capacity, of a tumor; reduction in the number or frequency of cancer stem cells in a tumor; differentiation of tumorigenic cells to a non-tumorigenic state; or some combination of effects.

"Polynucleotide," or "nucleic acid," as used interchangeably herein, refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase. A polynucleotide can comprise modified nucleotides, such as methylated nucleotides and their analogs. If present, modification to the nucleotide structure can be imparted before or after assembly of the polymer. The sequence of nucleotides can be interrupted by non-nucleotide components. A polynucleotide can be further modified after polymerization, such as by conjugation with a labeling component. Other types of modifications include, for example, "caps", substitution of one or more of the naturally occurring nucleotides with an analog, internucleotide modifications such as, for example, those with uncharged linkages (e.g., methyl phosphonates, phosphotriesters, phosphoamidates, cabamates, etc.) and with charged linkages (e.g., phosphorothioates, phosphorodithioates, etc.), those containing pendant moieties, such as, for example, proteins (e.g., nucleases, toxins, antibodies, signal peptides, ply-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide(s). Further, any of the hydroxyl groups ordinarily present in the sugars can be replaced, for example, by phosphonate groups, phosphate groups, protected by standard protecting groups, or activated to prepare additional linkages to additional nucleotides, or can be conjugated to solid supports. The 5' and 3' terminal OH can be phosphorylated or substituted with amines or organic capping group moieties of from 1 to 20 carbon atoms. Other hydroxyls can also be derivatized to standard protecting groups. Polynucleotides can also contain analogous forms of ribose or deoxyribose sugars that are generally known in the art, including, for example, 2'-O-methyl-, 2'-O-allyl, 2'-fluoro- or 2'-azido-ribose, carbocyclic sugar analogs, .alpha.-anomeric sugars, epimeric sugars such as arabinose, xyloses or lyxoses, pyranose sugars, furanose sugars, sedoheptuloses, acyclic analogs and abasic nucleoside analogs such as methyl riboside. One or more phosphodiester linkages can be replaced by alternative linking groups. These alternative linking groups include, but are not limited to, embodiments wherein phosphate is replaced by P(O)S ("thioate"), P(S)S ("dithioate"), "(O)$NR_2$ ("amidate"), P(O)R, P(O)OR', CO or $CH_2$ ("formacetal"), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. The preceding description applies to all polynucleotides referred to herein, including RNA and DNA.

The term "vector" means a construct, which is capable of delivering, and optionally expressing, one or more gene(s) or sequence(s) of interest in a host cell. Examples of vectors include, but are not limited to, viral vectors, naked DNA or RNA expression vectors, plasmid, cosmid or phage vectors, DNA or RNA expression vectors associated with cationic condensing agents, DNA or RNA expression vectors encapsulated in liposomes, and certain eukaryotic cells, such as producer cells.

The terms "polypeptide," "peptide," and "protein" are used interchangeably herein to refer to polymers of amino acids of any length. The polymer can be linear or branched, it can comprise modified amino acids, and it can be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art. It is understood that, because the polypeptides of this invention are based upon antibodies, in certain embodiments, the polypeptides can occur as single chains or associated chains.

The terms "identical" or percent "identity" in the context of two or more nucleic acids or polypeptides, refer to two or more sequences or subsequences that are the same or have a specified percentage of nucleotides or amino acid residues that are the same, when compared and aligned (introducing gaps, if necessary) for maximum correspondence, not considering any conservative amino acid substitutions as part of the sequence identity. The percent identity can be measured using sequence comparison software or algorithms or by visual inspection. Various algorithms and software are known in the art that can be used to obtain alignments of amino acid or nucleotide sequences. One such non-limiting example of a sequence alignment algorithm is the algorithm described in Karlin et al, 1990, *Proc. Natl. Acad. Sci.*, 87:2264-2268, as modified in Karlin et al., 1993, *Proc. Natl. Acad. Sci.*, 90:5873-5877, and incorporated into the NBLAST and XBLAST programs (Altschul et al., 1991, *Nucleic Acids Res.*, 25:3389-3402). In certain embodiments, Gapped BLAST can be used as described in Altschul et al., 1997, *Nucleic Acids Res.* 25:3389-3402. BLAST-2, WU-BLAST-2 (Altschul et al., 1996, *Methods in Enzymology*, 266:460-480), ALIGN, ALIGN-2 (Genentech, South San Francisco, Calif.) or Megalign (DNASTAR) are additional publicly available software programs that can be used to align sequences. In certain embodiments, the percent identity between two nucleotide sequences is determined using the GAP program in GCG software (e.g., using a NWSgapdna.CMP matrix and a gap weight of 40, 50, 60, 70, or 90 and a length weight of 1, 2, 3, 4, 5, or 6). In certain alternative embodiments, the GAP program in the GCG software package, which incorporates the algorithm of Needleman and Wunsch (*J. Mol. Biol.* (48): 444-453 (1970)) can be used to determine the percent identity between two amino acid sequences (e.g., using either a Blossum 62 matrix or a PAM250 matrix, and a gap weight of 16, 14, 12, 10, 8, 6, or 4 and a length weight of 1, 2, 3, 4, 5). Alternatively, in certain embodiments, the percent identity between nucleotide or amino acid sequences is determined using the algorithm of Myers and Miller (CABIOS, 4:11-17 (1989)). For example, the percent identity can be determined using the ALIGN program (version 2.0) and using a PAM120 with residue table, a gap length penalty of 12 and a gap penalty of 4. Appropriate parameters for maximal alignment by particular alignment software can be determined by one skilled in the art. In certain embodiments, the default parameters of the alignment software are used. In certain embodiments, the percentage identity "X" of a first amino acid sequence to a second sequence amino acid is calculated as $100\times(Y/Z)$, where Y is the number of amino acid residues scored as identical matches in the alignment of the first and second sequences (as aligned by visual inspection or a particular sequence alignment program) and Z is the total number of residues in the second sequence. If the length of a first sequence is longer than the second sequence, the percent identity of the first sequence to the second sequence will be longer than the percent identity of the second sequence to the first sequence.

As a non-limiting example, whether any particular polynucleotide has a certain percentage sequence identity (e.g., is at least 80% identical, at least 85% identical, at least 90% identical, and in some embodiments, at least 95%, 96%, 97%, 98%, or 99% identical) to a reference sequence can, in certain embodiments, be determined using the Bestfit program (Wisconsin Sequence Analysis Package, Version 8 for Unix, Genetics Computer Group, University Research Park, 575 Science Drive, Madison, Wis. 53711). Bestfit uses the local homology algorithm of Smith and Waterman, *Advances in Applied Mathematics* 2: 482 489 (1981), to find the best segment of homology between two sequences. When using Bestfit or any other sequence alignment program to determine whether a particular sequence is, for instance, 95% identical to a reference sequence according to the present invention, the parameters are set such that the percentage of identity is calculated over the full length of the reference nucleotide sequence and that gaps in homology of up to 5% of the total number of nucleotides in the reference sequence are allowed.

In some embodiments, two nucleic acids or polypeptides of the invention are substantially identical, meaning they have at least 70%, at least 75%, at least 80%, at least 85%, at least 90%, and in some embodiments at least 95%, 96%, 97%, 98%, 99% nucleotide or amino acid residue identity, when compared and aligned for maximum correspondence, as measured using a sequence comparison algorithm or by visual inspection. Identity can exist over a region of the sequences that is at least about 10, about 20, about 40-60 residues in length or any integral value therebetween, and can be over a longer region than 60-80 residues, for example, at least about 90-100 residues, and in some embodiments, the sequences are substantially identical over the full length of the sequences being compared, such as the coding region of a nucleotide sequence for example.

A "conservative amino acid substitution" is one in which one amino acid residue is replaced with another amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). For example, substitution of a phenylalanine for a tyrosine is a conservative substitution. In some embodiments, conservative substitutions in the sequences of the polypeptides and antibodies of the invention do not abrogate the binding of the polypeptide or antibody containing the amino acid sequence, to the antigen(s), i.e., the CD37 to which the polypeptide or antibody binds. Methods of identifying nucleotide and amino acid conservative substitutions which do not eliminate antigen binding are well-known in the art (see, e.g., Brummell et al., *Biochem.* 32: 1180-1187 (1993); Kobayashi et al. *Protein Eng.* 12(10):879-884 (1999); and Burks et al. *Proc. Natl. Acad. Sci. USA* 94:412-417 (1997)).

As used in the present disclosure and claims, the singular forms "a," "an," and "the" include plural forms unless the context clearly dictates otherwise.

It is understood that wherever embodiments are described herein with the language "comprising," otherwise analogous embodiments described in terms of "consisting of" and/or "consisting essentially of" are also provided.

The term "and/or" as used in a phrase such as "A and/or B" herein is intended to include both "A and B," "A or B," "A," and "B." Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

II. CD37 Binding Agents

The present invention provides agents that specifically bind CD37. These agents are referred to herein as "CD37 binding agents." The full-length amino acid sequences for human, macaca, and murine CD37 are known in the art and also provided herein as represented by SEQ ID NOs:1-3, respectively.

```
Human CD37:
                                        (SEQ ID NO: 1)
MSAQESCLSLIKYFLFVFNLFFFVLGSLIFCFGIWILIDKTSFVSFVGLA
FVPLQIWSKVLAISGIFTMGIALLGCVGALKELRCLLGLYFGMLLLLFAT
QITLGILISTQRAQLERSLRDVVEKTIQKYGTNPEETAAEESWDYVQFQL
RCCGWHYPQDWFQVLILRGNGSEAHRVPCSCYNLSATNDSTILDKVILPQ
LSRLGHLARSRHSADICAVPAESHIYREGCAQGLQKWLHNNLISIVGICL
GVGLLELGFMTLSIFLCRNLDHVYNRLAYR

Macaca CD37:
                                        (SEQ ID NO: 2)
MSAQESCLSLIKYFLFVFNLFFFVILGSLIFCFGIWILIDKTSFVSFVGL
AFVPLQIWSKVLAISGVFTMGLALLGCVGALKELRCLLGLYFGMLLLLFA
TQITLGILISTQRAQLERSLQDIVEKTIQRYHTNPEETAAEESWDYVQFQ
LRCCGWHSPQDWFQVLTLRGNGSEAHRVPCSCYNLSATNDSTILDKVILP
QLSRLGQLARSRHSTDICAVPANSHIYREGCARSLQKWLHNNLISIVGIC
LGVGLLELGFMTLSIFLCRNLDHVYNRLRYR

Murine CD37 (NP_031671):
                                        (SEQ ID NO: 3)
MSAQESCLSLIKYFLFVFNLFFFVLGGLIFCFGTWILIDKTSFVSFVGLS
FVPLQTWSKVLAVSGVLTMALALLGCVGALKELRCLLGLYFGMLLLLFAT
QITLGILISTQRVRLERRVQELVLRTIQSYRTNPDETAAEESWDYAQFQL
RCCGWQSPRDWNKAQMLKANESEEPFVPCSCYNSTATNDSTVFDKLFFSQ
LSRLGPRAKLRQTADICALPAKAHIYREGCAQSLQKWLHNNIISIVGICL
GVGLLELGFMTLSIFLCRNLDHVYDRLARYR
```

In certain embodiments, the CD37 binding agents are antibodies, immunoconjugates or polypeptides. In some embodiments, the CD37 binding agents are humanized antibodies.

In certain embodiments, the CD37-binding agents have one or more of the following effects: inhibit proliferation of tumor cells, reduce the tumorigenicity of a tumor by reducing the frequency of cancer stem cells in the tumor, inhibit tumor growth, increase survival, trigger cell death of tumor cells, differentiate tumorigenic cells to a non-tumorigenic state, or prevent metastasis of tumor cells.

In certain embodiments, the CD37-binding agents are capable of inducing complement dependent cytotoxicity. For example, treatment of cells with the CD37-binding agents can result in CDC activity that reduces cell viability to less than about 80%, less than about 70%, less than about 60%, less than about 50%, less than about 40% or less than about 35% of the cell viability of untreated cells. Treatment of cells with the CD37-binding agents can also result in CDC activity that reduces cell viability to about 70-80%, about 60-70%, about 50-60%, about 40-50%, or about 30-40% of the cell viability of untreated cells. In some particular embodiments, the CD37-binding agents are capable of inducing complement dependent cytotoxicity in Ramos cells.

In certain embodiments, the CD37-binding agents are capable of inducing antibody dependent cell mediated cytotoxicity (ADCC). For example, treatment of cells with the CD37-binding agents can result in ADCC activity that produces at least about 15%, at least about 20%, at least about 25%, at least about 30%, at least about 35%, at least about 40%, at least about 45%, at least about 50%, or at least about 60% cell lysis. Treatment of cells with the CD37-binding agents can result in ADCC activity that produces about 10-20%, about 20-30%, about 30-40%, or about 40-50% cell lysis. Treatment of cells with the CD37-binding agents can also result in ADCC activity that produces about 10-50%, about 20-50%, about 30-50%, or about 40-50% cell lysis. In some particular embodiments, the CD37-binding agents are capable of inducing ADCC in Daudi, Ramos, and/or Granata-519 cells.

In some embodiments, the CD37-binding agents are capable of inducing apoptosis. For example, treatment of cells with the CD37-binding agents can induce apoptosis in at least about 15%, at least about 20%, at least about 25%, at least about 30%, at least about 35%, at least about 40%, at least about 45%, at least about 50%, or at least about 55% of cells. In some particular embodiments, the CD37-binding agents are capable of inducing apoptosis in Ramos cells and/or Raji cells.

In some embodiments, the CD37-binding agents are capable of reducing tumor volume. The ability of a CD37-binding agent to reduce tumor volume can be assessed, for example, by measuring a % T/C value, which is the median tumor volume of treated subjects divided by the median tumor volume of the control subjects. In some embodiments, treatment with a CD37-binding agent results in a % T/C value that is less than about 55%, less than about 50%, less than about 45%, less than about 40%, less than about 35%, less than about 30%, less than about 25%, less than about 20%, less than about 15%, less than about 10%, or less than about 5%. In some particular embodiments, the CD37-binding agents can reduce tumor size in a BJAB xenograft model and/or a SU-DHL-4 xenograft model.

In certain embodiments, immunoconjugates or other agents that specifically bind human CD37 trigger cell death via a cytotoxic agent. For example, in certain embodiments, an antibody to a human CD37 antibody is conjugated to a maytansinoid that is activated in tumor cells expressing the CD37 by protein internalization. In certain alternative embodiments, the agent or antibody is not conjugated.

In certain embodiments, the CD37-binding agents are capable of inhibiting tumor growth. In certain embodiments, the CD37-binding agents are capable of inhibiting tumor growth in vivo (e.g., in a xenograft mouse model and/or in a human having cancer).

The CD37-binding agents include CD37 antibodies CD37-3, CD37-12, CD37-38, CD37-50, CD37-51, CD37-56 and CD37-57 and fragments, variants and derivatives thereof. The CD37-binding agents also include CD37-binding agents that specifically bind to the same CD37 epitope as an antibody selected from the group consisting of CD37-3, CD37-12, CD37-38, CD37-50, CD37-51, CD37-56 and CD37-57. The CD37-binding agents also include CD37-binding agents that competitively inhibit an antibody selected from the group consisting of CD37-3, CD37-12, CD37-38, CD37-50, CD37-51, CD37-56 and CD37-57.

In some particular embodiments, the binding of the CD37-binding agents to CD37 does not require human CD37 amino acids 109-138. Thus, some CD37-binding agents bind to a polypeptide comprising the amino acid sequence of SEQ ID NO:180. In other embodiments, the binding of the CD37-binding agents to CD37 is disrupted by mutation of human CD37 amino acids 202-243. Thus, some CD37-binding agents do not bind to a polypeptide comprising the amino acid sequence of SEQ ID NO:184.

In some embodiments, the CD37-binding agents bind to a polypeptide of SEQ ID NO:180 and to a polypeptide of SEQ ID NO:183, but do not bind to a polypeptide of SEQ ID NO:184.

In some embodiments, the CD37-binding agents bind to a polypeptide of SEQ ID NO:190. In some embodiments, the CD37-binding agents bind to a polypeptide of SEQ ID NO:190 and a polypeptide of SEQ ID NO:189. In some embodiments, the CD37-binding agents bind to a polypeptide of SEQ ID NO:190 and a polypeptide of SEQ ID NO:188.

In some embodiments, the CD37-binding agent binds to a polypeptide of SEQ ID NO:192, but does not bind to a polypeptide of SEQ ID NO:194. In some embodiments, the CD37-binding agent binds to a polypeptide of SEQ ID NO:193, but does not bind to a polypeptide of SEQ ID NO:194.

CD37 peptide fragments to which certain CD37-binding agents bind to include, but are not limited to, CD37 fragments comprising, consisting essentially of, or consisting of amino acids 200-243 of SEQ ID NO: 1, amino acids 202-220 or SEQ ID NO:1, or amino acids 221-243 of SEQ ID NO: 1. In some embodiments, the CD37-binding agent is specifically binds to a human CD37 epitope comprising amino acids 202-243 of SEQ ID NO:1. In some embodiments, the binding of the CD37-binding agent to CD37 requires amino acids 202-243 of SEQ ID NO:1. In some embodiments, the binding of the CD37-binding agent to CD37 requires amino acids 200-220 of SEQ ID NO: 1. In some embodiments, the binding of the CD37-binding agent to CD37 requires amino acids 221-243 of SEQ ID NO:1.

The CD37-binding agents also include CD37-binding agents that comprise the heavy and light chain CDR sequences of CD37-3, CD37-12, CD37-38, CD37-50, CD37-51, CD37-56 or CD37-57. The heavy and light chain CDRs of CD37-38, CD37-50, CD37-51, CD37-56 and CD37-57 contain related sequences. Therefore, the CD-37 binding agents can also comprise heavy and light chain CDR sequences that comprise a consensus sequence obtained by the alignment of CD37-38, CD37-50, CD37-51, CD37-56 and CD37-57. The CDR sequences of CD37-3, CD37-12, CD37-38, CD37-50, CD37-51, CD37-56 and CD37-57, as well as the consensus sequence of CD37-38, CD37-50, CD37-51, CD37-56 and CD37-57 are described in Tables 1 and 2 below.

TABLE 1

Variable heavy chain CDR amino acid sequences

| Antibody | VH-CDR1 | VH-CDR2 | VH-CDR3 |
|---|---|---|---|
| CD37-3 | TSGVS (SEQ ID NO: 4) | VIWGDGSTN (SEQ ID NO: 5) | GGYSLAH (SEQ ID NO: 6) |
| CD37-12 | KYGMN (SEQ ID NO: 7) | WINTNTGESR (SEQ ID NO: 8) | GTVVAD (SEQ ID NO: 9) |
| CD37-38 | SGFGWH (SEQ ID NO: 10) | YILYSGGTD (SEQ ID NO: 11) | GYYGYGAWFVY (SEQ ID NO: 12) |
| CD37-50 | SGFAWH (SEQ ID NO: 13) | YILYSGSTV (SEQ ID NO: 14) | GYYGYGAWFAY (SEQ ID NO: 15) |
| CD37-51 | SGFAWH (SEQ ID NO: 16) | YIHYSGSTN (SEQ ID NO: 17) | GYYGFGAWFVY (SEQ ID NO: 18) |
| CD37-56 | SGFAWH (SEQ ID NO: 19) | YIHYSGGTN (SEQ ID NO: 20) | GYYGFGAWFAY (SEQ ID NO: 21) |
| CD37-57 | SGFAWH (SEQ ID NO: 22) | YILYSGSTV (SEQ ID NO: 23) | GYYGYGAWFAY (SEQ ID NO: 24) |
| CONSENSUS | SGF[A or G]WH (SEQ ID NO: 25) | YI[L or H]YSG[G or S]T[D, V, or N] (SEQ ID NO: 26) | GYYG[Y or F]GAWF[V or A]Y (SEQ ID NO: 27) |

TABLE 2

Variable light chain CDR amino acid sequences

| Antibody | VL-CDR1 | VL-CDR2 | VL-CDR3 |
|---|---|---|---|
| CD37-3 | RASENIRSNLA (SEQ ID NO: 28) | VATNLAD (SEQ ID NO: 29) | QHYWGTTWT (SEQ ID NO: 30) |
| CD37-12 | RASQSVSTSSYSYLY (SEQ ID NO: 31) | YASNLAS (SEQ ID NO: 32) | QHSWEIPYT (SEQ ID NO: 33) |
| CD37-38 | SASSSVTYMH (SEQ ID NO: 34) | DTSKLAS (SEQ ID NO: 35) | QQWISNPPT (SEQ ID NO: 36) |
| CD37-50 | SATSSVTYMH (SEQ ID NO: 37) | DTSKLPY (SEQ ID NO: 38) Humanized DTSNLPY (SEQ ID NO: 40) | QQWSDNPPT (SEQ ID NO: 39) |
| CD37-51 | SATSSVTYMH (SEQ ID NO: 41) | DTSKLAS (SEQ ID NO: 42) | QQWSSNPPT (SEQ ID NO: 43) |
| CD37-56 | SASSSVTYMH (SEQ ID NO: 44) | DTSKLAS (SEQ ID NO: 45) Humanized DTSNLAS (SEQ ID NO: 47) | QQWISDPPT (SEQ ID NO: 46) |
| CD37-57 | SATSSVTYMH (SEQ ID NO: 48) | DTSKLAS (SEQ ID NO: 49) Humanized DTSNLAS (SEQ ID NO: 51) | QQWSDNPPT (SEQ ID NO: 50) |
| CONSENSUS | SA[T or S]SSVTYMH (SEQ ID NO: 52) | DTS[K or N]L[A or P][S or Y] (SEQ ID NO: 53) | QQW[I or S][S or D][N or D]PPT (SEQ ID NO: 54) |

The CD37 binding molecules can be antibodies or antigen binding fragments that specifically bind to CD37 that comprise the CDRs of CD37-3, CD37-12, CD37-50, CD37-51, CD37-56, or CD37-57 with up to four (i.e. 0, 1, 2, 3, or 4) conservative amino acid substitutions per CDR.

Polypeptides an comprise one of the individual variable light chains or variable heavy chains described herein. Antibodies and polypeptides can also comprise both a variable light chain and a variable heavy chain. The variable light chain and variable heavy chain sequences of murine, chimeric, and humanized CD37-3, CD37-12, CD37-50, CD37-51, CD37-56, and CD37-57 antibodies are provided in Tables 3 and 4 below.

TABLE 3

Variable heavy chain amino acid sequences

| Antibody | VH Amino Acid Sequence (SEQ ID NO) |
|---|---|
| muCD37-3 | QVQVKESGPGLVAPSQSLSITCTVSGFSLTTSGVSWVRQPPGKGLEWLGVIWGDGSTNYHSALKSRLSIKKDHSKSQVFLKLNSLQTDDTATYYCAKGGYSLAHWGQGTLVTVSA (SEQ ID NO: 55) |
| chCD37-3 | QVQVKESGPGLVAPSQSLSITCTVSGFSLTTSGVSWVRQPPGKGLEWLGVIWGDGSTNYHSALKSRLSIKKDHSKSQVFLKLNSLQTDDTATYYCAKGGYSLAHWGQGTLVTVSA (SEQ ID NO: 56) |
| huCD37-3v1.0 | QVQVQESGPGLVAPSQTLSITCTVSGFSLTTSGVSWVRQPPGKGLEWLGVIWGDGSTNYHPSLKSRLSIKKDHSKSQVFLKLNSLTAADTATYYCAKGGYSLAHWGQGTLVTVSS (SEQ ID NO: 57) |
| huCD37-3v1.1 | QVQVQESGPGLVAPSQTLSITCTVSGFSLTTSGVSWVRQPPGKGLEWLGVIWGDGSTNYHSSLKSRLSIKKDHSKSQVFLKLNSLTAADTATYYCAKGGYSLAHWGQGTLVTVSS (SEQ ID NO: 58) |
| muCD37-12 | QIQLVQSGPELKKPGETVKISCKASGYTFTKYGMNWVKQAQGKGLKWMGWINTNTGESRNAEEFKGRFAFSLETSASTAYLQINNLKYEDTATYFCGRGTVVADWGQGTTLTVSS (SEQ ID NO: 59) |
| chCD37-12 | QIQLVQSGPELKKPGETVKISCKASGYTFTKYGMNWVKQAQGKGLKWMGWINTNTGESRNAEEFKGRFAFSLETSASTAYLQINNLKYEDTATYFCGRGTVVADWGQGTTLTVSS (SEQ ID NO: 60) |
| muCD37-38 | DVQLQESGPDLVKPSQSLSLTCTVTGYSITSGFGWHWIRQFPGNKLEWMAYILYSGGTDYNPSLKSRISITRDTSKNQFFLRLSSVTTEDTATYYCARGYYGYGAWFVYWGQGTLVTVSA (SEQ ID NO: 61) |
| chCD37-38 | QVQLQESGPDLVKPSQSLSLTCTVTGYSITSGFGWHWIRQFPGNKLEWMAYILYSGGTDYNPSLKSRISITRDTSKNQFFLRLSSVTTEDTATYYCARGYYGYGAWFVYWGQGTLVTVSA (SEQ ID NO: 62) |
| huCD37-38 | QVQLQESGPGLVKPSQSLSLTCTVSGYSITSGFGWHWIRQFPGKGLEWMAYILYSGGTDYNPSLKSRISITRDTSKNQFFLRLSSVTAADTATYYCARGYYGYGAWFVYWGQGTLVTVSS (SEQ ID NO: 63) |
| muCD37-50 | DVQLQESGPDLLKPSQSLSLTCTVTGYSITSGFAWHWIRQFPGNKLEWMGYILYSGSTVYSPSLKSRISITRDTSKNHFFLQLNSVTTEDTATYYCARGYYGYGAWFAYWGQGTLVTVSA (SEQ ID NO: 64) |
| huCD37-50 | QVQLQESGPGLLKPSQSLSLTCTVSGYSITSGFAWHWIRQHPGNKLEWMGYILYSGSTVYSPSLKSRISITRDTSKNHFFLQLNSVTAADTATYYCARGYYGYGAWFAYWGQGTLVTVSA (SEQ ID NO: 65) |
| muCD37-51 | DVQLQESGPDLLKPSQSLSLTCTVTGYSISSGFAWHWIRQFPGNKLEWMGYIHYSGSTNYSPSLKSRISITRDSSKNQFFLQLNSVTTEDTATYYCARGYYGFGAWFVYWGQGTLVTVSA (SEQ ID NO: 66) |
| huCD37-51 | EVQLVESGPEVLKPGESLSLTCTVSGYSISSGFAWHWIRQFPGKGLEWMGYIHYSGSTNYSPSLQGRISITRDSSINQFFLQLNSVTASDTATYYCARGYYGFGAWFVYWGQGTLVTVSA (SEQ ID NO: 67) |

TABLE 3-continued

| Variable heavy chain amino acid sequences | |
|---|---|
| Antibody | VH Amino Acid Sequence (SEQ ID NO) |
| muCD37-56 | DVQLQESGPDLVKPSQSLSLTCTVTGYSITSGFAW<br>HWIRQFPGNKLEWMGYIHYSGGTNYNPSLKSRVSI<br>TRDTSKNQFFLQLNSVTTEDTATYYCARGYYGFGA<br>WFAYWGQGTLVPVSA<br>(SEQ ID NO: 68) |
| huCD37-56 | QVQLQESGPGLVKPSQSLSLTCTVSGYSITSGFAW<br>HWIRQFPGKGLEWMGYIHYSGGTNYNPSLKSRVSI<br>TRDTSKNQFFLQLNSVTAADTATYYCARGYYGFGA<br>WFAYWGQGTLVPVSA<br>(SEQ ID NO: 69) |
| muCD37-57 | DVQLQESGPDLLKPSQSLSLTCTVTGYSITSGFAW<br>HWIRQFPGNKLEWMGYILYSGSTVYSPSLKSRISI<br>TRDTSKNQFFLQLNSVTTEDTATYYCARGYYGYGA<br>WFAYWGQGTLVTVSA<br>(SEQ ID NO: 70) |
| huCD37-57 | QVQLQESGPGLLKPSQSLSLTCTVSGYSITSGFAW<br>HWIRQFPGKGLEWMGYILYSGSTVYSPSLKSRISI<br>TRDTSKNQFFLQLNSVTAADTATYYCARGYYGYGA<br>WFAYWGQGTLVTVSA<br>(SEQ ID NO: 71) |

TABLE 4

| Variable light chain amino acid sequences | |
|---|---|
| Antibody | VL Amino Acid Sequence (SEQ ID NO) |
| muCD37-3 | DIQMTQSPASLSVSVGETVTITCRASENIRSNLA<br>WYQQKQGKSPQLLVNVATNLADGVPSRFSGSGSG<br>TQYSLKINSLQSEDFGTYYCQHYWGTTWTFGGGT<br>KLEIKR<br>(SEQ ID NO: 72) |
| chCD37-3 | DIQMTQSPASLSVSVGETVTITCRASENIRSNLA<br>WYQQKQGKSPQLLVNVATNLADGVPSRFSGSGSG<br>TQYSLKINSLQSEDFGTYYCQHYWGTTWTFGGGT<br>KLEIKR<br>(SEQ ID NO: 73) |
| huCD37-3<br>(1.0 and 1.1) | DIQMTQSPSSLSVSVGERVTITCRASENIRSNLA<br>WYQQKPGKSPKLLVNVATNLADGVPSRFSGSGTD<br>YSLKINSLQPEDFGTYYCQHYWGTTWTFGQGTKL<br>EIKR<br>(SEQ ID NO: 74) |
| muCD37-12 | DIVLTQSPASLAVSLGQRATISCRASQSVSTSSY<br>SYLYWFQQKPGQPPKLLIKYASNLASGVPARFSG<br>SGSGTDFTLNIHPVEEEDTATYYCQHSWEIPYTF<br>GGGTKLEIKR<br>(SEQ ID NO: 75) |
| chCD37-12 | DIVLTQSPASLAVSLGQRATISCRASQSVSTSSY<br>SYLYWFQQKPGQPPKLLIKYASNLASGVPARFSG<br>SGSGTDFTLNIHPVEEEDTATYYCQHSWEIPYTF<br>GGGTKLEIKR<br>(SEQ ID NO: 76) |
| muCD37-38 | QIVLTQSPAIMSASPGEKVTMTCSASSSVTYMHW<br>YQQKSGTSPKRWIYDTSKLASGVPARFSGGGSGT<br>SYSLTISSMEAEDAATYYCQQWISNPPTFGGGTK<br>LEIKR<br>(SEQ ID NO: 77) |
| chCD37-38 | QIVLTQSPAIMSASPGEKVTMTCSASSSVTYMHW<br>YQQKSGTSPKRWIYDTSKLASGVPARFSGGGSGT<br>SYSLTISSMEAEDAATYYCQQWISNPPTFGGGTK<br>LEIKR<br>(SEQ ID NO: 78) |

TABLE 4-continued

| Variable light chain amino acid sequences | |
|---|---|
| Antibody | VL Amino Acid Sequence (SEQ ID NO) |
| huCD37-38 | DIVLTQSPASMSASPGERVTMTCSASSSVTYMHW<br>YQQKPGTSPKRWIYDTSKLASGVPARFSGSGSGT<br>SYSLTISSMEAEDAATYYCQQWISNPPTFGGGTK<br>LEIKR<br>(SEQ ID NO: 79) |
| muCD37-50 | QIVLTQSPAIMSASPGEKVTMTCSATSSVTYMHW<br>YQQKSGTSPKRWIYDTSKLPYGVPGRFSGSGSGT<br>SYSLTISSMEAEDAATYYCQQWSDNPPTFGSGTK<br>LEIKR<br>(SEQ ID NO: 80) |
| huCD37-50 | EIVLTQSPATMSASPGERVTMTCSATSSVTYMHW<br>YQQKPGQSPKRWIYDTSNLPYGVPARFSGSGSGT<br>SYSLTISSMEAEDAATYYCQQWSDNPPTFGQGTK<br>LEIKR<br>(SEQ ID NO: 81) |
| muCD37-51 | QIVLTQSPAIMSASPGEKVTMTCSATSSVTYMHW<br>YQQKSGTSPKRWIYDTSKLASGVPARFSGSGSGT<br>SYSLTISNMEAEDAATYYCQQWSSNPPTFGSGTK<br>LEIKR<br>(SEQ ID NO: 82) |
| huCD37-51 | EIVLTQSPATMSASPGERVTMTCSATSSVTYMHW<br>YQQKPGQSPKRWIYDTSKLASGVPARFSGSGSGT<br>SYSLTISSMEAEDAATYYCQQWSSNPPTFGQGTK<br>LEIKR<br>(SEQ ID NO: 83) |
| muCD37-56 | QIVLTQSPAFMSASPGDKVTMTCSASSSVTYMHW<br>YQQKSGTSPKRWIYDTSKLASGVPARFSGGGSGT<br>SYSLTISTMEAEDAATYYCQQWISDPPTFGGGTK<br>LEIKR<br>(SEQ ID NO: 84) |
| huCD37-56 | DIVLTQSPAFMSASPGEKVTMTCSASSSVTYMHW<br>YQQKPDQSPKRWIYDTSNLASGVPSRFSGGGSGT<br>DYSLTISSMEAEDAATYYCQQWISDPPTFGQGTK<br>LEIKR<br>(SEQ ID NO: 85) |
| muCD37-57 | QIVLTQSPAIMSASPGEKVTMTCSATSSVTYMHW<br>YQQKSGTSPKRWIYDTSKLASGVPARFSGSGSGT<br>SYSLTISSMEAEDAATYYCQQWSDNPPTFGSGTK<br>LEIKR<br>(SEQ ID NO: 86) |
| huCD37-57 | EIVLTQSPATMSASPGERVTMTCSATSSVTYMHW<br>YQQKPGQSPRRWIYDTSNLASGVPARFSGSGSGT<br>SYSLTISSMEAEDAATYYCQQWSDNPPTFGQGTK<br>LEIKR<br>(SEQ ID NO: 87) |

Also provided are polypeptides that comprise: (a) a polypeptide having at least about 90% sequence identity to SEQ ID NOs:55-71; and/or (b) a polypeptide having at least about 90% sequence identity to SEQ ID NOs:72-87. In certain embodiments, the polypeptide comprises a polypeptide having at least about 95%, at least about 96%, at least about 97%, at least about 98%, or at least about 99% sequence identity to SEQ ID NOs:55-87. Thus, in certain embodiments, the polypeptide comprises (a) a polypeptide having at least about 95% sequence identity to SEQ ID NOs:55-71, and/or (b) a polypeptide having at least about 95% sequence identity to SEQ ID NOs:72-87. In certain embodiments, the polypeptide comprises (a) a polypeptide having the amino acid sequence of SEQ ID NOs:55-71; and/or (b) a polypeptide having the amino acid sequence of SEQ ID NOs:72-87. In certain embodiments, the polypeptide is an antibody and/or the polypeptide specifically binds CD37. In certain embodiments, the polypeptide is a murine, chimeric, or humanized antibody that specifically binds CD37. In certain embodiments, the polypeptide having a certain percentage of sequence identity to SEQ ID NOs:55-87 differs from SEQ ID NOs:55-87 by conservative amino acid substitutions only.

Polypeptides can comprise one of the individual light chains or heavy chains described herein. Antibodies and polypeptides can also comprise both a light chain and a heavy chain. The light chain and variable chain sequences of murine, chimeric, and humanized CD37-3, CD37-12, CD37-50, CD37-51, CD37-56, and CD37-57 antibodies are provided in Tables 5 and 6 below.

TABLE 5

Full-length heavy chain amino acid sequences

| Antibody | Full-Length Heavy Chain Amino Acid Sequence (SEQ ID NO) |
|---|---|
| muCD37-3 | QVQVKESGPGLVAPSQSLSITCTVSGFSLTTSGVS<br>WVRQPPGKGLEWLGVIWGDGSTNYHSALKSRLSIK<br>KDHSKSQVFLKLNSLQTDDTATYYCAKGGYSLAHW<br>GQGTLVTVSAAKTTAPSVYPLAPVCGDTTGSSVTL<br>GCLVKGYFPEPVTLTWNSGSLSSGVHTFPAVLQSD<br>LYTLSSSVTVTSSTWPSQSITCNVAHPASSTKVDK<br>KIEPRGPTIKPCPPCKCPAPNLLGGPSVFIFPPKI<br>KDVLMISLSPIVTCVVVDVSEDDPDVQISWFVNNV<br>EVHTAQTQTHREDYNSTLRVVSALPIQHQDWMSGK<br>EFKCKVNNKDLPAPIERTISKPKGSVRAPQVYVLP<br>PPEEEMTKKQVTLTCMVTDFMPEDIYVEWTNNGKT<br>ELNYKNTEPVLDSDGSYFMYSKLRVEKKNWVERNS<br>YSCSVVHEGLHNHHTTKSFSRTPGK<br>(SEQ ID NO: 88) |
| chCD37-3 | QVQVKESGPGLVAPSQSLSITCTVSGFSLTTSGVS<br>WVRQPPGKGLEWLGVIWGDGSTNYHSALKSRLSIK<br>KDHSKSQVFLKLNSLQTDDTATYYCAKGGYSLAHW<br>GQGTLVTVSAASTKGPSVFPLAPSSKSTSGGTAAL<br>GCLVKDYFPEPVTVSWNSGALTSGVHTFPAVLQSS<br>GLYSLSSVVTVPSSSLGTQTYICNVNHKPSNTKVD<br>KKVEPKSCDKTHTCPPCPAPELLGGPSVFLFPPKP<br>KDTLMISRTPEVTCVVVDVSHEDPEVKFNWYVDGV<br>EVHNAKTKPREEQYNSTYRVVSVLTVLHQDWLNGK<br>EYKCKVSNKALPAPIEKTISKAKGQPREPQVYTLP<br>PSRDELTKNQVSLTCLVKGFYPSDIAVEWESNGQP<br>ENNYKTTPPVLDSDGSFFLYSKLTVDKSRWQQGNV<br>FSCSVMHEALHNHYTQKSLSLSPGK<br>(SEQ ID NO: 89) |
| huCD37-3v1.0 | QVQVQESGPGLVAPSQTLSITCTVSGFSLTTSGVS<br>WVRQPPGKGLEWLGVIWGDGSTNYHPSLKSRLSIK<br>KDHSKSQVFLKLNSLTAADTATYYCAKGGYSLAHW<br>GQGTLVTVSSASTKGPSVFPLAPSSKSTSGGTAAL<br>GCLVKDYFPEPVTVSWNSGALTSGVHTFPAVLQSS<br>GLYSLSSVVTVPSSSLGTQTYICNVNHKPSNTKVD<br>KKVEPKSCDKTHTCPPCPAPELLGGPSVFLFPPKP<br>KDTLMISRTPEVTCVVVDVSHEDPEVKFNWYVDGV<br>EVHNAKTKPREEQYNSTYRVVSVLTVLHQDWLNGK<br>EYKCKVSNKALPAPIEKTISKAKGQPREPQVYTLP<br>PSRDELTKNQVSLTCLVKGFYPSDIAVEWESNGQP<br>ENNYKTTPPVLDSDGSFFLYSKLTVDKSRWQQGNV<br>FSCSVMHEALHNHYTQKSLSLSPG<br>(SEQ ID NO: 90) |
| huCD37-3v1.1 | QVQVQESGPGLVAPSQTLSITCTVSGFSLTTSGVS<br>WVRQPPGKGLEWLGVIWGDGSTNYHSSLKSRLSIK<br>KDHSKSQVFLKLNSLTAADTATYYCAKGGYSLAHW<br>GQGTLVTVSSASTKGPSVFPLAPSSKSTSGGTAAL<br>GCLVKDYFPEPVTVSWNSGALTSGVHTFPAVLQSS<br>GLYSLSSVVTVPSSSLGTQTYICNVNHKPSNTKVD<br>KKVEPKSCDKTHTCPPCPAPELLGGPSVFLFPPKP<br>KDTLMISRTPEVTCVVVDVSHEDPEVKFNWYVDGV<br>EVHNAKTKPREEQYNSTYRVVSVLTVLHQDWLNGK<br>EYKCKVSNKALPAPIEKTISKAKGQPREPQVYTLP<br>PSRDELTKNQVSLTCLVKGFYPSDIAVEWESNGQP<br>ENNYKTTPPVLDSDGSFFLYSKLTVDKSRWQQGNV<br>FSCSVMHEALHNHYTQKSLSLSPG<br>(SEQ ID NO: 91) |
| muCD37-12 | QIQLVQSGPELKKPGETVKISCKASGYTFTKYGMN<br>WVKQAQGKGLKWMGWINTNTGESRNAEEFKGRFAF<br>SLETSASTAYLQINNLKYEDTATYFCGRGTVVADW<br>GQGTTLTVSSAKTTAPSVYPLAPVCGDTTGSSVTL<br>GCLVKGYFPEPVTLTWNSGSLSSGVHTFPAVLQSD<br>LYTLSSSVTVTSSTWPSQSITCNVAHPASSTKVDK<br>KIEPRGPTIKPCPPCKCPAPNLLGGPSVFIFPPKI<br>KDVLMISLSPIVTCVVVDVSEDDPDVQISWFVNNV<br>EVHTAQTQTHREDYNSTLRVVSALPIQHQDWMSGK<br>EFKCKVNNKDLPAPIERTISKPKGSVRAPQVYVLP<br>PPEEEMTKKQVTLTCMVTDFMPEDIYVEWTNNGKT<br>ELNYKNTEPVLDSDGSYFMYSKLRVEKKNWVERNS<br>YSCSVVHEGLHNHHTTKSFSRTPGK<br>(SEQ ID NO: 92) |
| chCD37-12 | QIQLVQSGPELKKPGETVKISCKASGYTFTKYGMN<br>WVKQAQGKGLKWMGWINTNTGESRNAEEFKGRFAF<br>SLETSASTAYLQINNLKYEDTATYFCGRGTVVADW<br>GQGTTLTVSSASTKGPSVFPLAPSSKSTSGGTAAL<br>GCLVKDYFPEPVTVSWNSGALTSGVHTFPAVLQSS<br>GLYSLSSVVTVPSSSLGTQTYICNVNHKPSNTKVD<br>KKVEPKSCDKTHTCPPCPAPELLGGPSVFLFPPKP<br>KDTLMISRTPEVTCVVVDVSHEDPEVKFNWYVDGV<br>EVHNAKTKPREEQYNSTYRVVSVLTVLHQDWLNGK<br>EYKCKVSNKALPAPIEKTISKAKGQPREPQVYTLP<br>PSRDELTKNQVSLTCLVKGFYPSDIAVEWESNGQP<br>ENNYKTTPPVLDSDGSFFLYSKLTVDKSRWQQGNV<br>FSCSVMHEALHNHYTQKSLSLSPGK<br>(SEQ ID NO: 93) |
| muCD37 -38 | DVQLQESGPDLVKPSQSLSLTCTVTGYSITSGFGW<br>HWIRQFPGNKLEWMAYILYSGGTDYNPSLKSRISI<br>TRDTSKNQFFLRLSSVTTEDTATYYCARGYYGYGA<br>WFVYWGQGTLVTVSAAKTTPPSVYPLAPGSAAQTN<br>SMVTLGCLVKGYFPEPVTVTWNSGSLSSGVHTFPA<br>VLESDLYTLSSSVTVPSSMRPSETVTCNVAHPASS<br>TKVDKKIVPRDCGCKPCICTVPEVSSVFIFPPKPK<br>DVLTITLTPKVTCVVVDISKDDPEVQFSWFVDDVE<br>VHTAQTQPREEQFNSTFRSVSELPIMHQDWLNGKE<br>FKCRVNSAAFPAPIEKTISKTKGRPKAPQVYTIPP<br>PKEQMAKDKVSLTCMITDFFPEDITVEWQWNGQPA<br>ENYKNTQPIMNTNGSYFVYSKLNVQKSNWEAGNTF<br>TCSVLHEGLHNHHTEKSLSHSPGK<br>(SEQ ID NO: 94) |
| chCD37-38 | QVQLQESGPDLVKPSQSLSLTCTVTGYSITSGFGW<br>HWIRQFPGNKLEWMAYILYSGGTDYNPSLKSRISI<br>TRDTSKNQFFLRLSSVTTEDTATYYCARGYYGYGA<br>WFVYWGQGTLVTVSAASTKGPSVFPLAPSSKSTSG<br>GTAALGCLVKDYFPEPVTVSWNSGALTSGVHTFPA<br>VLQSSGLYSLSSVVTVPSSSLGTQTYICNVNHKPS<br>NTKVDKKVEPKSCDKTHTCPPCPAPELLGGPSVFL<br>FPPKPKDTLMISRTPEVTCVVVDVSHEDPEVKFNW<br>YVDGVEVHNAKTKPREEQYNSTYRVVSVLTVLHQD<br>WLNGKEYKCKVSNKALPAPIEKTISKAKGQPREPQ<br>VYTLPPSRDELTKNQVSLTCLVKGFYPSDIAVEWE<br>SNGQPENNYKTTPPVLDSDGSFFLYSKLTVDKSRW<br>QQGNVFSCSVMHEALHNHYTQKSLSLSPG<br>(SEQ ID NO: 95) |
| huCD37-38 | QVQLQESGPGLVKPSQSLSLTCTVSGYSITSGFGW<br>HWIRQFPGKGLEWMAYILYSGGTDYNPSLKSRISI<br>TRDTSKNQFFLRLSSVTAADTATYYCARGYYGYGA<br>WFVYWGQGTLVTVSSASTKGPSVFPLAPSSKSTSG<br>GTAALGCLVKDYFPEPVTVSWNSGALTSGVHTFPA<br>VLQSSGLYSLSSVVTVPSSSLGTQTYICNVNHKPS<br>NTKVDKKVEPKSCDKTHTCPPCPAPELLGGPSVFL<br>FPPKPKDTLMISRTPEVTCVVVDVSHEDPEVKFNW<br>YVDGVEVHNAKTKPREEQYNSTYRVVSVLTVLHQD<br>WLNGKEYKCKVSNKALPAPIEKTISKAKGQPREPQ<br>VYTLPPSRDELTKNQVSLTCLVKGFYPSDIAVEWE<br>SNGQPENNYKTTPPVLDSDGSFFLYSKLTVDKSRW<br>QQGNVFSCSVMHEALHNHYTQKSLSLSPG<br>(SEQ ID NO: 96) |

TABLE 5-continued

| Full-length heavy chain amino acid sequences | |
|---|---|
| Antibody | Full-Length Heavy Chain Amino Acid Sequence (SEQ ID NO) |
| muCD37-50 | DVQLQESGPDLLKPSQSLSLTCTVTGYSITSGFAW<br>HWIRQFPGNKLEWMGYILYSGSTVYSPSLKSRISI<br>TRDTSKNHFFLQLNSVTTEDTATYYCARGYYGYGA<br>WFAYWGQGTLVTVSAAKTTAPSVYPLAPVCGDTTG<br>SSVTLGCLVKGYFPEPVTLTWNSGSLSSGVHTFPA<br>VLQSDLYTLSSSVTVTSSTWPSQSITCNVAHPASS<br>TKVDKKIEPRGPTIKPCPPCKCPAPNLLGGPSVFI<br>FPPKIKDVLMISLSPIVTCVVVDVSEDDPDVQISW<br>FVNNVEVHTAQTQTHREDYNSTLRVVSALPIQHQD<br>WMSGKEFKCKVNNKDLPAPIERTISKPKGSVRAPQ<br>VYVLPPPEEEMTKKQVTLTCMVTDFMPEDIYVEWT<br>NNGKTELNYKNTEPVLDSDGSYFMYSKLRVEKKNW<br>VERNSYSCSVVHEGLHNHHTTKSFSRTPGK<br>(SEQ ID NO: 97) |
| huCD37-50 | QVQLQESGPGLLKPSQSLSLTCTVSGYSITSGFAW<br>HWIRQHPGNKLEWMGYILYSGSTVYSPSLKSRISI<br>TRDTSKNHFFLQLNSVTAADTATYYCARGYYGYGA<br>WFAYWGQGTLVTVSAASTKGPSVFPLAPSSKSTSG<br>GTAALGCLVKDYFPEPVTVSWNSGALTSGVHTFPA<br>VLQSSGLYSLSSVVTVPSSSLGTQTYICNVNHKPS<br>NTKVDKKVEPKSCDKTHTCPPCPAPELLGGPSVFL<br>FPPKPKDTLMISRTPEVTCVVVDVSHEDPEVKFNW<br>YVDGVEVHNAKTKPREEQYNSTYRVVSVLTVLHQD<br>WLNGKEYKCKVSNKALPAPIEKTISKAKGQPREPQ<br>VYTLPPSRDELTKNQVSLTCLVKGFYPSDIAVEWE<br>SNGQPENNYKTTPPVLDSDGSFFLYSKLTVDKSRW<br>QQGNVFSCSVMHEALHNHYTQKSLSLSPG<br>(SEQ ID NO: 98) |
| muCD37-51 | DVQLQESGPDLLKPSQSLSLTCTVTGYSISSGFAW<br>HWIRQFPGNKLEWMGYIHYSGSTNYSPSLKSRISI<br>TRDSSKNQFFLQLNSVTTEDTATYYCARGYYGFGA<br>WFVYVVGQGTLVTVSAAKTTAPSVYPLAPVCGDTT<br>GSSVTLGCLVKGYFPEPVTLTWNSGSLSSGVHTFP<br>AVLQSDLYTLSSSVTVTSSTWPSQSITCNVAHPAS<br>STKVDKKIEPRGPTIKPCPPCKCPAPNLLGGPSVF<br>IFPPKIKDVLMISLSPIVTCVVVDVSEDDPDVQIS<br>WFVNNVEVHTAQTQTHREDYNSTLRVVSALPIQHQ<br>DWMSGKEFKCKVNNKDLPAPIERTISKPKGSVRAP<br>QVYVLPPPEEEMTKKQVTLTCMVTDFMPEDIYVEW<br>TNNGKTELNYKNTEPVLDSDGSYFMYSKLRVEKKN<br>WVERNSYSCSVVHEGLHNHHTTKSFSRTPGK<br>(SEQ ID NO: 99) |
| huCD37-51 | EVQLVESGPEVLKPGESLSLTCTVSGYSISSGFAW<br>HWIRQFPGKGLEWMGYIHYSGSTNYSPSLQGRISI<br>TRDSSINQFFLQLNSVTASDTATYYCARGYYGFGA<br>WFVYVVGQGTLVTVSAASTKGPSVFPLAPSSKSTS<br>GGTAALGCLVKDYFPEPVTVSWNSGALTSGVHTFP<br>AVLQSSGLYSLSSVVTVPSSSLGTQTYICNVNHKP<br>SNTKVDKKVEPKSCDKTHTCPPCPAPELLGGPSVF<br>LFPPKPKDTLMISRTPEVTCVVVDVSHEDPEVKFN<br>WYVDGVEVHNAKTKPREEQYNSTYRVVSVLTVLHQ<br>DWLNGKEYKCKVSNKALPAPIEKTISKAKGQPREP<br>QVYTLPPSRDELTKNQVSLTCLVKGFYPSDIAVEW<br>ESNGQPENNYKTTPPVLDSDGSFFLYSKLTVDKSR<br>WQQGNVFSCSVMHEALHNHYTQKSLSLSPG<br>(SEQ ID NO: 100) |
| muCD37-56 | DVQLQESGPDLVKPSQSLSLTCTVTGYSITSGFAW<br>HWIRQFPGNKLEWMGYIHYSGGTNYNPSLKSRVSI<br>TRDTSKNQFFLQLNSVTTEDTATYYCARGYYGFGA<br>WFAYWGQGTLVPVSAAKTTPPSVYPLAPGSAAQTN<br>SMVTLGCLVKGYFPEPVTVTWNSGSLSSGVHTFPA<br>VLESDLYTLSSSVTVPSSMRPSETVTCNVAHPASS<br>TKVDKKIVPRDCGCKPCICTVPEVSSVFIFPPKPK<br>DVLTITLTPKVTCVVVDISKDDPEVQFSWFVDDVE<br>VHTAQTQPREEQFNSTFRSVSELPIMHQDWLNGKE<br>FKCRVNSAAFPAPIEKTISKTKGRPKAPQVYTIPP<br>PKEQMAKDKVSLTCMITDFFPEDITVEWQWNGQPA<br>ENYKNTQPIMNTNGSYFVYSKLNVQKSNWEAGNTF<br>TCSVLHEGLHNHHTEKSLSHSPGK<br>(SEQ ID NO: 101) |
| huCD37-56 | QVQLQESGPGLVKPSQSLSLTCTVSGYSITSGFAW<br>HWIRQFPGKGLEWMGYIHYSGGTNYNPSLKSRVSI<br>TRDTSKNQFFLQLNSVTAADTATYYCARGYYGFGA<br>WFAYWGQGTLVPVSAASTKGPSVFPLAPSSKSTSG<br>GTAALGCLVKDYFPEPVTVSWNSGALTSGVHTFPA<br>VLQSSGLYSLSSVVTVPSSSLGTQTYICNVNHKPS<br>NTKVDKKVEPKSCDKTHTCPPCPAPELLGGPSVFL<br>FPPKPKDTLMISRTPEVTCVVVDVSHEDPEVKFNW<br>YVDGVEVHNAKTKPREEQYNSTYRVVSVLTVLHQD<br>WLNGKEYKCKVSNKALPAPIEKTISKAKGQPREPQ<br>VYTLPPSRDELTKNQVSLTCLVKGFYPSDIAVEWE<br>SNGQPENNYKTTPPVLDSDGSFFLYSKLTVDKSRW<br>QQGNVFSCSVMHEALHNHYTQKSLSLSPG<br>(SEQ ID NO: 102) |
| muCD37-57 | DVQLQESGPDLLKPSQSLSLTCTVTGYSITSGFAW<br>HWIRQFPGNKLEWMGYILYSGSTVYSPSLKSRISI<br>TRDTSKNQFFLQLNSVTTEDTATYYCARGYYGYGA<br>WFAYWGQGTLVTVSAAKTTAPSVYPLAPVCGDTTG<br>SSVTLGCLVKGYFPEPVTLTWNSGSLSSGVHTFPA<br>VLQSDLYTLSSSVTVTSSTWPSQSITCNVAHPASS<br>TKVDKKIEPRGPTIKPCPPCKCPAPNLLGGPSVFI<br>FPPKIKDVLMISLSPIVTCVVVDVSEDDPDVQISW<br>FVNNVEVHTAQTQTHREDYNSTLRVVSALPIQHQD<br>WMSGKEFKCKVNNKDLPAPIERTISKPKGSVRAPQ<br>VYVLPPPEEEMTKKQVTLTCMVTDFMPEDIYVEWT<br>NNGKTELNYKNTEPVLDSDGSYFMYSKLRVEKKNW<br>VERNSYSCSVVHEGLHNHHTTKSFSRTPGK<br>(SEQ ID NO: 103) |
| huCD37-57 | QVQLQESGPGLLKPSQSLSLTCTVSGYSITSGFAW<br>HWIRQFPGKGLEWMGYILYSGSTVYSPSLKSRISI<br>TRDTSKNQFFLQLNSVTAADTATYYCARGYYGYGA<br>WFAYWGQGTLVTVSAASTKGPSVFPLAPSSKSTSG<br>GTAALGCLVKDYFPEPVTVSWNSGALTSGVHTFPA<br>VLQSSGLYSLSSVVTVPSSSLGTQTYICNVNHKPS<br>NTKVDKKVEPKSCDKTHTCPPCPAPELLGGPSVFL<br>FPPKPKDTLMISRTPEVTCVVVDVSHEDPEVKFNW<br>YVDGVEVHNAKTKPREEQYNSTYRVVSVLTVLHQD<br>WLNGKEYKCKVSNKALPAPIEKTISKAKGQPREPQ<br>VYTLPPSRDELTKNQVSLTCLVKGFYPSDIAVEWE<br>SNGQPENNYKTTPPVLDSDGSFFLYSKLTVDKSRW<br>QQGNVFSCSVMHEALHNHYTQKSLSLSPG<br>(SEQ ID NO: 104) |

TABLE 6

| Full-length light chain amino acid sequences | |
|---|---|
| Antibody | Full-length Light Chain Amino Acid Sequence (SEQ ID NO) |
| muCD37-3 | DIQMTQSPASLSVSVGETVTITCRASENIRSNLAWYQQKQGKSPQLLVNVAT<br>NLADGVPSRFSGSGSGTQYSLKINSLQSEDFGTYYCQHYWGTTWTFGGGTK<br>LEIKRADAAPTVSIFPPSSEQLTSGGASVVCFLNNFYPKDINVKWKIDGSERQ<br>NGVLNSWTDQDSKDSTYSMSSTLTLTKDEYERHNSYTCEATHKTSTSPIVKS<br>FNRNEC<br>(SEQ ID NO: 105) |

TABLE 6-continued

Full-length light chain amino acid sequences

| Antibody | Full-length Light Chain Amino Acid Sequence (SEQ ID NO) |
| --- | --- |
| chCD37-3 | DIQMTQSPASLSVSVGETVTITCRASENIRSNLAWYQQKQGKSPQLLVNVAT NLADGVPSRFSGSGSGTQYSLKINSLQSEDFGTYYCQHYWGTTWTFGGGTK LEIKRTVAAPSVFIFPPSDEQLKSGTASVVCLLNNFYPREAKVQWKVDNALQ SGNSQESVTEQDSKDSTYSLSSTLTLSKADYEKHKVYACEVTHQGLSSPVTK SFNRGEC (SEQ ID NO: 106) |
| huCD37-3 (1.0 and 1.1) | DIQMTQSPSSLSVSVGERVTITCRASENIRSNLAWYQQKPGKSPKLLVNVAT NLADGVPSRFSGSGSGTDYSLKINSLQPEDFGTYYCQHYWGTTWTFGQGTK LEIKRTVAAPSVFIFPPSDEQLKSGTASVVCLLNNFYPREAKVQWKVDNALQ SGNSQESVTEQDSKDSTYSLSSTLTLSKADYEKHKVYACEVTHQGLSSPVTK SFNRGEC (SEQ ID NO: 107) |
| muCD37-12 | DIVLTQSPASLAVSLGQRATISCRASQSVSTSSYSYLYWFQQKPGQPPKLLIK YASNLASGVPARFSGSGSGTDFTLNIHPVEEEDTATYYCQHSWEIPYTFGGG TKLEIKRADAAPTVSIFPPSSEQLTSGGASVVCFLNNFYPKDINVKWKIDGSE RQNGVLNSWTDQDSKDSTYSMSSTLTLTKDEYERHNSYTCEATHKTSTSPI VKSFNRNEC (SEQ ID NO: 108) |
| chCD37-12 | DIVLTQSPASLAVSLGQRATISCRASQSVSTSSYSYLYWFQQKPGQPPKLLIK YASNLASGVPARFSGSGSGTDFTLNIHPVEEEDTATYYCQHSWEIPYTFGGG TKLEIKRTVAAPSVFIFPPSDEQLKSGTASVVCLLNNFYPREAKVQWKVDNA LQSGNSQESVTEQDSKDSTYSLSSTLTLSKADYEKHKVYACEVTHQGLSSPV TKSFNRGEC (SEQ ID NO: 109) |
| muCD37-38 | QIVLTQSPAIMSASPGEKVTMTCSASSSVTYMHWYQQKSGTSPKRWIYDTS KLASGVPARFSGGGSGTSYSLTISSMEAEDAATYYCQQWISNPPTFGGGTKL EIKRADAAPTVSIFPPSSEQLTSGGASVVCFLNNFYPKDINVKWKIDGSERQN GVLNSWTDQDSKDSTYSMSSTLTLTKDEYERHNSYTCEATHKTSTSPIVKSF NRNEC (SEQ ID NO: 110) |
| chCD37-38 | QIVLTQSPAIMSASPGEKVTMTCSASSSVTYMHWYQQKSGTSPKRWIYDTS KLASGVPARFSGGGSGTSYSLTISSMEAEDAATYYCQQWISNPPTFGGGTKL EIKRTVAAPSVFIFPPSDEQLKSGTASVVCLLNNFYPREAKVQWKVDNALQS GNSQESVTEQDSKDSTYSLSSTLTLSKADYEKHKVYACEVTHQGLSSPVTKS FNRGEC (SEQ ID NO: 111) |
| huCD37-38 | DIVLTQSPASMSASPGERVTMTCSASSSVTYMHWYQQKPGTSPKRWIYDTS KLASGVPARFSGSGSGTSYSLTISSMEAEDAATYYCQQWISNPPTFGGGTKL EIKRTVAAPSVFIFPPSDEQLKSGTASVVCLLNNFYPREAKVQWKVDNALQS GNSQESVTEQDSKDSTYSLSSTLTLSKADYEKHKVYACEVTHQGLSSPVTKS FNRGEC (SEQ ID NO: 112) |
| muCD37-50 | QIVLTQSPAIMSASPGEKVTMTCSATSSVTYMHWYQQKSGTSPKRWIYDTS KLPYGVPGRFSGSGSGTSYSLTISSMEAEDAATYYCQQWSDNPPTFGSGTKL EIKRADAAPTVSIFPPSSEQLTSGGASVVCFLNNFYPKDINVKWKIDGSERQN GVLNSWTDQDSKDSTYSMSSTLTLTKDEYERHNSYTCEATHKTSTSPIVKSF NRNEC (SEQ ID NO: 113) |
| huCD37-50 | EIVLTQSPATMSASPGERVTMTCSATSSVTYMHWYQQKPGQSPKRWIYDTS NLPYGVPARFSGSGSGTSYSLTISSMEAEDAATYYCQQWSDNPPTFGQGTKL EIKRTVAAPSVFIFPPSDEQLKSGTASVVCLLNNFYPREAKVQWKVDNALQS GNSQESVTEQDSKDSTYSLSSTLTLSKADYEKHKVYACEVTHQGLSSPVTKS FNRGEC (SEQ ID NO: 114) |
| muCD37-51 | QIVLTQSPAIMSASPGEKVTMTCSATSSVTYMHWYQQKSGTSPKRWIYDTS KLASGVPARFSGSGSGTSYSLTISNMEAEDAATYYCQQWSSNPPTFGSGTKL EIKRADAAPTVSIFPPSSEQLTSGGASVVCFLNNFYPKDINVKWKIDGSERQN GVLNSWTDQDSKDSTYSMSSTLTLTKDEYERHNSYTCEATHKTSTSPIVKSF NRNEC (SEQ ID NO: 115) |

TABLE 6-continued

Full-length light chain amino acid sequences

| Antibody | Full-length Light Chain Amino Acid Sequence (SEQ ID NO) |
| --- | --- |
| huCD37-51 | EIVLTQSPATMSASPGERVTMTCSATSSVTYMHWYQQKPGQSPKRWIYDTS<br>KLASGVPARFSGSGSGTSYSLTISSMEAEDAATYYCQQWSSNPPTFGQGTKL<br>EIKRTVAAPSVFIFPPSDEQLKSGTASVVCLLNNFYPREAKVQWKVDNALQS<br>GNSQESVTEQDSKDSTYSLSSTLTLSKADYEKHKVYACEVTHQGLSSPVTKS<br>FNRGEC<br>(SEQ ID NO: 116) |
| muCD37-56 | QIVLTQSPAFMSASPGDKVTMTCSASSSVTYMHWYQQKSGTSPKRWIYDTS<br>KLASGVPARFSGGGSGTSYSLTISTMEAEDAATYYCQQWISDPPTFGGGTKL<br>EIKRADAAPTVSIFPPSSEQLTSGGASVVCFLNNFYPKDINVKWKIDGSERQN<br>GVLNSWTDQDSKDSTYSMSSTLTLTKDEYERHNSYTCEATHKTSTSPIVKSF<br>NRNEC<br>(SEQ ID NO: 117) |
| huCD37-56 | DIVLTQSPAFMSASPGEKVTMTCSASSSVTYMHWYQQKPDQSPKRWIYDTS<br>NLASGVPSRFSGGGSGTDYSLTISSMEAEDAATYYCQQWISDPPTFGQGTKL<br>EIKRTVAAPSVFIFPPSDEQLKSGTASVVCLLNNFYPREAKVQWKVDNALQS<br>GNSQESVTEQDSKDSTYSLSSTLTLSKADYEKHKVYACEVTHQGLSSPVTKS<br>FNRGEC<br>(SEQ ID NO: 118) |
| muCD37-57 | QIVLTQSPAIMSASPGEKVTMTCSATSSVTYMHWYQQKSGTSPKRWIYDTS<br>KLASGVPARFSGSGSGTSYSLTISSMEAEDAATYYCQQWSDNPPTFGSGTKL<br>EIKRADAAPTVSIFPPSSEQLTSGGASVVCFLNNFYPKDINVKWKIDGSERQN<br>GVLNSWTDQDSKDSTYSMSSTLTLTKDEYERHNSYTCEATHKTSTSPIVKSF<br>NRNEC<br>(SEQ ID NO: 119) |
| huCD37-57 | EIVLTQSPATMSASPGERVTMTCSATSSVTYMHWYQQKPGQSPRRWIYDTS<br>NLASGVPARFSGSGSGTSYSLTISSMEAEDAATYYCQQWSDNPPTFGQGTKL<br>EIKRTVAAPSVFIFPPSDEQLKSGTASVVCLLNNFYPREAKVQWKVDNALQS<br>GNSQESVTEQDSKDSTYSLSSTLTLSKADYEKHKVYACEVTHQGLSSPVTKS<br>FNRGEC<br>(SEQ ID NO: 120) |

Also provided are polypeptides that comprise: (a) a polypeptide having at least about 90% sequence identity to SEQ ID NOs:88-104; and/or (b) a polypeptide having at least about 90% sequence identity to SEQ ID NOs:105-120. In certain embodiments, the polypeptide comprises a polypeptide having at least about 95%, at least about 96%, at least about 97%, at least about 98%, or at least about 99% sequence identity to SEQ ID NOs:88-120. Thus, in certain embodiments, the polypeptide comprises (a) a polypeptide having at least about 95% sequence identity to SEQ ID NOs:88-104, and/or (b) a polypeptide having at least about 95% sequence identity to SEQ ID NOs:105-120. In certain embodiments, the polypeptide comprises (a) a polypeptide having the amino acid sequence of SEQ ID NOs:88-104; and/or (b) a polypeptide having the amino acid sequence of SEQ ID NOs:105-120. In certain embodiments, the polypeptide is an antibody and/or the polypeptide specifically binds CD37. In certain embodiments, the polypeptide is a murine, chimeric, or humanized antibody that specifically binds CD37. In certain embodiments, the polypeptide having a certain percentage of sequence identity to SEQ ID NOs:88-120 differs from SEQ ID NOs:88-120 by conservative amino acid substitutions only.

In certain embodiments, the CD37 antibody can be the antibody produced from a hybridoma selected from the group consisting of consisting of ATCC Deposit Designation PTA-10664, deposited with the ATCC on Feb. 18, 2010, ATCC Deposit Designation PTA-10665, deposited with the ATCC on Feb. 18, 2010, ATCC Deposit Designation PTA-10666, deposited with the ATCC on Feb. 18, 2010, ATCC Deposit Designation PTA-10667 deposited with the ATCC on Feb. 18, 2010, ATCC Deposit Designation PTA-10668, deposited with the ATCC on Feb. 18, 2010, ATCC Deposit Designation PTA-10669, deposited with the ATCC on Feb. 18, 2010, and ATCC Deposit Designation PTA-10670, deposited with the ATCC on Feb. 18, 2010. In certain embodiments, the antibody comprises the VH-CDRs and the VL-CDRS of the antibody produced from a hydridoma selected from the group consisting of PTA-10665, PTA-10666, PTA-10667, PTA-10668, PTA-10669, and PTA-10670.

In certain embodiments, the CD37 antibody can comprise a light chain encoded by the recombinant plasmid DNA phuCD37-3LC (ATCC Deposit Designation PTA-10722, deposited with the ATCC on Mar. 18, 2010). In certain embodiments, the CD37 antibody can comprise a heavy chain encoded by the recombinant plasmid DNA phuCD37-3HCv.1.0 (ATCC Deposit Designation PTA-10723, deposited with the ATCC on Mar. 18, 2010). In certain embodiments, the CD37 antibody can comprise a light chain encoded by the recombinant plasmid DNA phuCD37-3LC (PTA-10722) and a heavy chain encoded by the recombinant plasmid DNA phuCD37-3HCv.1.0 (PTA-10723). In certain embodiments, the CD37 antibody can comprise the VL-CDRs encoded by the recombinant plasmid DNA phuCD37-3LC (PTA-10722) and the VH-CDRs encoded by the recombinant plasmid DNA phuCD37-3HCv.1.0 (PTA-10723).

Monoclonal antibodies can be prepared using hybridoma methods, such as those described by Kohler and Milstein (1975) Nature 256:495. Using the hybridoma method, a mouse, hamster, or other appropriate host animal, is immunized as described above to elicit the production by lymphocytes of antibodies that will specifically bind to an immunizing antigen. Lymphocytes can also be immunized in vitro. Following immunization, the lymphocytes are isolated and fused with a suitable myeloma cell line using, for example, polyethylene glycol, to form hybridoma cells that can then be selected away from unfused lymphocytes and myeloma cells. Hybridomas that produce monoclonal antibodies directed specifically against a chosen antigen as determined by immunoprecipitation, immunoblotting, or by an in vitro binding assay (e.g. radioimmunoassay (RIA); enzyme-linked immunosorbent assay (ELISA)) can then be propagated either in vitro culture using standard methods (Goding, Monoclonal Antibodies: Principles and Practice, Academic Press, 1986) or in vivo as ascites tumors in an animal. The monoclonal antibodies can then be purified from the culture medium or ascites fluid as described for polyclonal antibodies above.

Alternatively monoclonal antibodies can also be made using recombinant DNA methods as described in U.S. Pat. No. 4,816,567. The polynucleotides encoding a monoclonal antibody are isolated from mature B-cells or hybridoma cell, such as by RT-PCR using oligonucleotide primers that specifically amplify the genes encoding the heavy and light chains of the antibody, and their sequence is determined using conventional procedures. The isolated polynucleotides encoding the heavy and light chains are then cloned into suitable expression vectors, which when transfected into host cells such as *E. coli* cells, simian COS cells, Chinese hamster ovary (CHO) cells, or myeloma cells that do not otherwise produce immunoglobulin protein, monoclonal antibodies are generated by the host cells. Also, recombinant monoclonal antibodies or fragments thereof of the desired species can be isolated from phage display libraries expressing CDRs of the desired species as described (McCafferty et al., 1990, Nature, 348:552-554; Clackson et al., 1991, Nature, 352:624-628; and Marks et al., 1991, J. Mol. Biol., 222:581-597).

The polynucleotide(s) encoding a monoclonal antibody can further be modified in a number of different manners using recombinant DNA technology to generate alternative antibodies. In some embodiments, the constant domains of the light and heavy chains of, for example, a mouse monoclonal antibody can be substituted 1) for those regions of, for example, a human antibody to generate a chimeric antibody or 2) for a non-immunoglobulin polypeptide to generate a fusion antibody. In some embodiments, the constant regions are truncated or removed to generate the desired antibody fragment of a monoclonal antibody. Site-directed or high-density mutagenesis of the variable region can be used to optimize specificity, affinity, etc. of a monoclonal antibody.

In some embodiments, the monoclonal antibody against the human CD37 is a humanized antibody. In certain embodiments, such antibodies are used therapeutically to reduce antigenicity and HAMA (human anti-mouse antibody) responses when administered to a human subject. Humanized antibodies can be produced using various techniques known in the art. In certain alternative embodiments, the antibody to CD37 is a human antibody.

Human antibodies can be directly prepared using various techniques known in the art. Immortalized human B lymphocytes immunized in vitro or isolated from an immunized individual that produce an antibody directed against a target antigen can be generated (See, e.g., Cole et al., Monoclonal Antibodies and Cancer Therapy, Alan R. Liss, p. 77 (1985); Boerner et al., 1991, J. Immunol., 147 (1):86-95; and U.S. Pat. No. 5,750,373). Also, the human antibody can be selected from a phage library, where that phage library expresses human antibodies, as described, for example, in Vaughan et al., 1996, Nat. Biotech., 14:309-314, Sheets et al., 1998, Proc. Nat'l. Acad. Sci., 95:6157-6162, Hoogenboom and Winter, 1991, J. Mol. Biol., 227:381, and Marks et al., 1991, J. Mol. Biol., 222:581). Techniques for the generation and use of antibody phage libraries are also described in U.S. Pat. Nos. 5,969,108, 6,172,197, 5,885,793, 6,521,404; 6,544,731; 6,555,313; 6,582,915; 6,593,081; 6,300,064; 6,653,068; 6,706,484; and 7,264,963; and Rothe et al., 2007, J. Mol. Bio., doi:10.1016/j.jmb.2007.12.018 (each of which is incorporated by reference in its entirety). Affinity maturation strategies and chain shuffling strategies (Marks et al., 1992, Bio/Technology 10:779-783, incorporated by reference in its entirety) are known in the art and can be employed to generate high affinity human antibodies.

Humanized antibodies can also be made in transgenic mice containing human immunoglobulin loci that are capable upon immunization of producing the full repertoire of human antibodies in the absence of endogenous immunoglobulin production. This approach is described in U.S. Pat. Nos. 5,545,807; 5,545,806; 5,569,825; 5,625,126; 5,633,425; and 5,661,016.

This invention also encompasses bispecific antibodies that specifically recognize a CD37. Bispecific antibodies are antibodies that are capable of specifically recognizing and binding at least two different epitopes. The different epitopes can either be within the same molecule (e.g. the same CD37) or on different molecules such that both, for example, the antibodies can specifically recognize and bind a CD37 as well as, for example, 1) an effector molecule on a leukocyte such as a T-cell receptor (e.g. CD3) or Fc receptor (e.g. CD64, CD32, or CD16) or 2) a cytotoxic agent as described in detail below.

Exemplary bispecific antibodies can bind to two different epitopes, at least one of which originates in a polypeptide of the invention. Alternatively, an anti-antigenic arm of an immunoglobulin molecule can be combined with an arm which binds to a triggering molecule on a leukocyte such as a T cell receptor molecule (e.g. CD2, CD3, CD28, or B7), or Fc receptors for IgG so as to focus cellular defense mechanisms to the cell expressing the particular antigen. Bispecific antibodies can also be used to direct cytotoxic agents to cells which express a particular antigen. These antibodies possess an antigen-binding arm and an arm which binds a cytotoxic agent or a radionuclide chelator, such as EOTUBE, DPTA, DOTA, or TETA. Techniques for making bispecific antibodies are common in the art (Millstein et al., 1983, Nature 305:537-539; Brennan et al., 1985, Science 229:81; Suresh et al, 1986, Methods in Enzymol. 121:120; Traunecker et al., 1991, EMBO J. 10:3655-3659; Shalaby et al., 1992, J. Exp. Med. 175:217-225; Kostelny et al., 1992, J. Immunol. 148:1547-1553; Gruber et al., 1994, J. Immunol. 152:5368; and U.S. Pat. No. 5,731,168). Antibodies with more than two valencies are also contemplated. For example, trispecific antibodies can be prepared (Tutt et al., J. Immunol. 147:60 (1991)). Thus, in certain embodiments the antibodies to CD37 are multispecific.

In certain embodiments are provided an antibody fragment to, for example, increase tumor penetration. Various techniques are known for the production of antibody fragments. Traditionally, these fragments are derived via proteolytic digestion of intact antibodies (for example Morimoto et al., 1993, Journal of Biochemical and Biophysical Methods 24:107-117; Brennan et al., 1985, Science, 229:81). In certain embodiments, antibody fragments are produced recombinantly. Fab, Fv, and scFv antibody fragments can all be expressed in and secreted from *E. coli* or other host cells, thus allowing the production of large amounts of these fragments. Such antibody fragments can also be isolated from the antibody phage libraries discussed above. The antibody fragment can also be linear antibodies as described in U.S. Pat. No. 5,641,870, for example, and can be monospecific or bispecific. Other techniques for the production of antibody fragments will be apparent to the skilled practitioner.

According to the present invention, techniques can be adapted for the production of single-chain antibodies specific to CD37 (see U.S. Pat. No. 4,946,778). In addition, methods can be adapted for the construction of Fab expression libraries (Huse, et al., Science 246:1275-1281 (1989)) to allow rapid and effective identification of monoclonal Fab fragments with the desired specificity for CD37, or derivatives, fragments, analogs or homologs thereof. Antibody fragments can be produced by techniques in the art including, but not limited to: (a) a F(ab')2 fragment produced by pepsin digestion of an antibody molecule; (b) a Fab fragment generated by reducing the disulfide bridges of an F(ab')2 fragment, (c) a Fab fragment generated by the treatment of the antibody molecule with papain and a reducing agent, and (d) Fv fragments.

It can further be desirable, especially in the case of antibody fragments, to modify an antibody in order to increase its serum half-life. This can be achieved, for example, by incorporation of a salvage receptor binding epitope into the antibody fragment by mutation of the appropriate region in the antibody fragment or by incorporating the epitope into a peptide tag that is then fused to the antibody fragment at either end or in the middle (e.g., by DNA or peptide synthesis).

Heteroconjugate antibodies are also within the scope of the present invention. Heteroconjugate antibodies are composed of two covalently joined antibodies. Such antibodies have, for example, been proposed to target immune cells to unwanted cells (U.S. Pat. No. 4,676,980). It is contemplated that the antibodies can be prepared in vitro using known methods in synthetic protein chemistry, including those involving crosslinking agents. For example, immunotoxins can be constructed using a disulfide exchange reaction or by forming a thioether bond. Examples of suitable reagents for this purpose include iminothiolate and methyl-4-mercaptobutyrimidate.

For the purposes of the present invention, it should be appreciated that modified antibodies can comprise any type of variable region that provides for the association of the antibody with the polypeptides of a human CD37. In this regard, the variable region can comprise or be derived from any type of mammal that can be induced to mount a humoral response and generate immunoglobulins against the desired tumor associated antigen. As such, the variable region of the modified antibodies can be, for example, of human, murine, non-human primate (e.g. cynomolgus monkeys, macaques, etc.) or lupine origin. In some embodiments both the variable and constant regions of the modified immunoglobulins are human. In other embodiments the variable regions of compatible antibodies (usually derived from a non-human source) can be engineered or specifically tailored to improve the binding properties or reduce the immunogenicity of the molecule. In this respect, variable regions useful in the present invention can be humanized or otherwise altered through the inclusion of imported amino acid sequences.

In certain embodiments, the variable domains in both the heavy and light chains are altered by at least partial replacement of one or more CDRs and, if necessary, by partial framework region replacement and sequence changing. Although the CDRs can be derived from an antibody of the same class or even subclass as the antibody from which the framework regions are derived, it is envisaged that the CDRs will be derived from an antibody of different class and possibly from an antibody from a different species. It is not always necessary to replace all of the CDRs with the complete CDRs from the donor variable region to transfer the antigen binding capacity of one variable domain to another. Rather, in some cases it is only necessary to transfer those residues that are necessary to maintain the activity of the antigen binding site. Given the explanations set forth in U.S. Pat. Nos. 5,585,089, 5,693,761 and 5,693,762, it will be well within the competence of those skilled in the art, either by carrying out routine experimentation or by trial and error testing to obtain a functional antibody with reduced immunogenicity.

Alterations to the variable region notwithstanding, those skilled in the art will appreciate that the modified antibodies of this invention will comprise antibodies (e.g., full-length antibodies or immunoreactive fragments thereof) in which at least a fraction of one or more of the constant region domains has been deleted or otherwise altered so as to provide desired biochemical characteristics such as increased tumor localization or reduced serum half-life when compared with an antibody of approximately the same immunogenicity comprising a native or unaltered constant region. In some embodiments, the constant region of the modified antibodies will comprise a human constant region. Modifications to the constant region compatible with this invention comprise additions, deletions or substitutions of one or more amino acids in one or more domains. That is, the modified antibodies disclosed herein can comprise alterations or modifications to one or more of the three heavy chain constant domains (CH1, CH2 or CH3) and/or to the light chain constant domain (CL). In some embodiments, modified constant regions wherein one or more domains are partially or entirely deleted are contemplated. In some embodiments, the modified antibodies will comprise domain deleted constructs or variants wherein the entire CH2 domain has been removed (ΔCH2 constructs). In some embodiments, the omitted constant region domain will be replaced by a short amino acid spacer (e.g. 10 residues) that provides some of the molecular flexibility typically imparted by the absent constant region.

Besides their configuration, it is known in the art that the constant region mediates several effector functions. For example, binding of the C1 component of complement to antibodies activates the complement system. Activation of complement is important in the opsonisation and lysis of cell pathogens. The activation of complement also stimulates the inflammatory response and can also be involved in autoimmune hypersensitivity. Further, antibodies bind to cells via the Fc region, with a Fc receptor site on the antibody Fc region binding to a Fc receptor (FcR) on a cell. There are a number of Fc receptors which are specific for different classes of antibody, including IgG (gamma receptors), IgE (eta receptors), IgA (alpha receptors) and IgM (mu receptors). Binding of antibody to Fc receptors on cell surfaces triggers a number of important and diverse biological responses including engulfment and destruction of antibody-coated particles, clearance of immune complexes, lysis of antibody-coated target cells by killer cells (called antibody-dependent cell-mediated cytotoxicity, or ADCC), release of inflammatory mediators, placental transfer and control of immunoglobulin production.

In certain embodiments, the CD37-binding antibodies provide for altered effector functions that, in turn, affect the biological profile of the administered antibody. For example, the deletion or inactivation (through point mutations or other means) of a constant region domain can reduce Fc receptor binding of the circulating modified antibody thereby increasing tumor localization. In other cases, it can be that constant region modifications, consistent with this invention, moderate complement binding and thus reduce the serum half life and nonspecific association of a conjugated cytotoxin. Yet other modifications of the constant region can be used to eliminate disulfide linkages or oligosaccharide moieties that allow for enhanced localization due to increased antigen specificity or antibody flexibility. Similarly, modifications to the constant region in accordance with this invention can easily be made using well known biochemical or molecular engineering techniques well within the purview of the skilled artisan.

In certain embodiments, a CD37-binding agent that is an antibody does not have one or more effector functions. For instance, in some embodiments, the antibody has no antibody-dependent cellular cytotoxicity (ADCC) activity and/or no complement-dependent cytotoxicity (CDC) activity. In certain embodiments, the antibody does not bind to an Fc receptor and/or complement factors. In certain embodiments, the antibody has no effector function.

It will be noted that in certain embodiments, the modified antibodies can be engineered to fuse the CH3 domain directly to the hinge region of the respective modified antibodies. In other constructs it can be desirable to provide a peptide spacer between the hinge region and the modified CH2 and/or CH3 domains. For example, compatible constructs could be expressed wherein the CH2 domain has been deleted and the remaining CH3 domain (modified or unmodified) is joined to the hinge region with a 5-20 amino acid spacer. Such a spacer can be added, for instance, to ensure that the regulatory elements of the constant domain remain free and accessible or that the hinge region remains flexible. However, it should be noted that amino acid spacers can, in some cases, prove to be immunogenic and elicit an unwanted immune response against the construct. Accordingly, in certain embodiments, any spacer added to the construct will be relatively non-immunogenic, or even omitted altogether, so as to maintain the desired biochemical qualities of the modified antibodies.

Besides the deletion of whole constant region domains, it will be appreciated that the antibodies of the present invention can be provided by the partial deletion or substitution of a few or even a single amino acid. For example, the mutation of a single amino acid in selected areas of the CH2 domain can be enough to substantially reduce Fc binding and thereby increase tumor localization. Similarly, it can be desirable to simply delete that part of one or more constant region domains that control the effector function (e.g. complement CLQ binding) to be modulated. Such partial deletions of the constant regions can improve selected characteristics of the antibody (serum half-life) while leaving other desirable functions associated with the subject constant region domain intact. Moreover, as alluded to above, the constant regions of the disclosed antibodies can be modified through the mutation or substitution of one or more amino acids that enhances the profile of the resulting construct. In this respect it can be possible to disrupt the activity provided by a conserved binding site (e.g. Fc binding) while substantially maintaining the configuration and immunogenic profile of the modified antibody. Certain embodiments can comprise the addition of one or more amino acids to the constant region to enhance desirable characteristics such as decreasing or increasing effector function or provide for more cytotoxin or carbohydrate attachment. In such embodiments it can be desirable to insert or replicate specific sequences derived from selected constant region domains.

The present invention further embraces variants and equivalents which are substantially homologous to the chimeric, humanized and human antibodies, or antibody fragments thereof, set forth herein. These can contain, for example, conservative substitution mutations, i.e. the substitution of one or more amino acids by similar amino acids. For example, conservative substitution refers to the substitution of an amino acid with another within the same general class such as, for example, one acidic amino acid with another acidic amino acid, one basic amino acid with another basic amino acid or one neutral amino acid by another neutral amino acid. What is intended by a conservative amino acid substitution is well known in the art.

The polypeptides of the present invention can be recombinant polypeptides, natural polypeptides, or synthetic polypeptides comprising an antibody, or fragment thereof, against a human CD37. It will be recognized in the art that some amino acid sequences of the invention can be varied without significant effect of the structure or function of the protein. Thus, the invention further includes variations of the polypeptides which show substantial activity or which include regions of an antibody, or fragment thereof, against CD37 protein. Such mutants include deletions, insertions, inversions, repeats, and type substitutions.

The polypeptides and analogs can be further modified to contain additional chemical moieties not normally part of the protein. Those derivatized moieties can improve the solubility, the biological half life or absorption of the protein. The moieties can also reduce or eliminate any desirable side effects of the proteins and the like. An overview for those moieties can be found in REMINGTON'S PHARMACEUTICAL SCIENCES, 20th ed., Mack Publishing Co., Easton, Pa. (2000).

The isolated polypeptides described herein can be produced by any suitable method known in the art. Such methods range from direct protein synthetic methods to constructing a DNA sequence encoding isolated polypeptide sequences and expressing those sequences in a suitable transformed host. In some embodiments, a DNA sequence is constructed using recombinant technology by isolating or synthesizing a DNA sequence encoding a wild-type protein of interest. Optionally, the sequence can be mutagenized by site-specific mutagenesis to provide functional analogs thereof. See, e.g. Zoeller et al., Proc. Nat'l. Acad. Sci. USA 81:5662-5066 (1984) and U.S. Pat. No. 4,588,585.

In some embodiments a DNA sequence encoding a polypeptide of interest would be constructed by chemical synthesis using an oligonucleotide synthesizer. Such oligonucleotides can be designed based on the amino acid sequence of the desired polypeptide and selecting those codons that are favored in the host cell in which the recombinant polypeptide of interest will be produced. Standard methods can be applied to synthesize an isolated polynucleotide sequence encoding an isolated polypeptide of interest. For example, a complete amino acid sequence can be used to construct a back-translated gene. Further, a DNA oligomer containing a nucleotide sequence coding for the particular isolated polypeptide can be synthesized. For example, several small oligonucleotides coding for portions of the desired polypeptide can be synthesized and then ligated. The individual oligonucleotides typically contain 5' or 3' overhangs for complementary assembly.

Once assembled (by synthesis, site-directed mutagenesis or another method), the polynucleotide sequences encoding a particular isolated polypeptide of interest will be inserted into an expression vector and operatively linked to an expression control sequence appropriate for expression of the protein in a desired host. Proper assembly can be confirmed by nucleotide sequencing, restriction mapping, and expression of a biologically active polypeptide in a suitable host. As is well known in the art, in order to obtain high expression levels of a transfected gene in a host, the gene must be operatively linked to transcriptional and translational expression control sequences that are functional in the chosen expression host.

In certain embodiments, recombinant expression vectors are used to amplify and express DNA encoding antibodies, or fragments thereof, against human CD37. Recombinant expression vectors are replicable DNA constructs which have synthetic or cDNA-derived DNA fragments encoding a polypeptide chain of an anti-CD37 antibody, or fragment thereof, operatively linked to suitable transcriptional or translational regulatory elements derived from mammalian, microbial, viral or insect genes. A transcriptional unit generally comprises an assembly of (1) a genetic element or elements having a regulatory role in gene expression, for example, transcriptional promoters or enhancers, (2) a structural or coding sequence which is transcribed into mRNA and translated into protein, and (3) appropriate transcription and translation initiation and termination sequences, as described in detail below. Such regulatory elements can include an operator sequence to control transcription. The ability to replicate in a host, usually conferred by an origin of replication, and a selection gene to facilitate recognition of transformants can additionally be incorporated. DNA regions are operatively linked when they are functionally related to each other. For example, DNA for a signal peptide (secretory leader) is operatively linked to DNA for a polypeptide if it is expressed as a precursor which participates in the secretion of the polypeptide; a promoter is operatively linked to a coding sequence if it controls the transcription of the sequence; or a ribosome binding site is operatively linked to a coding sequence if it is positioned so as to permit translation. Structural elements intended for use in yeast expression systems include a leader sequence enabling extracellular secretion of translated protein by a host cell. Alternatively, where recombinant protein is expressed without a leader or transport sequence, it can include an N-terminal methionine residue. This residue can optionally be subsequently cleaved from the expressed recombinant protein to provide a final product.

The choice of expression control sequence and expression vector will depend upon the choice of host. A wide variety of expression host/vector combinations can be employed. Useful expression vectors for eukaryotic hosts, include, for example, vectors comprising expression control sequences from SV40, bovine papilloma virus, adenovirus and cytomegalovirus. Useful expression vectors for bacterial hosts include known bacterial plasmids, such as plasmids from *Esherichia coli*, including pCR 1, pBR322, pMB9 and their derivatives, wider host range plasmids, such as M13 and filamentous single-stranded DNA phages.

Suitable host cells for expression of a CD37-binding polypeptide or antibody (or a CD37 protein to use as an antigen) include prokaryotes, yeast, insect or higher eukaryotic cells under the control of appropriate promoters. Prokaryotes include gram negative or gram positive organisms, for example *E. coli* or bacilli. Higher eukaryotic cells include established cell lines of mammalian origin as described below. Cell-free translation systems could also be employed. Appropriate cloning and expression vectors for use with bacterial, fungal, yeast, and mammalian cellular hosts are described by Pouwels et al. (Cloning Vectors: A Laboratory Manual, Elsevier, N.Y., 1985), the relevant disclosure of which is hereby incorporated by reference. Additional information regarding methods of protein production, including antibody production, can be found, e.g., in U.S. Patent Publication No. 2008/0187954, U.S. Pat. Nos. 6,413,746 and 6,660,501, and International Patent Publication No. WO 04009823, each of which is hereby incorporated by reference herein in its entirety.

Various mammalian or insect cell culture systems are also advantageously employed to express recombinant protein. Expression of recombinant proteins in mammalian cells can be performed because such proteins are generally correctly folded, appropriately modified and completely functional. Examples of suitable mammalian host cell lines include the COS-7 lines of monkey kidney cells, described by Gluzman (Cell 23:175, 1981), and other cell lines capable of expressing an appropriate vector including, for example, L cells, C127, 3T3, Chinese hamster ovary (CHO), HeLa and BHK cell lines. Mammalian expression vectors can comprise nontranscribed elements such as an origin of replication, a suitable promoter and enhancer linked to the gene to be expressed, and other 5' or 3' flanking nontranscribed sequences, and 5' or 3' nontranslated sequences, such as necessary ribosome binding sites, a polyadenylation site, splice donor and acceptor sites, and transcriptional termination sequences. Baculovirus systems for production of heterologous proteins in insect cells are reviewed by Luckow and Summers, Bio/Technology 6:47 (1988).

The proteins produced by a transformed host can be purified according to any suitable method. Such standard methods include chromatography (e.g., ion exchange, affinity and sizing column chromatography), centrifugation, differential solubility, or by any other standard technique for protein purification. Affinity tags such as hexahistidine, maltose binding domain, influenza coat sequence and glutathione-S-transferase can be attached to the protein to allow easy purification by passage over an appropriate affinity column. Isolated proteins can also be physically characterized using such techniques as proteolysis, nuclear magnetic resonance and x-ray crystallography.

For example, supernatants from systems which secrete recombinant protein into culture media can be first concentrated using a commercially available protein concentration filter, for example, an Amicon or Millipore Pellicon ultrafiltration unit. Following the concentration step, the concentrate can be applied to a suitable purification matrix. Alternatively, an anion exchange resin can be employed, for example, a matrix or substrate having pendant diethylaminoethyl (DEAE) groups. The matrices can be acrylamide, agarose, dextran, cellulose or other types commonly employed in protein purification. Alternatively, a cation exchange step can be employed. Suitable cation exchangers include various insoluble matrices comprising sulfopropyl or carboxymethyl groups. Finally, one or more reversed-phase high performance liquid chromatography (RP-HPLC) steps employing hydrophobic RP-HPLC media, e.g., silica gel having pendant methyl or other aliphatic groups, can be employed to further purify a CD37-binding agent. Some or all of the foregoing purification steps, in various combinations, can also be employed to provide a homogeneous recombinant protein.

Recombinant protein produced in bacterial culture can be isolated, for example, by initial extraction from cell pellets, followed by one or more concentration, salting-out, aqueous ion exchange or size exclusion chromatography steps. High performance liquid chromatography (HPLC) can be employed for final purification steps. Microbial cells employed in expression of a recombinant protein can be disrupted by any convenient method, including freeze-thaw cycling, sonication, mechanical disruption, or use of cell lysing agents.

Methods known in the art for purifying antibodies and other proteins also include, for example, those described in U.S. Patent Publication No. 2008/0312425, 2008/0177048, and 2009/0187005, each of which is hereby incorporated by reference herein in its entirety.

In certain embodiments, the CD37-binding agent is a polypeptide that is not an antibody. A variety of methods for identifying and producing non-antibody polypeptides that bind with high affinity to a protein target are known in the art. See, e.g., Skerra, Curr. Opin. Biotechnol., 18:295-304 (2007), Hosse et al., Protein Science, 15:14-27 (2006), Gill et al., Curr. Opin. Biotechnol., 17:653-658 (2006), Nygren, FEBS J., 275:2668-76 (2008), and Skerra, FEBS J., 275:2677-83 (2008), each of which is incorporated by reference herein in its entirety. In certain embodiments, phage display technology has been used to identify/produce the CD37-binding polypeptide. In certain embodiments, the polypeptide comprises a protein scaffold of a type selected from the group consisting of protein A, a lipocalin, a fibronectin domain, an ankyrin consensus repeat domain, and thioredoxin.

In some embodiments, the agent is a non-protein molecule. In certain embodiments, the agent is a small molecule. Combinatorial chemistry libraries and techniques useful in the identification of non-protein CD37-binding agents are known to those skilled in the art. See, e.g., Kennedy et al., J. Comb. Chem, 10:345-354 (2008), Dolle et al, J. Comb. Chem., 9:855-902 (2007), and Bhattacharyya, Curr. Med. Chem., 8:1383-404 (2001), each of which is incorporated by reference herein in its entirety. In certain further embodiments, the agent is a carbohydrate, a glycosaminoglycan, a glycoprotein, or a proteoglycan.

In certain embodiments, the agent is a nucleic acid aptamer. Aptamers are polynucleotide molecules that have been selected (e.g., from random or mutagenized pools) on the basis of their ability to bind to another molecule. In some embodiments, the aptamer comprises a DNA polynucleotide. In certain alternative embodiments, the aptamer comprises an RNA polynucleotide. In certain embodiments, the aptamer comprises one or more modified nucleic acid residues. Methods of generating and screening nucleic acid aptamers for binding to proteins are well known in the art. See, e.g., U.S. Pat. No. 5,270,163, U.S. Pat. No. 5,683,867, U.S. Pat. No. 5,763,595, U.S. Pat. No. 6,344,321, U.S. Pat. No. 7,368,236, U.S. Pat. No. 5,582,981, U.S. Pat. No. 5,756,291, U.S. Pat. No. 5,840,867, U.S. Pat. No. 7,312,325, U.S. Pat. No. 7,329,742, International Patent Publication No. WO 02/077262, International Patent Publication No. WO 03/070984, U.S. Patent Application Publication No. 2005/0239134, U.S. Patent Application Publication No. 2005/0124565, and U.S. Patent Application Publication No. 2008/0227735, each of which is incorporated by reference herein in its entirety.

III. Immunoconjugates

The present invention is also directed to conjugates (also referred to herein as immunoconjugates), comprising the anti-CD37 antibodies, antibody fragments, and their functional equivalents as disclosed herein, linked or conjugated to a drug or prodrug. Suitable drugs or prodrugs are known in the art. The drugs or prodrugs can be cytotoxic agents. The cytotoxic agent used in the cytotoxic conjugate of the present invention can be any compound that results in the death of a cell, or induces cell death, or in some manner decreases cell viability, and includes, for example, maytansinoids and maytansinoid analogs. Other suitable cytotoxic agents are for example benzodiazepines, taxoids, CC-1065 and CC-1065 analogs, duocarmycins and duocarmycin analogs, enediynes, such as calicheamicins, dolastatin and dolastatin analogs including auristatins, tomaymycin derivatives, leptomycin derivatives, methotrexate, cisplatin, carboplatin, daunorubicin, doxorubicin, vincristine, vinblastine, melphalan, mitomycin C, chlorambucil and morpholino doxorubicin.

Such conjugates can be prepared by using a linking group in order to link a drug or prodrug to the antibody or functional equivalent. Suitable linking groups are well known in the art and include, for example, disulfide groups, thioether groups, acid labile groups, photolabile groups, peptidase labile groups and esterase labile groups.

The drug or prodrug can, for example, be linked to the anti-CD37 antibody or fragment thereof through a disulfide bond. The linker molecule or crosslinking agent comprises a reactive chemical group that can react with the anti-CD37 antibody or fragment thereof. The reactive chemical groups for reaction with the cell-binding agent can be N-succinimidyl esters and N-sulfosuccinimidyl esters. Additionally the linker molecule comprises a reactive chemical group, which can be a dithiopyridyl group that can react with the drug to form a disulfide bond. Linker molecules include, for example, N-succinimidyl 3-(2-pyridyldithio) propionate (SPDP) (see, e.g., Carlsson et al., *Biochem. J.,* 173: 723-737 (1978)), N-succinimidyl 4-(2-pyridyldithio)butanoate (SPDB) (see, e.g., U.S. Pat. No. 4,563,304), N-succinimidyl 4-(2-pyridyldithio)-2-sulfobutanoate (sulfo-SPDB) (see US Publication No. 20090274713), N-succinimidyl 4-(2-pyridyldithio) pentanoate (SPP) (see, e.g., CAS Registry number 341498-08-6), 2-iminothiolane, or acetylsuccinic anhydride. For example, the antibody or cell binding agent can be modified with crosslinking reagents and the antibody or cell binding agent containing free or protected thiol groups thus derived is then reacted with a disulfide- or thiol-containing maytansinoid to produce conjugates. The conjugates can be purified by chromatography, including but not limited to HPLC, size-exclusion, adsorption, ion exchange and affinity capture, dialysis or tangential flow filtration.

In another aspect of the present invention, the anti-CD37 antibody is linked to cytotoxic drugs via disulfide bonds and a polyethylene glycol spacer in enhancing the potency, solubility or the efficacy of the immunoconjugate. Such cleavable hydrophilic linkers are described in WO2009/0134976. The additional benefit of this linker design is the desired high monomer ratio and the minimal aggregation of the antibody-drug conjugate. Specifically contemplated in this aspect are conjugates of cell-binding agents and drugs linked via disulfide group (—S—S—) bearing polyethylene glycol spacers ($(CH_2CH_2O)_{n=1-14}$) with a narrow range of drug load of 2-8 are described that show relatively high potent biological activity toward cancer cells and have the desired biochemical properties of high conjugation yield and high monomer ratio with minimal protein aggregation.

Specifically contemplated in this aspect is an anti-CD37 antibody drug conjugate of formula (I) or a conjugate of formula (I'):

$$CB—[X_1—(—CH_2—CH_2O—)_n—Y\text{-}D]_m \quad (I)$$

$$[D\text{-}Y—(—CH_2—CH_2O—)_n—X_1]_m—CB \quad (I')$$

wherein:

CB represents an anti-CD37 antibody or fragment;

D represents a drug;

X represents an aliphatic, an aromatic or a heterocyclic unit attached to the cell-binding agent via a thioether bond, an amide bond, a carbamate bond, or an ether bond;

Y represents an aliphatic, an aromatic or a heterocyclic unit attached to the drug via a disulfide bond;

1 is 0 or 1;

m is an integer from 2 to 8; and n is an integer from 1 to 24.

In some embodiments, m is an integer from 2 to 6.

In some embodiments, m is an integer from 3 to 5.

In some embodiments, n is an integer form 2 to 8. Alternatively, as disclosed in, for example, U.S. Pat. Nos. 6,441,163 and 7,368,565, the drug can be first modified to introduce a reactive ester suitable to react with a cell-binding agent. Reaction of these drugs containing an activated linker moiety with a cell-binding agent provides another method of producing a cell-binding agent drug conjugate. Maytansinoids can also be linked to anti-CD37 antibody or fragment using PEG linking groups, as set forth for example in U.S. Pat. No. 6,716,821. These PEG non-cleavable linking groups are soluble both in water and in non-aqueous solvents, and can be used to join one or more cytotoxic agents to a cell binding agent. Exemplary PEG linking groups include heterobifunctional PEG linkers that react with cytotoxic agents and cell binding agents at opposite ends of the linkers through a functional sulfhydryl or disulfide group at one end, and an active ester at the other end. As a general example of the synthesis of a cytotoxic conjugate using a PEG linking group, reference is again made to U.S. Pat. No. 6,716,821 which is incorporated entirely by reference herein. Synthesis begins with the reaction of one or more cytotoxic agents bearing a reactive PEG moiety with a cell-binding agent, resulting in displacement of the terminal active ester of each reactive PEG moiety by an amino acid residue of the cell binding agent, to yield a cytotoxic conjugate comprising one or more cytotoxic agents covalently bonded to a cell binding agent through a PEG linking group. Alternatively, the cell binding can be modified with the bifunctional PEG crosslinker to introduce a reactive disulfide moiety (such as a pyridyldisulfide), which can then be treated with a thiol-containing maytansinoid to provide a conjugate. In another method, the cell binding can be modified with the bifunctional PEG crosslinker to introduce a thiol moiety which can then can be treated with a reactive disulfide-containing maytansinoid (such as a pyridyldisulfide), to provide a conjugate.

Antibody-maytansinoid conjugates with non-cleavable links can also be prepared. Such crosslinkers are described in the art (see US Publication No. 20050169933) and include but are not limited to, N-succinimidyl 4-(maleimidomethyl) cyclohexanecarboxylate (SMCC). In some embodiments, the antibody is modified with crosslinking reagents such as succinimidyl 4-(N-maleimidomethyl)-cyclohexane-1-carboxylate (SMCC), sulfo-SMCC, maleimidobenzoyl-N-hydroxysuccinimide ester (MBS), sulfo-MBS or succinimidyl-iodoacetate, as described in the literature, to introduce 1-10 reactive groups (Yoshitake et al, Eur. J. Biochem., 101:395-399 (1979); Hashida et al, J. Applied Biochem., 56-63 (1984); and Liu et al, Biochem., 18:690-697 (1979)). The modified antibody is then reacted with the thiol-containing maytansinoid derivative to produce a conjugate. The conjugate can be purified by gel filtration through a Sephadex G25 column or by dialysis or tangential flow filtration. The modified antibodies are treated with the thiol-containing maytansinoid (1 to 2 molar equivalent/maleimido group) and antibody-maytansinoid conjugates are purified by gel filtration through a Sephadex G-25 column, chromatography on a ceramic hydroxyapatite column, dialysis or tangential flow filtration or a combination of methods thereof. Typically, an average of 1-10 maytansinoids per antibody are linked. One method is to modify antibodies with succinimidyl 4-(N-maleimidomethyl)-cyclohexane-1-carboxylate (SMCC) to introduce maleimido groups followed by reaction of the modified antibody with a thiol-containing maytansinoid to give a thioether-linked conjugate. Again conjugates with 1 to 10 drug molecules per antibody molecule result. Maytansinoid conjugates of antibodies, antibody fragments, and other proteins are made in the same way.

In another aspect of the invention, the CD37 antibody is linked to the drug via a non-cleavable bond through the intermediacy of a PEG spacer. Suitable crosslinking reagents comprising hydrophilic PEG chains that form linkers between a drug and the anti-CD37 antibody or fragment are also well known in the art, or are commercially available (for example from Quanta Biodesign, Powell, Ohio). Suitable PEG-containing crosslinkers can also be synthesized from commercially available PEGs themselves using standard synthetic chemistry techniques known to one skilled in the art. The drugs can be reacted with bifunctional PEG-containing cross linkers to give compounds of the following formula, $Z—X_1—(—CH_2—CH_2O—)_n—Y_p$-D, by methods described in detail in US Patent Publication 20090274713 and in WO2009/0134976, which can then react with the cell binding agent to provide a conjugate. Alternatively, the cell binding can be modified with the bifunctional PEG crosslinker to introduce a thiol-reactive group (such as a maleimide or haloacetamide) which can then be treated with a thiol-containing maytansinoid to provide a conjugate. In another method, the cell binding can be modified with the bifunctional PEG crosslinker to introduce a thiol moiety which can then be treated with a thiol-reactive maytansinoid (such as a maytansinoid bearing a maleimide or haloacetamide), to provide a conjugate.

Accordingly, another aspect of the present invention is an anti-CD37 antibody drug conjugate of formula (II) or of formula (II'):

$$CB—[X_1—(—CH_2—CH_2—O—)_n—Y_p\text{-}D]_m \quad (II)$$

$$[D\text{-}Y_p—(—CH_2—CH_2—O—)_n—X_1]_m—CB \quad (II')$$

wherein, CB represents an anti-CD37 antibody or fragment;

D represents a drug;

X represents an aliphatic, an aromatic or a heterocyclic unit bonded to the cell-binding agent via a thioether bond, an amide bond, a carbamate bond, or an ether bond;

Y represents an aliphatic, an aromatic, or a heterocyclic unit bonded to the drug via a covalent bond selected from the group consisting of a thioether bond, an amide bond, a carbamate bond, an ether bond, an amine bond, a carbon-carbon bond and a hydrazone bond;

1 is 0 or 1;

p is 0 or 1;

m is an integer from 2 to 15; and n is an integer from 1 to 2000.

In some embodiments, m is an integer from 2 to 8; and

In some embodiments, n is an integer from 1 to 24.

In some embodiments, m is an integer from 2 to 6.

In some embodiments, m is an integer from 3 to 5.

In some embodiments, n is an integer from 2 to 8. Examples of suitable PEG-containing linkers include linkers having an N-succinimidyl ester or N-sulfosuccinimidyl ester moiety for reaction with the anti-CD37 antibody or fragment thereof, as well as a maleimido- or haloacetyl-based moiety for reaction with the compound. A PEG spacer can be incorporated into any crosslinker known in the art by the methods described herein.

Many of the linkers disclosed herein are described in detail in U.S. Patent Publication Nos. 20050169933 and 20090274713, and in WO2009/0134976; the contents of which are entirely incorporated herein by reference.

The present invention includes aspects wherein about 2 to about 8 drug molecules ("drug load"), for example, maytansinoid, are linked to an anti-CD37 antibody or fragment thereof, the anti-tumor effect of the conjugate is much more efficacious as compared to a drug load of a lesser or higher number of drugs linked to the same cell binding agent. "Drug load", as used herein, refers to the number of drug molecules (e.g., a maytansinoid) that can be attached to a cell binding agent (e.g., an anti-CD37 antibody or fragment thereof). In one aspect, the number of drug molecules that can be attached to a cell binding agent can average from about 2 to about 8 (e.g., 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1). $N^{2'}$-deacetyl-$N^{2'}$-(3-mercapto-1-oxopropyl)-maytansine (DM1) and $N^{2'}$-deacetyl-$N^{2'}$-(4-mercapto-4-methyl-1-oxopentyl) maytansine (DM4) can be used.

Thus, in one aspect, an immunocongugate comprises 1 maytansinoid per antibody. In another aspect, an immunocongugate comprises 2 maytansinoids per antibody. In another aspect, an immunocongugate comprises 3 maytansinoids per antibody. In another aspect, an immunocongugate comprises 4 maytansinoids per antibody. In another aspect, an immunocongugate comprises 5 maytansinoids per antibody. In another aspect, an immunocongugate comprises 6 maytansinoids per antibody. In another aspect, an immunocongugate comprises 7 maytansinoids per antibody. In another aspect, an immunocongugate comprises 8 maytansinoids per antibody.

In one aspect, an immunoconjugate comprises about 1 to about 8 maytansinoids per antibody. In another aspect, an immunoconjugate comprises about 2 to about 7 maytansinoids per antibody. In another aspect, an immunoconjugate comprises about 2 to about 6 maytansinoids per antibody. In another aspect, an immunoconjugate comprises about 2 to about 5 maytansinoids per antibody. In another aspect, an immunoconjugate comprises about 3 to about 5 maytansinoids per antibody. In another aspect, an immunoconjugate comprises about 3 to about 4 maytansinoids per antibody.

In one aspect, a composition comprising immunoconjugates has an average of about 2 to about 8 (e.g., 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1) drug molecules (e.g., maytansinoids) attached per antibody. In one aspect, a composition comprising immunoconjugates has an average of about 1 to about 8 drug molecules (e.g., maytansinoids) per antibody. In one aspect, a composition comprising immunoconjugates has an average of about 2 to about 7 drug molecules (e.g., maytansinoids) per antibody. In one aspect, a composition comprising immunoconjugates has an average of about 2 to about 6 drug molecules (e.g., maytansinoids) per antibody. In one aspect, a composition comprising immunoconjugates has an average of about 2 to about 5 drug molecules (e.g., maytansinoids) per antibody. In one aspect, a composition comprising immunoconjugates has an average of about 3 to about 5 drug molecules (e.g., maytansinoids) per antibody. In one aspect, a composition comprising immunoconjugates has an average of about 3 to about 4 drug molecules (e.g., maytansinoids) per antibody.

In one aspect, a composition comprising immunoconjugates has an average of about 2±0.5, about 3±0.5, about 4±0.5, about 5±0.5, about 6±0.5, about 7±0.5, or about 8±0.5 drug molecules (e.g., maytansinoids) attached per antibody. In one aspect, a composition comprising immunoconjugates has an average of about 3.5±0.5 drug molecules (e.g., maytansinoids) per antibody.

The anti-CD37 antibody or fragment thereof can be modified by reacting a bifunctional crosslinking reagent with the anti-CD37 antibody or fragment thereof, thereby resulting in the covalent attachment of a linker molecule to the anti-CD37 antibody or fragment thereof. As used herein, a "bifunctional crosslinking reagent" is any chemical moiety that covalently links a cell-binding agent to a drug, such as the drugs described herein. In another method, a portion of the linking moiety is provided by the drug. In this respect, the drug comprises a linking moiety that is part of a larger linker molecule that is used to join the cell-binding agent to the drug. For example, to form the maytansinoid DM1, the side chain at the C-3 hydroxyl group of maytansine is modified to have a free sulfhydryl group (SH). This thiolated form of maytansine can react with a modified cell-binding agent to form a conjugate. Therefore, the final linker is assembled from two components, one of which is provided by the crosslinking reagent, while the other is provided by the side chain from DM1.

The drug molecules can also be linked to the antibody molecules through an intermediary carrier molecule such as serum albumin.

As used herein, the expression "linked to a cell-binding agent" or "linked to an anti-CD37 antibody or fragment" refers to the conjugate molecule comprising at least one drug derivative bound to a cell-binding agent anti-CD37 antibody or fragment via a suitable linking group, or a precursor thereof. One linking group is SMCC.

In certain embodiments, cytotoxic agents useful in the present invention are maytansinoids and maytansinoid analogs. Examples of suitable maytansinoids include esters of maytansinol and maytansinol analogs. Included are any drugs that inhibit microtubule formation and that are highly toxic to mammalian cells, as are maytansinol and maytansinol analogs.

Examples of suitable maytansinol esters include those having a modified aromatic ring and those having modifications at other positions. Such suitable maytansinoids are disclosed in U.S. Pat. Nos. 4,424,219; 4,256,746; 4,294,757; 4,307,016; 4,313,946; 4,315,929; 4,331,598; 4,361,650; 4,362,663; 4,364,866; 4,450,254; 4,322,348; 4,371,533; 5,208,020; 5,416,064; 5,475,092; 5,585,499; 5,846,545; 6,333,410; 7,276,497 and 7,473,796.

In a certain embodiment, the immunoconjugates of the invention utilize the thiol-containing maytansinoid (DM1), formally termed $N^{2'}$-deacetyl-$N^{2'}$-(3-mercapto-1-oxopropyl)-maytansine, as the cytotoxic agent. DM1 is represented by the following structural formula (III):

(III)

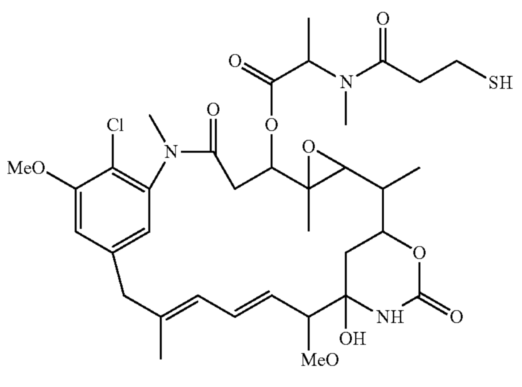

In another embodiment, the conjugates of the present invention utilize the thiol-containing maytansinoid $N^{2'}$-deacetyl-$N^{2'}$ (4-methyl-4-mercapto-1-oxopentyl)-maytansine (e.g., DM4) as the cytotoxic agent. DM4 is represented by the following structural formula (IV):

(IV)

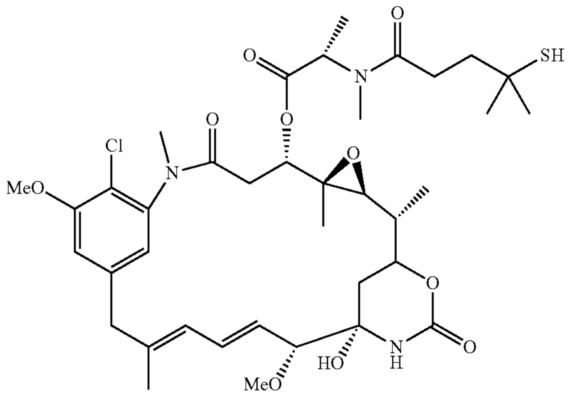

Another maytansinoid comprising a side chain that contains a sterically hindered thiol bond is $N^{2'}$-deacetyl-$N^{2'}$(4-mercapto-1-oxopentyl)-maytansine (termed DM3), represented by the following structural formula (V):

(V)

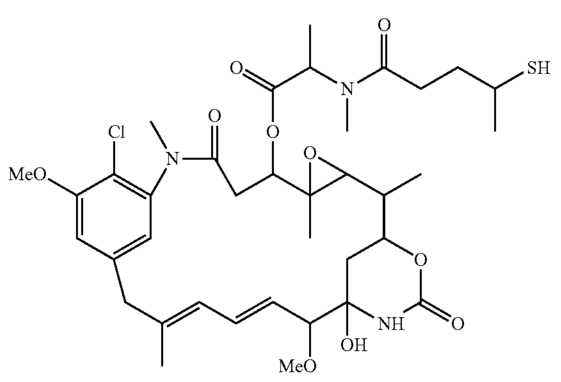

Each of the maytansinoids taught in U.S. Pat. Nos. 5,208,020 and 7,276,497, can also be used in the conjugate of the present invention. In this regard, the entire disclosure of U.S. Pat. No. 5,208,020 and U.S. Pat. No. 7,276,697 is incorporated herein by reference.

Many positions on maytansinoids can serve as the position to chemically link the linking moiety. For example, the C-3 position having a hydroxyl group, the C-14 position modified with hydroxymethyl, the C-15 position modified with hydroxy and the C-20 position having a hydroxy group are all expected to be useful. In some embodiments, the C-3 position serves as the position to chemically link the linking moiety, and in some particular embodiments, the C-3 position of maytansinol serves as the position to chemically link the linking moiety.

Structural representations of some conjugates are shown below:

(VI)

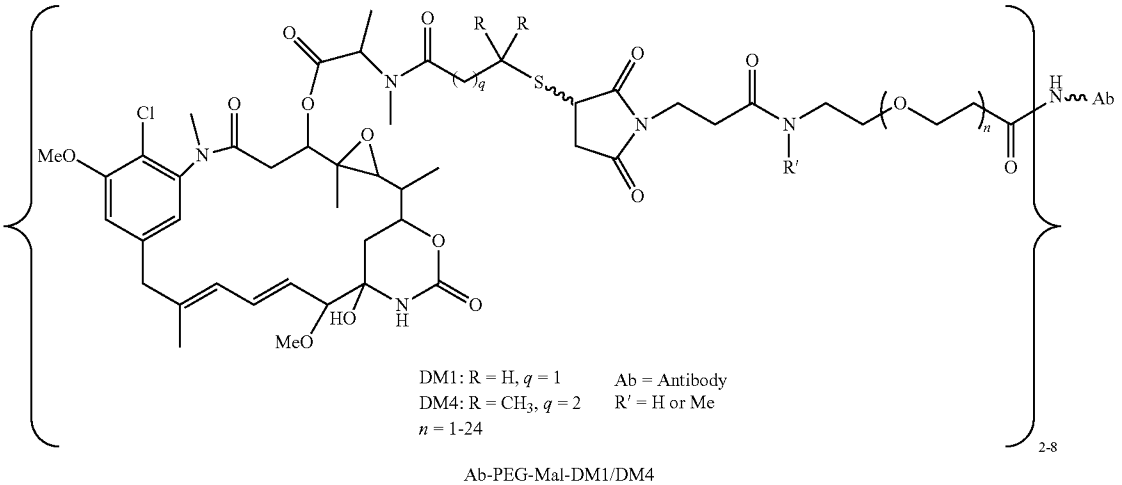

Ab-PEG-Mal-DM1/DM4

-continued
(VII)
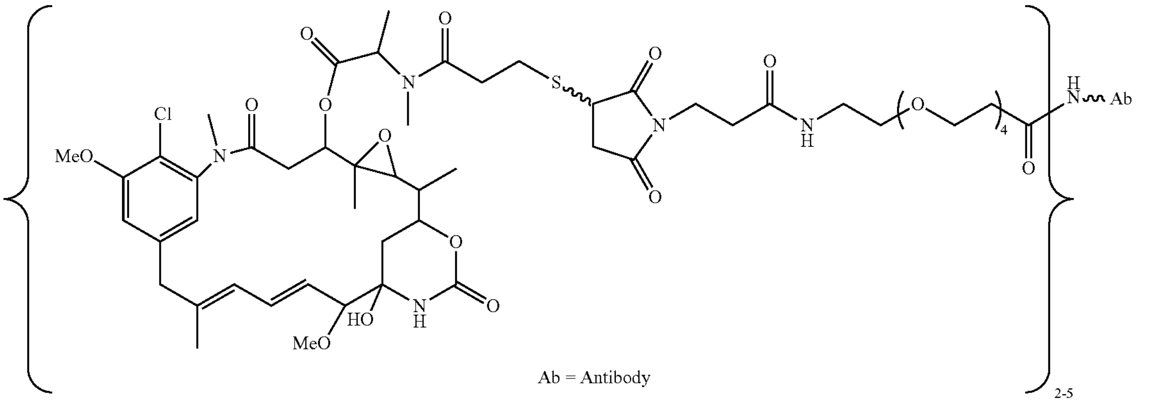
Ab = Antibody
Ab-PEG4-Mal-DM1
(VIII)
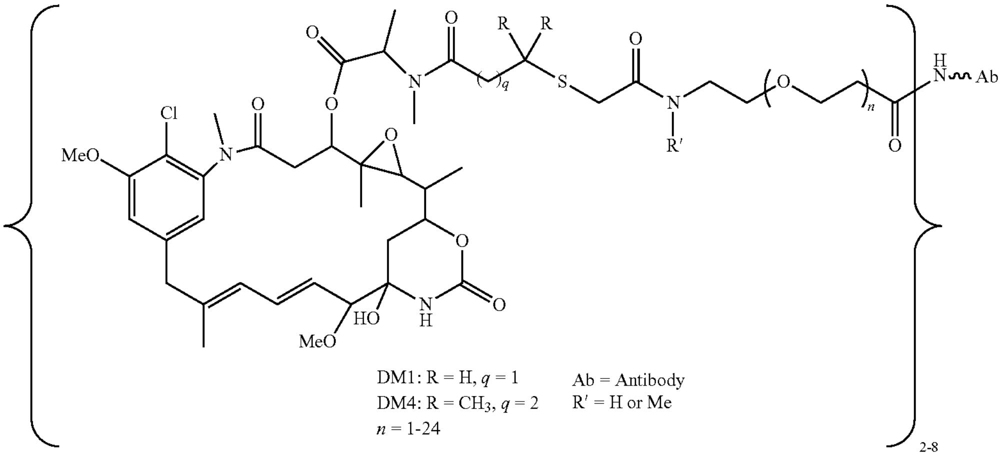
DM1: R = H, *q* = 1
DM4: R = $CH_3$, *q* = 2
*n* = 1-24
Ab = Antibody
R′ = H or Me
Ab-PEG-SIA-DM1/DM4
(IX)
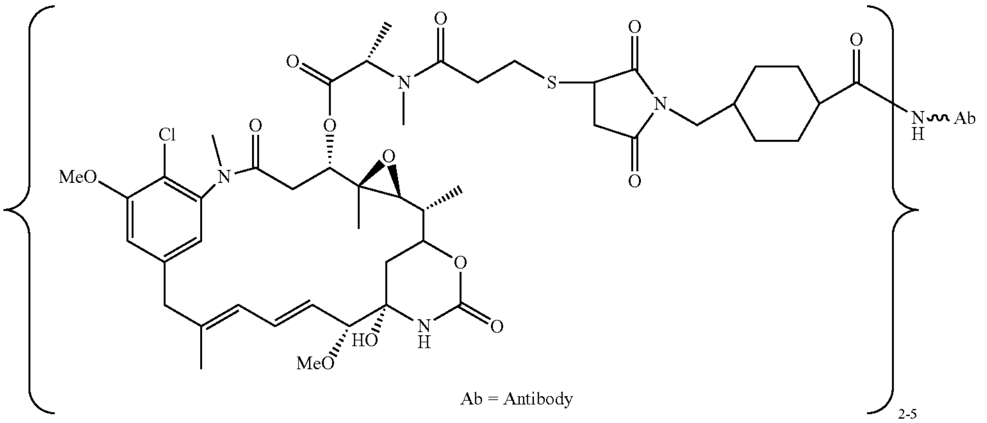
Ab = Antibody
Ab-SMCC-DM1

-continued
(X)
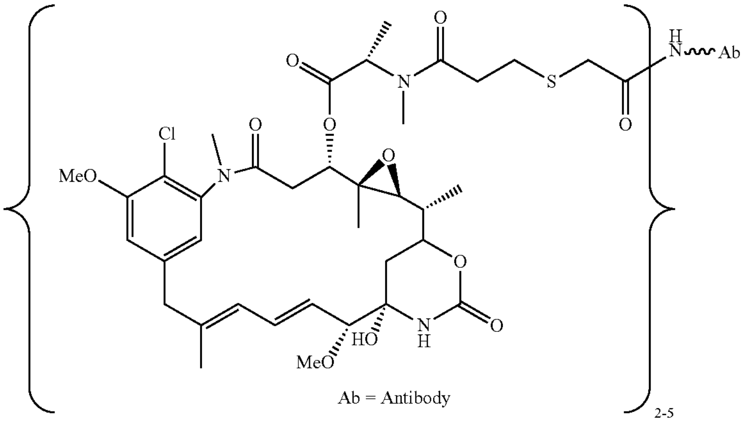
Ab = Antibody
Ab-SIA-DM1
(XI)
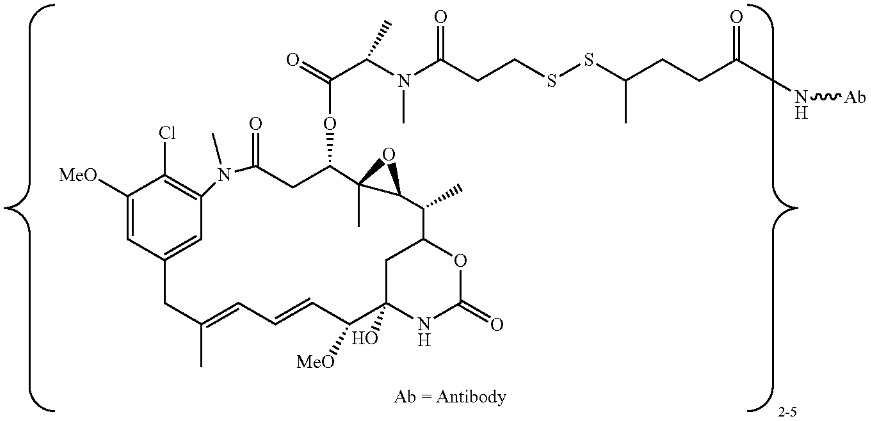
Ab = Antibody
Ab-SPP-DM1
(XII)
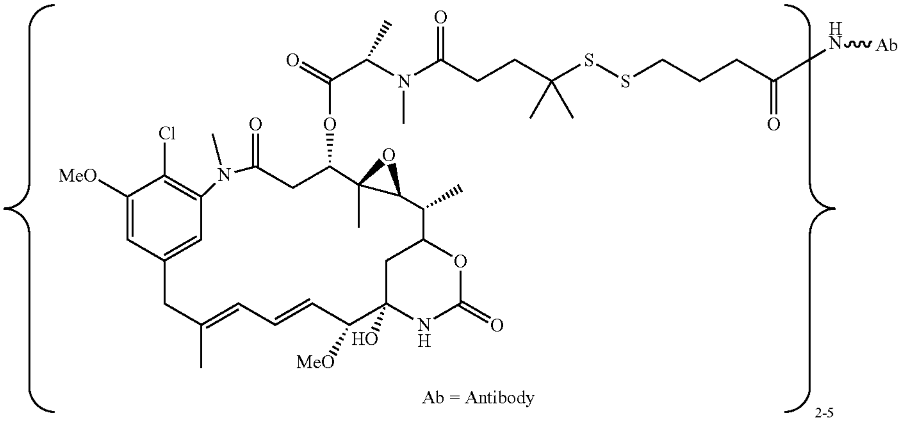
Ab = Antibody
Ab-SPDB-DM4

-continued (XIII)

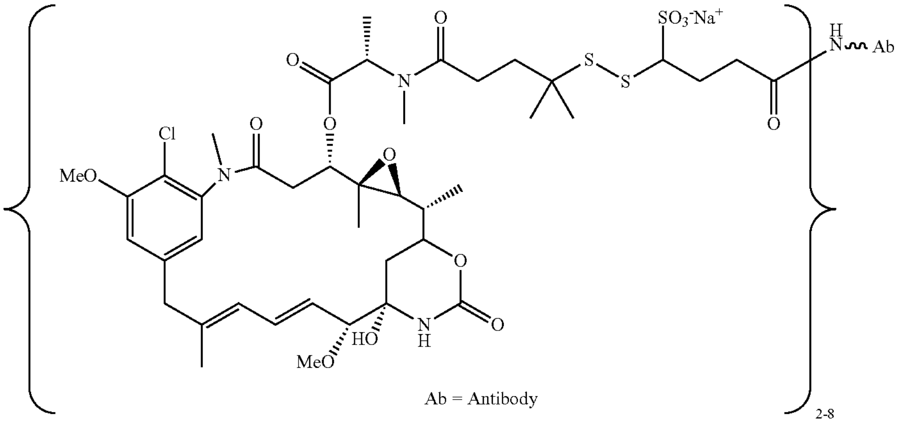

Ab = Antibody

Ab-sulfo-SPDB-DM4

Several descriptions for producing such antibody-maytansinoid conjugates are provided in U.S. Pat. Nos. 6,333,410, 6,441,163, 6,716,821, and 7,368,565, each of which is incorporated herein in its entirety.

In general, a solution of an antibody in aqueous buffer can be incubated with a molar excess of maytansinoids having a disulfide moiety that bears a reactive group. The reaction mixture can be quenched by addition of excess amine (such as ethanolamine, taurine, etc.). The maytansinoid-antibody conjugate can then be purified by gel filtration.

The number of maytansinoid molecules bound per antibody molecule can be determined by measuring spectrophotometrically the ratio of the absorbance at 252 nm and 280 nm. The average number of maytansinoid molecules/antibody can be, for example, about 1-10, 2-5, 3-4, or about 3.5. In one aspect, the average number of maytansinoid molecules/antibody is about 3.5±0.5.

Anthracycline compounds, as well as derivatives, intermediates and modified versions thereof, can also be used to prepare anti-CD37 immunoconjugates. For example, doxorubicin, doxorubicin derivatives, doxorubicin intermediates, and modified doxorubicins can be used in anti-CD37 conjugates. Exemplary compounds are described in WO 2010/009124, which is herein incorporated by reference in its entirety. Such compounds include, for example, compounds of the following formula:

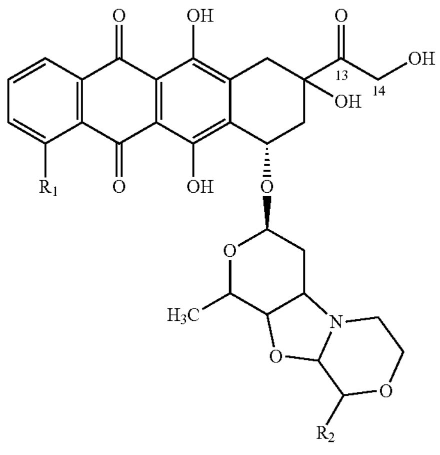

wherein $R_1$ is a hydrogen atom, hydroxy or methoxy group and $R_2$ is a $C_1$-$C_5$ alkoxy group, or a pharmaceutically acceptable salt thereof.

Conjugates of antibodies with maytansinoid or other drugs can be evaluated for their ability to suppress proliferation of various unwanted cell lines in vitro. For example, cell lines such as the human lymphoma cell line Daudi and the human lymphoma cell line Ramos, can easily be used for the assessment of cytotoxicity of these compounds. Cells to be evaluated can be exposed to the compounds for 4 to 5 days and the surviving fractions of cells measured in direct assays by known methods. $IC_{50}$ values can then be calculated from the results of the assays.

The immunoconjugates can, according to some embodiments described herein, be internalized into cells. The immunocongugate, therefore, can exert a therapeutic effect when it is taken up by, or internalized, by a CD37-expressing cell. In some particular embodiments, the immunoconjugate comprises an antibody, antibody fragment, or polypeptide, linked to a cytotoxic agent by a cleavable linker, and the cytotoxic agent is cleaved from the antibody, antibody fragment, or polypeptide, wherein it is internalized by a CD37-expressing cell.

In some embodiments, the immunoconjugates are capable of reducing tumor volume. For example, in some embodiments, treatment with an immunoconjugate results in a % T/C value that is less than about 50%, less than about 45%, less than about 40%, less than about 35%, less than about 30%, less than about 25%, less than about 20%, less than about 15%, less than about 10%, or less than about 5%. In some particular embodiments, the immunoconjugates can reduce tumor size in a BJAB xenograft model and/or a SU-DHL-4 xenograft model.

In another aspect of the invention siRNA molecules can be linked to the antibodies of the present invention instead of a drug. siRNAs can be linked to the antibodies of the present invention by methods commonly used for the modification of oligonucleotides (see, for example, US Patent Publications 20050107325 and 20070213292). Thus the siRNA in its 3' or 5'-phosphoromidite form can be reacted with one end of the crosslinker bearing a hydroxyl functionality to give an ester bond between the siRNA and the crosslinker. Similarly reaction of the siRNA phosphoramidite with a crosslinker bearing a terminal amino group results in linkage of the crosslinker to the siRNA through an amine. Alternatively, the siRNA can be derivatized by standard chemical methods to introduce a thiol group. This thiol-containing siRNA can be reacted with an antibody, that has been modified to introduce an active disulfide or maleimide moiety, to produce a cleavable or non cleavable conjugate. Between 1-20 siRNA molecules can be linked to an antibody by this method.

III. Polynucleotides

In certain embodiments, the invention encompasses polynucleotides comprising polynucleotides that encode a polypeptide that specifically binds CD37 or a fragment of such a polypeptide. For example, the invention provides a polynucleotide comprising a nucleic acid sequence that encodes an antibody to a human CD37 or encodes a fragment of such an antibody. The polynucleotides of the invention can be in the form of RNA or in the form of DNA. DNA includes cDNA, genomic DNA, and synthetic DNA; and can be double-stranded or single-stranded, and if single stranded can be the coding strand or non-coding (anti-sense) strand.

In certain embodiments, the polynucleotides are isolated. In certain embodiments, the polynucleotides are substantially pure.

The invention provides a polynucleotide comprising a polynucleotide encoding a polypeptide comprising a sequence selected from the group consisting of SEQ ID NOs: 4-120.

The invention further provides a polynucleotide comprising a sequence selected from those shown in Tables 7-10 below.

TABLE 7

Variable heavy chain polynucleotide sequences

| Antibody | VH Polynucleotide Sequence (SEQ ID NO) |
|---|---|
| muCD37-3 | caggtgcaggtgaaggagtcaggacctggcctggtggcgccctcacagagcctgtccattacatgcactg<br>tctcagggttctcattaaccacctctggtgtaagctgggttcgccagcctccaggaaagggtctggagtg<br>gctgggagtaatatggggtgacgggagcacaaactatcattcagctctcaaatccagactgagcatcaag<br>aaggatcactccaagagccaagttttcttaaaactgaacagtctgcaaactgatgacacagccacgtact<br>actgtgccaaaggaggctactcgttggctcactggggccaagggactctggtcacagtctctgca<br>(SEQ ID NO: 121) |
| chCD37-3 | aagcttgccaccatggctgtcctggcactgctcctctgcctggtgacatacccaagctgtgtcctatcacaggtgcaggt<br>gaaggagtcaggacctggcctggtggcgccctcacagagcctgtccattacatgcactgtctcagggttctcattaacca<br>cctctggtgtaagctgggttcgccagcctccaggaaagggtctggagtggctgggagtaatatggggtgacgggagcac<br>aaactatcattcagctctcaaatccagactgagcatcaagaaggatcactccaagagccaagttttcttaaaactgaaca<br>gtctgcaaactgatgacacagccacgtactactgtgccaaaggaggctactcgttggctcactggggccaagggactctg<br>gtcacagtctctgcagcctctacgaagggccc<br>(SEQ ID NO: 122) |
| huCD37-3v1.0 | aagcttgccaccatgggttggagctgcattattctgtttctggtggccaccgccaccggtgtgcactcacaagtccaagt<br>ccaagaatctggtccaggtctggtggccccttcccaaactctgagcatcacctgtaccgtttctggttttagccttacca<br>cctctggtgtgagttgggtacgccaaccacccggtaagggtctcgaatggctgggtgtaatctggggtgatggttccaca<br>aattaccatccttccctcaagtcccgccttagcatcaaaaaggatcacagcaaaagtcaagttttcctgaaactgaatag<br>tctgacagcagccgatacagccacctactattgcgccaagggtggttatagtcttgcacactggggtcaaggtaccctcg<br>ttaccgtctcctcagctagtaccaagggccc<br>(SEQ ID NO: 123) |
| huCD37-3v1.1 | aagcttgccaccatgggctggagctgtatcattctgtttctggtggcgacagctactggggtccactcccaagtgcaggt<br>acaagagtccgggcctggattggtcgcaccaagccagaccctctctatcacttgtaccgttagcgggttctctctgacaa<br>ccagtggagtgagttgggtgaggcagccaccaggaaagggactggagtggctgggggtgatttggggcgacggcagca<br>caaactatcattccagtcttaaatctcggttgtccattaaaaagaccatagtaaatctcaagttttcctgaaactcaat<br>agcctgacagccgcagacactgctacgtattactgcgccaaaggaggatacagtctggctcactggggacaggggaccct<br>ggtgaccgtgtcatccgcatcaacaaagggccc<br>(SEQ ID NO: 124) |
| muCD37-12 | cagatccagttggtgcagtctggacctgagctgaagaagcctggagagacagtcaagatctcctgcaagg<br>cttctgggtataccttcacaaagtatggaatgaactgggtgaagcaggctcaaggaaagggtttaaagtg<br>gatgggctggataaacaccaacactggagagtcaagaaatgctgaagaattcaagggacggtttgccttc<br>tctttggaaacctctgccagcactgcctatttgcagatcaacaacctcaaatatgaggacacggctacat<br>atttctgtggaaggggcacggtagtagcggactggggccaaggcaccactctcacagtctcctca<br>(SEQ ID NO: 125) |
| chCD37-12 | aagcttgccaccatggggtggtcatgcataatcctctttctggtcgctactgctaccggtgtgcactcacagattcagct<br>ggttcaaagtggcccagagctgaaaaagccaggggaaacagtgaaaataagttgcaaggcatccggttacactttcacaa<br>agtacggcatgaactgggtcaagcaggcccagggcaaggggctcaaatggatgggttggatcaataccaacactggcg<br>agtctaggaatgctgaggagtttaagggccggtttgccttcagcctggagacaagtgccagcacagcttacctgcaaatc<br>aacaatctgaagtatgaggatacagcaacctatttctgcggccgcggcactgtcgttgcagactggggacaaggtacca<br>ccttgactgtatccagtgccagcactaagggccc<br>(SEQ ID NO: 126) |
| muCD37-38 | gatgtgcagcttcaggagtcaggacctgacctggtgaaaccttctcagtcactttcactcacctgcactg<br>tcactggctactccatcaccagtggttttggctggcactggatccggcagtttccaggaaacaagctgga<br>atggatggcctacatactctacagtggtggcactgactacaacccatctctcaaaagtcgaatctctatc<br>actcgagacacttccaagaaccagttcttcctgcggttgagttctgtgactactgaggacacagccacat<br>attactgtgcaagaggctactatggttacggggcctggtttgtttactggggccaagggactctggtcac<br>tgtctctgca<br>(SEQ ID NO: 127) |
| chCD37-38 | aagcttgccaccatgggctggagttgtatcattctgtttttggtggccaccgccactggagtccattcccaagtgcaact<br>ccaggaatctggccctgacctggttaagccatctcagagcctctccctgacctgcactgttacaggatactcaatcacat<br>caggctttggctggcactggatcagacaatttcccgggaacaagttggaatggatggcttacattctgtatagcggggt<br>accgattacaatccttccctcaagagccgaatctctatcaccagggatacaagcaagaaccaatttttctccgcctcag |

TABLE 7-continued

| Variable heavy chain polynucleotide sequences | |
|---|---|
| Antibody | VH Polynucleotide Sequence (SEQ ID NO) |
| | ctctgtgactaccgaagataccgctacttactattgtgccaggggctactatggatatggtgcatggttcgtctattggg<br>gccagggaaccctggtgactgtgagcgctgcctctaccaagggccc<br>(SEQ ID NO: 128) |
| huCD37-38 | aagcttgccaccatgggttggagctgcatcattcttttcctggtcgctactgcaactggagtccactcacaggtccagct<br>gcaagagtccggtcctgggcttgtgaaacccagccagtccctcagtctcacctgtactgtctctggctactctattacca<br>gtgggttcggctggcattggattaggcagtttcccggtaaggggctggagtggatggcatatatcctgtacagcggagga<br>accgattacaacccaagtctgaagagcaggatcagcattacccgggacacaagcaaaaaccagttttccttcggctgtc<br>tagtgttacagctgcagacaccgctacttactattgtgctcggggttactatggctatggggcttggtttgtgtattggg<br>gacaaggcactcttgtgaccgtgagcagcgcctcaacaaagggccc<br>(SEQ ID NO: 129) |
| muCD37-50 | gatgtgcagcttcaggagtcaggacctgacctgttgaaaccttctcagtcactttcactcacctgcactg<br>tcactggctactccatcaccagtggttttgcctggcactggatccggcagtttccaggaaacaaactgga<br>atggatgggctacatactctacagtggtagcactgtctacagcccatctctcaaaagtcgaatctctatc<br>actcgagacacatccaagaaccacttcttcctgcagttgaattctgtgactactgaggacacagccacat<br>attactgtgcaagagggtactatggttacggcgcctggtttgcttactggggccaagggactctggtcac<br>tgtctctgca<br>(SEQ ID NO: 130) |
| huCD37-50 | aagcttgccaccatggggtggtcctgcataatccttttcctggttgctactgctaccggagtccattcacaggtgcagct<br>gcaggagtccggccccggcctgctcaagccttctcagagtctgagtctgacttgtactgtttctggctacagcataacca<br>gcggtttcgcttggcactggatcagacagcatcccggcaacaaactggagtggatgggatacatactgtactcaggctca<br>actgtctattcccccctccctgaaatcccggatcagtattacccgtgacacttctaagaaccatttttttctgcagctgaa<br>cagcgttaccgcagctgacactgcaacctactactgtgcccggggatattatggatacggagcttggttcgcttactggg<br>gccaaggcaccctcgtaactgtgagtgctgcttccaccaagggccc<br>(SEQ ID NO: 195) |
| muCD37-51 | gatgtgcagcttcaggagtcaggacctgacctgttgaaaccttctcagtcactttcactcacctgcactg<br>tcactggctactccatctccagtggttttgcctggcactggatccggcagtttccaggaaacaaactgga<br>atggatgggctacatacactacagtggtagcactaactacagcccatctctcaaaagtcgaatctctatc<br>actcgagactcatccaagaaccagttcttcctgcagttgaattctgtgactactgaggacacagccacat<br>attactgtgcaagaggatactatggtttcggcgcctggtttgtttactggggccaagggactctggtcac<br>tgtctctgca<br>(SEQ ID NO: 131) |
| huCD37-51 | Aagcttgccaccatgggttggtcttgcatcatcctgttcctggtggccactgccactggcgtgcattcagaagttcagtt<br>ggtggagtccggcccagaagtgctgaaacccggcgaatcactgtccctgacttgtaccgtgtcaggttatagcatcagca<br>gcggctttgcttggcactggattcggcagtttccaggcaagggactggaatggatgggctacatccattacagtggctca<br>accaattacagccctagcctgcagggccgaatctctattaccagggatagttctattaaccagtttttcctgcagcttaa<br>ttccgtgactgcctctgacacagcaacttactattgcgcccgtggctactacgggttcggagcctggtttgtatactggg<br>gtcagggcaccctggtcactgtctcagccgcctctaccaagggccc<br>(SEQ ID NO: 196) |
| muCD37-56 | gatgtgcagcttcaggagtcaggacctgacctggtgaaaccttctcagtcactttcactcacctgcactg<br>tcactggctactccatcaccagtggttttgcctggcactggatccggcagtttccaggaaacaaactgga<br>atggatgggctacatacactacagtggtggcactaactacaacccatctctcaaaagtcgagtctctatc<br>actcgagacacatccaagaaccagttcttcctgcagttgaattctgtgactactgaggacacagccacat<br>attactgtgcaagaggctactatggtttcggggcctggtttgcttactggggccaagggactctggtccc<br>tgtctctgca<br>(SEQ ID NO: 132) |
| huCD37-56 | aagcttgccaccatggggtggagctgcattatcctgttcctcgtcgccaccgcaaccggcgtccactcccaggtgcagct<br>gcaagaaagcgggccaggattggtaaaaccttcccagtctctgagtcttacttgtaccgtatctggatacagtatcacat<br>ctggcttcgcctggcattggattcgccagtttcccggcaaggggcttgagtggatggggtatattcattattctggaggt<br>accaactacaacccttccctgaagagtcgagtctcaattaccagggacacttccaagaaccaattctttttgcagcttaa<br>ttcagtgaccgctgccgacaccgctacttactactgcgcccggggctactatgggtttggtgcctggttcgcctactggg<br>gccaggggaccctggtgcccgtgtctgctgcctccacaaagggccc<br>(SEQ ID NO: 133) |
| muCD37-57 | gatgtgcagcttcaggagtcaggacctgacctgttgaaaccttctcagtcactttcactcacctgcactg<br>tcactggctactccatcaccagtggttttgcctggcactggatccggcagtttccaggaaacaaactgga<br>atggatgggctacatactctacagtggtagcactgtctacagcccatctctcaaaagtcgaatctctatc<br>actcgagacacatccaagaaccagttcttcctgcagttgaattctgtgactactgaggacacagccacat<br>attactgtgcaagagggtactatggttacggcgcctggtttgcttactggggccaagggactctggtcac<br>tgtctctgca<br>(SEQ ID NO: 134) |
| huCD37-57 | aagcttgccaccatgggctggagctgcatcattctgtttctggtggccacagcaactggcgttcacagtcaagtccaact<br>gcaggagagcggccccggactcctgaaaccatctcagtcactcagtctgacatgtactgtgagcggctacagcattacct<br>caggcttcgcttggcattggatcaggcagttccccggaaaaggtctggagtggatggggtacattctgtacagcggcagt<br>acagtgtattcaccctccttgaaatctaggatatcaatcacacgtgatacaagcaaaaatcagttcttcctccagctgaa<br>ctccgtcaccgccgcagacacagcaacctattattgtgctcgcggatactacggatatggcgcatggttcgcctattggg<br>gccaggggacactcgtgaccgtttccgccgcctccacaaagggccc<br>(SEQ ID NO: 135) |

TABLE 8

Variable light chain polynucleotide sequences

| Antibody | VL Polynucleotide Sequence (SEQ ID NO) |
|---|---|
| muCD37-3 | gacatccagatgactcagtctccagcctccctttctgtatctgtgggagaaactgtcaccatcacatgtc<br>gagcaagtgagaatattcgcagtaatttagcatggtatcagcagaaacagggaaaatctcctcagctcct<br>ggtcaatgttgcaacaaacttagcagatggtgtgccatcaaggttcagtggcagtggatcaggcacacag<br>tattccctcaagatcaacagcctgcagtctgaagattttgggacttattactgtcaacattattggggta<br>ctacgtggacgttcggtggaggcaccaagctggaaatcaaacgt<br>(SEQ ID NO: 136) |
| chCD37-3 | gaattcgccaccatgagtgtgcccactcaggtcctggggttgctgctgctgtggcttacagatgccagatgtgacatcca<br>gatgactcagtctccagcctccctttctgtatctgtgggagaaactgtcaccatcacatgtcgagcaagtgagaatattc<br>gcagtaatttagcatggtatcagcagaaacagggaaaatctcctcagctcctggtcaatgttgcaacaaacttagcagat<br>ggtgtgccatcaaggttcagtggcagtggatcaggcacacagtattccctcaagatcaacagcctgcagtctgaagattt<br>tgggacttattactgtcaacattattggggtactacgtggacgttcggtggaggcaccaagctggaaatcaaacgtacg<br>(SEQ ID NO: 137) |
| huCD37-3<br>(1.0 and 1.1) | gaattcgccaccatgggttggtcctgcatcatcttgtttctcgtggccacagccaccggtgttcactctgatatacaaat<br>gactcaaagcccttccagtttgagcgtaagtgtgggtgaacgcgtaacaatcacctgtagagctagtgaaaacatccgca<br>gtaatctcgcatggtaccaacaaaagccaggtaagtcacctaagctcctcgtgaatgttgctaccaacctcgctgatggt<br>gtgccttcacgattctctggttcaggttccggtaccgattattcacttaagatcaactcactccaaccagaagatttcgg<br>tacatattactgtcaacactactggggtacgacctggacattcggtcaaggtactaagctggaaatcaagcgtacg<br>(SEQ ID NO: 138) |
| muCD37-12 | gacattgtgctaacacagtctcctgcttccttagctgtatctctggggcagagggccaccatctcatgca<br>gggccagccaaagtgtcagtacatctagctatagttatttgtactggttccagcagaaaccaggacagcc<br>acccaaactcctcatcaagtatgcatccaacctagcatctggggtccctgccaggttcagtggcagtggg<br>tctgggacagacttcaccctcaacatccatcctgtggaggaggaggatactgcaacatattactgtcaac<br>acagttgggagattccgtacacgttcggaggggggaccaaactggaaataaaacgg<br>(SEQ ID NO: 139) |
| chCD37-12 | gaattcgccaccatgggttggtcctgtataatcctgttcttggtggccaccgctactggcgttcatagtgatattgtact<br>cactcagtcaccagccagtctggcagtgtccctgggccagcgtgccaccatctcctgccgggcctcacagtccgtgagca<br>ctagctcttattcctatctctactggtttcaacagaagccaggacagccccctaagctgctgatcaagtacgcctccaac<br>ctcgccagcggcgttcccgctagattctctggttccggtagcggaactgatttcactttgaacatccaccccgttgagga<br>agaggataccgccacttactattgtcaacactcttgggagattccttacacctttggaggaggaacaaagctcgaaatta<br>agcgtacg<br>(SEQ ID NO: 140) |
| muCD37-38 | caaattgttctcacccagtctccagcaatcatgtctgcatctccaggggagaaggtcaccatgacctgca<br>gtgccagctcaagtgtaacttacatgcactggtaccagcagaagtcaggcacctcccccaaaagatggat<br>ttatgacacatccaaactggcttctggagtccctgctcgcttcagtggcggtgggtctgggacctcttac<br>tctctcacaatcagcagcatggaggctgaagatgctgccacttattactgccagcagtggattagtaacc<br>cacccacgttcggaggggggaccaagctggaaattaaacgg<br>(SEQ ID NO: 141) |
| chCD37-38 | gaattcgccaccatgggctggtcctgtatcatcctgtttctcgtggccacagctacaggtgttcattctcagattgtgct<br>gacccaatcaccagctattatgtccgctagccccggcgagaaagtgacaatgacatgtagcgctagctcttctgtgactt<br>acatgcattggtatcaacagaagtcaggtaccagtcccaagcgttggatctacgacacatccaaactggcctccggagtc<br>cctgccaggttcagcggaggtgggtccggcaccagttattcactgaccatatcctctatggaagctgaagatgctgctac<br>ttattattgtcaacaatggatttctaacccccccacctttggtggcggaacaaagctggagatcaagcgtacg<br>(SEQ ID NO: 142) |
| huCD37-38 | gaattcgccaccatgggatggtcctgcattattctgttcttggtcgccactgctactggcgttcactctgacattgtgct<br>cacacagtctccagcctcaatgtctgcttcccccggtgagcgggtgaccatgacatgctctgccagttcctccgtgacat<br>atatgcattggtatcagcaaaaacccggtacctctccaaaaagatggatctacgacacttcaaagcttgcatcaggcgtt<br>cctgccagattttccgggtctgggtctggcacttcatacagtctgaccattagttccatggaagctgaagatgcagccac<br>ctattactgtcagcagtggatttcaaatcctcctaccttcggcggcggaaccaaactggagataaagcgtacg<br>(SEQ ID NO: 143) |
| muCD37-50 | caaattgttctcacccagtctccagcaatcatgtctgcatctccaggggagaaggtcaccatgacctgca<br>gtgccacctcaagtgtgacttacatgcactggtaccagcagaagtcaggcacctcccccaaaagatggatttatgacaca<br>tccaaactgccttatggagtccctggtcgtttcagtggtagtgggtctgggacctcttactctctcacaatcagcagcat<br>ggaggctgaagatgctgccacttattactgccagcagtggagtgataacccacccacgttcggctcggggacaaagttgg<br>aaataaagcgg<br>(SEQ ID NO: 144) |
| huCD37-50 | gaattcgccaccatgggttggtcatgcattattctgttcctggttgctaccgcaacaggagtacatagtgagatagtcct<br>cacccaaagtcctgctactatgtctgccagcccaggagagcgtgtgaccatgacttgctctgcaacctcaagtgtgacat<br>acatgcattggtatcagcaaaagcctggccaatcccctaaaaggtggatctacgatacttctaatctgccatacggtgtg<br>cccgcaaggttctccgggagtggcagtggcaccagttatagtctgaccatcagttcaatggaagcagaggatgcagcaac<br>ctattattgtcagcagtggtccgataatccccctacttttggtcagggtacaaagctggagattaagcgtacg<br>(SEQ ID NO: 145) |

TABLE 8-continued

| Variable light chain polynucleotide sequences | |
|---|---|
| Antibody | VL Polynucleotide Sequence (SEQ ID NO) |
| muCD37-51 | caaattgttctcacccagtctccagcaatcatgtctgcatctccaggggagaaggtcaccatgacctgca<br>gtgccacctcaagtgtgacttacatgcactggtaccagcagaagtcaggcacctcccccaaaagatggatttatgacaca<br>tccaaactggcttctggagtccctgctcgcttcagtggcagtgggtctgggacctcttactctctcacaatcagcaacat<br>ggaggctgaagatgctgccacttattactgccagcagtggagtagtaacccacccacgttcggctcggggacaaagttgg<br>aaataaagcgg<br>(SEQ ID NO: 146) |
| huCD37-51 | gaattcgccaccatgggatggagctgtattattctgttcctggttgctactgctactggcgtccattccgagatagtcct<br>cacccagagccccgcaaccatgagtgcctcccctggggagcgagtgactatgacttgttccgccacttcttcagttacct<br>atatgcattggtatcagcagaaacctggacagtctccaaagcgttggatttacgacacctccaacctggcttcaggagtt<br>cctgctaggttcagcggatctgggtctggcacaagttattcactcaccattagttccatggaggccgaagatgccgctac<br>ttactactgtcagcagtggagcagcaaccccctacattcgggcagggaactaagctggagatcaaacgtacg<br>(SEQ ID NO: 147) |
| muCD37-56 | caaattgttctcacccagtctccagcattcatgtctgcatctccaggggataaggtcaccatgacctgca<br>gtgccagttcaagtgttacttacatgcactggtatcagcagaagtcaggcacctcccccaaaagatggatttatgacaca<br>tccaaactggcttctggagtccctgctcgcttcagtggcggtgggtctgggacctcttac<br>tctctcacaatcagcaccatggaggctgaagatgctgccacttattactgccagcagtggattagtgacc<br>cacccacgttcggaggggggaccaagctggaaataaaacgg<br>(SEQ ID NO: 148) |
| huCD37-56 | gaattcgccaccatgggctggtcctgtatcatcctgtttctggtggcaaccgctactggggttcactctgatattgtcct<br>gacacagagtccagccttcatgagtgcttctcccggagaaaaggtcacaatgacttgttcagcttcctcctccgtcacat<br>acatgcattggtaccagcagaagcctgaccagagtcctaagaggtggatctatgatacaagcaatctggcttccggtgtc<br>ccctcccgcttttcaggcggcggaagcggaactgactatagccttaccatctcctcaatggaagccgaggacgctgctac<br>atattactgccagcaatggatcagcgaccctcctactttcggacagggaacaaaattggaaattaagcgtacg<br>(SEQ ID NO: 149) |
| muCD37-57 | caaattgttctcacccagtctccagcaatcatgtctgcatctccaggggagaaggtcaccatgacctgca<br>gtgccacctcaagtgtgacttacatgcactggtaccagcagaagtcaggcacctcccccaaaagatggatttatgacaca<br>tccaaactggcttctggagtccctgctcgcttcagtggcagtgggtctgggacctcttactctctcacaatcagcagcat<br>ggaggctgaagatgctgccacttattactgccagcagtggagtgataacccacccacgttcggctcggggacaaagttgg<br>aaataaagcgg<br>(SEQ ID NO: 150) |
| huCD37-57 | gaattcgccaccatggggtggtcctgtattatcctgttcctggtcgcaaccgccacaggcgttcactccgagatcgtgtt<br>gactcagagcccagccaccatgtccgcttcccccggggagagagtgacaatgacttgttccgccacaagttctgtaacct<br>acatgcattggtaccagcaaaaaccaggacagagtccccgtcgttggatttatgatacctctaacctggcttcaggcgtt<br>cctgcccgcttttctggtagtggatctgggacttcctatagccttaccataagctctatggaagccgaggacgccgctac<br>atactactgccagcagtggagtgataacccccccaccttcgggcagggaaccaaattggagatcaaacgtacg<br>(SEQ ID NO: 151) |

TABLE 9

| Full-length heavy chain polynucleotide sequences | |
|---|---|
| Antibody | Full-Length Heavy Chain Polynucleotide Sequence (SEQ ID NO) |
| chCD37-3 | aagcttgccaccatggctgtcctggcactgctcctctgcctggtgacatacccaagctgtgtcctatcacaggtgcaggt<br>gaaggagtcaggacctggcctggtggcgccctcacagagcctgtccattacatgcactgtctcagggttctcattaacca<br>cctctggtgtaagctgggttcgccagcctccaggaaagggtctggagtggctgggagtaatatggggtgacgggagcac<br>aaactatcattcagctctcaaatccagactgagcatcaagaaggatcactccaagagccaagttttcttaaaactgaaca<br>gtctgcaaactgatgacacagccacgtactactgtgccaaggaggctactcgttggctcactggggccaagggactctg<br>gtcacagtctctgcagcctctacgaagggcccatcagttttccccttggctccaagttctaaatccacaagcggtggaac<br>agctgcactgggatgcctcgttaaagattatttccctgagcctgtgacagtgagctggaatagcggagcattgacttcag<br>gtgtgcacacttttcccgctgtgttgcagtcctccggtctgtactcactgtccagtgtcgtaaccgtcccttctagcagc<br>ttgggaacccagacctacatctgtaacgtcaaccataaaccatccaacacaaaggtggataagaaggttgaaccaaagag<br>ctgtgataagacacatacatgccctccttgtcctgcaccagagctcctcggaggtccatctgtgttcctgtttcccccca<br>aacccaaggacactcttatgatctctcgtactccagaggtcacctgtgttgttgtcgacgtgagccatgaagatcccgag<br>gttaaattcaactggtacgtggatggagtcgaggttcacaatgccaagaccaagcccagggaggagcaatataattctac<br>atatcgggtagtgagcgttctgaccgtgctccaccaagattggctcaatggaaaagagtacaagtgcaaggtgtccaaca<br>aggctcttcccgctcccattgagaaaactatctccaaagccaaggggcagccacgggaaccccaggtgtatacattgccc<br>ccatctagagacgagctgaccaagaaccaggtgagtctcacttgtctggtcaaggggttttacccttctgacattgctgt<br>agagtgggagtctaacggacagccagaaaacaactacaagacaactcccccagtgctggacagcgacgggagcttcttcc<br>tctactccaagttgactgtagacaagtctagatggcagcaaggaaacgttttctcctgctcagtaatgcatgaggctctg<br>cacaatcactatacccagaaatcactgtcccttagcccagggtgactcgag<br>(SEQ ID NO: 152) |
| huCD37-3v1.0 | aagcttgccaccatgggttggagctgcattattctgtttctggtggccaccgccaccggtgtgcactcacaagtccaagt<br>ccaagaatctggtccaggtctggtggccccttcccaaactctgagcatcacctgtaccgtttctggttttagccttacca<br>cctctggtgtgagttgggtacgccaaccacccggtaagggtctcgaatggctgggtgtaatctggggtgatggttccaca<br>aattaccatccttccctcaagtcccgccttagcatcaaaaaggatcacagcaaaagtcaagttttcctgaaactgaatag<br>tctgacagcagccgatacagccacctactattgcgccaagggtggttatagtcttgcacactggggtcaaggtaccctcg<br>ttaccgtctcctcagctagtaccaagggcccatcagttttccccttggctccaagttctaaatccacaagcggtggaaca |

TABLE 9-continued

Full-length heavy chain polynucleotide sequences

| Antibody | Full-Length Heavy Chain Polynucleotide Sequence (SEQ ID NO) |
|---|---|
| | gctgcactgggatgcctcgttaaagattatttccctgagcctgtgacagtgagctggaatagcggagcattgacttcagg<br>tgtgcacacttttcccgctgtgttgcagtcctccggtctgtactcactgtccagtgtcgtaaccgtcccttctagcagct<br>tgggaacccagacctacatctgtaacgtcaaccataaaccatccaacacaaaggtggataagaaggttgaaccaaagagc<br>tgtgataagacacatacatgccctccttgtcctgcaccagagctcctcggaggtccatctgtgttcctgtttcccccaa<br>acccaaggacactcttatgatctctcgtactccagaggtcacctgtgttgttgtcgacgtgagccatgaagatcccgagg<br>ttaaattcaactggtacgtggatggagtcgaggttcacaatgccaagaccaagcccagggaggagcaatataattctaca<br>tatcgggtagtgagcgttctgaccgtgctccaccaagattggctcaatggaaaagagtacaagtgcaaggtgtccaacaa<br>ggctcttcccgctcccattgagaaaactatctccaaagccaaggggcagccacgggaaccccaggtgtatacattgcccc<br>catctagagacgagctgaccaagaaccaggtgagtctcacttgtctggtcaaggggttttacccttctgacattgctgta<br>gagtgggagtctaacggacagccagaaaacaactacaagacaactcccccagtgctggacagcgacgggagcttcttcct<br>ctactccaagttgactgtagacaagtctagatggcagcaaggaaacgttttctcctgctcagtaatgcatgaggctctgc<br>acaatcactatacccagaaatcactgtcccttagcccagggtgactcgag<br>(SEQ ID NO: 153) |
| huCD37-3v1.1 | aagcttgccaccatgggctggagctgtatcattctgtttctggtggcgacagctactggggtccactcccaagtgcaggt<br>acaagagtccgggcctggattggtcgcaccaagccagaccctctctatcacttgtaccgttagcgggttctctctgacaa<br>ccagtggagtgagttgggtgaggcagccaccaggaaagggactggagtggctgggggtgatttggggcgacggcagca<br>caaactatcattccagtcttaaatctcggttgtccattaaaaaagaccatagtaaatctcaagttttcctgaaactcaat<br>agcctgacagccgcagacactgctacgtattactgcgccaaaggaggatacagtctggctcactggggacaggggaccct<br>ggtgaccgtgtcatccgcatcaacaaagggcccatcagttttccccttggctccaagttctaaatccacaagcggtggaa<br>cagctgcactgggatgcctcgttaaagattatttccctgagcctgtgacagtgagctggaatagcggagcattgacttca<br>ggtgtgcacacttttcccgctgtgttgcagtcctccggtctgtactcactgtccagtgtcgtaaccgtcccttctagcag<br>cttgggaacccagacctacatctgtaacgtcaaccataaaccatccaacacaaaggtggataagaaggttgaaccaaaga<br>gctgtgataagacacatacatgccctccttgtcctgcaccagagctcctcggaggtccatctgtgttcctgtttcccccc<br>aaacccaaggacactcttatgatctctcgtactccagaggtcacctgtgttgttgtcgacgtgagccatgaagatcccga<br>ggttaaattcaactggtacgtggatggagtcgaggttcacaatgccaagaccaagcccagggaggagcaatataattcta<br>catatcgggtagtgagcgttctgaccgtgctccaccaagattggctcaatggaaaagagtacaagtgcaaggtgtccaac<br>aaggctcttcccgctcccattgagaaaactatctccaaagccaaggggcagccacgggaaccccaggtgtatacattgcc<br>cccatctagagacgagctgaccaagaaccaggtgagtctcacttgtctggtcaaggggttttacccttctgacattgctg<br>tagagtgggagtctaacggacagccagaaaacaactacaagacaactcccccagtgctggacagcgacgggagcttcttc<br>ctctactccaagttgactgtagacaagtctagatggcagcaaggaaacgttttctcctgctcagtaatgcatgaggctct<br>gcacaatcactatacccagaaatcactgtcccttagcccagggtgactcgag<br>(SEQ ID NO: 154) |
| chCD37-12 | aagcttgccaccatggggtggtcatgcataatcctctttctggtcgctactgctaccggtgtgcactcacagattcagct<br>ggttcaaagtggcccagagctgaaaaagccaggggaaacagtgaaaataagttgcaaggcatccggttacactttcacaa<br>agtacggcatgaactgggtcaagcaggcccagggcaaggggctcaaatggatgggttggatcaataccaacactggcg<br>agtctaggaatgctgaggagtttaagggccggtttgccttcagcctggagacaagtgccagcacagcttacctgcaaatc<br>aacaatctgaagtatgaggatacagcaacctatttctgcggccgcggcactgtcgttgcagactggggacaaggtacca<br>ccttgactgtatccagtgccagcactaagggcccatcagttttccccttggctccaagttctaaatccacaagcggtgga<br>acagctgcactgggatgcctcgttaaagattatttccctgagcctgtgacagtgagctggaatagcggagcattgacttc<br>aggtgtgcacacttttcccgctgtgttgcagtcctccggtctgtactcactgtccagtgtcgtaaccgtcccttctagca<br>gcttgggaacccagacctacatctgtaacgtcaaccataaaccatccaacacaaaggtggataagaaggttgaaccaaag<br>agctgtgataagacacatacatgccctccttgtcctgcaccagagctcctcggaggtccatctgtgttcctgtttccccc<br>caaacccaaggacactcttatgatctctcgtactccagaggtcacctgtgttgttgtcgacgtgagccatgaagatcccg<br>aggttaaattcaactggtacgtggatggagtcgaggttcacaatgccaagaccaagcccagggaggagcaatataattct<br>acatatcgggtagtgagcgttctgaccgtgctccaccaagattggctcaatggaaaagagtacaagtgcaaggtgtccaa<br>caaggctcttcccgctcccattgagaaaactatctccaaagccaaggggcagccacgggaaccccaggtgtatacattgc<br>ccccatctagagacgagctgaccaagaaccaggtgagtctcacttgtctggtcaaggggttttacccttctgacattgct<br>gtagagtgggagtctaacggacagccagaaaacaactacaagacaactcccccagtgctggacagcgacgggagcttctt<br>cctctactccaagttgactgtagacaagtctagatggcagcaaggaaacgttttctcctgctcagtaatgcatgaggctc<br>tgcacaatcactatacccagaaatcactgtcccttagcccagggtgactcgag<br>(SEQ ID NO: 155) |
| chCD37-38 | aagcttgccaccatgggctggagttgtatcattctgtttttggtggccaccgccactggagtccattcccaagtgcaact<br>ccaggaatctggccctgacctggttaagccatctcagagcctctccctgacctgcactgttacaggatactcaatcacat<br>caggctttggctggcactggatcagacaatttcccgggaacaagttggaatggatggcttacattctgtatagcggggt<br>accgattacaatccttccctcaagagccgaatctctatcaccagggatacaagcaagaaccaatttttctccgcctcag<br>ctctgtgactaccgaagataccgctacttactattgtgccaggggctactatggatatggtgcatggttcgtctattggg<br>gccagggaaccctggtgactgtgagcgctgcctctaccaagggcccatcagttttccccttggctccaagttctaaatcc<br>acaagcggtggaacagctgcactgggatgcctcgttaaagattatttccctgagcctgtgacagtgagctggaatagcgg<br>agcattgacttcaggtgtgcacacttttcccgctgtgttgcagtcctccggtctgtactcactgtccagtgtcgtaaccg<br>tcccttctagcagcttgggaacccagacctacatctgtaacgtcaaccataaaccatccaacacaaaggtggataagaag<br>gttgaaccaaagagctgtgataagacacatacatgccctccttgtcctgcaccagagctcctcggaggtccatctgtgtt<br>cctgtttcccccaaacccaaggacactcttatgatctctcgtactccagaggtcacctgtgttgttgtcgacgtgagcc<br>atgaagatcccgaggttaaattcaactggtacgtggatggagtcgaggttcacaatgccaagaccaagcccagggaggag<br>caatataattctacatatcgggtagtgagcgttctgaccgtgctccaccaagattggctcaatggaaaagagtacaagtg<br>caaggtgtccaacaaggctcttcccgctcccattgagaaaactatctccaaagccaaggggcagccacgggaaccccagg<br>tgtatacattgcccccatctagagacgagctgaccaagaaccaggtgagtctcacttgtctggtcaaggggttttaccct<br>tctgacattgctgtagagtgggagtctaacggacagccagaaaacaactacaagacaactcccccagtgctggacagcga<br>cgggagcttcttcctctactccaagttgactgtagacaagtctagatggcagcaaggaaacgttttctcctgctcagtaa<br>tgcatgaggctctgcacaatcactatacccagaaatcactgtcccttagcccagggtgactcgag<br>(SEQ ID NO: 156) |

TABLE 9-continued

Full-length heavy chain polynucleotide sequences

| Antibody | Full-Length Heavy Chain Polynucleotide Sequence (SEQ ID NO) |
|---|---|
| huCD37-38 | aagcttgccaccatgggttggagctgcatcattcttttcctggtcgctactgcaactggagtccactcacaggtccagct<br>gcaagagtccggtcctgggcttgtgaaacccagccagtccctcagtctcacctgtactgtctctggctactctattacca<br>gtgggttcggctggcattggattaggcagtttcccggtaaggggctggagtggatggcatatatcctgtacagcggagga<br>accgattacaacccaagtctgaagagcaggatcagcattacccgggacacaagcaaaaaccagtttttccttcggctgtc<br>tagtgttacagctgcagacaccgctacttactattgtgctcggggttactatggctatggggcttggtttgtgtattggg<br>gacaaggcactcttgtgaccgtgagcagcgcctcaacaaagggcccatcagttttccccttggctccaagttctaaatcc<br>acaagcggtggaacagctgcactgggatgcctcgttaaagattatttccctgagcctgtgacagtgagctggaatagcgg<br>agcattgacttcaggtgtgcacacttttcccgctgtgttgcagtcctccggtctgtactcactgtccagtgtcgtaaccg<br>tcccttctagcagcttgggaacccagacctacatctgtaacgtcaaccataaaccatccaacacaaaggtggataagaag<br>gttgaaccaaagagctgtgataagacacatacatgccctccttgtcctgcaccagagctcctcggaggtccatctgtgtt<br>cctgtttcccccaaacccaaggacactcttatgatctctcgtactccagaggtcacctgtgttgttgtcgacgtgagcc<br>atgaagatcccgaggttaaattcaactggtacgtggatggagtcgaggttcacaatgccaagaccaagcccagggaggag<br>caatataattctacatatcgggtagtgagcgttctgaccgtgctccaccaagattggctcaatggaaaagagtacaagtg<br>caaggtgtccaacaaggctcttcccgctcccattgagaaaactatctccaaagccaaggggcagccacgggaaccccagg<br>tgtatacattgcccccatctagagacgagctgaccaagaaccaggtgagtctcacttgtctggtcaaggggttttaccct<br>tctgacattgctgtagagtgggagtctaacggacagccagaaaacaactacaagacaactcccccagtgctggacagcga<br>cgggagcttcttcctctactccaagttgactgtagacaagtctagatggcagcaaggaaacgttttctcctgctcagtaa<br>tgcatgaggctctgcacaatcactatacccagaaatcactgtcccttagcccagggtgactcgag<br>(SEQ ID NO: 157) |
| huCD37-50 | aagcttgccaccatggggtggtcctgcataatccttttcctggttgctactgctaccggagtccattcacaggtgcagct<br>gcaggagtccggccccggcctgctcaagccttctcagagtctgagtctgacttgtactgtttctggctacagcataacca<br>gcggtttcgcttggcactggatcagacagcatcccggcaacaaactggagtggatgggatacatactgtactcaggctca<br>actgtctattcccctccctgaaatcccggatcagtattacccgtgacacttctaagaaccatttttttctgcagctgaa<br>cagcgttaccgcagctgacactgcaacctactactgtgcccggggatattatggatacggagcttggttcgcttactggg<br>gccaaggcaccctcgtaactgtgagtgctgcttccaccaagggcccatcagttttccccttggctccaagttctaaatcc<br>acaagcggtggaacagctgcactgggatgcctcgttaaagattatttccctgagcctgtgacagtgagctggaatagcgg<br>agcattgacttcaggtgtgcacacttttcccgctgtgttgcagtcctccggtctgtactcactgtccagtgtcgtaaccg<br>tcccttctagcagcttgggaacccagacctacatctgtaacgtcaaccataaaccatccaacacaaaggtggataagaag<br>gttgaaccaaagagctgtgataagacacatacatgccctccttgtcctgcaccagagctcctcggaggtccatctgtgtt<br>cctgtttcccccaaacccaaggacactcttatgatctctcgtactccagaggtcacctgtgttgttgtcgacgtgagcc<br>atgaagatcccgaggttaaattcaactggtacgtggatggagtcgaggttcacaatgccaagaccaagcccagggaggag<br>caatataattctacatatcgggtagtgagcgttctgaccgtgctccaccaagattggctcaatggaaaagagtacaagtg<br>caaggtgtccaacaaggctcttcccgctcccattgagaaaactatctccaaagccaaggggcagccacgggaaccccagg<br>tgtatacattgcccccatctagagacgagctgaccaagaaccaggtgagtctcacttgtctggtcaaggggttttaccct<br>tctgacattgctgtagagtgggagtctaacggacagccagaaaacaactacaagacaactcccccagtgctggacagcga<br>cgggagcttcttcctctactccaagttgactgtagacaagtctagatggcagcaaggaaacgttttctcctgctcagtaa<br>tgcatgaggctctgcacaatcactatacccagaaatcactgtcccttagcccagggtgactcgag<br>(SEQ ID NO: 158) |
| huCD37-51 | aagcttgccaccatgggttggtcttgcatcatcctgttcctggtggccactgccactggcgtgcattcagaagttcagtt<br>ggtggagtccggcccagaagtgctgaaacccggcgaatcactgtccctgacttgtaccgtgtcaggttatagcatcagca<br>gcggctttgcttggcactggattcggcagtttccaggcaagggactggaatggatgggctacatccattacagtggctca<br>accaattacagccctagcctgcagggccgaatctctattaccagggatagttctattaaccagtttttcctgcagcttaa<br>ttccgtgactgcctctgacacagcaacttactattgcgcccgtggctactacgggttcggagcctggtttgtatactggg<br>gtcagggcaccctggtcactgtctcagccgcctctaccaagggcccatcagttttcccttggctccaagttctaaatcca<br>caagcggtggaacagctgcactgggatgcctcgttaaagattatttccctgagcctgtgacagtgagctggaatagcgga<br>gcattgacttcaggtgtgcacacttttcccgctgtgttgcagtcctccggtctgtactcactgtccagtgtcgtaaccgt<br>cccttctagcagcttgggaacccagacctacatctgtaacgtcaaccataaaccatccaacacaaaggtggataagaagg<br>ttgaaccaaagagctgtgataagacacatacatgccctccttgtcctgcaccagagctcctcggaggtccatctgtgttc<br>ctgtttcccccaaacccaaggacactcttatgatctctcgtactccagaggtcacctgtgttgttgtcgacgtgagcca<br>tgaagatcccgaggttaaattcaactggtacgtggatggagtcgagttcacaatgccaagaccaagcccagggaggagca<br>atataattctacatatcgggtagtgagcgttctgaccgtgctccaccaagattggctcaatggaaaagagtacaagtgca<br>aggtgtccaacaaggctcttcccgctcccattgagaaaactatctccaaagccaaggggcagccacgggaaccccaggtg<br>tatacattgcccccatctagagacgagctgaccaagaaccaggtgagtctcacttgtctggtcaaggggttttacccttc<br>tgacattgctgtagagtgggagtctaacggacagccagaaaacaactacaagacaactcccccagtgctggacagcgacg<br>ggagcttcttcctctactccaagttgactgtagacaagtctagatggcagcaaggaaacgttttctcctgctcagtaatg<br>catgaggctctgcacaatcactatacccagaaatcactgtcccttagcccagggtgactcgag<br>(SEQ ID NO: 159) |
| huCD37-56 | aagcttgccaccatggggtggagctgcattatcctgttcctcgtcgccaccgcaaccggcgtccactcccaggtgcagct<br>gcaagaaagcgggccaggattggtaaaaccttcccagtctctgagtcttacttgtaccgtatctggatacagtatcacat<br>ctggcttcgcctggcattggattcgccagtttcccggcaaggggcttgagtggatggggtatattcattattctggaggt<br>accaactacaacccttccctgaagagtcgagtctcaattaccagggacacttccaagaaccaattcttttttgcagcttaa<br>ttcagtgaccgctgccgacaccgctacttactactgcgcccggggctactatgggtttggtgcctggttcgcctactggg<br>gccaggggaccctggtgcccgtgtctgctgcctccacaaagggcccatcagttttccccttggctccaagttctaaatcc<br>acaagcggtggaacagctgcactgggatgcctcgttaaagattatttccctgagcctgtgacagtgagctggaatagcgg<br>agcattgacttcaggtgtgcacacttttcccgctgtgttgcagtcctccggtctgtactcactgtccagtgtcgtaaccg<br>tcccttctagcagcttgggaacccagacctacatctgtaacgtcaaccataaaccatccaacacaaaggtggataagaag<br>gttgaaccaaagagctgtgataagacacatacatgccctccttgtcctgcaccagagctcctcggaggtccatctgtgtt<br>cctgtttcccccaaacccaaggacactcttatgatctctcgtactccagaggtcacctgtgttgttgtcgacgtgagcc<br>atgaagatcccgaggttaaattcaactggtacgtggatggagtcgaggttcacaatgccaagaccaagcccagggaggag<br>caatataattctacatatcgggtagtgagcgttctgaccgtgctccaccaagattggctcaatggaaaagagtacaagtg |

TABLE 9-continued

| Full-length heavy chain polynucleotide sequences | |
|---|---|
| Antibody | Full-Length Heavy Chain Polynucleotide Sequence (SEQ ID NO) |
| | caaggtgtccaacaaggctcttcccgctcccattgagaaaactatctccaaagccaaggggcagccacgggaaccccagg<br>tgtatacattgcccccatctagagacgagctgaccaagaaccaggtgagtctcacttgtctggtcaaggggttttaccct<br>tctgacattgctgtagagtgggagtctaacggacagccagaaaacaactacaagacaactcccccagtgctggacagcga<br>cgggagcttcttcctctactccaagttgactgtagacaagtctagatggcagcaaggaaacgttttctcctgctcagtaa<br>tgcatgaggctctgcacaatcactatacccagaaatcactgtcccttagcccagggtgactcgag<br>(SEQ ID NO: 160) |
| huCD37-57 | aagcttgccaccatgggctggagctgcatcattctgtttctggtggccacagcaactggcgttcacagtcaagtccaact<br>gcaggagagcggccccggactcctgaaaccatctcagtcactcagtctgacatgtactgtgagcggctacagcattacct<br>caggcttcgcttggcattggatcaggcagttccccggaaaaggtctggagtggatggggtacattctgtacagcggcagt<br>acagtgtattcaccctccttgaaatctaggatatcaatcacacgtgatacaagcaaaaatcagttcttcctccagctgaa<br>ctccgtcaccgccgcagacacagcaacctattattgtgctcgcggatactacggatatggcgcatggttcgcctattggg<br>gccaggggacactcgtgaccgtttccgccgcctccacaaagggcccatcagttttccccttggctccaagttctaaatcc<br>acaagcggtggaacagctgcactgggatgcctcgttaaagattatttccctgagcctgtgacagtgagctggaatagcgg<br>agcattgacttcaggtgtgcacacttttcccgctgtgttgcagtcctccggtctgtactcactgtccagtgtcgtaaccg<br>tcccttctagcagcttgggaacccagacctacatctgtaacgtcaaccataaaccatccaacacaaaggtggataagaag<br>gttgaaccaaagagctgtgataagacacatacatgccctccttgtcctgcaccagagctcctcggaggtccatctgtgtt<br>cctgtttcccccaaacccaaggacactcttatgatctctcgtactccagaggtcacctgtgttgttgtcgacgtgagcc<br>atgaagatcccgaggttaaattcaactggtacgtggatggagtcgaggttcacaatgccaagaccaagcccagggaggag<br>caatataattctacatatcgggtagtgagcgttctgaccgtgctccaccaagattggctcaatggaaaagagtacaagtg<br>caaggtgtccaacaaggctcttcccgctcccattgagaaaactatctccaaagccaaggggcagccacgggaaccccagg<br>tgtatacattgcccccatctagagacgagctgaccaagaaccaggtgagtctcacttgtctggtcaaggggttttaccct<br>tctgacattgctgtagagtgggagtctaacggacagccagaaaacaactacaagacaactcccccagtgctggacagcga<br>cgggagcttcttcctctactccaagttgactgtagacaagtctagatggcagcaaggaaacgttttctcctgctcagtaa<br>tgcatgaggctctgcacaatcactatacccagaaatcactgtcccttagcccagggtgactcgag<br>(SEQ ID NO: 161) |

TABLE 10

| Full-length light chain polynucleotide sequences | |
|---|---|
| Antibody | Full-length Light Chain Polynucleotide Sequence (SEQ ID NO) |
| chCD37-3 | gaattcgccaccatgagtgtgcccactcaggtcctggggttgctgctgctgtggcttacagatgccagatgtgacatcca<br>gatgactcagtctccagcctccctttctgtatctgtgggagaaactgtcaccatcacatgtcgagcaagtgagaatattc<br>gcagtaatttagcatggtatcagcagaaacagggaaaatctcctcagctcctggtcaatgttgcaacaaacttagcagat<br>ggtgtgccatcaaggttcagtggcagtggatcaggcacacagtattccctcaagatcaacagcctgcagtctgaagattt<br>tgggacttattactgtcaacattattggggtactacgtggacgttcggtggaggcaccaagctggaaatcaaacgtacgg<br>tggctgcaccatctgtcttcatcttcccgccatctgatgagcagttgaaatctggaactgcctctgttgtgtgcctgctg<br>aataacttctatcccagagaggccaaagtacagtggaaggtggataacgccctccaatcgggtaactcccaggagagtgt<br>cacagagcaggacagcaaggacagcacctacagcctcagcagcaccctgacgctgagcaaagcagactacgagaaacaca<br>aagtctacgcctgcgaagtcacccatcagggcctgagctcgcccgtcacaaagagcttcaacaggggagagtgttag<br>(SEQ ID NO: 162) |
| huCD37-3<br>(1.0 and 1.1) | gaattcgccaccatgggttggtcctgcatcatcttgtttctcgtggccacagccaccggtgttcactctgatatacaaat<br>gactcaaagcccttccagtttgagcgtaagtgtgggtgaacgcgtaacaatcacctgtagagctagtgaaaacatccgca<br>gtaatctcgcatggtaccaacaaaagccaggtaagtcacctaagctcctcgtgaatgttgctaccaacctcgctgatggt<br>gtgccttcacgattctctggttcaggttccggtaccgattattcacttaagatcaactcactccaaccagaagatttcgg<br>tacatattactgtcaacactactggggtacgacctggacattcggtcaaggtactaagctggaaatcaagcgtacggtgg<br>ctgcaccatctgtcttcatcttcccgccatctgatgagcagttgaaatctggaactgcctctgttgtgtgcctgctgaat<br>aacttctatcccagagaggccaaagtacagtggaaggtggataacgccctccaatcgggtaactcccaggagagtgtcac<br>agagcaggacagcaaggacagcacctacagcctcagcagcaccctgacgctgagcaaagcagactacgagaaacacaaag<br>tctacgcctgcgaagtcacccatcagggcctgagctcgcccgtcacaaagagcttcaacaggggagagtgttag<br>(SEQ ID NO: 163) |
| chCD37-12 | gaattcgccaccatgggttggtcctgtataatcctgttcttggtggccaccgctactggcgttcatagtgatattgtact<br>cactcagtcaccagccagtctggcagtgtccctgggccagcgtgccaccatctcctgccgggcctcacagtccgtgagca<br>ctagctcttattcctatctctactggtttcaacagaagccaggacagcccccctaagctgctgatcaagtacgcctccaac<br>ctcgccagcggcgttcccgctagattctctggttccggtagcggaactgatttcactttgaacatccaccccgttgagga<br>agaggataccgccacttactattgtcaacactcttgggagattccttacacctttggaggaggaacaaagctcgaaatta<br>agcgtacggtggctgcaccatctgtcttcatcttcccgccatctgatgagcagttgaaatctggaactgcctctgttgtg<br>tgcctgctgaataacttctatcccagagaggccaaagtacagtggaaggtggataacgccctccaatcgggtaactccca<br>ggagagtgtcacagagcaggacagcaaggacagcacctacagcctcagcagcaccctgacgctgagcaaagcagactacg<br>agaaacacaaagtctacgcctgcgaagtcacccatcagggcctgagctcgcccgtcacaaagagcttcaacaggggagag<br>tgttag<br>(SEQ ID NO: 164) |
| chCD37-38 | gaattcgccaccatgggctggtcctgtatcatcctgtttctcgtggccacagctacaggtgttcattctcagattgtgct<br>gacccaatcaccagctattatgtccgctagccccggcgagaaagtgacaatgacatgtagcgctagctcttctgtgactt<br>acatgcattggtatcaacagaagtcaggtaccagtcccaagcgttggatctacgacacatccaaactggcctccggagtc<br>cctgccaggttcagcggaggtgggtccggcaccagttattcactgaccatatcctctatggaagctgaagatgctgctac<br>ttattattgtcaacaatggatttctaacccccccacctttggtggcggaacaaagctggagatcaagcgtacggtggctg<br>caccatctgtcttcatcttcccgccatctgatgagcagttgaaatctggaactgcctctgttgtgtgcctgctgaataac |

TABLE 10-continued

| Full-length light chain polynucleotide sequences | |
|---|---|
| Antibody | Full-length Light Chain Polynucleotide Sequence (SEQ ID NO) |
| | ttctatcccagagaggccaaagtacagtggaaggtggataacgccctccaatcgggtaactcccaggagagtgtcacaga<br>gcaggacagcaaggacagcacctacagcctcagcagcaccctgacgctgagcaaagcagactacgagaaacacaaagtct<br>acgcctgcgaagtcacccatcagggcctgagctcgcccgtcacaaagagcttcaacaggggagagtgttag<br>(SEQ ID NO: 165) |
| huCD37-38 | gaattcgccaccatgggatggtcctgcattattctgttcttggtcgccactgctactggcgttcactctgacattgtgct<br>cacacagtctccagcctcaatgtctgcttcccccggtgagcgggtgaccatgacatgctctgccagttcctccgtgacat<br>atatgcattggtatcagcaaaaacccggtacctctccaaaaagatggatctacgacacttcaaagcttgcatcaggcgtt<br>cctgccagattttccgggtctgggtctggcacttcatacagtctgaccattagttccatggaagctgaagatgcagccac<br>ctattactgtcagcagtggatttcaaatcctcctaccttcggcggcggaaccaaactggagataaagcgtacggtggctg<br>caccatctgtcttcatcttcccgccatctgatgagcagttgaaatctggaactgcctctgttgtgtgcctgctgaataac<br>ttctatcccagagaggccaaagtacagtggaaggtggataacgccctccaatcgggtaactcccaggagagtgtcacaga<br>gcaggacagcaaggacagcacctacagcctcagcagcaccctgacgctgagcaaagcagactacgagaaacacaaagtct<br>acgcctgcgaagtcacccatcagggcctgagctcgcccgtcacaaagagcttcaacaggggagagtgttag<br>(SEQ ID NO: 166) |
| huCD37-50 | gaattcgccaccatgggttggtcatgcattattctgttcctggttgctaccgcaacaggagtacatagtgagatagtcct<br>cacccaaagtcctgctactatgtctgccagcccaggagagcgtgtgaccatgacttgctctgcaacctcaagtgtgacat<br>acatgcattggtatcagcaaaagcctggccaatcccctaaaaggtggatctacgatacttctaatctgccatacggtgtg<br>cccgcaaggttctccgggagtggcagtggcaccagttatagtctgaccatcagttcaatggaagcagaggatgcagcaac<br>ctattattgtcagcagtggtccgataatcccccctacttttggtcagggtacaaagctggagattaagcgtacggtggctg<br>caccatctgtcttcatcttcccgccatctgatgagcagttgaaatctggaactgcctctgttgtgtgcctgctgaataac<br>ttctatcccagagaggccaaagtacagtggaaggtggataacgccctccaatcgggtaactcccaggagagtgtcacaga<br>gcaggacagcaaggacagcacctacagcctcagcagcaccctgacgctgagcaaagcagactacgagaaacacaaagtct<br>acgcctgcgaagtcacccatcagggcctgagctcgcccgtcacaaagagcttcaacaggggagagtgttag<br>(SEQ ID NO: 167) |
| huCD37-51 | gaattcgccaccatgggttggtcatgcattattctgttcctggttgctaccgcaacaggagtacatagtgagatagtcct<br>cacccagagccccgcaaccatgagtgcctcccctggggagcgagtgactatgacttgttccgccacttcttcagttacct<br>atatgcattggtatcagcagaaacctggacagtctccaaagcgttggatttacgacacctccaacctggcttcaggagtt<br>cctgctaggttcagcggatctgggtctggcacaagttattcactcaccattagttccatggaggccgaagatgccgctac<br>ttactactgtcagcagtggagcagcaacccccctacattcgggcagggaactaagctggagatcaaacgtacggtggctg<br>caccatctgtcttcatcttcccgccatctgatgagcagttgaaatctggaactgcctctgttgtgtgcctgctgaataac<br>ttctatcccagagaggccaaagtacagtggaaggtggataacgccctccaatcgggtaactcccaggagagtgtcacaga<br>gcaggacagcaaggacagcacctacagcctcagcagcaccctgacgctgagcaaagcagactacgagaaacacaaagtct<br>acgcctgcgaagtcacccatcagggcctgagctcgcccgtcacaaagagcttcaacaggggagagtgttag<br>(SEQ ID NO: 168) |
| huCD37-56 | gaattcgccaccatgggctggtcctgtatcatcctgtttctggtggcaaccgctactggggttcactctgatattgtcct<br>gacacagagtccagccttcatgagtgcttctcccggagaaaaggtcacaatgacttgttcagcttcctcctccgtcacat<br>acatgcattggtaccagcagaagcctgaccagagtcctaagaggtggatctatgatacaagcaatctggcttccggtgtc<br>cctcccgcttttcaggcggcggaagcggaactgactatagccttaccatctcctcaatggaagccgaggacgctgctac<br>atattactgccagcaatggatcagcgaccctcctactttcggacagggaacaaaattggaaattaagcgtacggtggctg<br>caccatctgtcttcatcttcccgccatctgatgagcagttgaaatctggaactgcctctgttgtgtgcctgctgaataac<br>ttctatcccagagaggccaaagtacagtggaaggtggataacgccctccaatcgggtaactcccaggagagtgtcacaga<br>gcaggacagcaaggacagcacctacagcctcagcagcaccctgacgctgagcaaagcagactacgagaaacacaaagtct<br>acgcctgcgaagtcacccatcagggcctgagctcgcccgtcacaaagagcttcaacaggggagagtgttag<br>(SEQ ID NO: 169) |
| huCD37-57 | gaattcgccaccatggggtggtcctgtattatcctgttcctggtcgcaaccgccacaggcgttcactccgagatcgtgtt<br>gactcagagcccagccaccatgtccgcttcccccggggagagagtgacaatgacttgttccgccacaagttctgtaacct<br>acatgcattggtaccagcaaaaaccaggacagagtccccgtcgttggatttatgatacctctaacctggcttcaggcgtt<br>cctgcccgcttttctggtagtggatctgggacttcctatagccttaccataagctctatggaagccgaggacgccgctac<br>atactactgccagcagtggagtgataacccccccaccttcgggcagggaaccaaattggagatcaaacgtacggtggctg<br>caccatctgtcttcatcttcccgccatctgatgagcagttgaaatctggaactgcctctgttgtgtgcctgctgaataac<br>ttctatcccagagaggccaaagtacagtggaaggtggataacgccctccaatcgggtaactcccaggagagtgtcacaga<br>gcaggacagcaaggacagcacctacagcctcagcagcaccctgacgctgagcaaagcagactacgagaaacacaaagtct<br>acgcctgcgaagtcacccatcagggcctgagctcgcccgtcacaaagagcttcaacaggggagagtgttag<br>(SEQ ID NO: 170) |

Also provided is a polynucleotide having at least about 95%, at least about 96%, at least about 97%, at least about 98%, or at least about 99% sequence identity to SEQ ID NOs:121-170. Thus, in certain embodiments, the polypeptide comprises (a) a polypeptide having at least about 95% sequence identity to SEQ ID NOs:121-135 or 152-161, and/or (b) a polypeptide having at least about 95% sequence identity to SEQ ID NOs:136-151 or 162-170. In certain embodiments, the polypeptide comprises (a) a polypeptide having the amino acid sequence of SEQ ID NOs: 121-135 or 152-161; and/or (b) a polypeptide having the amino acid sequence of SEQ ID NOs: 136-151 or 162-170.

In some embodiments, the polynucleotide encodes the light chain encoded by the recombinant plasmid DNA phuCD37-3LC (ATCC Deposit Designation PTA-10722, deposited with the ATCC on Mar. 18, 2010) or a light chain that is at least about 85%, at least about 90%, at least about 95%, or at least about 99% to the light chain encoded by phuCD37-3LC (PTA-10722). In some embodiments, the polynucleotide encodes the heavy chain encoded by the recombinant plasmid DNA phuCD37-3HCv.1.0 (ATCC Deposit Designation PTA-10723, deposited with the ATCC on Mar. 18, 2010) or a heavy chain that is at least about 85%, at least about 90%, at least about 95%, or at least about 99% identical to the heavy chain encoded by phuCD37-3HCv.1.0 (PTA-10723). In certain embodiments the polynucleotide is the recombinant plasmid DNA phuCD37-3LC (PTA-10722) or the recombinant plasmid phuCD37-3HCv.1.0 (PTA-10723).

In certain embodiments the polynucleotides comprise the coding sequence for the mature polypeptide fused in the same reading frame to a polynucleotide which aids, for example, in expression and secretion of a polypeptide from a host cell (e.g. a leader sequence which functions as a secretory sequence for controlling transport of a polypeptide from the cell). The polypeptide having a leader sequence is a preprotein and can have the leader sequence cleaved by the host cell to form the mature form of the polypeptide. The polynucleotides can also encode for a proprotein which is the mature protein plus additional 5' amino acid residues. A mature protein having a prosequence is a proprotein and is an inactive form of the protein. Once the prosequence is cleaved an active mature protein remains.

In certain embodiments the polynucleotides comprise the coding sequence for the mature polypeptide fused in the same reading frame to a marker sequence that allows, for example, for purification of the encoded polypeptide. For example, the marker sequence can be a hexa-histidine tag supplied by a pQE-9 vector to provide for purification of the mature polypeptide fused to the marker in the case of a bacterial host, or the marker sequence can be a hemagglutinin (HA) tag derived from the influenza hemagglutinin protein when a mammalian host (e.g. COS-7 cells) is used.

The present invention further relates to variants of the hereinabove described polynucleotides encoding, for example, fragments, analogs, and derivatives.

The polynucleotide variants can contain alterations in the coding regions, non-coding regions, or both. In some embodiments the polynucleotide variants contain alterations which produce silent substitutions, additions, or deletions, but do not alter the properties or activities of the encoded polypeptide. In some embodiments, nucleotide variants are produced by silent substitutions due to the degeneracy of the genetic code. Polynucleotide variants can be produced for a variety of reasons, e.g., to optimize codon expression for a particular host (change codons in the human mRNA to those preferred by a bacterial host such as *E. coli*).

Vectors and cells comprising the polynucleotides described herein are also provided.

IV. Methods of Use and Pharmaceutical Compositions

The CD37-binding agents (including antibodies, immunoconjugates, and polypeptides) of the invention are useful in a variety of applications including, but not limited to, therapeutic treatment methods, such as the treatment of cancer, such as B-cell malignancies. In certain embodiments, the agents are useful for inhibiting tumor growth, inducing differentiation, reducing tumor volume, and/or reducing the tumorigenicity of a tumor. The methods of use can be in vitro, ex vivo, or in vivo methods. In certain embodiments, the CD37-binding agent or antibody or immunoconjugate, or polypeptide is an antagonist of the human CD37 to which it binds.

In one aspect, anti-CD37 antibodies and immunoconjugates of the invention are useful for detecting the presence of CD37 in a biological sample. The term "detecting" as used herein encompasses quantitative or qualitative detection. In certain embodiments, a biological sample comprises a cell or tissue. In certain embodiments, such tissues include normal and/or cancerous tissues that express CD37 at higher levels relative to other tissues, for example, B cells and/or B cell associated tissues.

In one aspect, the invention provides a method of detecting the presence of CD37 in a biological sample. In certain embodiments, the method comprises contacting the biological sample with an anti-CD37 antibody under conditions permissive for binding of the anti-CD37 antibody to CD37, and detecting whether a complex is formed between the anti-CD37 antibody and CD37.

In one aspect, the invention provides a method of diagnosing a disorder associated with increased expression of CD37. In certain embodiments, the method comprises contacting a test cell with an anti-CD37 antibody; determining the level of expression (either quantitatively or qualitatively) of CD37 by the test cell by detecting binding of the anti-CD37 antibody to CD37; and comparing the level of expression of CD37 by the test cell with the level of expression of CD37 by a control cell (e.g., a normal cell of the same tissue origin as the test cell or a cell that expresses CD37 at levels comparable to such a normal cell), wherein a higher level of expression of CD37 by the test cell as compared to the control cell indicates the presence of a disorder associated with increased expression of CD37. In certain embodiments, the test cell is obtained from an individual suspected of having a disorder associated with increased expression of CD37. In certain embodiments, the disorder is a cell proliferative disorder, such as a cancer or a tumor.

In certain embodiments, a method of diagnosis or detection, such as those described above, comprises detecting binding of an anti-CD37 antibody to CD37 expressed on the surface of a cell or in a membrane preparation obtained from a cell expressing CD37 on its surface. In certain embodiments, the method comprises contacting a cell with an anti-CD37 antibody under conditions permissive for binding of the anti-CD37 antibody to CD37, and detecting whether a complex is formed between the anti-CD37 antibody and CD37 on the cell surface. An exemplary assay for detecting binding of an anti-CD37 antibody to CD37 expressed on the surface of a cell is a "FACS" assay.

Certain other methods can be used to detect binding of anti-CD37 antibodies to CD37. Such methods include, but are not limited to, antigen-binding assays that are well known in the art, such as western blots, radioimmunoassays, ELISA (enzyme linked immunosorbent assay), "sandwich" immunoassays, immunoprecipitation assays, fluorescent immunoassays, protein A immunoassays, and immunohistochemistry (IHC).

In certain embodiments, anti-CD37 antibodies are labeled. Labels include, but are not limited to, labels or moieties that are detected directly (such as fluorescent, chromophoric, electron-dense, chemiluminescent, and radioactive labels), as well as moieties, such as enzymes or ligands, that are detected indirectly, e.g., through an enzymatic reaction or molecular interaction.

In certain embodiments, anti-CD37 antibodies are immobilized on an insoluble matrix. Immobilization entails separating the anti-CD37 antibody from any CD37 that remains free in solution. This conventionally is accomplished by either insolubilizing the anti-CD37 antibody before the assay procedure, as by adsorption to a water-insoluble matrix or surface (Bennich et al., U.S. Pat. No. 3,720,760), or by covalent coupling (for example, using glutaraldehyde cross-linking), or by insolubilizing the anti-CD37 antibody after formation of a complex between the anti-CD37 antibody and CD37, e.g., by immunoprecipitation.

Any of the above embodiments of diagnosis or detection can be carried out using an immunoconjugate of the invention in place of or in addition to an anti-CD37 antibody.

In certain embodiments, the disease treated with the CD37-binding agent or antagonist (e.g., an anti-CD37 antibody) is a cancer. In certain embodiments, the cancer is characterized by CD37 expressing cells to which the CD37-binding agent (e.g., antibody) binds.

The present invention provides for methods of treating cancer comprising administering a therapeutically effective amount of a CD37-binding agent to a subject (e.g., a subject in need of treatment). In certain embodiments, the cancer is a B-cell malignancy. In certain embodiments, the cancer is selected from the group consisting of B cell lymphomas, NHL, precursor B cell lymphoblastic leukemia/lymphoma and mature B cell neoplasms, B cell chronic lymphocytic leukemia (CLL)/small lymphocytic lymphoma (SLL), B cell prolymphocytic leukemia, lymphoplasmacytic lymphoma, mantle cell lymphoma (MCL), follicular lymphoma (FL), low grade, intermediate-grade and high-grade (FL), cutaneous follicle center lymphoma, marginal zone B cell lymphoma, MALT type marginal zone B cell lymphoma, nodal marginal zone B cell lymphoma, splenic type marginal zone B cell lymphoma, hairy cell leukemia, diffuse large B cell lymphoma, Burkitt's lymphoma, plasmacytoma, plasma cell myeloma, post-transplant lymphoproliferative disorder, Waldenstrom's macroglobulinemia, and anaplastic large-cell lymphoma (ALCL). In certain embodiments, the subject is a human.

The present invention further provides methods for inhibiting tumor growth using the antibodies or other agents described herein. In certain embodiments, the method of inhibiting the tumor growth comprises contacting the cell with a CD37-binding agent (e.g., antibody) in vitro. For example, an immortalized cell line or a cancer cell line that expresses CD37 is cultured in medium to which is added the antibody or other agent to inhibit tumor growth. In some embodiments, tumor cells are isolated from a patient sample such as, for example, a tissue biopsy, pleural effusion, or blood sample and cultured in medium to which is added an CD37-binding agent to inhibit tumor growth.

In some embodiments, the method of inhibiting tumor growth comprises contacting the tumor or tumor cells with the CD37-binding agent (e.g., antibody) in vivo. In certain embodiments, contacting a tumor or tumor cell with a CD37-binding agent is undertaken in an animal model. For example, CD37-binding agents can be administered to xenografts expressing one or more CD37s that have been grown in immunocompromised mice (e.g. NOD/SCID mice) to inhibit tumor growth. In some embodiments, cancer stem cells are isolated from a patient sample such as, for example, a tissue biopsy, pleural effusion, or blood sample and injected into immunocompromised mice that are then administered a CD37-binding agent to inhibit tumor cell growth. In some embodiments, the CD37-binding agent is administered at the same time or shortly after introduction of tumorigenic cells into the animal to prevent tumor growth. In some embodiments, the CD37-binding agent is administered as a therapeutic after the tumorigenic cells have grown to a specified size.

In certain embodiments, the method of inhibiting tumor growth comprises administering to a subject a therapeutically effective amount of a CD37-binding agent. In certain embodiments, the subject is a human. In certain embodiments, the subject has a tumor or has had a tumor removed.

In certain embodiments, the tumor expresses the CD37 to which the CD37-binding agent or antibody binds. In certain embodiments, the tumor overexpresses the human CD37.

In addition, the invention provides a method of reducing the tumorigenicity of a tumor in a subject, comprising administering a therapeutically effective amount of a CD37-binding agent to the subject. In certain embodiments, the tumor comprises cancer stem cells. In certain embodiments, the frequency of cancer stem cells in the tumor is reduced by administration of the agent.

The invention further provides methods of differentiating tumorigenic cells into non-tumorigenic cells comprising contacting the tumorigenic cells with a CD37-binding agent (for example, by administering the CD37-binding agent to a subject that has a tumor comprising the tumorigenic cells or that has had such a tumor removed.

The use of the CD37-binding agents, polypeptides, or antibodies described herein to induce the differentiation of cells, including, but not limited to tumor cells, is also provided. For example, methods of inducing cells to differentiate comprising contacting the cells with an effective amount of a CD37-binding agent (e.g., an anti-CD37 antibody) described herein are envisioned. Methods of inducing cells in a tumor in a subject to differentiate comprising administering a therapeutically effective amount of a CD37-binding agent, polypeptide, or antibody to the subject are also provided. In certain embodiments, the tumor is a pancreatic tumor. In certain other embodiments, the tumor is a colon tumor. In some embodiments, the treatment methods comprise administering a therapeutically effective amount of the CD37-binding agent, polypeptide, or antibody to the subject.

The present invention further provides pharmaceutical compositions comprising one or more of the CD37-binding agents described herein. In certain embodiments, the pharmaceutical compositions further comprise a pharmaceutically acceptable vehicle. These pharmaceutical compositions find use in inhibiting tumor growth and treating cancer in human patients.

In certain embodiments, formulations are prepared for storage and use by combining a purified antibody or agent of the present invention with a pharmaceutically acceptable vehicle (e.g. carrier, excipient) (Remington, The Science and Practice of Pharmacy 20th Edition Mack Publishing, 2000). Suitable pharmaceutically acceptable vehicles include, but are not limited to, nontoxic buffers such as phosphate, citrate, and other organic acids; salts such as sodium chloride; antioxidants including ascorbic acid and methionine; preservatives (e.g. octadecyldimethylbenzyl ammonium chloride; hexamethonium chloride; benzalkonium chloride; benzethonium chloride; phenol, butyl or benzyl alcohol; alkyl parabens, such as methyl or propyl paraben; catechol; resorcinol; cyclohexanol; 3-pentanol; and m-cresol); low molecular weight polypeptides (e.g. less than about 10 amino acid residues); proteins such as serum albumin, gelatin, or immunoglobulins; hydrophilic polymers such as polyvinylpyrrolidone; amino acids such as glycine, glutamine, asparagine, histidine, arginine, or lysine; carbohydrates such as monosacchandes, disaccharides, glucose, mannose, or dextrins; chelating agents such as EDTA; sugars such as sucrose, mannitol, trehalose or sorbitol; salt-forming counter-ions such as sodium; metal complexes (e.g. Zn-protein complexes); and non-ionic surfactants such as TWEEN or polyethylene glycol (PEG).

The pharmaceutical compositions of the present invention can be administered in any number of ways for either local or systemic treatment. Administration can be topical (such as to mucous membranes including vaginal and rectal delivery) such as transdermal patches, ointments, lotions, creams, gels, drops, suppositories, sprays, liquids and powders; pulmonary (e.g., by inhalation or insufflation of powders or aerosols, including by nebulizer; intratracheal, intranasal, epidermal and transdermal); oral; or parenteral including intravenous, intraarterial, subcutaneous, intraperitoneal or intramuscular injection or infusion; or intracranial (e.g., intrathecal or intraventricular) administration.

An antibody or immunoconjugate of the invention can be combined in a pharmaceutical combination formulation, or dosing regimen as combination therapy, with a second compound having anti-cancer properties. The second compound of the pharmaceutical combination formulation or dosing regimen can have complementary activities to the ADC of the combination such that they do not adversely affect each other. Pharmaceutical compositions comprising the CD37-binding agent and the second anti-cancer agent are also provided. For example, CD37-binding agents can be administered in combination with CD20 antagonists, such as Rituximab.

For the treatment of the disease, the appropriate dosage of an antibody or agent of the present invention depends on the type of disease to be treated, the severity and course of the disease, the responsiveness of the disease, whether the antibody or agent is administered for therapeutic or preventative purposes, previous therapy, patient's clinical history, and so on all at the discretion of the treating physician. The antibody or agent can be administered one time or over a series of treatments lasting from several days to several months, or until a cure is effected or a diminution of the disease state is achieved (e.g. reduction in tumor size). Optimal dosing schedules can be calculated from measurements of drug accumulation in the body of the patient and will vary depending on the relative potency of an individual antibody or agent. The administering physician can easily determine optimum dosages, dosing methodologies and repetition rates. In certain embodiments, dosage is from 0.01 μg to 100 mg per kg of body weight, and can be given once or more daily, weekly, monthly or yearly. In certain embodiments, the antibody or other CD37-binding agent is given once every two weeks or once every three weeks. In certain embodiments, the dosage of the antibody or other CD37-binding agent is from about 0.1 mg to about 20 mg per kg of body weight. The treating physician can estimate repetition rates for dosing based on measured residence times and concentrations of the drug in bodily fluids or tissues.

The combination therapy can provide "synergy" and prove "synergistic", i.e. the effect achieved when the active ingredients used together is greater than the sum of the effects that results from using the compounds separately. A synergistic effect can be attained when the active ingredients are: (1) co-formulated and administered or delivered simultaneously in a combined, unit dosage formulation; (2) delivered by alternation or in parallel as separate formulations; or (3) by some other regimen. When delivered in alternation therapy, a synergistic effect can be attained when the compounds are administered or delivered sequentially, e.g. by different injections in separate syringes. In general, during alternation therapy, an effective dosage of each active ingredient is administered sequentially, i.e. serially, whereas in combination therapy, effective dosages of two or more active ingredients are administered together.

VI. Kits Comprising CD37 Binding Agents

The present invention provides kits that comprise the antibodies, immunoconjugates or other agents described herein and that can be used to perform the methods described herein. In certain embodiments, a kit comprises at least one purified antibody against CD37 in one or more containers. In some embodiments, the kits contain all of the components necessary and/or sufficient to perform a detection assay, including all controls, directions for performing assays, and any necessary software for analysis and presentation of results. One skilled in the art will readily recognize that the disclosed antibodies, immunoconjugates or other agents of the present invention can be readily incorporated into one of the established kit formats which are well known in the art.

Further provided are kits comprising a CD37-binding agent (e.g., a CD37-binding antibody), as well as a second anti-cancer agent. In certain embodiments, the second anti-cancer agent is a chemotherapeutic agent (e.g., rituximab).

Embodiments of the present disclosure can be further defined by reference to the following non-limiting examples, which describe in detail preparation of certain antibodies of the present disclosure and methods for using antibodies of the present disclosure. It will be apparent to those skilled in the art that many modifications, both to materials and methods, can be practiced without departing from the scope of the present disclosure.

EXAMPLES

It is understood that the examples and embodiments described herein are for illustrative purposes only and that various modifications or changes in light thereof will be suggested to persons skilled in the art and are to be included within the spirit and purview of this application Cell Lines and Growth

| Cell line | Origin | Source |
|---|---|---|
| Ramos | Burkitt lymphoma | DSMZ (ACC 603) |
| Raji | Burkitt lymphoma | DSMZ (ACC 319) |
| Daudi | Burkitt lymphoma | DSMZ (ACC 78) |
| Namalwa | Burkitt lymphoma | ATCC (CRL-1432) |
| BJAB | B-NHL | A gift from Elliot Kieff (Harvard) |
| WSU-DLCL-2 | B-NHL, diffuse large B-cell lymphoma | DSMZ (ACC 575) |
| RL | B-NHL, diffuse large B-cell lymphoma | DSMZ (ACC 613) |
| SU-DHL-4 | B-NHL, diffuse histiocytic lymphoma | DSMZ (ACC 495) |
| DOHH-2 | refractory immunoblastic B cell lymphoma, follicular lymphoma | DSMZ (ACC 47) |
| Granta-519 | B-NHL, mantle cell lymphoma | DSMZ (ACC 342) |

All cell lines were grown in RPMI-1640 media supplemented with 10% fetal bovine serum, 2 mM glutamine and 1% penicillin-streptomycin (all reagents from Invitrogen) at 37° C. in a humidified 5% $CO_2$ incubator. Cells were passaged by diluting into fresh media twice per week and maintained between 0.2 to $1\times10^6$ cells/ml.

Example 1

Production of Murine CD37 Antibodies

An expression plasmid pSRa-CD37 was constructed that contained the entire CD37 coding sequence (CDS) flanked by XbaI and BamHI restriction sites that allowed expression of human CD37. 300-19 cells, a pre-B cell line derived from a Balb/c mouse (M. G. Reth et al. 1985, *Nature,* 317: 353-355), were transfected with this expression plasmid to stably express high levels of human CD37 on the cell surface and used for immunization of Balb/c VAF mice. Mice were subcutaneously immunized with approximately $5\times10^6$ CD37-expressing 300-19 cells per mouse every 2-3 weeks by standard immunization protocols used at ImmunoGen, Inc. The immunized mice were boosted with another dose of antigen three days before being sacrificed for hybridoma generation. The spleen from the mouse was collected according to standard animal protocols and was ground between two sterile, frosted microscopic slides to obtain a single cell suspension in RPMI-1640 medium. The spleen cells were pelleted, washed, and fused with murine myeloma P3X63Ag8.653 cells (J. F. Kearney et al. 1979, *J Immunol,* 123: 1548-1550) by using polyethylene glycol-1500 (Roche 783 641). The fused cells were resuspended in RPMI-1640 selection medium containing hypoxanthine-aminopterin-thymidine (HAT) (Sigma H-0262) and selected for growth in 96-well flat-bottomed culture plates (Corning-Costar 3596, 200 μL of cell suspension per well) at 37° C. with 5% $CO_2$. After 5 days of incubation, 100 μL of culture supernatant were removed from each well and replaced with 100 μL of RPMI-1640 medium containing hypoxanthine-thymidine (HT) supplement (Sigma H-0137). Incubation at 37° C. with 5% $CO_2$ was continued until hydridoma clones were ready for antibody screening. Other techniques of immunization and hybridoma production can also be used, including those described in J. Langone and H. Vunakis (Eds., Methods in Enzymology, Vol. 121, "Immunochemical Techniques, Part I"; Academic Press, Florida) and E. Harlow and D. Lane ("Antibodies: A Laboratory Manual"; 1988; Cold Spring Harbor Laboratory Press, New York).

Hybridoma Screening and Selection

Culture supernatants from the hybridoma were screened by flow cytometry for secretion of mouse monoclonal antibodies that bind to the CD37-expressing 300-19 cells, but not to the non-transfected 300-19 cells. 100 μl of hybridoma supernatants was incubated for 3 h with either CD37-expressing 300-19 cells or the non-transfected 300-19 cells ($1\times10^5$ cells per sample) in 100 μL FACS buffer (RPMI-1640 medium supplemented with 2% normal goat serum). Then, the cells were pelleted, washed, and incubated for 1 h with 100 μL of PE-conjugated goat anti-mouse IgG-antibody (Jackson Laboratory, 6 μg/mL in FACS buffer). The cells were pelleted again, washed with FACS buffer and resuspended in 200 μL of PBS containing 1% formaldehyde. Samples were acquired using a FACSCalibur flow cytometer with the HTS multiwell sampler or a FACS array flow cytometer and analyzed using CellQuest Pro (all from BD Biosciences, San Diego, US).

The hybridoma clones that tested positive were subcloned by limiting dilution. One subclone from each hybridoma, which showed the same reactivity against CD37 as the parental cells by flow cytometry, was chosen for subsequent analysis. Stable subclones were cultured and the isotype of each secreted anti-CD37 antibody was identified using commercial isotyping reagents (Roche 1493027).

A total of 45 separate fusion experiments were conducted over the course of this investigation. A single fusion experiment routinely yielded approximately between 200 and 1000 hybridoma clones. All the resulting hybridoma clones were screened for CD37 binding by flow cytometry and a total of 184 hybridoma clones showed specific binding to CD37.

Antibody Purification

Antibodies were purified from hybridoma subclone supernatants using standard methods, such as, for example Protein A or G chromatography (HiTrap Protein A or G HP, 1 mL, Amersham Biosciences). Briefly, supernatant was prepared for chromatography by the addition of 1/10 volume of 1 M Tris/HCl buffer, pH 8.0. The pH-adjusted supernatant was filtered through a 0.22 μm filter membrane and loaded onto column equilibrated with binding buffer (PBS, pH 7.3). The column was washed with binding buffer until a stable baseline was obtained with no absorbance at 280 nm. Antibody was eluted with 0.1 M acetic acid buffer containing 0.15 M NaCl, pH 2.8, using a flow rate of 0.5 mL/min. Fractions of approximately 0.25 mL were collected and neutralized by the addition of 1/10 volume of 1M Tris/HCl, pH 8.0. The peak fraction(s) was dialyzed overnight twice against 1×PBS and sterilized by filtering through a 0.2 μm filter membrane. Purified antibody was quantified by absorbance at A280.

Protein A purified fractions were further polished using ion exchange chromatography (IEX) with quaternary ammonium (Q) chromatography for murine antibodies. Briefly, samples from protein A purification were buffer exchanged into binding buffer (10 mM Tris, 10 mM sodium chloride, pH 8.0) and filtered through 0.22 μm filer. The prepared sample was then loaded onto a Q fast flow resin (GE Lifesciences) that was equilibrated with binding buffer at a flow rate of 120 cm/hr. Column size was chosen to have sufficient capacity to bind all the MAb in the sample. The column was then washed with binding buffer until a stable baseline was obtained with no absorbance at 280 nm. Antibody was eluted by initiating a gradient from 10 mM to 500 mM sodium chloride in 20 column volume (CV). Peak fractions were collected based on absorbance measurement at 280 nm (A280). The percentage of monomer was assessed with size exclusion chromatography (SEC) on a TSK gel G3000SWXL, 7.8×300 mm with a SWXL guard column, 6.0×40 mm (Tosoh Bioscience, Montgomeryville, Pa.) using an Agilent HPLC 1100 system (Agilent, Santa Clara, Calif.). Fractions with monomer content above 95% were pooled, buffer exchanged to PBS (pH 7.4) using a TFF system, and sterilized by filtering through a 0.2 μm filter membrane. The IgG concentration of purified antibody was determined by A280 using an extinction coefficient of 1.47. Alternative methods such as ceramic hydroxyapatite (CHT) were also used to polish antibodies with good selectivity. Type II CHT resin with 40 μm particle size (Bio-Rad Laboratories) were used with a similar protocol as described for IEX chromatography. The binding buffer for CHT corresponds to 20 mM sodium phosphate, pH 7.0 and antibody was eluted with a gradient of 20-160 mM sodium phosphate over 20 CV.

Example 2

Binding Characterization by Flow Cytometry

Figure 1:
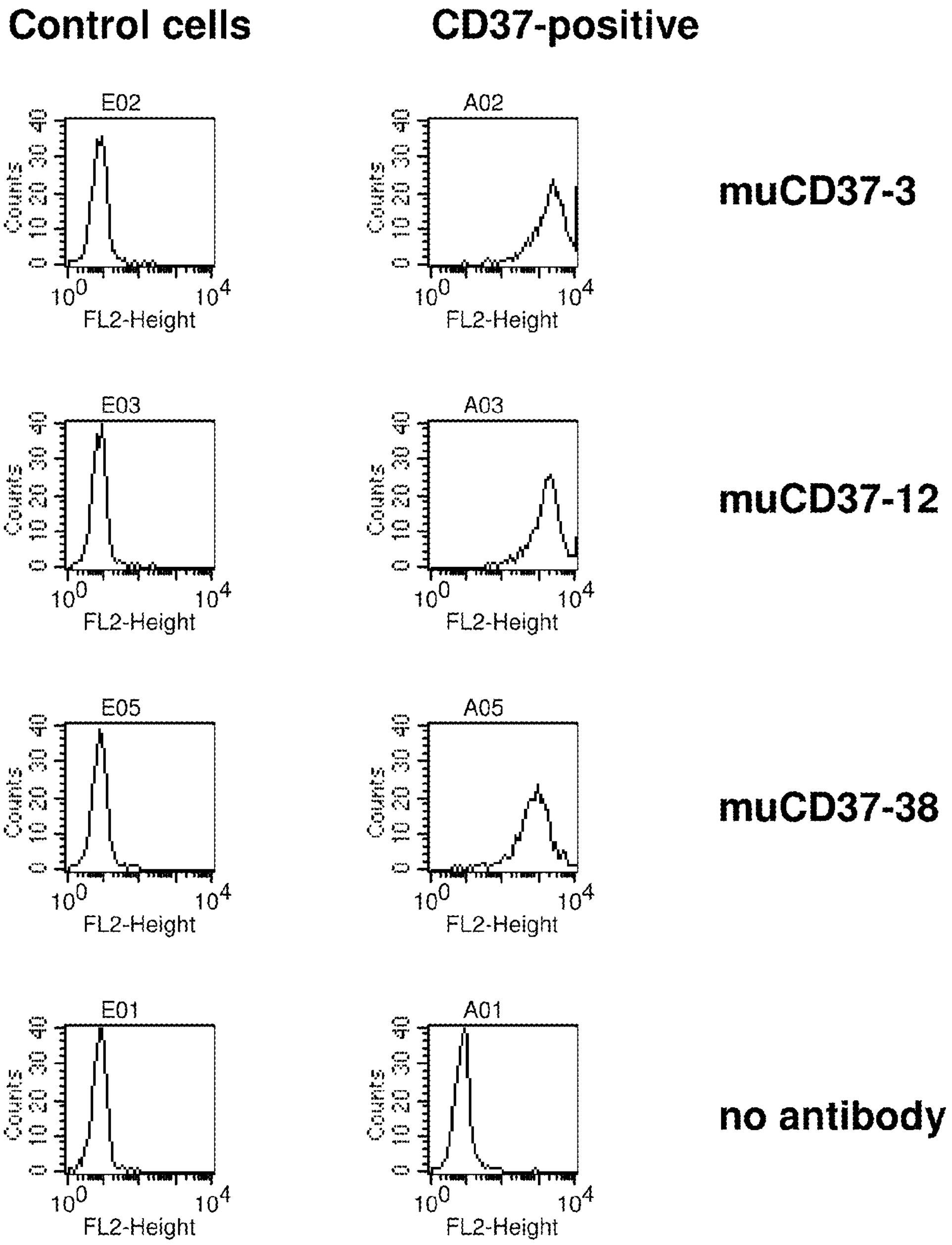
Figure 2:
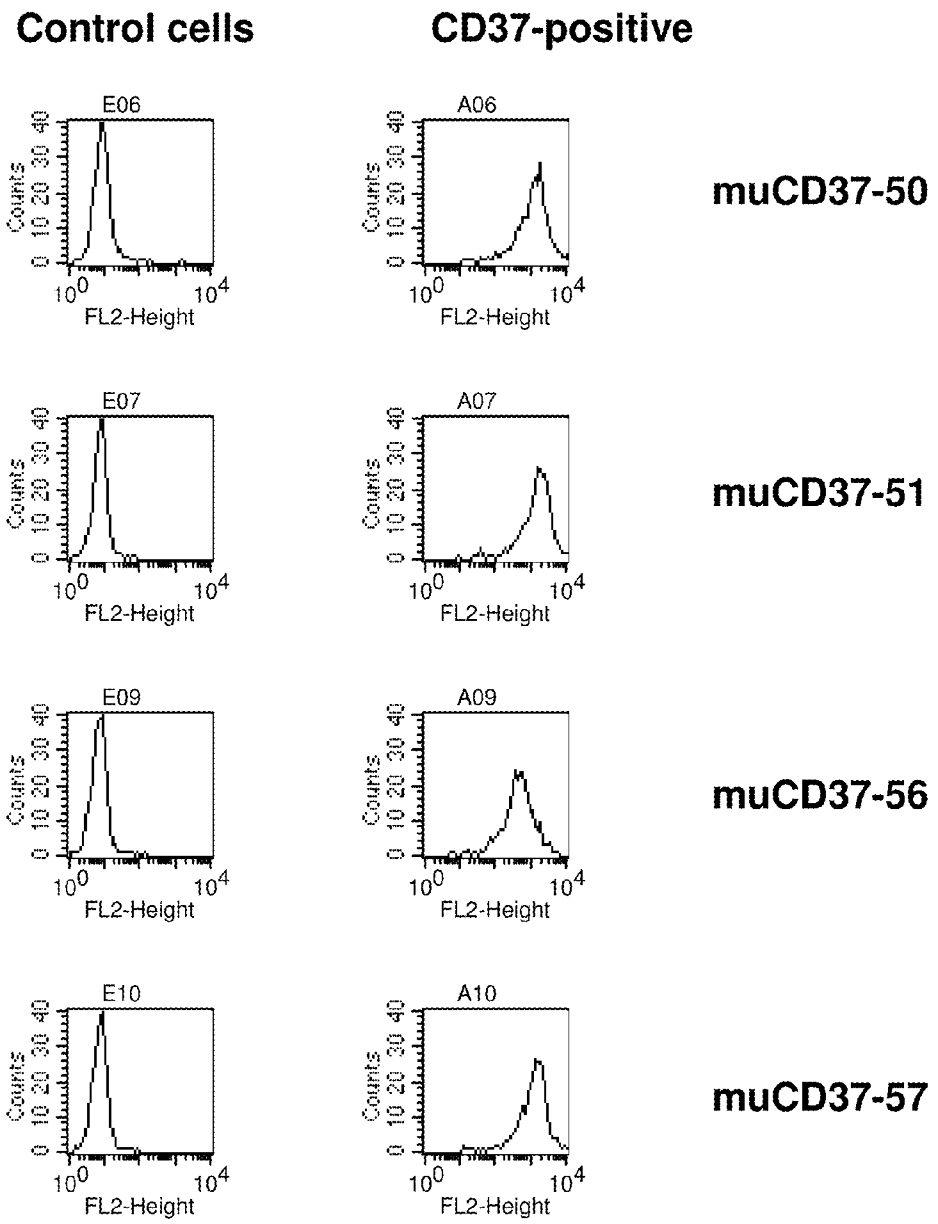

Binding specificity was tested by flow cytometry using purified antibodies. FACS histograms demonstrating the binding of muCD37-3, muCD37-12, muCD37-38, muCD37-50, muCD37-51, muCD37-56 and muCD37-57 to CD37-expressing 300-19 cells and the absence of binding to the parental 300-19 cells are shown in FIG. 1 and FIG. 2. All murine antibodies were incubated for 3 h with either CD37-expressing 300-19 cells or the non-transfected 300-19 cells ($1\times10^5$ cells per sample) in 100 μL FACS buffer (RPMI-1640 medium supplemented with 2% normal goat serum). Then, the cells were pelleted, washed, and incubated for 1 h with 100 μL of FITC-conjugated goat anti-mouse IgG-antibody (Jackson Laboratory, 6 μg/mL in FACS buffer). The cells were pelleted again, washed with FACS buffer and resuspended in 200 μL of PBS containing 1% formaldehyde. Samples were acquired using a FACSCalibur flow cytometer with the HTS multiwell sampler or a FACS array flow cytometer and analyzed using CellQuest Pro (all from BD Biosciences, San Diego, US).

The FACS histograms of CD37-expressing 300-19 cells incubated with muCD37-3, muCD37-12, muCD37-38, muCD37-50, muCD37-51, muCD37-56 or muCD37-57 showed a fluorescence shift, while parental 300-19 cells did not. Also, no significant fluorescence shift was detected when either cell lines was incubated only with FITC-conjugated goat anti-mouse IgG-antibody alone (FIG. 1 bottom).

Figure 3:
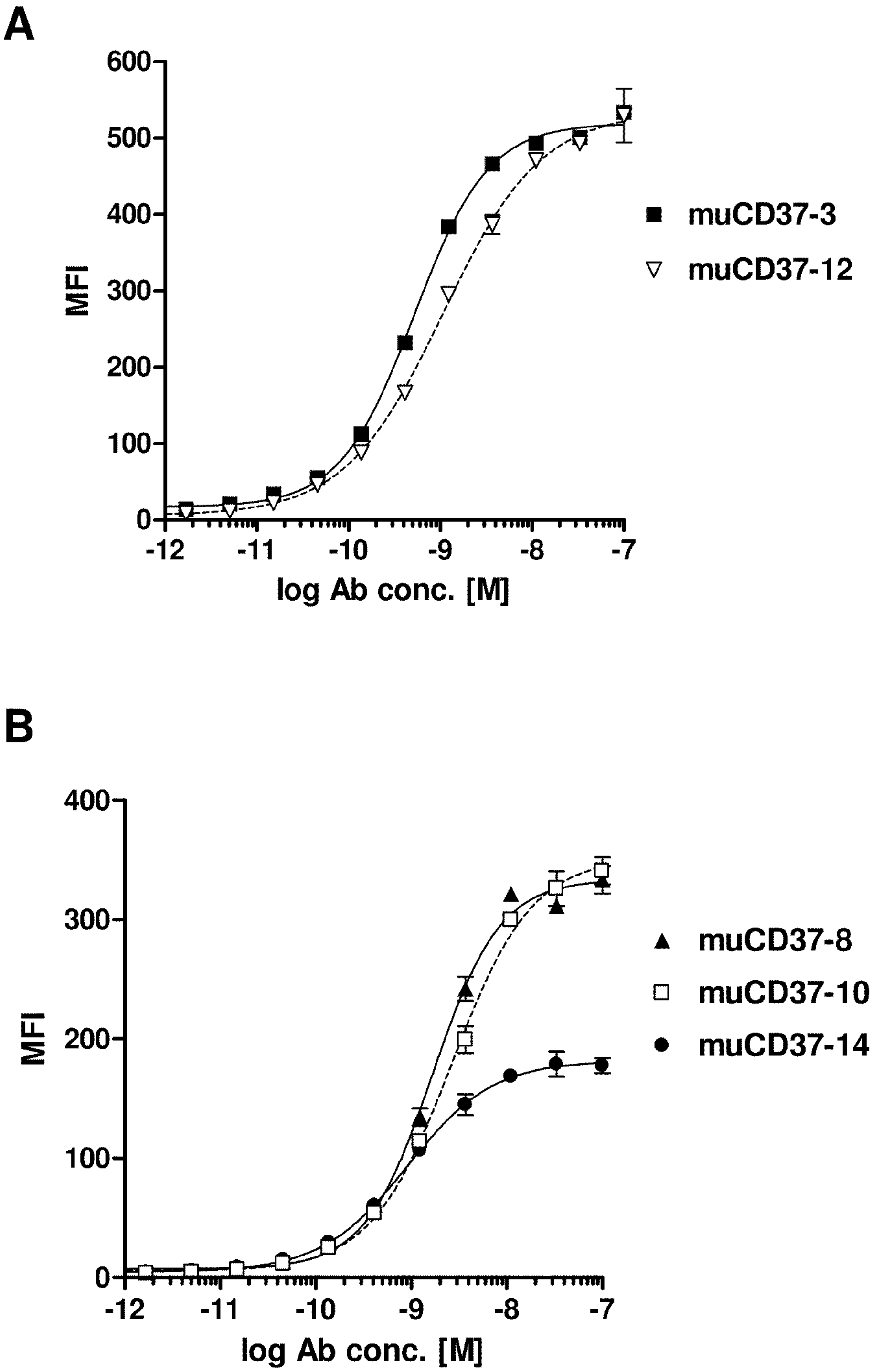

To verify that the antibodies can also bind to endogenously expressed CD37, binding experiments were performed with CD37-positive WSU-DLCL-2 lymphoma cells and the muCD37-3, muCD37-12, muCD37-8, muCD37-10 or muCD37-14 antibodies. WSU-DLCL-2 cells were incubated with varying concentrations of murine antibodies and processed as described above for flow cytometry analysis. Data analysis was performed using CellQuest Pro (BD Biosciences, San Diego, US) and for each sample the mean fluorescence intensity for FL1 (MFI) was exported and plotted against the antibody concentration in a semi-log plot (FIG. 3). A dose-response curve was generated by non-linear regression and the EC50 value of each curve, which corresponds to the apparent dissociation constant (Kd) of each antibody, was calculated using GraphPad Prism v4 (GraphPad software, San Diego, Calif.). A strong shift in fluorescence was observed for all antibodies tested and the Kd values correspond to 0.52 nM, 1.7 nM, 2.7 nM, 1.1 nM or 0.91 nM for muCD37-3, muCD37-8, muCD37-10, muCD37-12 or muCD37-14 antibodies, respectively.

Likewise, strong binding was also observed when CD37-positive BJAB lymphoma cells were used for the same flow cytometry assay described above. The Kd values were calculated as described above and correspond to 0.2 nM, 0.4 nM, 0.6 nM, 0.4 nM and 1 nM for muCD37-3, muCD37-38, muCD37-50, muCD37-51, muCD37-56 and muCD37-57, respectively.

Example 3

Pro-Apoptotic Activity of Murine Antibodies

The murine anti-CD37 antibodies induced apoptosis of Ramos and Raji lymphoma cell lines. The degree of apoptosis was measured by flow cytometry analysis after staining with FITC conjugates of Annexin-V (Invitrogen) and with TO-PRO-3 (Invitrogen). In healthy, normal cells, phosphatidylserine is expressed on the inside of the membrane bilayer, and the transition of phosphatidylserine from the inner to the outer leaflet of the plasma membrane is one of the earliest detectable signals of apoptosis. Annexin V binds phosphatidylserine on the outside but not on the inside of the cell membrane bilayer of intact cells. The degree of Annexin V binding is therefore an indicator of the induction of apoptosis. TO-PRO-3 is a monomeric cyanine nucleic acid stain that can only penetrate the plasma membrane when the membrane integrity is breached, as occurs in the later stages of apoptosis. Three populations of cells are distinguishable in two-color flow cytometry: Non-apoptotic cells (Annexin-V negative and TO-PRO-3 negative), early apoptotic cells (Annexin-V positive and TO-PRO-3 negative) and necrotic cells or late apoptotic cells (Annexin-V positive and TO-PRO-3 positive).

Exponentially growing cells were plated at about $2\times10^5$ cells/mL in 24-well plates in RMPI-1640 medium supplemented with 10% fetal bovine serum (FBS), 2 mM L glutamine, and 50 μg/mL gentamycin (denoted below as complete RMPI-1640 medium). Cells were generally grown in complete RMPI-1640 medium, unless stated otherwise. Cells were incubated with 10 nM of anti-CD37 antibodies for 20 to 24 h at 37° C. in a humidified 5% $CO_2$ incubator. The cells were then pelleted, washed twice with 500 μl PBS, resuspended in 100 μL binding buffer (10 mM Hepes-NaOH, pH 7.4, 140 mM NaCl, 2.5 mM CaCl2), and stained with 5 μL of Annexin V-FITC for 15 min on ice. Then, 400 μL of binding buffer with 1 μM of TO-PRO-3 was added to the mix, and the cell-associated fluorescence of FITC and TO-PRO-3 was immediately measured by flow cytometry. Five thousand events were collected for each sample. The dot plots for fluorescence of TO-PRO-3 (FL4-H; y-axis) and fluorescence of Annexin V-FITC (FL1-H; x-axis) were generated using BD CellQuest software.

The percentage of Annexin-V positive cells (includes both TO-PRO-3 positive and negative cells) were determined for each sample from these plots and are shown in FIG. 4 for Ramos cells. Several antibodies isolated from our antibody screen were tested for pro-apoptotic activity in comparison to rituximab. Unexpectedly, some of the isolated murine anti-CD37 antibodies, such as muCD37-3 and muCD37-12, showed very strong pro-apoptotic activity. Approximately 39% of Ramos cells exposed to muCD37-3 and 46% of Ramos cells exposed to muCD37-12 were Annexin-V positive. In contrast, treatment with the anti-CD20 antibody rituximab resulted in only 13% of Annexin-V positive cells, while untreated control samples contained 5% Annexin-V positive cells. Several of the isolated murine anti-CD37 antibodies did not show any pro-apoptotic activity. For example, treatment of Ramos cells with muCD37-8, muCD37-10 or muCD37-14 resulted in a minor or no increase in the percentage of Annexin-V positive as compared to untreated cells. This is in spite of their comparable binding affinity to CD37 as seen in FIG. 3.

Additional antibodies were isolated and screened for their ability to induce apoptosis in Ramos cells. Of many antibodies isolated that bound CD37 with high affinity, only some had pro-apoptotic activity. The results of a Annexin-V assay are shown in FIG. 4B. The murine antibodies muCD37-38, muCD37-50, muCD37-51, muCD37-56 and muCD37-57 were able to induce apoptosis and resulted in 38-45% of Annexin-V positive Ramos cells as compared with 5% in untreated control samples. Similar to the previous assay, treatment with the anti-CD20 antibody rituximab resulted in only 18% Annexin-V positive cells.

In addition, the murine antibodies were tested their ability to induce apoptosis in Raji lymphoma cells. As seen for Ramos cells, of the many antibodies isolated that bound CD37 with high affinity, only some had pro-apoptotic activity. Treatment with muCD37-3 or muCD37-12 resulted in 36% or 49% Annexin-V positive cells, respectively. In contrast, treatment with the anti-CD20 antibody rituximab resulted in only 20% of Annexin-V positive cells, while untreated control samples contained 4% Annexin-V positive cells.

Likewise, approximately 60% of Raji cells treated with muCD37-3, muCD37-38, muCD37-50, muCD37-51, muCD37-56 or muCD37-57 were Annexin-V positive cells compared to 15% of untreated cells.

Example 4

Proliferation Assays

The ability of anti-CD37 antibodies to inhibit cell growth was measured using in vitro cytotoxicity assays. Target cells were plated at 5,000 cells per well in 100 μL in complete RPMI media (RPMI-1640, 10% fetal bovine serum, 2 mM glutamine, 1% penicillin-streptomycin, all reagents from Invitrogen). Antibodies were diluted into complete RPMI media using 3-fold dilution series and 100 μL were added per well. The final concentration typically ranged from $3\times10^{-8}$ M to $4.6\times10^{-12}$ M. Cells were incubated at 37° C. in a humidified 5% $CO_2$ incubator for 4 to 5 days. Viability of remaining cells was determined by colorimetric WST-8 assay (Dojindo Molecular Technologies, Inc., Rockville, Md., US). WST-8 is reduced by dehydrogenases in living cells to an orange formazan product that is soluble in tissue culture medium. The amount of formazan produced is directly proportional to the number of living cells. WST-8 was added to 10% of the final volume and plates were incubated at 37° C. in a humidified 5% CO2 incubator for an additional 2-4 hours. Plates were analyzed by measuring the absorbance at 450 nm (A450) in a multiwell plate reader. Background A450 absorbance of wells with media and WST-8 only was subtracted from all values. The percent viability was calculated by dividing each treated sample value by the average value of wells with untreated cells. Percent viability=100*(A450 treated sample−A450 background)/(A450 untreated sample−A450 background). The percent viability value was plotted against the antibody concentration in a semi-log plot for each treatment.

Figure 5:
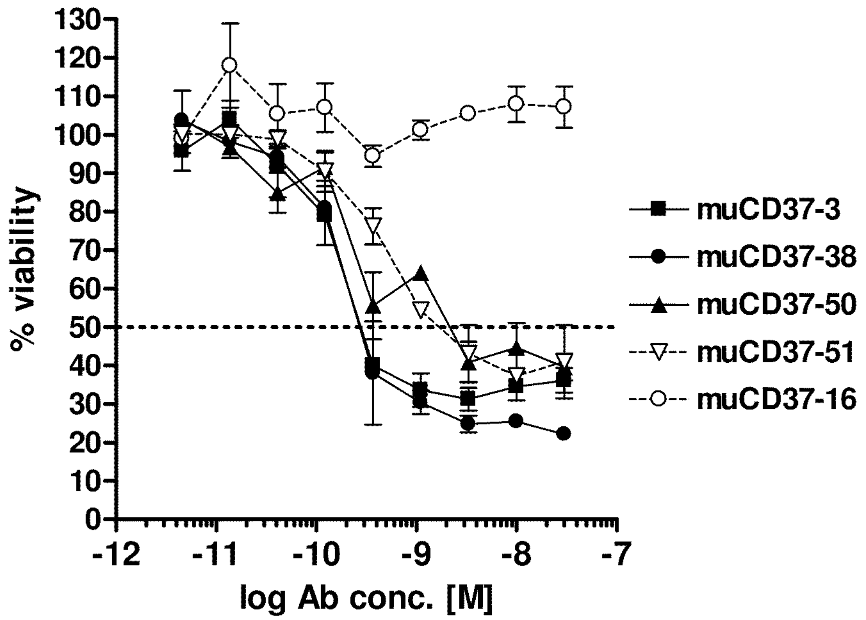
FIG. 5 depicts the results from WST-8 proliferation assays on SU-DHL-4 lymphoma cells incubated with varying concentrations of muCD37-3, muCD37-38, muCD37-50, muCD37-51 and muCD37-16 antibodies for 5 days.

The results from a typical proliferation assay using murine CD37 antibodies and SU-DHL-4 lymphoma cells are presented in FIG. 5. It is apparent, that several murine antibodies were able to inhibit proliferation of SU-DHL-4 cells substantially and in a dose-dependent manner, while others had no such effect. For example, treatment with muCD37-3 reduced the cell viability to 34% at the highest antibody concentration tested with an EC50 of 0.17 nM. Similarly, treatment with muCD37-38 reduced the cell viability to 25% at the highest antibody concentration tested with an EC50 of 0.19 nM. Likewise, treatment with muCD37-50 or muCD37-51 reduced the cell viability to 38% at the highest antibody concentration tested with an EC50 of 0.25 nM or 0.5 nM, respectively. In contrast, treatment with for example CD37-16 did not reduce cell viability in a dose-dependent manner.

Example 5

Cloning and Sequencing of the VL and VH Regions of the CD37-3 Antibody

Total cellular RNA was prepared from $5\times10^6$ cells of the CD37-3 hybridoma using an RNeasy kit (QIAgen) according to the manufacturer's protocol. cDNA was subsequently synthesized from total RNA using the SuperScript II cDNA synthesis kit (Invitrogen).

The procedure for the first round degenerate PCR reaction on the cDNA derived from hybridoma cells was based on methods described in Wang et al. ((2000) *J Immunol Methods.* 233:167-77) and Co et al. ((1992) *J Immunol.* 148:1149-54). VH sequences were amplified by PCR using the following degenerate primers: EcoMH1 CTTCCGGAATTCSARGTNMAGCTGSAGSAGTC (SEQ ID NO:171), EcoMH2 CTTCCGGAATTCSARGTNMAGCTGSAGSAGTCWGG (SEQ ID NO:172) and BamIgG1 GGAGGATCCATAGACAGATGGGGGTGTCGTTTTGGC (SEQ ID NO:173). VL sequences were amplified by PCR using the following degenerate primers: SacIMK GGAGCTCGAYATTGTGMTSACMCARWCTMCA (SEQ ID NO:174) and HindKL TATAGAGCTCAAGCTTGGATGGTGGGAAGATGGATACAGTTGGTGC (SEQ ID NO:175). (Mixed bases are defined as follows: N=G+A+T+C, S=G+C, Y=C+T, M=A+C, R=A+G, W=A+T). The PCR reaction mixtures were then run on a 1% low melt agarose gel, the 300 to 400 bp bands were excised, purified using Zymo DNA mini columns, and sent to Agencourt Biosciences for sequencing. The respective 5' and 3' PCR primers were used as sequencing primers to generate the variable region cDNAs from both directions. The amino acid sequences of VH and VL regions were predicted from the DNA sequencing results.

Since the degenerate primers used to clone the VL and VH cDNA sequences alters the 5' end sequences, additional sequencing efforts were needed to verify the complete sequences. The preliminary cDNA sequences were used to search the NCBI IgBlast site (http://www.ncbi.nlm.nih.gov/igblast/) for the murine germline sequences from which the antibody sequences are derived. PCR primers were then designed to anneal to the germline linked leader sequence of the murine antibody so that this new PCR reaction would yield a complete variable region cDNA sequence, unaltered by the PCR primers. The PCR reactions, band purifications, and sequencing were performed as described above.

Mass Determination for Sequence Confirmation

The cDNA sequence information for the variable region was combined with the germline constant region sequence to obtain full length antibody cDNA sequences. The molecular weights of the heavy chain and light chain were then calculated and compared with the molecular weights obtained by LC/MS analyses of the murine CD37-3 antibody. The molecular weight measurements are consistent with the cDNA sequences for both the CD37-3 light and heavy chain.

Chimerization

The variable sequence for the light chain variable region is cloned into EcoRI and BsiWI sites in the pchCD37-3LCZ plasmid. The heavy chain variable region is cloned into the HindIII and Apa1 sites in the pchCD37-3HCN plasmid. Equivalent plasmids were constructed for chCD37-12. These plasmids were used to express chimeric antibodies in HEK-293T cells using a standard calcium phosphate procedure (BD Biosciences, CalPhos Mammalian Transfection Kit, Cat #631312). Supernatant was purified using standard Protein A chromatography procedures as described above, but the polishing chromatography steps were performed using either carboxymethyl (CM) fast flow ion exchange (IEX) resin (GE Lifesciences) and 10 mM potassium phosphate, 10 mM sodium chloride binding buffer (pH 7.5) or the alternative CHT methods described above.

Example 6

Antibody Humanization

The CD37-3 and huCD37-50 antibodies were humanized following resurfacing methods previously described, such as, for example in Roguska et al., Proc. Natl. Acad. Sci., USA, 91(3):969-973 (1994) and Roguska et al., Protein Eng. 9(10): 895-904 (1996), which are incorporated in their entirety herein by reference. Resurfacing generally involves identification of the variable region framework surface residues in both light and heavy chains and replacing them with human equivalents. The murine CDR's are preserved in the resurfaced antibody. Exemplary CDRs of CD37-3 and CD37-50 are defined as indicated in Table 11. In addition to the heavy chain CDR2 definition employed for resurfacing, the table provides exemplary Kabat defined heavy chain CDR2's for both the murine and human CD37-3 and CD37-50. The underlined sequence marks the portion of the Kabat heavy chain CDR2 not considered a CDR for resurfacing.

TABLE 11

| CD37-3 CDR's | CD37-50 CDR's |
|---|---|
| Light Chain | Light Chain |
| CDR1:<br>RASENIRSNLA<br>(SEQ ID NO: 28) | CDR1:<br>SATSSVTYMH<br>(SEQ ID NO: 37) |

TABLE 11-continued

| CD37-3 CDR's | CD37-50 CDR's |
|---|---|
| CDR2: VATNLAD (SEQ ID NO: 29) | Murine CDR2: DTS*K*LPY (SEQ ID NO: 38) |
| CDR3: YWGTTWT (SEQ ID NO: 30) | Human CDR2: DTS*N*LPY (SEQ ID NO: 40) |
| | CDR3: QQWSDNPPT (SEQ ID NO: 39) |
| Heavy Chain | Heavy Chain |
| CDR1: TSGVS (SEQ ID NO: 4) | CDR1: SGFAWH (SEQ ID NO: 13) |
| CDR2: VIWGDGSTN (SEQ ID NO: 5) | CDR2: YILYSGSTV (SEQ ID NO: 14) |
| CDR3: GGYSLAH (SEQ ID NO: 6) | CDR3: GYYGYGAWFAY (SEQ ID NO: 15) |
| Kabat Defined CD37-3 HC CDR2 | Kabat Defined CD37-50 HC CDR2 |
| Murine HC CDR2: VIWGDGSTNYHSALKS (SEQ ID NO: 176) | Murine HC CDR2: YILYSGSTVYSPSLKS (SEQ ID NO: 178) |
| Human HC CDR2: VIWGDGSTNYHPSLKS (SEQ ID NO: 177) | Human HC CDR2: YILYSGSTVYSPSLKS (SEQ ID NO: 179) |

The CD37-3 and CD7-50 light and heavy chain CDR's as defined for the resurfacing are given by way of example in Table 11. Lysine 53 in murine CD37-50 light chain CDR2 was replaced with asparagine in humanized CD37-50 (shown in italic) so both versions of the LC CDR2 are given. The Kabat definition for heavy chain CDR2 is also given for both the murine and human CD37-3. The underlined sequence marks the portion of the Kabat heavy chain CDR2 not considered a CDR for resurfacing.

Surface residue positions are defined as any position with its relative accessibility of 30% or greater (Pedersen J. T. et. Al, J. Mol. Biol. 1994; 235: 959-973). Surface residues are then aligned with human germline surface sequences to identify the most homologous human surface sequence. For CD37-3, the human germline sequences used as the replacement surfaces were IGKV1/OR2-0*01 and IGHV4-34*09 for VL and VH, respectively. For CD37-50, the human germline sequences used as the replacement surfaces were IGKV3/OR2-268*01 and IGHV4-31*03 for VL and VH, respectively. As can be seen from the lists in FIG. 6, a total of seven surface residues in the light chain and seven in the heavy chain were replaced with the human counterparts in CD37-3. As seen in FIG. 7 for CD37-50, the total surface residues that were replaced with human counterparts are seven and five in VL and VH, respectively. In CD37-3, the heavy chain residue 61 is in close proximity to CDR-H2 and since its substitution to the human residue proline might result in reduced binding affinity, a second resurfaced version was generated with murine serine residue retained. Since these antibodies were being tested as cytotoxic conjugates, the CD37-50 light chain CDR2 lysine 53 was replaced with an asparagine to avoid the concerns that lysine conjugation could impact binding affinity. FIG. 8 shows the alignment of the resurfaced sequences for the CD37-3 and CD37-50 variable domain of both light chain and heavy chain with their murine counterparts.

Recombinant Expression of huCD37-3 Antibody

The variable region sequences for huCD37-3 and CD37-50 were codon-optimized and synthesized by Blue Heron Biotechnology. The sequences are flanked by restriction enzyme sites for cloning in-frame with the respective constant sequences in single chain mammalian expression plasmids. The light chain variable region is cloned into EcoRI and BsiWI sites in the pAbKZeo plasmid. The heavy chain variable region is cloned into the HindIII and Apa1 sites in the pAbG1Neo plasmid. These plasmids can be used to express the recombinant antibodies in either transient or stable mammalian cell transfections. Transient transfections to express recombinant antibodies in HEK 293T cells were performed using a modified PEI procedure (Durocher, Y. et al., *Nucleic Acids Res.* 30:E9 (2002)). Supernatant was purified by Protein A and polishing chromatography steps using standard procedures as described above for chimerized antibodies.

Expression of TRU-016

In order to compare the activity of the isolated anti-CD37 antibodies, previously identified anti-CD37 antibodies were cloned and expressed. The DNA sequence for the anti-CD37 SMIP was drawn from US2007/0059306 using SEQ ID 51. The sequence was flanked by HindIII and Xho1 restriction enzyme sites for cloning into the pAbG1Neo mammalian expression plasmids. Expression and purification was carried out as described for huCD37-3 above.

Example 7

Binding Affinity of Chimeric Antibodies

The chimeric antibodies chCD37-3 and chCD37-12 were assayed for their binding affinity to Ramos cells in comparison to their murine counterparts. Flow cytometry binding assays using Ramos cells and muCD37-3, chCD37-3, muCD37-12 and chCD37-12 antibodies were carried out and analyzed as described in Example 2 using secondary FITC-conjugated goat-anti-murine and -anti-human antibodies. FIG. 9A depicts the dose-response curves generated by non-linear regression for each antibody. The value for the apparent dissociation constant (Kd) of each antibody was calculated using GraphPad Prism v4 (GraphPad software, San Diego, Calif.). It is apparent that chimerization did not greatly affect the binding affinity of either antibody as the Kd for muCD37-3, chCD37-3, muCD37-12 and chCD37-12 corresponds to 0.4 nM, 0.8 nM, 0.8 nM and 1.2 nM, respectively.

Binding Affinity of huCD37-3v1.0 and huCD37-3v1.01

Flow cytometry binding assays using BJAB cells and a competitive binding format were used to evaluate binding affinity of chimeric and humanized versions of CD37-3. BJAB cells were incubated with a 1 nM concentration of PE-labeled muCD37-3 antibody and competition was measured by adding varying amounts of muCD37-3, chCD37-3, huCD37-3v1.0 or huCD37-3v1.01. The samples were incubated for 3 hrs at 4° C. Then, the cells were pelleted, washed with FACS buffer and resuspended in 200 μL of PBS containing 1% formaldehyde. Samples were acquired using a FACSCalibur flow cytometer with the HTS multiwell sampler and analyzed using CellQuest Pro (all from BD Biosciences, San Diego, US). The resulting mean PE fluorescence was plotted against the amount of competing antibody used in a semi-log plot. FIG. 9B depicts the dose-response curves generated by non-linear regression for each antibody. The value for the apparent dissociation constant (Kd) of each antibody was calculated using GraphPad Prism v4 (GraphPad software, San Diego, Calif.). It is apparent that chimerization or humanization did not affect the binding affinity of CD37-3 as all version compete equally well for binding with the murine parent antibody. The EC50 of competition binding for muCD37-3, chCD37-3, huCD37-3v1.0 or huCD37-3v1.01 corresponds to 0.8 nM, 0.7 nM, 1 nM and 0.6 nM, respectively.

Binding Affinity of Humanized Antibodies

The humanized antibodies huCD37-38, huCD37-50, huCD37-51, huCD37-56 and chCD37-57 were assayed for their binding affinity to BJAB cells in comparison to their murine counterparts. Flow cytometry binding assays were carried out using secondary FITC-conjugated goat-anti-murine and -anti-human antibodies, analyzed as described in Example 2 and dose-response curves were generated by non-linear regression for each antibody. The value for the apparent dissociation constant (Kd) of each antibody was calculated using GraphPad Prism v4 (GraphPad software, San Diego, Calif.). It is apparent that humanization did not greatly affect the binding affinity of any antibody. The Kd for muCD37-3 and huCD37-3 corresponds to 0.2 nM, while the Kd for muCD37-38 and huCD37-38 corresponds to 0.4 nM and 0.3 nM, respectively. Similarly, the Kd for muCD37-50 and huCD37-50 corresponds to 0.6 nM and 0.2 nM, respectively, while the Kd for muCD37-51 and huCD37-51 corresponds to 0.6 nM and 0.8 nM, respectively. Finally, the Kd for muCD37-56 and huCD37-56 corresponds to 0.4 nM and 0.2 nM, respectively, while the Kd for muCD37-57 and huCD37-57 corresponds to 1.0 nM and 0.3 nM, respectively.

Example 8

Expression of Macaque CD37

The CD37 AA sequence of macaque CD37 was obtained from Genbank (G1: 718718). The sequence was codon-optimized and synthesized by Blue Heron Biotechnology. An expression plasmid pSRa-CD37mac was constructed that contained the entire CD37 coding sequence (CDS) from macaque flanked by XbaI and BamHI restriction sites that allowed expression of macaque CD37. 300-19 cells, a pre-B cell line derived from a Balb/c mouse (M. G. Reth et al. 1985, *Nature,* 317: 353-355), was transfected with this expression plasmid to stably express macaque CD37 on the cell surface.

Binding Affinity of Murine Antibodies to Macaque CD37

The murine antibodies muCD37-3, muCD37-12, muCD37-38, huCD37-50, muCD37-51, muCD37-56 and muCD37-57 were assayed for their ability to bind to 300-19/CD37mac cells expressing macaque CD37. Flow cytometry binding assays were carried out using secondary FITC-conjugated goat-anti-murine or goat-anti-human antibodies, analyzed as described in Example 2. Binding was compared to the previously described anti-CD37 antibody WR17 and the anti-CD37 SMIP TRU-016. As can be seen from FIG. 10A, several isolated anti-CD37 antibodies, muCD37-38, huCD37-50, muCD37-51, muCD37-56 and muCD37-57 can bind to the macaque derived CD37 antigen. In contrast, muCD37-3, muCD37-12, the previously described anti-CD37 antibody WR17 and the anti-CD37 SMIP TRU-016 are unable to bind the macaque derived CD37 antigen.

Binding Affinity of Humanized Antibodies to Macaque CD37

The humanized antibodies huCD37-38, huCD37-50, huCD37-51, huCD37-56 and huCD37-57 were assayed for their binding affinity to 300-19/CD37mac cells expressing macaque CD37. Flow cytometry binding assays were carried out using secondary FITC-conjugated goat-anti-human antibodies, analyzed as described in Example 2 and dose-response curves were generated by non-linear regression for each antibody. The value for the apparent dissociation constant (Kd) of each antibody was calculated using GraphPad Prism v4 (GraphPad software, San Diego, Calif.). It is apparent from FIG. 10B, that several isolated humanized antibodies bind to macaque CD37 while huCD37-3 does not. The Kd value for huCD37-38, huCD37-50, huCD37-51, huCD37-56 and huCD37-57 correspond to 1.1 nM, 1.8 nM, 14 nM, 5 nM, and 2 nM, respectively. Therefore, humanization does not affect the binding specificity of the isolated antibodies.

Example 9

Pro-Apoptotic Activity of Chimeric and Humanized Antibodies

The pro-apoptotic activity of chimeric and humanized antibodies was evaluated on Ramos cells. Cells were incubated with 10 nM concentration of antibodies or an huIgG isotype control antibody for 20 hrs followed by Annexin-V-FITC and TO-PRO-3 staining and flow cytometry analysis. ChCD37-12 retained strong pro-apoptotic activity of muCD37-12. Approximately 40% of Ramos cells are Annexin-V positive after treatment with either muCD37-12 or chCD37-12 antibody as compared to 4% of untreated control cells. Similarly, approximately 40% of Ramos cells are Annexin-V positive after treatment with huCD37-3, huCD37-38, huCD37-50, huCD37-51, huCD37-56 or huCD37-57 antibody as compared to 4% of isotype control treated or untreated cells. In contrast, treatment with the anti-CD20 antibody rituximab resulted in only 13% of Annexin-V positive cells. This result demonstrates that the strong pro-apoptotic activity of the murine anti-CD37 antibodies isolated here is retained by the chimeric or humanized antibodies derived from them. Therefore, the unique functional property of this group of anti-CD37 antibodies, strong pro-apoptotic activity in the absence of cross-linking, is not negatively affected by chimerization or humanization.

Pro-Apoptotic Activity of huCD37-3 and TRU-016

The pro-apoptotic activity of huCD37-3 against Ramos and Raji lymphoma cells was compared to the anti-CD37 SMIP TRU-016. TRU-016 has been described as a compound with no pro-apoptotic activity unless cross-linked with a secondary antibody. It is apparent that exemplary anti-CD37 antibodies huCD37-3 and chCD37-38 have much stronger pro-apoptotic activity against both lymphoma cell lines. Treatment with huCD37-3 or chCD37-38 resulted in 40% or 49% Annexin-V positive Ramos cells, as compared to 3% of untreated control cells. Rituximab treatment resulted in only 15% Annexin-V positive Ramos cells. In contrast, TRU-016 treatment did not increase the percentage of Annexin-V positive Ramos cells. Likewise, Treatment with huCD37-3 or chCD37-38 resulted in 34% or 30% Annexin-V positive Raji cells, as compared to 7% of untreated control cells. Rituximab treatment resulted in only 19% Annexin-V positive Raji cells. In contrast, TRU-016 treatment did not increase the percentage of Annexin-V positive Ramos cells.

Dose Response for Pro-Apoptotic Activity of Humanized Antibodies

Varying amounts of each antibody were incubated with Ramos cells for 20 hrs followed by Annexin-V-FITC and TO-PRO-3 staining and flow cytometry analysis. The percentage of Annexin-V positive cells was plotted against the antibody concentration in a semi-log plot, and EC50 values were calculated from curves fitted using non-linear regression analysis. It is apparent that all humanized antibodies have strong pro-apoptotic activity with a maximum percentage of Annexin-V positive cells of at least 40%. FIG. 11. The EC50 for this activity corresponds to 0.08, 0.08 and 0.11 nM for huCD37-3, huCD37-38 and huCD37-50, respectively. In addition, the EC50 for this activity corresponds to 0.41, 0.57 and 1.01 nM for huCD37-51, huCD37-56 and huCD37-57, respectively. In contrast, treatment with the anti-CD20 antibody rituximab resulted in a maximum percentage of Annexin-V positive cells of only 15% compared with 4% of cells treated with isotype control antibody.

Example 10

Proliferation Assays for Chimeric and Humanized Anti-CD37 Antibodies

The ability of chimeric and humanized anti-CD37 antibodies to inhibit cell growth was measured using in vitro cytotoxicity assays as described in Example 4. The results from a typical proliferation assay using SU-DHL-4 and DOHH-2 lymphoma cells are presented in FIG. 12. It is apparent, that all antibodies were able to inhibit proliferation of SU-DHL-4 cells substantially and in a dose-dependent manner. For example, treatment with muCD37-3 reduced the viability of SU-DHL-4 cells to 35% with an EC50 of 0.07 nM. Similarly, treatment with chCD37-3, huCD37-3v1.0 or huCD37-3v1.01 reduced the viability of SU-DHL-4 cells to approximately 30% at the highest antibody concentration tested with an EC50 of 0.03 nM, 0.06 nM or 0.03 nM, respectively. Likewise, all antibodies were able to inhibit proliferation of DOHH-2 follicular lymphoma cells substantially and in a dose-dependent manner. For example, treatment with muCD37-3 reduced the viability of DOHH-2 cells to 45% with an EC50 of 0.05 nM. Similarly, treatment with chCD37-3, huCD37-3v1.0 or huCD37-3v1.01 reduced the viability of DOHH-2 cells to approximately 35% with an EC50 of 0.06 nM, 0.07 nM or 0.05 nM, respectively. This result demonstrates that the various version of the CD37-3 antibody have similar anti-proliferative activity that is not affected by chimerization or humanization.

Additional humanized anti-CD37 antibodies were tested in similar in vitro cytotoxicity assays. All humanized antibodies tested were able to inhibit proliferation of SU-DHL-4 cells substantially and in a dose-dependent manner. For example, treatment with huCD37-38 reduced the viability of SU-DHL-4 cells to 24% with an EC50 of 0.42 nM, while treatment with huCD37-50 reduced the viability of SU-DHL-4 cells to 31% with an EC50 of 0.39 nM. In contrast, treatment with the anti-CD20 antibody rituximab reduced the viability of SU-DHL-4 cells to 35% with an EC50 of 1.6 nM. In addition, treatment with huCD37-51 or huCD37-56 reduced the viability of SU-DHL-4 cells to 24% with an EC50 of 0.60 nM or 0.68 nM, respectively. Furthermore, treatment with huCD37-57 reduced the viability of SU-DHL-4 cells to 31% with an EC50 of 0.42 nM. Treatment with an isotype control antibody did not have an effect on the viability of SU-DHL-4 cells.

Anti-Proliferative Activity of huCD37-3 in Comparison to Other Antibodies

To further characterize the anti-proliferative activity of the isolated anti-CD37 antibodies, we compared the effect of the exemplary huCD37-3 antibody to that of the anti-CD37 SMIP TRU-16 compound. Immunohistochemistry using tumor microarrays confirmed that CD37 and CD20 exhibited similar expression patterns and prevalances in subtypes of NHL. See Table 12 below. Thus, comparisons were also made to the anti-CD20 antibody rituximab. The panel of cell lines included Granta-519, SU-DHL-4, Namalwa and Daudi lymphoma cells. FIG. 13.

TABLE 12

CD37 staining on lymphoma tumor microarrays in comparison to CD20 staining.

| Tumor histology | # of pos. cores (≥1 hetero) CD37 | CD20 | # total cores |
|---|---|---|---|
| T-cell lymphoma | 0 | 0 | 4 |
| Multiple myeloma | 0 | 0 | 10 |
| Hodgkin's B-cell lymphoma | 1 (8%) | 1 (8%) | 12 |
| Non-Hodgkin B cell lymphoma (unspecified) | 21 (95%) | 21 (95%) | 22 |
| Follicular lymphoma | 3 (100%) | 3 (100%) | 3 |
| MALT lymphoma | 3 (100%) | 3 (100%) | 3 |
| Diffuse large B cell lymphoma | 13 (93%) | 13 (93%) | 14 |
| Burkitt's lymphoma | 6 (75%) | 7 (88%) | 8 |
| Mantle cell lymphoma | 3 (50%) | 6 (100%) | 6 |

In all case, huCD37-3 treatment resulted in a reduction in cell viability in a dose-dependent manner. For example, treatment with huCD37-3 reduced the viability of Granta-519 cells to approximately 37% with an EC50 of 0.062 nM. Rituximab treatment reduced the viability of Granta-519 cells to approximately 47% with an EC50 of 0.36 nM. Treatment with huCD37-3 reduced the viability of SU-DHL-4 cells to approximately 17% with an EC50 of 0.053 nM. Rituximab treatment reduced the viability of SU-DHL-4 cells to approximately 20% with an EC50 of 0.2 nM. In striking contrast, treatment with TRU-016 did not reduce the viability of Granta-519 or SU-DHL-4 cells to a significant degree or in a dose-dependent manner. In further examples, treatment with huCD37-3 reduced the viability of Namalwa cells to approximately 47% with an EC50 of 0.1 nM and reduced the viability of Daudi cells to approximately 68% with an EC50 of 0.25 nM. Rituximab treatment did not have an effect on Namalwa cells but reduced the viability of Daudi cells to approximately 69% with an EC50 of 2.6 nM. In striking contrast, treatment with TRU-016 did not reduce the viability of Namalwa or Daudi cells to a significant degree or in a dose-dependent manner. Finally, treatment with huCD37-3 reduced the viability of Ramos cells to approximately 53% with an EC50 of 0.08 nM, while neither TRU-016 nor rituximab treatment had any effect on Ramos cell viability. This result underscores the uniqueness of the anti-proliferative activity of the isolated anti-CD37 antibodies.

Example 11

CDC Activity of CD37 Antibodies

To assess complement-dependent cytotoxicity (CDC) activities of chimeric and humanized anti-CD37 antibodies, cell based assays were performed according to a published method (Gazzano-Santoro H, *J Immunol Methods.* 1997 202 (2):163-71). Antibodies were aliquoted in duplicate at 50 μL/well into a flat-bottom 96-well tissue culture plate at various concentrations typically ranging from 5 μg/mL (=3.3×$10^{-8}$ M) to 2.3 ng/mL (=1.5×$10^{-11}$ M) in RHBP (RPMI-1640, 20 mM HEPES, 0.1% BSA, 1% penicillin-streptomycin) medium. Target cells were added to the antibodies at 5×$10^4$ cells in 100 μL of RHBP medium per well. Lyophilized human complement (Sigma-Aldrich, St. Louis, US) was reconstituted with 1 mL sterile purified water per vial and diluted 5-fold to a 20% stock with RHBP media immediately before use. 50 μL/well of complement solution was added to each well for a final concentration of 5%. Plates were incubated for 2 h at 37° C. in 5% $CO_2$ humidified incubator to allow for complement mediated lysis. After this incubation time, Alamar Blue reagent (Invitrogen) was added to each well at a final concentration of 10% to measure the viability of the remaining cells. The plate was incubated for 16 to 20 hours at 37° C. before measuring the fluorescence (in relative fluorescence units, RFU) at EX540/EM590 nm. Controls included triplicate wells with media and complement but without cells (media only, 0% viability) and wells with cells and complement but without antibody (cells only, 100% viability). The percentage of specific cell viability for each sample was determined by to the following formula: Percent viability=(sample−media only)/(cells only−media only).

The result of an exemplary CDC assay using Ramos cells is presented in FIG. 14. Strikingly, chCD37-12 has potent CDC activity against Ramos cells. It reduced the viability of Ramos cells to 32% at the highest antibody concentration tested with an EC50 of 0.037 μg/mL. In addition, several isolated antibodies showed CDC activity against Ramos to a varying degree. Treatment with huCD37-3, huCD37-38, huCD37-50 resulted in a reduction in cell viability to 59%, 50% and 45%, respectively. Treatment with huCD37-51, huCD37-56 or huCD37-56 moderately reduced cell viability of Ramos cells to approximately 70-80% at the highest antibody concentration tested.

Example 12

ADCC Activity of CD37 Antibodies

A lactate dehydrogenase (LDH) release assay was used to measure antibody-dependent cell mediated cytotoxicity (ADCC) of tumor cells lines using freshly isolated human natural killer (NK) cells as effector cells (Shields R L, *J Biol Chem.* 2001 276(9):6591-604). The NK cells were first isolated from human blood from a normal donor (Research Blood Components, Inc., Brighton, Mass.) using a modified protocol for the NK Isolation Kit II (Miltenyi Biotech, 130-091-152). Blood was diluted 2-fold with 1×PBS. 25 mL of diluted blood was carefully layered over 25 mL of Ficoll Paque in a 50 mL conical tube and centrifuged at 400 g for 45 min at RT. The peripheral blood mononuclear cells (PBMC) were collected from the interface, transferred into a new conical 50 mL tube, and washed once with 1×PBS. The PBMC were resuspended in 2 mL of NK-isolation buffer (1×PBS, 0.5% BSA, 2 mM EDTA), and then 500 μL of Biotin-Antibody Cocktail were added to the cell suspension. The Biotin-Antibody Cocktail contains biotinylated antibodies that bind to the lymphocytes, except for NK cells, resulting in a negative selection of NK cells. The mixture was incubated at 4° C. for 10 min, and then 1.5 mL of NK-isolation buffer and 1 mL of Anti-Biotin Micro Beads were added. The cell-antibody mixture was incubated for another 15 min at 4° C. Next, cells were washed once with 50 mL of NK-isolation buffer and resuspended in 3 mL of NK-isolation buffer. Then, a MACS LS column was mounted on the autoMACS separator (Miltenyi Biotech) and pre-washed with 3 mL of NK-isolation Buffer. The cell suspension was automatically applied onto the column, washed and the effluent fraction with unlabeled NK cells was collected into a new 50-mL conical tube. The resulting NK cells were plated into 30 mL of complete RPMI media (RPMI-1640 supplemented with 5% fetal bovine serum, 1% penicillin-streptomycin, 1 mM HEPES, 1 mM Sodium Pyruvate, 1% 100×MEM non-essential Amino Acid Solution) overnight. The subsequent assay and all dilutions were carried out in RHBP medium (RPMI-1640 medium supplemented with 20 mM HEPES, pH 7.4, 0.1% BSA and 1% penicillin-streptomycin).

Various concentrations of antibodies in RHBP medium were aliquoted in duplicate at 50 μL/well into a round bottom 96-well plate. The target cells were resuspended at 106 cells/mL in RHBP medium and added at 100 μL/well to each well containing antibody dilutions. The plate containing target cells and antibody dilutions was incubated for 30 min at 37° C. NK cells were then added to the wells containing the target cells at 50 μL/well. The typical ratio was 1 target cell to 3-4 NK cells. The following controls were set up for each experiment: NK cells alone, target cells alone (spontaneous LDH release), target cells with NK cells (antibody independent LDH release), target cells with 10% Triton X-100 (maximum LDH release). The mixtures were incubated at 37° C. for 4 h to allow for cell lysis. Plates were centrifuged for 10 min at 1200 rpm, and 100 μL of the supernatant was carefully transferred to a new flat-bottom 96-well plate. LDH reaction mixture (100 μL/well) from the Cytotoxicity Detection Kit (Roche 1 644 793) was added to each well and incubated at room temperature for 5 to 30 min. The optical density of samples was measured at 490 nm (OD490). The percent specific lysis of each sample was determined using the following formula: percent specific lysis=(sample value−spontaneous release)/(maximum release−spontaneous release) *100.

Incubation with humanized antibodies lead to good ADCC activity against Daudi, Ramos and Granta-519 lymphoma cells in the presence of human NK effector cells. Their ADCC activity against Daudi lymphoma cells was compared with the ADCC activity of TRU-016 (FIG. 15).

Treatment with huCD37-3, huCD37-38 or huCD37-50 antibodies resulted in approximately 41%, 39% or 40% Daudi cell lysis with an EC50 value of 0.42 ng/mL, 1.31 ng/mL, or 2.42 ng/mL, respectively. This activity was similar to that resulting from TRU-016 treatment with 42% Daudi cell lysis observed and an EC50 value of 0.93 ng/mL. In addition, treatment with huCD37-51, huCD37-56 and huCD37-57 resulted in approximately 39%, 36% or 36% of Daudi cell lysis with an EC50 value of 5.7 ng/mL, 4.3 ng/mL, or 7.9 ng/mL, respectively.

The ADCC activity of the isolated antibodies against Ramos lymphoma cells was compared with the ADCC activity of TRU-016. Treatment with huCD37-3, huCD37-38 or huCD37-50 antibodies resulted in approximately 43%, 42% or 46% Ramos cell lysis with an EC50 value of 0.95 ng/mL, 2.0 ng/mL, or 3.0 ng/mL respectively. This activity was similar to that resulting from TRU-016 treatment with 59% Ramos cell lysis observed and an EC50 value of 1.53 ng/mL. In addition, treatment with huCD37-51, huCD37-56 and huCD37-57 resulted in approximately 53%, 43% or 44% of Ramos cell lysis with an EC50 value of 5.7 ng/mL, 4.3 ng/mL, or 7.9 ng/mL, respectively.

In additional experiments the ADCC activity of huCD37-3 and chCD37-38 against Granta-519 cells was compared with the ADCC activity of TRU-016. Treatment with huCD37-3 or chCD37-38 antibodies resulted in approximately 19% or 18% Granta-519 cell lysis with an EC50 value of 0.13 ng/mL, or 0.73 ng/mL respectively. TRU-016 treatment resulted in 16% Granta-519 cell lysis observed and an EC50 value of 0.83 ng/mL.

Example 13

Epitope Mapping

The localization of amino acid requirements for the epitopes of different CD37 antibodies can help tie common or unique functional characteristics to specific molecular interactions. The extracellular domain of CD37 contains two extracellular loops, a small loop of about 18 residues, and a larger one consisting of approximately 135 amino acids. Epitope requirements have not been described for previously published CD37 antibodies. To further characterize the isolated CD37 antibodies of this invention, we constructed several CD37 antigen variants with AA substitution in the larger extracellular loop.

CD37 Variant Cloning and Expression

Mammalian expression plasmids were built containing either the entire human or macaca CD37 cDNA sequences, codon optimized and synthesized by Blue Heron Biotechnologies, and flanked by XbaI and BamHI restriction sites to facilitate cloning into the pSRa vector multiple cloning site. Since the human and macaca CD37 sequences are highly homologous (FIG. 16), the expression of these constructs could distinguish the human and macaca cross reactive antibodies from those that recognize epitopes requiring at least one of the 11 extracellular CD37 amino acid differences between in these two species as described in Example 8.

To further characterize the CD37 antibody epitopes, a series of murine and human chimeric CD37 constructs were built. Because of the size and high homology of the small CD37 extracellular loop, epitope localization efforts were limited to the large extracellular loop. An EcoRV to Pst1 cassette encoding residues 1108 to Q235 of the large extracellular loop was redesigned to be further segmented into 5 sections by incorporating 4 unique restriction sites that could be conserved between the human, murine, and macaca CD37 sequences (FIG. 17). The following human and mouse chimeric CD37 constructs were created:

```
hCD37-M1
                                (SEQ ID NO: 180)
MSAQESCLSLIKYFLFVFNLFFFVLGSLIFCFGIWILIDKTSFVSFVG
LAFVPLQIWSKVLAISGIFTMGIALLGCVGALKELRCLLGLYFGMLLL
LFATQITLGILISTQRVRLERRVQELVLRTIQSYRTNPDETAAEESWD
YVQFQLRCCGWHYPQDWFQVLILRGNGSEAHRVPCSCYNLSATNDSTI
LDKVILPQLSRLGHLARSRHSADICAVPAESHIYREGCAQGLQKWLHN
NLISIVGICLGVGLLELGFMTLSIFLCRNLDHVYNRLARYR

hCD37-M2
                                (SEQ ID NO: 181)
MSAQESCLSLIKYFLFVFNLFFFVLGSLIFCFGIWILIDKTSFVSFVG
LAFVPLQIWSKVLAISGIFTMGIALLGCVGALKELRCLLGLYFGMLLL
LFATQITLGILISTQRAQLERSLRDVVEKTIQKYGTNPEETAAEESWD
YAQFQLRCCGWQSPRDWNKAQMLKANESEEPRVPCSCYNLSATNDSTI
LDKVILPQLSRLGHLARSRHSADICAVPAESHIYREGCAQGLQKWLHN
NLISIVGICLGVGLLELGFMTLSIFLCRNLDHVYNRLARYR

hCD37-M3
                                (SEQ ID NO: 182)
MSAQESCLSLIKYFLFVFNLFFFVLGSLIFCFGIWILIDKTSFVSFVG
LAFVPLQIWSKVLAISGIFTMGIALLGCVGALKELRCLLGLYFGMLLL
LFATQITLGILISTQRAQLERSLRDVVEKTIQKYGTNPEETAAEESWD
YVQFQLRCCGWHYPQDWFQVLILRGNGSEAHRVPCSCYNSTATNDSTV
FDKLFFSQLSRLGHLARSRHSADICAVPAESHIYREGCAQGLQKWLHN
NLISIVGICLGVGLLELGFMTLSIFLCRNLDHVYNRLARYR

hCD37-M45
                                (SEQ ID NO: 183)
MSAQESCLSLIKYFLFVFNLFFFVLGSLIFCFGIWILIDKTSFVSFVG
LAFVPLQIWSKVLAISGIFTMGIALLGCVGALKELRCLLGLYFGMLLL
LFATQITLGILISTQRAQLERSLRDVVEKTIQKYGTNPEETAAEESWD
YVQFQLRCCGWHYPQDWFQVLILRGNGSEAHRVPCSCYNLSATNDSTI
LDKVILPQLSRLGPRAKLRQTADICALPAKAHIYREGCAQSLQKWLHN
NLISIVGICLGVGLLELGFMTLSIFLCRNLDHVYNRLARYR

muCD37-R176
                                (SEQ ID NO: 184)
ISTQRVRLERRVQELVLRTIQSYRTNPDETAAEESWDYAQFQLRCCGW
QSPRDWNKAQMLKANESEEPRVPCSCYNSTATNDSTVFDKLFFSQLSR
LGPRAKLRQTADICALPAKAHIYREGCAQSLQ.
```

In order to preserve one such restriction site, Kpn1, the human R176 was included in all of the murine/human chimeric constructs. The murine and human CD37 cassettes were ordered from Blue Heron and cloned into the pSRa vector together with a 5' end fragment of the original human CD37 construct generated by PCR to incorporate the EcoRV site and the 3' end Pst1 to Xba1 restriction fragment taken from the original macaca CD37 construct. The murine and human chimeric CD37 cassettes were then built using standard restriction digests and ligations taking advantage of the common unique restriction sites.

The hCD37-M1 variant was created by inserting a EcoRV-SacII restriction fragment encoding the AA 5109 to A138 of the analogous murine CD37 sequence. Likewise the hCD37-M3 variant was created by inserting a KpnI-B1 µl restriction fragment encoding the AA V177 to L201 of the analogous murine CD37 sequence. The hCD37-M45 variant was created by inserting a BlpI-PstI restriction fragment encoding the AA 5202 to 1243 of the analogous murine CD37 sequence. The resulting clones were verified by restriction enzyme digestion followed by DNA sequencing.

Stable cell lines were obtained by transfection of the murine and human chimeric CD37 variant expression plasmids into 300-19 cells using standard electroporation procedures. Briefly, $5\times10^6$ 300-19 cells were electroporated in cold RPMI-1640 media using a BioRad Gene Pulser set at 260V and 960 µF. Subsequently, cells were diluted and plated into 96-well plates in RPMI-1640 media supplemented with 10% FBS and 50 µM β-mercaptoethanol. After 24 hours G418 (Invitrogen) was added at a final concentration of 2 mg/mL to select for transfected cells. After 2 weeks, single colonies were isolated, analyzed for CD37 surface expression by flow cytometry and expanded.

Antibody Binding to CD37 Variants

Binding of various CD37 antibodies to cells expressing human CD37 wildtype and variants was analyzed by flow cytometry using 1.5 µg/mL of each antibody. The isolated antibodies of this invention were compared to commercially available CD37 antibody WR17, as well as the TRU-016 SMIP. As can be seen in FIG. 18A, all antibodies bound to wild type CD37 expressing cells. Likewise, all antibodies tested bound the hCD37-M3 variant (FIG. 18B). In contrast, the isolated antibodies of this invention bound the hCD37-M1 variant, while TRU-016 and WR17 were unable to bind hCD37-M1 variant (FIG. 19A). The CD37-50 and CD37-51 antibodies and TRU-016 were also able to bind the hCD37-M45 variant. WR17 showed partial binding to the hCD37-M45 variant, while the other antibodies CD37-3, CD37-12, CD37-38, CD37-56 and CD37-57 were unable to bind (FIG. 19B). This suggests that all of the isolated antibodies of this invention do not require the 12 AA residues in the hCD37-M1 variant that were changed to the corresponding murine AA residues for binding to the CD37 antigen. In contrast, the CD37-3, CD37-12, CD37-38, CD37-56 and CD37-57 antibodies require at least one of the AA residues in the hCD37-M45 variant that were changed to the corresponding murine AA residues for binding to the CD37 antigen.

This unexpected result indicates that the isolated antibodies of this invention represent a novel class of CD37 antibodies with a unique combination of functional characteristics.

In addition, similar constructs are built following the same design. The constructs contain various combinations of murine, human and/or macaca sequences encoding the large extracellular loop of CD37 (see FIG. 17). Examples of constructs with a single human section inserted into the murine large extracellular loop sequence are:

hCD37mECD-H1:
(SEQ ID NO: 185)
MSAQESCLSLIKYFLFVFNLFFFVLGSLIFCFGIWILIDKTSFVSFVG
LAFVPLQIWSKVLAISGIFTMGIALLGCVGALKELRCLLGLYFGMLLL
LFATQITLGILISTQRAQLERSLRDVVEKTIQKYGTNPEETAAEESWD
YAQFQLRCCGWQSPRDWNKAQMLKANESEEPRVPCSCYNSTATNDSTV
FDKLFFSQLSRLGPRAKLRQTADICALPAKAHIYREGCAQSLQKWLHN
NLISIVGICLGVGLLELGFMTLSIFLCRNLDHVYNRLARY hCD37mECD-H2:
(SEQ ID NO: 186)
MSAQESCLSLIKYFLFVFNLFFFVLGSLIFCFGIWILIDKTSFVSFVG
LAFVPLQIWSKVLAISGIFTMGIALLGCVGALKELRCLLGLYFGMLLL
LFATQITLGILISTQRVRLERRVQELVLRTIQSYRTNPDETAAEESWD
YVQFQLRCCGWHYPQDWFQVLILRGNGSEAHRVPCSCYNSTATNDSTV
FDKLFFSQLSRLGPRAKLRQTADICALPAKAHIYREGCAQSLQKWLHN
NLISIVGICLGVGLLELGFMTLSIFLCRNLDHVYNRLARYR hCD37mECD-H3:
(SEQ ID NO: 187)
MSAQESCLSLIKYFLFVFNLFFFVLGSLIFCFGIWILIDKTSFVSFVG
LAFVPLQIWSKVLAISGIFTMGIALLGCVGALKELRCLLGLYFGMLLL
LFATQITLGILISTQRVRLERRVQELVLRTIQSYRTNPDETAAEESWD
YAQFQLRCCGWQSPRDWNKAQMLKANESEEPRVPCSCYNLSATNDSTI
LDKVILPQLSRLGPRAKLRQTADICALPAKAHIYREGCAQSLQKWLHN
NLISIVGICLGVGLLELGFMTLSIFLCRNLDHVYNRLARYR hCD37mECD-H4:
(SEQ ID NO: 188)
MSAQESCLSLIKYFLFVFNLFFFVLGSLIFCFGIWILIDKTSFVSFVG
LAFVPLQIWSKVLAISGIFTMGIALLGCVGALKELRCLLGLYFGMLLL
LFATQITLGILISTQRVRLERRVQELVLRTIQSYRTNPDETAAEESWD
YAQFQLRCCGWQSPRDWNKAQMLKANESEEPRVPCSCYNSTATNDSTV
FDKLFFSQLSRLGHLARSRHSADICALPAKAHIYREGCAQSLQKWLHN
NLISIVGICLGVGLLELGFMTLSIFLCRNLDHVYNRLARYR hCD37mECD-H5
(SEQ ID NO: 189)
MSAQESCLSLIKYFLFVFNLFFFVLGSLIFCFGIWILIDKTSFVSFVG
LAFVPLQIWSKVLAISGIFTMGIALLGCVGALKELRCLLGLYFGMLLL
LFATQITLGILISTQRVRLERRVQELVLRTIQSYRTNPDETAAEESWD
YAQFQLRCCGWQSPRDWNKAQMLKANESEEPRVPCSCYNSTATNDSTV
FDKLFFSQLSRLGPRAKLRQTADICAVPAESHIYREGCAQGLQKWLHN
NLISIVGICLGVGLLELGFMTLSIFLCRNLDHVYNRLARYR
and hCD37mECD-H45
(SEQ ID NO: 190)
MSAQESCLSLIKYFLFVFNLFFFVLGSLIFCFGIWILIDKTSFVSFVG
LAFVPLQIWSKVLAISGIFTMGIALLGCVGALKELRCLLGLYFGMLLL
LFATQITLGILISTQRVRLERRVQELVLRTIQSYRTNPDETAAEESWD
YAQFQLRCCGWQSPRDWNKAQMLKANESEEPRVPCSCYNSTATNDSTV
FDKLFFSQLSRLGHLARSRHSADICAVPAESHIYREGCAQGLQKWLHN
NLISIVGICLGVGLLELGFMTLSIFLCRNLDHVYNRLARYR.

Further examples are constructs with a single macaca section inserted into the human large extracellular loop sequence such as:

hCD37-Mac12:
(SEQ ID NO: 191)
MSAQESCLSLIKYFLFVFNLFFFVLGSLIFCFGIWILIDKTSFVSFVG
LAFVPLQIWSKVLAISGIFTMGIALLGCVGALKELRCLLGLYFGMLLL
LFATQITLGILISTQRAQLERSLQDIVEKTIQRYHTNPEETAAEESWD
YVQFQLRCCGWHSPQDWFQVLTLRGNGSEAHRVPCSCYNLSATNDSTI
LDKVILPQLSRLGHLARSRHSADICAVPAESHIYREGCAQGLQKWLHN
NLISIVGICLGVGLLELGFMTLSIFLCRNLDHVYNRLARYR hCD37-Mac4:
(SEQ ID NO: 192)
MSAQESCLSLIKYFLFVFNLFFFVLGSLIFCFGIWILIDKTSFVSFVG
LAFVPLQIWSKVLAISGIFTMGIALLGCVGALKELRCLLGLYFGMLLL
LFATQITLGILISTQRAQLERSLRDVVEKTIQKYGTNPEETAAEESWD
YVQFQLRCCGWHYPQDWFQVLILRGNGSEAHRVPCSCYNLSATNDSTI
LDKVILPQLSRLGQLARSRHSTDICAVPAESHIYREGCAQGLQKWLHN
NLISIVGICLGVGLLELGFMTLSIFLCRNLDHVYNRLARYR

-continued hCD37-Mac5:
(SEQ ID NO: 193)
MSAQESCLSLIKYFLFVFNLFFFVLGSLIFCFGIWILIDKTSFVSFVG
LAFVPLQIWSKVLAISGIFTMGIALLGCVGALKELRCLLGLYFGMLLL
LFATQITLGILISTQRAQLERSLRDVVEKTIQKYGTNPEETAAEESWD
YVQFQLRCCGWHYPQDWFQVLILRGNGSEAHRVPCSCYNLSATNDSTI
LDKVILPQLSRLGHLARSRHSADICAVPANSHIYREGCARSLQKWLHN
NLISIVGICLGVGLLELGFMTLSIFLCRNLDHVYNRLARYR
and hCD37-Mac45:
(SEQ ID NO: 194)
MSAQESCLSLIKYFLFVFNLFFFVLGSLIFCFGIWILIDKTSFVSFVG
LAFVPLQIWSKVLAISGIFTMGIALLGCVGALKELRCLLGLYFGMLLL
LFATQITLGILISTQRAQLERSLRDVVEKTIQKYGTNPEETAAEESWD
YVQFQLRCCGWHYPQDWFQVLILRGNGSEAHRVPCSCYNLSATNDSTI
LDKVILPQLSRLGQLARSRHSTDICAVPANSHIYREGCARSLQKWLHN
NLISIVGICLGVGLLELGFMTLSIFLCRNLDHVYNRLARY.

Furthermore, single point mutations are generated in the human large extracellular loop sequence to identify residues important for antibody binding.

Binding of CD37 binding agents to cells expressing SEQ ID NOs: 185-194 is analyzed by flow cytometry as described above.

Example 14

Preparation of huCD37-3-SPP-DM1

The N-succinimidyl 4-(2-pyridyldithio)pentanoate (SPP) linker was dissolved in ethanol. The huCD37-3 antibody was incubated at 5 mg/mL with a 7 fold molar excess of SPP linker for approximately 100 minutes at room temperature in 50 mM potassium phosphate buffer (pH 6.5) containing 50 mM NaCl, 2 mM EDTA, and 5% ethanol. The reaction mixture was purified using a SEPHADEX™ G25F column equilibrated with the aforementioned potassium phosphate buffer. Antibody containing fractions were pooled and used for subsequent steps.

The maytansinoid DM1 was dissolved in dimethylacetamide (DMA, final concentration is 3%) and a 1.7 fold molar excess relative to the linker was added drop wise to the SPP modified antibody. After overnight incubation at room temperature, the conjugated antibody was purified by chromatography on SEPHADEX™ G25F equilibrated in phosphate buffered saline (PBS), pH 6.5. The huCD37-3-SPP-DM1 conjugate was then dialyzed into buffer containing 10 mM histidine, 250 mM glycine, 1% sucrose pH 5.5. The number of DM1 molecules linked per antibody molecule was determined using the previously reported extinction coefficients for antibody and DM1 (Liu et al., *Proc. Natl. Acad. Sci. USA,* 93, 8618-8623 (1996)). The percentage of free maytansinoid present after the conjugation reaction was determined by injecting 20-50 µg conjugate onto a HiSep column equilibrated in 25% acetonitrile in 100 mM ammonium acetate buffer, pH 7.0, and eluting in acetonitrile. The peak area of total free maytansinoid species (eluted in the gradient and identified by comparison of elution time with known standards) was measured using an absorbance detector set to a wavelength of 252 nm and compared with the peak area related to bound maytansinoid (eluted in the conjugate peak in the column flow-through fractions) to calculate the percentage of total free maytansinoid species. Conjugates with 3.5-4 DM1 molecules per huCD37-3 antibody were obtained with <1% present as unconjugated maytansinoid.

Preparation of huCD37-3-SMCC-DM1

The (Succinimidyl 4-(N-maleimidomethyl)cyclohexane-1-carboxylate (SMCC, Pierce Biotechnology, Inc) linker was dissolved in DMA. The huCD37-3 antibody was modified with SMCC to introduce maleimides into the antibody by incubating the antibody at 5 mg/mL in 50 mM potassium phosphate, 50 mM NaCl, 2 mM EDTA, pH 6.5 with a 10 molar excess of SMCC. After approximately 100 minutes at ambient temperature, the reaction mixture was purified using a SEPHADEX™ G25 column equilibrated with the same potassium phosphate buffer. Antibody containing fractions were pooled and used for subsequent steps.

The SMCC-modified antibody was reacted with a 10 mM solution of DM1 at a 1.7 molar excess relative to the maleimide linker. The reaction was stirred at ambient temperature under for approximately 18 hours. The conjugation reaction mixture was filtered through a SEPHADEX™ G25 gel filtration column equilibrated with 1×PBS at pH 6.5. The huCD37-3-SMCC-DM1 conjugate was then dialyzed into buffer containing 10 mM histidine, 250 mM glycine, 1% sucrose pH 5.5. The number of DM1 molecules linked per antibody molecule and the percentage of total free maytansinoid species were determined as described above. Conjugates with 3.5-4 DM1 molecules per huCD37-3 antibody were obtained with <1% present as unconjugated maytansinoid.

Preparation of huCD37-3-Sulfo-Mal-DM4

Solutions of DM4 thiol and the heterobifunctional linker 1-(2,5-dioxo-2,5-dihydro-1H-pyrrol-1-yl)-4-(2,5-dioxopyrrolidin-1-yloxy)-4-oxobutane-2-sulfonic acid (3-sulfo-mal) were made up in N,N-dimethylacetamide (DMA) at concentrations of 30-60 mM. The linker and DM4 were mixed together in DMA containing up to 40% v/v of 200 mM succinate buffer, 2 mM EDTA, pH 5.0 to give a ratio of DM4 to linker of 1.6 and a final concentration of DM4 equal to 15 mM. After mixing, the reaction was left for 2 h added to a mixture of huCD37-3 antibody in phosphate buffer (pH 7.5) under final conjugation conditions of 4 mg/ml Ab, 90% phosphate buffer/10% DMA, pH 7.5. The conjugation reaction was allowed to proceed at ambient temperature for 2 h. The huCD37-3-sulfo-mal-DM4 conjugate was purified from excess unreacted DM4 and unconjugated linker products dialysis in PBS, followed by a final dialysis into buffer containing 10 mM histidine, 250 mM glycine, 1% sucrose pH 5.5. The conjugate was filtered through a 0.22 μm filter for final storage. The number of DM4 molecules per huCD37-3 antibody molecule (average) in the final conjugate the percentage of total free maytansinoid species were determined as described above. Conjugates with 3.5-4 DM4 molecules per huCD37-3 antibody were obtained with <1% present as unconjugated maytansinoid.

Preparation of huCD37-3-PEG4-Mal-DM1

The N-hydroxysuccinimidyl-(polyethylene glycol)4-(N-maleimidomethyl)-DM1 (NHS-PEG4-mal-DM1) reagent was dissolved in DMA. The huCD37-3 antibody was incubated at 5 mg/mL in 50 mM potassium phosphate, 150 mM NaCl, 2 mM EDTA, pH 7.5 with a 7 fold molar excess of NHS-PEG4-mal-DM1 (10% DMA total). After approximately 2 hours at ambient temperature, the reaction mixture was purified using a SEPHADEX™ G25 column equilibrated in 1×PBS, pH 7.4. Antibody containing fractions were pooled and dialyzed into buffer containing 10 mM histidine, 250 mM glycine, 1% sucrose, pH 5.5. The number of DM1 molecules linked per antibody and the percentage of total free maytansinoid species were determined as described above. Conjugates with 3.5-4 DM4 molecules per huCD37-3 antibody were obtained with <1% present as unconjugated maytansinoid.

Example 15

Binding Affinity of Maytansinoid Conjugates

Binding affinity of the exemplary huCD37-3 after conjugation to SMCC-DM1, SPP-DM1 or sulfo-mal-DM4 was assayed by flow cytometry as described in the above example. The value for the apparent dissociation constants (Kd) were calculated from the binding curves shown in FIG. 20A and correspond to 0.26 nM for huCD37-3, 0.46 for huCD37-3-SMCC-DM1, 0.56 nM for huCD37-3-SPP-DM1, and 0.89 nM for huCD37-3-sulfo-mal-DM4 conjugates. This result demonstrates that SMCC-DM1, SPP-DM1 or sulfo-mal-DM4 conjugation does not notably alter the affinity of the exemplary huCD37-3 antibody.

Binding affinity of huCD37-38 after conjugation to SMCC-DM1 was assayed by flow cytometry as described in the above example. The value for the apparent dissociation constants (Kd) were calculated from the binding curves shown in FIG. 20B and correspond to 1.04 nM for huCD37-38 and 1.2 nM for huCD37-38-SMCC-DM1 conjugates. This result demonstrates that SMCC-DM1 conjugation does not notably alter the affinity of the huCD38 antibody. Likewise, binding affinity of huCD37-50, huCD37-51, huCD37-56 and huCD37-57 after conjugation to SMCC-DM1 was assayed by flow cytometry. The value for the apparent dissociation constants (Kd) were calculated from binding curves and correspond to 0.43 nM for huCD37-50, 0.70 nM for huCD37-50-SMCC-DM1, 2.0 nM for huCD37-51, 1.6 nM for huCD37-51-SMCC-DM1, 0.3 nM for huCD37-56, 0.34 nM for huCD37-56-SMCC-DM1, 0.30 for huCD37-57 and 0.34 for huCD37-57-SMCC-DM1. This result demonstrates that SMCC-DM1 conjugation also does not notably alter the affinity of the huCD37-50, huCD37-51, huCD37-56 or huCD37-57 antibodies.

Binding Affinity of PEG4-Mal-DM1 Conjugates

Binding affinity of the exemplary huCD37-3 and huCD37-50 antibodies after conjugation to PEG4-mal-DM1 was assayed by flow cytometry as described in the above example. The value for the apparent dissociation constants (Kd) were calculated from binding curves and correspond to 0.28 nM for huCD37-3, 0.35 nM for huCD37-3-PEG4-mal-DM1, 0.68 nM for huCD37-50 and 1.1 nM for huCD37-50-PEG4-mal-DM1 conjugates. This result demonstrates that PEG4-mal-DM1 conjugation does not notably alter the affinity of the exemplary huCD37-3 or huCD50 antibodies.

Pro-Apoptotic Activity of huCD37-3-SMCC-DM1 Conjugates

Pro-apoptotic activity of huCD37-3 after conjugation to SMCC-DM1 was evaluated by Annexin-V staining on Ramos cells as described above. Treatment with either huCD37-3 antibody or huCD37-3-SMCC-DM1 conjugate resulted in approximately 40% Annexin-V positive Ramos cells with an EC50 value of approximately 0.09 nM (FIG. 21A). Ramos cells treated with a non-binding control antibody or a non-binding SMCC-DM1 control conjugate contained only up to 4% Annexin-V positive cells. In comparison, treatment with the anti-CD20 antibody rituximab resulted in only 16% Annexin-V positive cells with an EC50 value of approximately 2 nM. In contrast, TRU-016 treatment did not increase the percentage of Annexin-V positive Ramos cells. This demonstrates that the strong pro-apoptotic activity of the human anti-CD37 antibody huCD37-3 is retained after conjugation to SMCC-DM1.

CDC Activity of huCD37-3-SMCC-DM1 Conjugates

CDC activity of huCD37-3 after conjugation to SMCC-DM1 was evaluated on Ramos cells in the presence of 5% human complement. Treatment with huCD37-3 or huCD37-3-SMCC-DM1 resulted in a reduction in cell viability to 53% and 73%, respectively (FIG. 21B). Therefore, the CDC activity of the exemplary huCD37-3 antibody is maintained after maytansinoid conjugation.

ADCC Activity of Conjugates

ADCC activity of huCD37-3 after conjugation to SMCC-DM1 or PEG4-mal-DM1 was evaluated on Daudi and Ramos cells in the presence of human NK effector cells by LDH release assay as described above. As can be seen in FIG. 22A, huCD37-3-SMCC-DM1 or huCD37-3-PEG4-mal-DM1 conjugates have similar ADCC activity as the unconjugated huCD37-3 antibody on Daudi cells. Treatment with huCD37-3, huCD37-3 SMCC-DM1 or huCD37-3-PEG4-mal-DM1 resulted in approximately 41%, 39% or 36% Daudi cell lysis with an EC50 value of 0.42 ng/mL, 1.13 ng/mL, or 0.91 ng/mL, respectively. Similar results were obtained using Ramos cells as target cells. As before, huCD37-3-SMCC-DM1 or huCD37-3-PEG4-mal-DM1 conjugates have comparable ADCC activity to the unconjugated huCD37-3 antibody on Ramos cells (FIG. 22B). Treatment with huCD37-3, huCD37-3 SMCC-DM1 or huCD37-3-PEG4-mal-DM1 resulted in approximately 43%, 41% or 42% Ramos cell lysis with an EC50 value of 0.95 ng/mL, 1.33 ng/mL, or 1.57 ng/mL, respectively. Therefore, the potent ADCC activity of the exemplary huCD37-3 antibody is maintained after maytansinoid conjugation.

Induction of Cell Cycle Arrest by huCD37-3-SMCC-DM1

The potential of anti-CD37 antibodies and conjugates to induce cell cycle arrest in cell lines was evaluated by propridium iodide (PI) staining followed by flow cytometry analysis. Exponentially growing cells were harvested by centrifugation at 1,300 rpm for 5 minutes at RT and resuspended at 0.5×106 cells/mL in complete RPMI media. Cells were transferred at 1 mL per well to a 24-well plate (Falcon 3077) to equal $0.5\times10^6$ cells/assay. The test compounds were added to each well in a final concentration of 10 nM. Complete RPMI media was added to untreated control wells. Cells were incubated overnight for 16 to 20 hrs at 37° C. in a humidified 5% $CO_2$ incubator. The next day, cells were harvested by transferring into 5 mL polystyrene tubes, washed once with 3 mL PBS, and fixed in 1 mL 70% ethanol for 30 minutes on ice. The samples were then washed again with 3 mL PBS once and resuspended in 0.5 mL PBS. RNase was added to the sample at 5 μL/mL and incubated at 37° C. for 30 minutes. The samples were then stained with propidium iodide at a final concentration of 50 μg/mL. Samples were acquired within 24 hours of PI staining. Samples were run on a FACS Calibur (BD Biosciences, San Diego). The FL2-A parameter was set to linear scale and the FL2 PTM was adjusted to position the G1 peak around 200. Samples were acquired at a low flow rate and 10,000 events were collected per sample. Distribution of cells in the different phases of the cell cycle was determined using ModFit software (Version 5.11, Verity Software House Inc., USA). This program utilizes peak fitting techniques to automatically model the PI data and provides the desired quantitative data. The data was analyzed with standard program settings.

The effect of huCD37-3 and huCD37-3-SMCC-DM1 on cell cycle arrest of BJAB and RL lymphoma cells was evaluated after a 16-20 hour incubation with either compound at a 10 nM concentration followed by propridium iodide (PI) staining and flow cytometry analysis. Incubation with huCD37-3-SMCC-DM1 resulted in an increase in the percentage of cells in G2/M phase from 13% for untreated BJAB lymphoma cells to 95% for huCD37-3-SMCC-DM1 treated cells (FIG. 23A). Similarly, incubation with huCD37-3-SMCC-DM1 resulted in an increase in the percentage of cells in G2/M phase from 12% for untreated RL lymphoma cells to 33% for huCD37-3-SMCC-DM1 treated cells (FIG. 23B). In contrast, the huCD37-3 antibody had no effect on the cell cycles of either BJAB or RL cells. In addition, a non-binding SMCC-DM1 conjugate tested at the same concentration also had no effect on the cell cycle of either cell type. This demonstrated that maytansinoid conjugates made with isolated anti-CD37 antibodies caused specific cell cycle arrest of CD37-positive lymphoma cell lines.

Example 16

In Vitro Cytotoxicity Assays

The ability of antiCD37 antibody-conjugates to inhibit cell growth was measured using in vitro cytotoxicity assays as described in Example 10 for antibodies. Briefly, target cells were plated at 5,000 cells per well in 100 μL in complete RPMI media (RPMI-1640, 10% fetal bovine serum, 2 mM glutamine, 1% penicillin-streptomycin, all reagents from Invitrogen). Conjugates were diluted into complete RPMI media using 3-fold dilution series and 100 μL were added per well. The final concentration typically ranged from $3\times10^{-8}$ M to $4.6\times10^{-12}$ M. Cells were incubated at 37° C. in a humidified 5% $CO_2$ incubator for 4 to 5 days. Viability of remaining cells was determined by colorimetric WST-8 assay as described for antibody assays and the absorbance at 450 nm (A450) was measured in a multiwell plate reader (Dojindo Molecular Technologies, Inc., Rockville, Md., US). The percent viability was calculated by dividing each treated sample value by the average value of wells with untreated cells. The percent viability value was plotted against the antibody-conjugate concentration in a semi-log plot for each treatment.

In Vitro Cytotoxicity of SMCC-DM1 Conjugates of Various Antibodies

The in vitro cytotoxicity of SMCC-DM1 conjugates made with various anti-CD37 antibodies was compared to the activity of a non-specific huIgG-SMCC-DM1 conjugate. The results from a typical cytotoxicity assay are shown in FIG. 24A for Daudi cells incubated with huCD37-3-SMCC-DM1, huCD37-38-SMCC-DM1, huCD37-50-SMCC-DM1, huCD37-51-SMCC-DM1, huCD37-56-SMCC-DM1, huCD37-57-SMCC-DM1, or a non-binding huIgG1-SMCC-DM1 control conjugate. All specific conjugates resulted in specific cell killing as compared to the control conjugate and reduced the cell viability completely at the highest concentration tested. The EC50 values correspond to 0.067 nM, 0.098 nM, 0.13 nM, 0.20 nM, 0.31 nM and 0.35 nM for SMCC-DM1 conjugates of huCD37-3, huCD37-38, huCD37-50, huCD37-51, huCD37-56 and huCD37-57, respectively. In contrast, SMCC-DM1 conjugates of a non-binding isotype control antibody resulted in cell killing with an EC50 value of only 20 nM.

Likewise, FIG. 24B shows the results of a typical cytotoxicity assay using Granta-519 cells incubated with huCD37-3-SMCC-DM1, huCD37-38-SMCC-DM1, huCD37-50-SMCC-DM1, huCD37-51-SMCC-DM1, or a non-binding huIgG1-SMCC-DM1 control conjugate for 5 days. Treatment with all specific SMCC-DM1 completely reduced viability at the highest concentration tested with an EC50 of 0.047 nM, 0.074 nM, 0.12 nM and 0.25 nM for SMCC-DM1 conjugates of huCD37-3, huCD37-38, huCD37-50, and huCD37-51, respectively. In contrast, SMCC-DM1 conjugates of a non-binding isotype control antibody resulted in cell killing with an EC50 value of only 20 nM.

In Vitro Cytotoxicity of huCD37-3-SMCC-DM1, —SPP-DM1 and Sulfo-Mal-DM4 Conjugates The in vitro cytotoxicity of huCD37-3-SMCC-DM1, —SPP-DM1 and sulfo-mal-DM4 conjugates against Daudi, Granta-519 and BJAB cells was compared to the activity of a non-specific huIgG-MCC-DM1 conjugate. All conjugates tested reduced viability of Daudi cells completely at the highest concentration tested with an EC50 value of 0.065 nM, 0.12 nM and 0.14 nM for huCD37-3-SMCC-DM1, huCD37-3-SPP-DM1 and huCD37-3-sulfo-mal-DM4, respectively. In contrast, the non-specific huIgG-SMCC-DM1 conjugate had an EC50 of 19 nM. Likewise, all conjugates tested reduced viability of Granta-519 cells completely at the highest concentration tested with an EC50 value of 0.047 nM, 0.13 nM and 0.088 nM for huCD37-3-SMCC-DM1, huCD37-3-SPP-DM1 and huCD37-3-sulfo-mal-DM4, respectively. In contrast, the non-specific huIgG-SMCC-DM1 conjugate had an EC50 of 19 nM. Finally, all conjugates tested reduced viability of BJAB cells completely at the highest concentration tested with an EC50 value of 0.041 nM, 0.11 nM and 0.11 nM for huCD37-3-SMCC-DM1, huCD37-3-SPP-DM1 and huCD37-3-sulfo-mal-DM4, respectively. In contrast, the non-specific huIgG-SMCC-DM1 conjugate had an EC50 of 16 nM.

In Vitro Cytotoxicity of huCD37-3-SMCC-DM1 and huCD37-3-PEG4-Mal-DM1 Conjugates

The in vitro cytotoxicity of huCD37-3-SMCC-DM1 and huCD37-3-PEG4-mal-DM1 conjugates against a panel of lymphoma cell lines was compared to the activity of a non-specific huIgG-SMCC-DM1 conjugate. Treatment with huCD37-3 conjugates completely reduced Daudi cell viability at the highest concentration tested with an EC50 of 0.036 nM or 0.018 nM for huCD37-3-SMCC-DM1 or huCD37-3-PEG4-mal-DM1 conjugates, respectively. In contrast, the non-binding isotype control conjugates reduced viability with an EC50 of 16 nM or greater than 30 nM for huIgG-SMCC-DM1 or huIgG-PEG4-mal-DM1, respectively. Likewise, treatment with huCD37-3 conjugates completely reduced Granta-519 cell viability at the highest concentration tested with an EC50 of 0.014 nM or 0.012 nM for huCD37-3-SMCC-DM1 or huCD37-3-PEG4-mal-DM1 conjugates, respectively. In contrast, the non-binding isotype control conjugates reduced viability with an EC50 of 6.5 nM or greater than 12 nM for huIgG-SMCC-DM1 or huIgG-PEG4-mal-DM1, respectively.

The in vitro cytotoxicity of huCD37-3-SMCC-DM1 and huCD37-3-PEG4-mal-DM1 conjugates against a panel of lymphoma cell lines was compared to the activity of a non-specific huIgG-SMCC-DM1 conjugate. Treatment with huCD37-3 conjugates completely reduced BJAB cell viability at the highest concentration tested with an EC50 of 0.019 nM or 0.010 nM for huCD37-3-SMCC-DM1 or huCD37-3-PEG4-mal-DM1 conjugates, respectively. In contrast, the non-binding isotype control conjugates reduced viability with an EC50 of 13 nM or 17 nM for huIgG-SMCC-DM1 or huIgG-PEG4-mal-DM1, respectively. Likewise, treatment with huCD37-3 conjugates completely reduced SU-DHL-4 cell viability at the highest concentration tested with an EC50 of 0.031 nM or 0.024 nM for huCD37-3-SMCC-DM1 or huCD37-3-PEG4-mal-DM1 conjugates, respectively. In contrast, the non-binding isotype control conjugates reduced viability with an EC50 of greater than 30 nM for both huIgG-SMCC-DM1 or huIgG-PEG4-mal-DM1. The huCD37-3-SMCC-DM1 conjugate also showed potency against the FL cell line DOHH-2 as well as CLL cell lines such as JVM-2 and JVM-3 (FIG. 32B).

Treatment with huCD37-3 conjugates completely reduced Raji cell viability at the highest concentration tested with an EC50 of 0.071 nM or 0.045 nM for huCD37-3-SMCC-DM1 or huCD37-3-PEG4-mal-DM1 conjugates, respectively. In contrast, the non-binding isotype control conjugates reduced viability with an EC50 of 24 nM or 47 nM for huIgG-SMCC-DM1 or huIgG-PEG4-mal-DM1, respectively. Next, the same conjugates were tested in a vincristine-resistant Raji clone termed Raji-VCR. As seen for the parental Raji cell, both conjugates showed specific cell killing Treatment with huCD37-3 conjugates completely reduced Raji-VCR cell viability at the highest concentration tested with an EC50 of 0.11 nM or 0.037 nM for huCD37-3-SMCC-DM1 or huCD37-3-PEG4-mal-DM1 conjugates, respectively. In contrast, the non-binding isotype control conjugates reduced viability with an EC50 of 46 nM or 100 nM for huIgG-SMCC-DM1 or huIgG-PEG4-mal-DM1, respectively.

Treatment with huCD37-3 conjugates completely reduced Namalwa cell viability at the highest concentration tested with an EC50 of 0.033 nM or 0.024 nM for huCD37-3-SMCC-DM1 or huCD37-3-PEG4-mal-DM1 conjugates, respectively. In contrast, the non-binding isotype control conjugates reduced viability with an EC50 of 20 nM or greater than 30 nM for huIgG-SMCC-DM1 or huIgG-PEG4-mal-DM1, respectively. Likewise, treatment with huCD37-3 conjugates completely reduced Ramos cell viability at the highest concentration tested with an EC50 of 0.16 nM or 0.069 nM for huCD37-3-SMCC-DM1 or huCD37-3-PEG4-mal-DM1 conjugates, respectively. In contrast, the non-binding isotype control conjugates reduced viability with an EC50 of 20 nM for huIgG-SMCC-DM1 and greater than 30 nM for huIgG-PEG4-mal-DM1.

In Vitro Cytotoxicity of huCD37-3-SMCC-DM1 on Antigen Negative Molt-4 Cells

To further verify the specificity of huCD37-3-SMCC-DM1 cytotoxicity, its activity was compared to a non-specific huIgG-MCC-DM1 conjugate against non-CD37 expressing Molt-4 T-cell acute lymphoblastic leukemia cell line. An increased concentration of both conjugates was used in this experiment to capture the relatively poor non-specific cytotoxicity. HuCD37-3-SMCC-DM1 and the non-specific conjugate showed the same cytotoxicity with an EC50 of 38 nM and 42 nM, respectively.

Summary of In Vitro Cytotoxicity of Anti-CD37 Antibody Maytansinoid Conjugates

Taken these cytotoxicity results together, it is apparent that conjugates made with the isolated anti-CD37 antibodies showed specific cytotoxicity against a panel of CD37-positive lymphoma cell lines (FIG. 32B). In each case tested a good specificity window is observed for each CD37-expressing cell line, suggesting that cytotoxicity is a result of specific anti-CD37 antibody binding to target cells. In addition, huCD37-3-SMCC-DM1 and the non-specific conjugate showed the same poor cytotoxicity against antigen-negative Molt-4 cells. This demonstrates that the cytotoxicity observed for this exemplary conjugate is dependent on CD37 expression. The huCD37-3 antibody was also active against many cell lines including DOHH-2, Granata-519, SU-DHL-4, JVM-2, and JVM-3. In contrast, the anti-CD37 SMIP TRU-016 compound had no direct effect on survival of any of these cell lines. The anti-CD20 antibody showed less direct activity than huCD37-3 in most of these cell lines despite the often higher CD20 expression levels as measured by quantitative flow cytometry (FIG. 32A).

Example 17

In Vivo Efficacy of Anti-CD37 Antibodies and their SMCC-DM1 Conjugates in a BJAB Xenograft Model Anti-CD37 antibodies and their SMCC-DM1 conjugates were tested in an established xenograft model using BJAB lymphoma cells implanted subcutaneous into SCID mice.

Animals were randomized by tumor volume into treatment groups when tumors reached a mean tumor volume of approximately 120 $mm^3$ and treated once on day 12 post cell inoculation with either 10 mg/kg of (A) huCD37-3 Ab, huCD37-3-SMCC-DM1, huCD37-50 Ab, huCD37-50-SMCC-DM1 or (B) huCD37-38 Ab, huCD37-38-SMCC-DM1, huCD37-56 Ab, huCD37-56-SMCC-DM1. The mean tumor volume of the different treatment groups is plotted against time post tumor cell inoculation in FIG. 25. It is apparent that treatment with any of the antibodies resulted in a moderate reduction in mean tumor volume, while treatment with any of the SMCC-DM1 conjugates resulted in a more significant reduction in mean tumor volume. In addition, for each treatment a % T/C value was calculated which corresponds to the median tumor volume of each treated group divided by the median tumor volume of the vehicle treated group. A treatment with a % T/C value of below 42% is considered active, while a treatment with a % T/C value of below 12% is considered highly active. Treatment with all SMCC-DM1 conjugates tested resulted in a significant reduction in median tumor volume. The % T/C value on day 29 post cell inoculation corresponded to 20%, 20%, 9% or 4% for huCD37-3-SMCC-DM1, huCD37-50-SMCC-DM1, huCD37-38-SMCC-DM1 or huCD37-56-SMCC-DM1, respectively.

In Vivo Efficacy of huCD37-3 Antibody, Sulfo-Mal-DM4, —SPP-DM1 and SMCC-DM1 Conjugates in a BJAB Xenograft Model In order to evaluate the in vivo efficacy of additional maytansioid conjugates, the sulfo-mal-DM4 and SPP-DM1 conjugates of the exemplary huCD37-3 antibody were compared to SMCC-DM1 conjugates in a xenograft model using BJAB lymphoma cells implanted intravenously into SCID mice.

Animals were randomized by tumor volume into treatment groups when tumors reached a mean tumor volume of approximately 120 $mm^3$ and treated once on day 9 post cell inoculation with either 10 mg/kg of huCD37-3 Ab, huCD37-3-SMCC-DM1, huCD37-3-sulfo-mal-DM4 or 5 mg/kg of huCD37-3-SPP-DM1. The mean tumor volume of the different treatment groups is plotted against time post tumor cell inoculation in FIG. 26. It is apparent that treatment with any of the conjugates resulted in a significant reduction in mean tumor volume. The % T/C value was calculated as described above for each treatment using the median tumor volume for each treatment group. The % T/C value on day 21 post cell inoculation corresponded to 49%, 5%, 7% or 4% for huCD37-3, huCD37-3-SMCC-DM1, huCD37-3-sulfo-mal-DM4 or huCD37-3-SPP-DM1, respectively. At the end of the study on day 121, huCD37-3-sulfo-mal-DM4 treatment resulted in 3 of 8 tumor-free survivors (TFS), while huCD37-3-SPP-DM1 treatment resulted in 1 of 8 TFS. No TFS were observed in the huCD37-3 antibody, huCD37-3-SMCC-DM1 or PBS vehicle control groups. This indicated that maytansinoid conjugates of the huCD37-3 antibody, such as for example SMCC-DM1, sulfo-mal-DM4 or SPP-DM1 conjugates, were highly active in the BJAB model.

In Vivo Efficacy of huCD37-3 Antibody, Sulfo-Mal-DM4, —SPP-DM1 and SMCC-DM1 Conjugates in a SU-DHL-4 Xenograft Model A second xenograft model using SU-DHL-4 diffuse large B-cell lymphoma cells implanted subcutaneous into SCID mice was utilized to evaluate the in vivo efficacy of the sulfo-mal-DM4 and SPP-DM1 conjugates of the exemplary huCD37-3 antibody as compared to SMCC-DM1 conjugates Animals were randomized by body weight into treatment groups when tumors were established and treated once on day 17 post cell inoculation with either 10 mg/kg of huCD37-3 Ab, huCD37-3-SMCC-DM1, huCD37-3-sulfo-mal-DM4 or 5 mg/kg of huCD37-3-SPP-DM1. The median tumor volume of the different treatment groups is plotted against time post tumor cell inoculation in FIG. 27. It is apparent that treatment with the huCD37-3 antibody resulted in a reduction in median tumor volume, while treatment with any of the conjugates resulted in a more significant reduction in median tumor volume. The % T/C value was calculated as described above for each treatment. The % T/C value on day 37 post cell inoculation corresponded to 32%, 1%, 1% or 3% for huCD37-3, huCD37-3-SMCC-DM1, huCD37-3-sulfo-mal-DM4 or huCD37-3-SPP-DM1, respectively. At the end of the study on day 125, huCD37-3-SMCC-DM1 or huCD37-3-sulfo-mal-DM4 treatment resulted in 8 of 10 tumor-free survivors (TFS), while huCD37-3-SPP-DM1 treatment resulted in 9 of 10 TFS. No TFS were observed in the huCD37-3 antibody or PBS vehicle control groups. This indicated that the huCD37-3 antibody itself was active with a single 10 mg/kg dose in the SU-DHL-4 model. In addition, maytansinoid conjugates, such as for example SMCC-DM1, sulfo-mal-DM4 or SPP-DM1 conjugates, added efficacy to the antibody and result in even greater potency in this model.

In Vivo Efficacy of huCD37-3 Antibody, PEG4-Mal-DM1 and SMCC-DM1 Conjugates in a BJAB Xenograft Model The huCD37-3 antibody and its PEG4-mal-DM1 and SMCC-DM1 conjugates were tested in an established xenograft model using BJAB lymphoma cells implanted subcutaneous into SCID mice. Animals were randomized by tumor volume into treatment groups when tumors reached a mean tumor volume of approximately 120 $mm^3$ and treated once on day 9 post cell inoculation with either 10 mg/kg of huCD37-3 Ab, huCD37-3-SMCC-DM1 or huCD37-3-PEG4-mal-DM1. As seen in FIG. 28, treatment with either conjugate resulted in a significant reduction in mean tumor volume. The % T/C value was calculated as described above for each treatment using the median tumor volume for each treatment group. The % T/C value on day 24 post cell inoculation corresponded to 48%, 16% or 5% for huCD37-3, huCD37-3-SMCC-DM1 or huCD37-3-PEG4-mal-DM1, respectively. On day 74 post cell inoculation, huCD37-3-SMCC-DM1 treatment resulted in 1 of 9 tumor-free survivors (TFS), while huCD37-PEG4-mal-DM1 treatment resulted in 1 of 9 TFS. No TFS were observed in the huCD37-3 antibody or PBS vehicle control groups. In addition, huCD37-3-SMCC-DM1 was also active at a single dose of 5 mg/kg in this model with a % T/C value on day 24 post cell inoculation of 34%. This indicated that maytansinoid conjugates of the huCD37-3 antibody, such as for example SMCC-DM1 or PEG4-mal-DM1 conjugates, were highly active in the BJAB model.

In Vivo Efficacy of huCD37-3 Antibody, PEG4-Mal-DM1 and SMCC-DM1 Conjugates in a SU-DHL-4 Xenograft Model The huCD37-3 antibody and its PEG4-mal-DM1 and SMCC-DM1 conjugates were tested in an established xenograft model using SU-DHL-4 diffuse large B-cell lymphoma cells implanted subcutaneous into SCID mice. Animals were randomized by body weight into treatment groups and treated once on day 15 post cell inoculation with either 10 mg/kg of huCD37-3 Ab, huCD37-3-SMCC-DM1 or huCD37-3-PEG4-mal-DM1. The mean tumor volume of the different treatment groups is plotted against time post tumor cell inoculation FIG. 29. It is apparent that treatment with the huCD37-3 antibody resulted in a reduction in mean tumor volume, while treatment with either conjugate resulted in a more significant reduction in mean tumor volume. The % T/C value was calculated as described above for each treatment using the median tumor volume for each treatment group. The % T/C value on day 38 post cell inoculation corresponded to 34%, 4% or 2% for huCD37-3, huCD37-3-SMCC-DM1, or huCD37-3-PEG4-mal-DM1, respectively. On day 74 post cell inoculation, huCD37-3-SMCC-DM1 treatment resulted in 8 of 10 tumor-free survivors (TFS), while huCD37-3-PEG4-mal-DM1 treatment resulted in 10 of 10 TFS. No TFS were observed in the huCD37-3 antibody or PBS vehicle control groups. This indicated that the huCD37-3 antibody itself was active with a single 10 mg/kg dose in the SU-DHL-4 model. In addition, maytansinoid conjugates, such as for example SMCC-DM1 or PEG4-mal-DM1 conjugates, showed enhanced efficacy as compared to the unconjugated antibody efficacy to the antibody and resulted in even greater potency in this model. The huCD37-3-SMCC-DM1 conjugate also showed strong efficacy at single doses of 2.5 or 5 mg/kg in this model with % T/C values on day 37 post cell inoculation of 18% and 6%, respectively.

In Vivo Efficacy of huCD37-3 Antibody, huCD37-3-SMCC-DM1 Conjugate, Rituximab Antibody, and a Regime of Cyclophosphamide, Vincristine, and Prednisone (CVP) in a DoHH2 Xenograft Model The huCD37-3 antibody and its SMCC-DM1 conjugate were tested in an established xenograft model using DoHH2 follicular lymphoma cells implanted subcutaneously into SCID mice. Animals were randomized by tumor volume into treatment groups, and treatments started on day 12 post inoculation with either a single dose of 10 mg/kg of huCD37-3 antibody or huCD37-3-SMCC-DM1 conjugate; six doses of 2 mg/kg of Rituximab twice per week for three weeks; or with a regimen of a single 40 mg/kg dose of cyclophosphamide, and 0.5 mg/kg of vincristine, along with five daily 0.2 mg/kg doses of prednisone (CVP). The median tumor volume of the different treatment groups was plotted against time post tumor cell inoculation in FIG. 30. Treatment with the huCD37-3 antibody resulted in a reduction in median tumor volume, while treatment with huCD37-3-SMCC-DM1 conjugate resulted in a more significant reduction in median tumor volume. The huCD37-3-SMCC-DM1 conjugate resulted in a median tumor reduction similar to treatment with Rituximab and a more durable median tumor reduction as compared to treatment with CVP. The tumor growth delay (T-C value) was defined as the median time (in days), required for the treatment group (T) and the control group (C) tumors to reach a predetermined size and was calculated for each treatment group excluding the tumor free survivors. The T-C value for median treatment tumors to reach 800 $mm^3$ corresponded to 8, 25, 24, and 13 days for huCD37-3, huCD37-3-SMCC-DM1, rituximab and CVP, respectively. At the end of the study, on day 130 post cell inoculation, huCD37-3-SMCC-DM1 treatment resulted in 1 of 9 tumor-free survivors (TFS). No TFS were observed in the huCD37-3 antibody, rituximab, CVP, or PBS vehicle control groups. The SMCC-DM1 conjugate showed comparable tumor growth delay to rituximab and enhanced tumor growth delay as compared to the unconjugated antibody and treatment with CVP in the DoHH2 model.

In Vivo Efficacy of huCD37-3 Antibody, huCD37-3-SMCC-DM1 Conjugate, Ofatumumab Antibody and Bendamustine in a JVM-3 Xenograft Model The huCD37-3 antibody and its huCD37-3-SMCC-DM1 conjugate were tested in an established xenograft model using JVM-3 chronic lymphocytic leukemia cells implanted subcutaneously into SCID mice. Animals were randomized by tumor volume into treatment groups, and treatments started on day 7 post inoculation with either a single dose of 10 mg/kg of huCD37-3 antibody, a 5 or a 10 mg/kg dose of huCD37-3-SMCC-DM1 conjugate, six doses of 5 mg/kg of ofatumumab twice per week for three weeks, or a single 50 mg/kg dose of bendamustine. The median tumor volume of the different treatment groups was plotted against time post tumor cell inoculation in FIG. 31. Treatment with the huCD37-3 antibody resulted in a reduction in median tumor volume, while treatment with huCD37-3-SMCC-DM1 conjugate resulted in a more significant reduction in median tumor volume. The % T/C value was calculated as described above for each treatment using the median tumor volume for each treatment group. The % T/C value on day 20 post cell inoculation corresponded to 31%, 19%, 10%, 35%, and 38% for huCD37-3, 5 mg/kg huCD37-3-SMCC-DM1, 10 mg/kg huCD37-3-SMCC-DM1, ofatumumab, and bendamustine, respectively. At the end of the study, on day 76 post cell inoculation, huCD37 and ofatumumab antibody treatments both resulted in 1 of 10 tumor-free survivors (TFS), while huCD37-3-SMCC-DM1 at 5 and 10 mg/kg resulted in 1 and 2 out of 10 TFS, respectively. No TFS were observed in the bendamustine or PBS vehicle control groups. This indicated that the huCD37-3 antibody itself was active at a single 10 mg/kg dose in the JVM-3 model. The maytansinoid conjugate, huCD37-3-SMCC-DM1, showed enhanced efficacy as compared to the unconjugated antibody. In addition, treatment with the huCD37-3-SMCC-DM1 maytansinoid conjugate resulted in even greater potency than ofatumumab or bendamustine treatment in this model.

Summary of In Vivo Efficacy of Anti-CD37 Antibody Conjugates

CD37 has not been evaluated as a target for maytansinoid immunoconjugates, however CD20 has. CD37 is structurally similar to CD20 as both antigens are cell surface proteins that contain 4 transmembrane domains and one small and one large extracellular loop. Antibodies against either antigen have been shown to be internalized slowly and have a slow to moderate rate of intracellular metabolism (Press et al. 1989, Cancer Res. 49(17):4906-12, and Press et al. 1994, Blood. 83(5):1390-7). Immunoconjugates of CD20 antibodies have been evaluated previously. In one case, non-cleavable MCC-DM1 conjugates of an anti-CD20 antibody showed the same efficacy as the unconjugated antibody, while a cleavable SPP-DM1 conjugate of the same antibody showed improved efficacy in a Granta-519 xenograft model in SCID mice (Polson A G, Cancer Res 2009; 69:2358-64). Similarly, calicheamicin conjugates of rituximab made with an acid-stable amide linker were did not show improved in vivo efficacy in a Ramos xenograft model in nude mice. Only calicheamicin conjugates of rituximab made with an acid-labile dimethyl hydrazide Ac-But linker showed improved in vivo efficacy in this study (DiJoseph J F, Cancer Immunol Immunotherapy 2007; 56:1107-1117).

In striking contrast non-cleavable SMCC-DM1 conjugates of several isolated anti-CD37 antibodies of this invention show dramatically improved in vivo efficacy in BJAB, SU-DHL-4, DoHH2 and JVM-3 xenograft model as compared to the unconjugated antibody. This suggests that the isolated antibodies have unique properties that allow them to be more efficacious as maytansinoid conjugates, such as for example SMCC-DM1 conjugates, in vivo.

It is to be appreciated that the Detailed Description section, and not the Summary and Abstract sections, is intended to be used to interpret the claims. The Summary and Abstract sections sets forth one or more, but not all, exemplary embodiments of the present invention as contemplated by the inventor(s), and thus, are not intended to limit the present invention and the appended claims in any way.

The present invention has been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

What is claimed is:

1. An antibody produced by the hybridoma of ATCC Deposit Designation PTA-10664 or an antigen-binding fragment thereof.

2. An isolated antibody or antigen binding fragment thereof that specifically binds to CD37, wherein said antibody, or antigen binding fragment comprises the VH-CDR1, VH-CDR2, VH-CDR3, VL-CDR1, VL-CDR2, and VL-CDR3 polypeptide sequences of SEQ ID NOs: 4, 5, and 6 and SEQ ID NOs: 28, 29, and 30 respectively.

3. An isolated cell producing the antibody or antigen binding fragment thereof of claim 2.

4. A method of making an anti-CD37 antibody or antigen-binding fragment thereof comprising (a) culturing the cell of claim 3; and (b) isolating said antibody, or antigen-binding fragment thereof from said cultured cell.

5. An immunoconjugate having the formula (A)-(L)-(C), wherein:

(A) is the antibody or antigen binding fragment of claim 2;

(L) is a linker; and (C) is a cytotoxic agent; and wherein said linker (L) links (A) to (C).

6. The immunoconjugate of claim 5 comprising 3-4 (C) per (A).

7. The immunoconjugate of claim 5, wherein said linker is selected from the group consisting: N-succinimidyl 4-(2-pyridyldithio)pentanoate (SPP); N-succinimidyl 4-(2-pyridyldithio)butanoate (SPDB) or N-succinimidyl 4-(2-pyridyldithio)-2-sulfobutanoate (sulfo-SPDB); N-succinimidyl 4-(maleimidomethyl)cyclohexanecarboxylate (SMCC); N-sulfosuccinimidyl 4-(maleimidomethyl)cyclohexanecarboxylate (sulfoSMCC); N-succinimidyl-4-(iodoacetyl)-aminobenzoate (SIAB); and N-succinimidyl-[(N-maleimidopropionamido)-tetraethyleneglycol]ester (NHS-PEG4-maleimide).

8. The immunoconjugate of claim 5, wherein said cytotoxic agent is selected from the group consisting of a maytansinoid, maytansinoid analog, doxorubicin, a modified doxorubicin, benzodiazepine, taxoid, CC-1065, CC-1065 analog, duocarmycin, duocarmycin analog, calicheamicin, dolastatin, dolastatin analog, aristatin, tomaymycin derivative, and leptomycin derivative or a prodrug of the agent.

9. The immunoconjugate of claim 8, wherein said cytotoxic agent is N(2')-deacetyl-N(2')-(3-mercapto-1-oxopropyl)-maytansine (DM1) or N(2')-deacetyl-N2-(4-mercapto-4-methyl-1-oxopentyl)-maytansine (DM4).

10. A pharmaceutical composition comprising the antibody or antigen binding fragment thereof of claim 2 and a pharmaceutically acceptable carrier.

11. A pharmaceutical composition comprising the immunoconjugates of claim 5, wherein the immunoconjugates have an average of about 3 to about 4 (C) per (A).

12. A diagnostic reagent comprising the antibody or antigen binding fragment thereof of claim 2.

13. A kit comprising the antibody or antigen binding fragment thereof of claim 2.

14. The immunoconjugate of claim 5, wherein the antibody comprises the polypeptide sequences of SEQ ID NO:57 and SEQ ID NO:74.

15. The antibody or antigen binding fragment of claim 2, wherein the antibody or antigen binding fragment comprises the polypeptide sequences of SEQ ID NO:57 and SEQ ID NO:74.

16. The immunoconjugate of claim 5, wherein said linker is SMCC.

17. The immunoconjugate of claim 16, wherein said cytotoxic agent is N(2')-deacetyl-N(2')-(3-mercapto-1-oxopropyl)-maytansine (DM1).

18. The immunoconjugate of claim 14, wherein said linker is SMCC.

19. The immunoconjugate of claim 14, wherein said cytotoxic agent is N(2')-deacetyl-N(2')-(3-mercapto-1-oxopropyl)-maytansine (DM1).

20. The immunoconjugate of claim 18, wherein said cytotoxic agent is N(2')-deacetyl-N(2')-(3-mercapto-1-oxopropyl)-maytansine (DM1).

21. An immunoconjugate having the formula (A)-(L)-(C), wherein:

(A) is the antibody or antigen binding fragment of claim 15;

(L) is a linker; and (C) is a cytotoxic agent; and wherein said linker (L) links (A) to (C).

22. A pharmaceutical composition comprising the antibody or antigen binding fragment of claim 15 and a pharmaceutically acceptable carrier.

23. A pharmaceutical composition comprising the immunoconjugate of claim 17 and a pharmaceutically acceptable carrier.

24. A pharmaceutical composition comprising the immunoconjugate of claim 20 and a pharmaceutically acceptable carrier.

25. A pharmaceutical composition comprising the immunoconjugates of claim 17, wherein the immunoconjugates have an average of about 3 to about 4 (C) per (A).

26. A pharmaceutical composition comprising the immunoconjugates of claim 20, wherein the immunoconjugates have an average of about 3 to about 4 (C) per (A).

* * * * *

UNITED STATES PATENT AND TRADEMARK OFFICE

CERTIFICATE OF CORRECTION

PATENT NO. : 8,765,917 B2
APPLICATION NO. : 13/045693
DATED : July 1, 2014
INVENTOR(S) : Deckert et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 562 days.

Signed and Sealed this
Eighth Day of March, 2016

Michelle K. Lee
*Director of the United States Patent and Trademark Office*

SEQUENCE LISTING

```
<160> NUMBER OF SEQ ID NOS: 196

<210> SEQ ID NO 1
<211> LENGTH: 280
<212> TYPE: PRT
<213> ORGANISM: Homo sapiens
<220> FEATURE:
<223> OTHER INFORMATION: CD37

<400> SEQUENCE: 1

Met Ser Ala Gln Glu Ser Cys Leu Ser Leu Ile Lys Tyr Phe Leu Phe
1               5                   10                  15

Val Phe Asn Leu Phe Phe Phe Val Leu Gly Ser Leu Ile Phe Cys Phe
            20                  25                  30

Gly Ile Trp Ile Leu Ile Asp Lys Thr Ser Phe Val Ser Phe Val Gly
        35                  40                  45

Leu Ala Phe Val Pro Leu Gln Ile Trp Ser Lys Val Leu Ala Ile Ser
    50                  55                  60

Gly Ile Phe Thr Met Gly Ile Ala Leu Leu Gly Cys Val Gly Ala Leu
65                  70                  75                  80

Lys Glu Leu Arg Cys Leu Leu Gly Leu Tyr Phe Gly Met Leu Leu Leu
                85                  90                  95

Leu Phe Ala Thr Gln Ile Thr Leu Gly Ile Leu Ile Ser Thr Gln Arg
            100                 105                 110

Ala Gln Leu Glu Arg Ser Leu Arg Asp Val Val Glu Lys Thr Ile Gln
        115                 120                 125

Lys Tyr Gly Thr Asn Pro Glu Glu Thr Ala Ala Glu Glu Ser Trp Asp
    130                 135                 140

Tyr Val Gln Phe Gln Leu Arg Cys Cys Gly Trp His Tyr Pro Gln Asp
145                 150                 155                 160

Trp Phe Gln Val Leu Ile Leu Arg Gly Asn Gly Ser Glu Ala His Arg
                165                 170                 175

Val Pro Cys Ser Cys Tyr Asn Leu Ser Ala Thr Asn Asp Ser Thr Ile
            180                 185                 190

Leu Asp Lys Val Ile Leu Pro Gln Leu Ser Arg Leu Gly His Leu Ala
        195                 200                 205

Arg Ser Arg His Ser Ala Asp Ile Cys Ala Val Pro Ala Glu Ser His
    210                 215                 220

Ile Tyr Arg Glu Gly Cys Ala Gln Gly Leu Gln Lys Trp Leu His Asn
225                 230                 235                 240

Asn Leu Ile Ser Ile Val Gly Ile Cys Leu Gly Val Gly Leu Leu Glu
                245                 250                 255

Leu Gly Phe Met Thr Leu Ser Ile Phe Leu Cys Arg Asn Leu Asp His
            260                 265                 270
```

```
Val Tyr Asn Arg Leu Ala Tyr Arg
        275                 280


<210> SEQ ID NO 2
<211> LENGTH: 281
<212> TYPE: PRT
<213> ORGANISM: Macaca mulatta
<220> FEATURE:
<223> OTHER INFORMATION: CD37

<400> SEQUENCE: 2

Met Ser Ala Gln Glu Ser Cys Leu Ser Leu Ile Lys Tyr Phe Leu Phe
1               5                   10                  15

Val Phe Asn Leu Phe Phe Phe Val Ile Leu Gly Ser Leu Ile Phe Cys
            20                  25                  30

Phe Gly Ile Trp Ile Leu Ile Asp Lys Thr Ser Phe Val Ser Phe Val
        35                  40                  45

Gly Leu Ala Phe Val Pro Leu Gln Ile Trp Ser Lys Val Leu Ala Ile
    50                  55                  60

Ser Gly Val Phe Thr Met Gly Leu Ala Leu Leu Gly Cys Val Gly Ala
65                  70                  75                  80

Leu Lys Glu Leu Arg Cys Leu Leu Gly Leu Tyr Phe Gly Met Leu Leu
                85                  90                  95

Leu Leu Phe Ala Thr Gln Ile Thr Leu Gly Ile Leu Ile Ser Thr Gln
            100                 105                 110

Arg Ala Gln Leu Glu Arg Ser Leu Gln Asp Ile Val Glu Lys Thr Ile
        115                 120                 125

Gln Arg Tyr His Thr Asn Pro Glu Glu Thr Ala Ala Glu Glu Ser Trp
    130                 135                 140

Asp Tyr Val Gln Phe Gln Leu Arg Cys Cys Gly Trp His Ser Pro Gln
145                 150                 155                 160

Asp Trp Phe Gln Val Leu Thr Leu Arg Gly Asn Gly Ser Glu Ala His
                165                 170                 175

Arg Val Pro Cys Ser Cys Tyr Asn Leu Ser Ala Thr Asn Asp Ser Thr
            180                 185                 190

Ile Leu Asp Lys Val Ile Leu Pro Gln Leu Ser Arg Leu Gly Gln Leu
        195                 200                 205

Ala Arg Ser Arg His Ser Thr Asp Ile Cys Ala Val Pro Ala Asn Ser
    210                 215                 220

His Ile Tyr Arg Glu Gly Cys Ala Arg Ser Leu Gln Lys Trp Leu His
225                 230                 235                 240

Asn Asn Leu Ile Ser Ile Val Gly Ile Cys Leu Gly Val Gly Leu Leu
                245                 250                 255

Glu Leu Gly Phe Met Thr Leu Ser Ile Phe Leu Cys Arg Asn Leu Asp
            260                 265                 270

His Val Tyr Asn Arg Leu Arg Tyr Arg
        275                 280


<210> SEQ ID NO 3
<211> LENGTH: 281
<212> TYPE: PRT
<213> ORGANISM: Mus musculus
<220> FEATURE:
<223> OTHER INFORMATION: CD37

<400> SEQUENCE: 3

Met Ser Ala Gln Glu Ser Cys Leu Ser Leu Ile Lys Tyr Phe Leu Phe
```

```
1               5                   10                  15

Val Phe Asn Leu Phe Phe Phe Val Leu Gly Gly Leu Ile Phe Cys Phe
            20                  25                  30

Gly Thr Trp Ile Leu Ile Asp Lys Thr Ser Phe Val Ser Phe Val Gly
        35                  40                  45

Leu Ser Phe Val Pro Leu Gln Thr Trp Ser Lys Val Leu Ala Val Ser
    50                  55                  60

Gly Val Leu Thr Met Ala Leu Ala Leu Leu Gly Cys Val Gly Ala Leu
65                  70                  75                  80

Lys Glu Leu Arg Cys Leu Leu Gly Leu Tyr Phe Gly Met Leu Leu Leu
                85                  90                  95

Leu Phe Ala Thr Gln Ile Thr Leu Gly Ile Leu Ile Ser Thr Gln Arg
            100                 105                 110

Val Arg Leu Glu Arg Arg Val Gln Glu Leu Val Leu Arg Thr Ile Gln
        115                 120                 125

Ser Tyr Arg Thr Asn Pro Asp Glu Thr Ala Ala Glu Glu Ser Trp Asp
    130                 135                 140

Tyr Ala Gln Phe Gln Leu Arg Cys Cys Gly Trp Gln Ser Pro Arg Asp
145                 150                 155                 160

Trp Asn Lys Ala Gln Met Leu Lys Ala Asn Glu Ser Glu Glu Pro Phe
                165                 170                 175

Val Pro Cys Ser Cys Tyr Asn Ser Thr Ala Thr Asn Asp Ser Thr Val
            180                 185                 190

Phe Asp Lys Leu Phe Phe Ser Gln Leu Ser Arg Leu Gly Pro Arg Ala
        195                 200                 205

Lys Leu Arg Gln Thr Ala Asp Ile Cys Ala Leu Pro Ala Lys Ala His
    210                 215                 220

Ile Tyr Arg Glu Gly Cys Ala Gln Ser Leu Gln Lys Trp Leu His Asn
225                 230                 235                 240

Asn Ile Ile Ser Ile Val Gly Ile Cys Leu Gly Val Gly Leu Leu Glu
                245                 250                 255

Leu Gly Phe Met Thr Leu Ser Ile Phe Leu Cys Arg Asn Leu Asp His
            260                 265                 270

Val Tyr Asp Arg Leu Ala Arg Tyr Arg
        275                 280


<210> SEQ ID NO 4
<211> LENGTH: 5
<212> TYPE: PRT
<213> ORGANISM: Artificial Sequence
<220> FEATURE:
<223> OTHER INFORMATION: Variable heavy chain CDR amino acid sequence;
      Antibody CD37-3, VH-CDR1

<400> SEQUENCE: 4

Thr Ser Gly Val Ser
1               5


<210> SEQ ID NO 5
<211> LENGTH: 9
<212> TYPE: PRT
<213> ORGANISM: Artificial Sequence
<220> FEATURE:
<223> OTHER INFORMATION: Variable heavy chain CDR amino acid sequence;
      Antibody CD37-3, VH-CDR2

<400> SEQUENCE: 5

Val Ile Trp Gly Asp Gly Ser Thr Asn
```

-continued 1 5

<210> SEQ ID NO 6
<211> LENGTH: 7
<212> TYPE: PRT
<213> ORGANISM: Artificial Sequence
<220> FEATURE:
<223> OTHER INFORMATION: Variable heavy chain CDR amino acid sequence; Antibody CD37-3, VH-CDR3

<400> SEQUENCE: 6

Gly Gly Tyr Ser Leu Ala His
1 5

<210> SEQ ID NO 7
<211> LENGTH: 5
<212> TYPE: PRT
<213> ORGANISM: Artificial Sequence
<220> FEATURE:
<223> OTHER INFORMATION: Variable heavy chain CDR amino acid sequence; Antibody CD37-12, VH-CDR1

<400> SEQUENCE: 7

Lys Tyr Gly Met Asn
1 5

<210> SEQ ID NO 8
<211> LENGTH: 10
<212> TYPE: PRT
<213> ORGANISM: Artificial Sequence
<220> FEATURE:
<223> OTHER INFORMATION: Variable heavy chain CDR amino acid sequence; Antibody CD37-12, VH-CDR2

<400> SEQUENCE: 8

Trp Ile Asn Thr Asn Thr Gly Glu Ser Arg
1 5 10

<210> SEQ ID NO 9
<211> LENGTH: 6
<212> TYPE: PRT
<213> ORGANISM: Artificial Sequence
<220> FEATURE:
<223> OTHER INFORMATION: Variable heavy chain CDR amino acid sequence; Antibody CD37-12, VH-CDR3

<400> SEQUENCE: 9

Gly Thr Val Val Ala Asp
1 5

<210> SEQ ID NO 10
<211> LENGTH: 6
<212> TYPE: PRT
<213> ORGANISM: Artificial Sequence
<220> FEATURE:
<223> OTHER INFORMATION: Variable heavy chain CDR amino acid sequence; Antibody CD37-38, VH-CDR1

<400> SEQUENCE: 10

Ser Gly Phe Gly Trp His
1 5

<210> SEQ ID NO 11
<211> LENGTH: 9
<212> TYPE: PRT
<213> ORGANISM: Artificial Sequence
<220> FEATURE:
<223> OTHER INFORMATION: Variable heavy chain CDR amino acid sequence;

Antibody CD37-38, VH-CDR2

<400> SEQUENCE: 11

Tyr Ile Leu Tyr Ser Gly Gly Thr Asp
1 5

<210> SEQ ID NO 12
<211> LENGTH: 11
<212> TYPE: PRT
<213> ORGANISM: Artificial Sequence
<220> FEATURE:
<223> OTHER INFORMATION: Variable heavy chain CDR amino acid sequence; Antibody CD37-38, VH-CDR3

<400> SEQUENCE: 12

Gly Tyr Tyr Gly Tyr Gly Ala Trp Phe Val Tyr
1 5 10

<210> SEQ ID NO 13
<211> LENGTH: 6
<212> TYPE: PRT
<213> ORGANISM: Artificial Sequence
<220> FEATURE:
<223> OTHER INFORMATION: Variable heavy chain CDR amino acid sequence; Antibody CD37-50, VH-CDR1

<400> SEQUENCE: 13

Ser Gly Phe Ala Trp His
1 5

<210> SEQ ID NO 14
<211> LENGTH: 9
<212> TYPE: PRT
<213> ORGANISM: Artificial Sequence
<220> FEATURE:
<223> OTHER INFORMATION: Variable heavy chain CDR amino acid sequence; Antibody CD37-50, VH-CDR2

<400> SEQUENCE: 14

Tyr Ile Leu Tyr Ser Gly Ser Thr Val
1 5

<210> SEQ ID NO 15
<211> LENGTH: 11
<212> TYPE: PRT
<213> ORGANISM: Artificial Sequence
<220> FEATURE:
<223> OTHER INFORMATION: Variable heavy chain CDR amino acid sequence; Antibody CD37-50, VH-CDR3

<400> SEQUENCE: 15

Gly Tyr Tyr Gly Tyr Gly Ala Trp Phe Ala Tyr
1 5 10

<210> SEQ ID NO 16
<211> LENGTH: 6
<212> TYPE: PRT
<213> ORGANISM: Artificial Sequence
<220> FEATURE:
<223> OTHER INFORMATION: Variable heavy chain CDR amino acid sequence; Antibody CD37-51, VH-CDR1

<400> SEQUENCE: 16

Ser Gly Phe Ala Trp His
1 5

<210> SEQ ID NO 17

<211> LENGTH: 9
<212> TYPE: PRT
<213> ORGANISM: Artificial Sequence
<220> FEATURE:
<223> OTHER INFORMATION: Variable heavy chain CDR amino acid sequence;
Antibody CD37-51, VH-CDR2

<400> SEQUENCE: 17

Tyr Ile His Tyr Ser Gly Ser Thr Asn
1 5

<210> SEQ ID NO 18
<211> LENGTH: 11
<212> TYPE: PRT
<213> ORGANISM: Artificial Sequence
<220> FEATURE:
<223> OTHER INFORMATION: Variable heavy chain CDR amino acid sequence;
Antibody CD37-51, VH-CDR3

<400> SEQUENCE: 18

Gly Tyr Tyr Gly Phe Gly Ala Trp Phe Val Tyr
1 5 10

<210> SEQ ID NO 19
<211> LENGTH: 6
<212> TYPE: PRT
<213> ORGANISM: Artificial Sequence
<220> FEATURE:
<223> OTHER INFORMATION: Variable heavy chain CDR amino acid sequence;
Antibody CD37-56, VH-CDR1

<400> SEQUENCE: 19

Ser Gly Phe Ala Trp His
1 5

<210> SEQ ID NO 20
<211> LENGTH: 9
<212> TYPE: PRT
<213> ORGANISM: Artificial Sequence
<220> FEATURE:
<223> OTHER INFORMATION: Variable heavy chain CDR amino acid sequence;
Antibody CD37-56, VH-CDR2

<400> SEQUENCE: 20

Tyr Ile His Tyr Ser Gly Gly Thr Asn
1 5

<210> SEQ ID NO 21
<211> LENGTH: 11
<212> TYPE: PRT
<213> ORGANISM: Artificial Sequence
<220> FEATURE:
<223> OTHER INFORMATION: Variable heavy chain CDR amino acid sequence;
Antibody CD37-56, VH-CDR3

<400> SEQUENCE: 21

Gly Tyr Tyr Gly Phe Gly Ala Trp Phe Ala Tyr
1 5 10

<210> SEQ ID NO 22
<211> LENGTH: 6
<212> TYPE: PRT
<213> ORGANISM: Artificial Sequence
<220> FEATURE:
<223> OTHER INFORMATION: Variable heavy chain CDR amino acid sequence;
Antibody CD37-57, VH-CDR1

<400> SEQUENCE: 22

```
Ser Gly Phe Ala Trp His
1               5


<210> SEQ ID NO 23
<211> LENGTH: 9
<212> TYPE: PRT
<213> ORGANISM: Artificial Sequence
<220> FEATURE:
<223> OTHER INFORMATION: Variable heavy chain CDR amino acid sequence;
      Antibody CD37-57, VH-CDR2

<400> SEQUENCE: 23

Tyr Ile Leu Tyr Ser Gly Ser Thr Val
1               5


<210> SEQ ID NO 24
<211> LENGTH: 11
<212> TYPE: PRT
<213> ORGANISM: Artificial Sequence
<220> FEATURE:
<223> OTHER INFORMATION: Variable heavy chain CDR amino acid sequence;
      Antibody CD37-57, VH-CDR3

<400> SEQUENCE: 24

Gly Tyr Tyr Gly Tyr Gly Ala Trp Phe Ala Tyr
1               5                   10


<210> SEQ ID NO 25
<211> LENGTH: 6
<212> TYPE: PRT
<213> ORGANISM: Artificial Sequence
<220> FEATURE:
<223> OTHER INFORMATION: Variable heavy chain CDR amino acid sequence;
      Consensus, VH-CDR1
<220> FEATURE:
<221> NAME/KEY: MISC_FEATURE
<222> LOCATION: (4)..(4)
<223> OTHER INFORMATION: Where Xaa is Ala or Gly

<400> SEQUENCE: 25

Ser Gly Phe Xaa Trp His
1               5


<210> SEQ ID NO 26
<211> LENGTH: 9
<212> TYPE: PRT
<213> ORGANISM: Artificial Sequence
<220> FEATURE:
<223> OTHER INFORMATION: Variable heavy chain CDR amino acid sequence;
      Consensus, VH-CDR2
<220> FEATURE:
<221> NAME/KEY: MISC_FEATURE
<222> LOCATION: (3)..(3)
<223> OTHER INFORMATION: Where Xaa is Leu or His
<220> FEATURE:
<221> NAME/KEY: MISC_FEATURE
<222> LOCATION: (7)..(7)
<223> OTHER INFORMATION: Where Xaa is Gly or Ser
<220> FEATURE:
<221> NAME/KEY: MISC_FEATURE
<222> LOCATION: (9)..(9)
<223> OTHER INFORMATION: Where Xaa is Asp, Val or Asn

<400> SEQUENCE: 26

Tyr Ile Xaa Tyr Ser Gly Xaa Thr Xaa
1               5


<210> SEQ ID NO 27
<211> LENGTH: 11
<212> TYPE: PRT
```

```
<213> ORGANISM: Artificial Sequence
<220> FEATURE:
<223> OTHER INFORMATION: Variable heavy chain CDR amino acid sequence;
      Consensus, VH-CDR3
<220> FEATURE:
<221> NAME/KEY: MISC_FEATURE
<222> LOCATION: (5)..(5)
<223> OTHER INFORMATION: Where Xaa is Tyr or Phe
<220> FEATURE:
<221> NAME/KEY: MISC_FEATURE
<222> LOCATION: (10)..(10)
<223> OTHER INFORMATION: Where Xaa is Val or Ala

<400> SEQUENCE: 27

Gly Tyr Tyr Gly Xaa Gly Ala Trp Phe Xaa Tyr
1               5                   10


<210> SEQ ID NO 28
<211> LENGTH: 11
<212> TYPE: PRT
<213> ORGANISM: Artificial Sequence
<220> FEATURE:
<223> OTHER INFORMATION: Variable light chain CDR amino acid sequence;
      CD37-3, VL-CDR1

<400> SEQUENCE: 28

Arg Ala Ser Glu Asn Ile Arg Ser Asn Leu Ala
1               5                   10


<210> SEQ ID NO 29
<211> LENGTH: 7
<212> TYPE: PRT
<213> ORGANISM: Artificial Sequence
<220> FEATURE:
<223> OTHER INFORMATION: Variable light chain CDR amino acid sequence;
      CD37-3, VL-CDR2

<400> SEQUENCE: 29

Val Ala Thr Asn Leu Ala Asp
1               5


<210> SEQ ID NO 30
<211> LENGTH: 9
<212> TYPE: PRT
<213> ORGANISM: Artificial Sequence
<220> FEATURE:
<223> OTHER INFORMATION: Variable light chain CDR amino acid sequence;
      CD37-3, VL-CDR3

<400> SEQUENCE: 30

Gln His Tyr Trp Gly Thr Thr Trp Thr
1               5


<210> SEQ ID NO 31
<211> LENGTH: 15
<212> TYPE: PRT
<213> ORGANISM: Artificial Sequence
<220> FEATURE:
<223> OTHER INFORMATION: Variable light chain CDR amino acid sequence;
      CD37-12, VL-CDR1

<400> SEQUENCE: 31

Arg Ala Ser Gln Ser Val Ser Thr Ser Ser Tyr Ser Tyr Leu Tyr
1               5                   10                  15


<210> SEQ ID NO 32
<211> LENGTH: 7
<212> TYPE: PRT
<213> ORGANISM: Artificial Sequence
```

<220> FEATURE:
<223> OTHER INFORMATION: Variable light chain CDR amino acid sequence;
      CD37-12, VL-CDR2

<400> SEQUENCE: 32

Tyr Ala Ser Asn Leu Ala Ser
1               5

<210> SEQ ID NO 33
<211> LENGTH: 9
<212> TYPE: PRT
<213> ORGANISM: Artificial Sequence
<220> FEATURE:
<223> OTHER INFORMATION: Variable light chain CDR amino acid sequence;
      CD37-12, VL-CDR3

<400> SEQUENCE: 33

Gln His Ser Trp Glu Ile Pro Tyr Thr
1               5

<210> SEQ ID NO 34
<211> LENGTH: 10
<212> TYPE: PRT
<213> ORGANISM: Artificial Sequence
<220> FEATURE:
<223> OTHER INFORMATION: Variable light chain CDR amino acid sequence;
      CD37-38, VL-CDR1

<400> SEQUENCE: 34

Ser Ala Ser Ser Ser Val Thr Tyr Met His
1               5                   10

<210> SEQ ID NO 35
<211> LENGTH: 7
<212> TYPE: PRT
<213> ORGANISM: Artificial Sequence
<220> FEATURE:
<223> OTHER INFORMATION: Variable light chain CDR amino acid sequence;
      CD37-38, VL-CDR2

<400> SEQUENCE: 35

Asp Thr Ser Lys Leu Ala Ser
1               5

<210> SEQ ID NO 36
<211> LENGTH: 9
<212> TYPE: PRT
<213> ORGANISM: Artificial Sequence
<220> FEATURE:
<223> OTHER INFORMATION: Variable light chain CDR amino acid sequence;
      CD37-38, VL-CDR3

<400> SEQUENCE: 36

Gln Gln Trp Ile Ser Asn Pro Pro Thr
1               5

<210> SEQ ID NO 37
<211> LENGTH: 10
<212> TYPE: PRT
<213> ORGANISM: Artificial Sequence
<220> FEATURE:
<223> OTHER INFORMATION: Variable light chain CDR amino acid sequence;
      CD37-50, VL-CDR1

<400> SEQUENCE: 37

Ser Ala Thr Ser Ser Val Thr Tyr Met His
1               5                   10

<210> SEQ ID NO 38
<211> LENGTH: 7
<212> TYPE: PRT
<213> ORGANISM: Artificial Sequence
<220> FEATURE:
<223> OTHER INFORMATION: Variable light chain CDR amino acid sequence;
CD37-50, VL-CDR2

<400> SEQUENCE: 38

Asp Thr Ser Lys Leu Pro Tyr
1 5

<210> SEQ ID NO 39
<211> LENGTH: 9
<212> TYPE: PRT
<213> ORGANISM: Artificial Sequence
<220> FEATURE:
<223> OTHER INFORMATION: Variable light chain CDR amino acid sequence;
CD37-50, VL-CDR3

<400> SEQUENCE: 39

Gln Gln Trp Ser Asp Asn Pro Pro Thr
1 5

<210> SEQ ID NO 40
<211> LENGTH: 7
<212> TYPE: PRT
<213> ORGANISM: Artificial Sequence
<220> FEATURE:
<223> OTHER INFORMATION: Variable light chain CDR amino acid sequence;
CD37-50, VL-CDR2, Humanized

<400> SEQUENCE: 40

Asp Thr Ser Asn Leu Pro Tyr
1 5

<210> SEQ ID NO 41
<211> LENGTH: 10
<212> TYPE: PRT
<213> ORGANISM: Artificial Sequence
<220> FEATURE:
<223> OTHER INFORMATION: Variable light chain CDR amino acid sequence;
CD37-51, VL-CDR1

<400> SEQUENCE: 41

Ser Ala Thr Ser Ser Val Thr Tyr Met His
1 5 10

<210> SEQ ID NO 42
<211> LENGTH: 7
<212> TYPE: PRT
<213> ORGANISM: Artificial Sequence
<220> FEATURE:
<223> OTHER INFORMATION: Variable light chain CDR amino acid sequence;
CD37-51, VL-CDR2

<400> SEQUENCE: 42

Asp Thr Ser Lys Leu Ala Ser
1 5

<210> SEQ ID NO 43
<211> LENGTH: 9
<212> TYPE: PRT
<213> ORGANISM: Artificial Sequence
<220> FEATURE:
<223> OTHER INFORMATION: Variable light chain CDR amino acid sequence;
CD37-51, VL-CDR3

<400> SEQUENCE: 43

Gln Gln Trp Ser Ser Asn Pro Pro Thr
1 5

<210> SEQ ID NO 44
<211> LENGTH: 10
<212> TYPE: PRT
<213> ORGANISM: Artificial Sequence
<220> FEATURE:
<223> OTHER INFORMATION: Variable light chain CDR amino acid sequence; CD37-56, VL-CDR1

<400> SEQUENCE: 44

Ser Ala Ser Ser Ser Val Thr Tyr Met His
1 5 10

<210> SEQ ID NO 45
<211> LENGTH: 7
<212> TYPE: PRT
<213> ORGANISM: Artificial Sequence
<220> FEATURE:
<223> OTHER INFORMATION: Variable light chain CDR amino acid sequence; CD37-56, VL-CDR2

<400> SEQUENCE: 45

Asp Thr Ser Lys Leu Ala Ser
1 5

<210> SEQ ID NO 46
<211> LENGTH: 9
<212> TYPE: PRT
<213> ORGANISM: Artificial Sequence
<220> FEATURE:
<223> OTHER INFORMATION: Variable light chain CDR amino acid sequence; CD37-56, VL-CDR3

<400> SEQUENCE: 46

Gln Gln Trp Ile Ser Asp Pro Pro Thr
1 5

<210> SEQ ID NO 47
<211> LENGTH: 7
<212> TYPE: PRT
<213> ORGANISM: Artificial Sequence
<220> FEATURE:
<223> OTHER INFORMATION: Variable light chain CDR amino acid sequence; CD37-56, VL-CDR2, Humanized

<400> SEQUENCE: 47

Asp Thr Ser Asn Leu Ala Ser
1 5

<210> SEQ ID NO 48
<211> LENGTH: 10
<212> TYPE: PRT
<213> ORGANISM: Artificial Sequence
<220> FEATURE:
<223> OTHER INFORMATION: Variable light chain CDR amino acid sequence; CD37-57, VL-CDR1

<400> SEQUENCE: 48

Ser Ala Thr Ser Ser Val Thr Tyr Met His
1 5 10

<210> SEQ ID NO 49
<211> LENGTH: 7
<212> TYPE: PRT

<213> ORGANISM: Artificial Sequence
<220> FEATURE:
<223> OTHER INFORMATION: Variable light chain CDR amino acid sequence;
CD37-57, VL-CDR2

<400> SEQUENCE: 49

Asp Thr Ser Lys Leu Ala Ser
1 5

<210> SEQ ID NO 50
<211> LENGTH: 9
<212> TYPE: PRT
<213> ORGANISM: Artificial Sequence
<220> FEATURE:
<223> OTHER INFORMATION: Variable light chain CDR amino acid sequence;
CD37-57, VL-CDR3

<400> SEQUENCE: 50

Gln Gln Trp Ser Asp Asn Pro Pro Thr
1 5

<210> SEQ ID NO 51
<211> LENGTH: 7
<212> TYPE: PRT
<213> ORGANISM: Artificial Sequence
<220> FEATURE:
<223> OTHER INFORMATION: Variable light chain CDR amino acid sequence;
CD37-57, VL-CDR2, Humanized

<400> SEQUENCE: 51

Asp Thr Ser Asn Leu Ala Ser
1 5

<210> SEQ ID NO 52
<211> LENGTH: 10
<212> TYPE: PRT
<213> ORGANISM: Artificial Sequence
<220> FEATURE:
<223> OTHER INFORMATION: Variable light chain CDR amino acid sequence;
Consensus, VL-CDR1
<220> FEATURE:
<221> NAME/KEY: MISC_FEATURE
<222> LOCATION: (3)..(3)
<223> OTHER INFORMATION: Where Xaa is Thr or Ser

<400> SEQUENCE: 52

Ser Ala Xaa Ser Ser Val Thr Tyr Met His
1 5 10

<210> SEQ ID NO 53
<211> LENGTH: 7
<212> TYPE: PRT
<213> ORGANISM: Artificial Sequence
<220> FEATURE:
<223> OTHER INFORMATION: Variable light chain CDR amino acid sequence;
Consensus, VL-CDR2
<220> FEATURE:
<221> NAME/KEY: MISC_FEATURE
<222> LOCATION: (4)..(4)
<223> OTHER INFORMATION: Where Xaa is Lys or Asn
<220> FEATURE:
<221> NAME/KEY: MISC_FEATURE
<222> LOCATION: (6)..(6)
<223> OTHER INFORMATION: Where Xaa is Ala or Pro
<220> FEATURE:
<221> NAME/KEY: MISC_FEATURE
<222> LOCATION: (7)..(7)
<223> OTHER INFORMATION: Where Xaa is Ser or Tyr

<400> SEQUENCE: 53

-continued

```
Asp Thr Ser Xaa Leu Xaa Xaa
1               5


<210> SEQ ID NO 54
<211> LENGTH: 9
<212> TYPE: PRT
<213> ORGANISM: Artificial Sequence
<220> FEATURE:
<223> OTHER INFORMATION: Variable light chain CDR amino acid sequence;
      Consensus, VL-CDR3
<220> FEATURE:
<221> NAME/KEY: MISC_FEATURE
<222> LOCATION: (4)..(4)
<223> OTHER INFORMATION: Where Xaa is Ile or Ser
<220> FEATURE:
<221> NAME/KEY: MISC_FEATURE
<222> LOCATION: (5)..(5)
<223> OTHER INFORMATION: Where Xaa is Ser or Asp
<220> FEATURE:
<221> NAME/KEY: MISC_FEATURE
<222> LOCATION: (6)..(6)
<223> OTHER INFORMATION: Where Xaa is Asn or Asp

<400> SEQUENCE: 54

Gln Gln Trp Xaa Xaa Xaa Pro Pro Thr
1               5


<210> SEQ ID NO 55
<211> LENGTH: 115
<212> TYPE: PRT
<213> ORGANISM: Artificial Sequence
<220> FEATURE:
<223> OTHER INFORMATION: Variable heavy chain amino acid sequences;
      muCD37-3 antibody

<400> SEQUENCE: 55

Gln Val Gln Val Lys Glu Ser Gly Pro Gly Leu Val Ala Pro Ser Gln
1               5                   10                  15

Ser Leu Ser Ile Thr Cys Thr Val Ser Gly Phe Ser Leu Thr Thr Ser
            20                  25                  30

Gly Val Ser Trp Val Arg Gln Pro Pro Gly Lys Gly Leu Glu Trp Leu
        35                  40                  45

Gly Val Ile Trp Gly Asp Gly Ser Thr Asn Tyr His Ser Ala Leu Lys
    50                  55                  60

Ser Arg Leu Ser Ile Lys Lys Asp His Ser Lys Ser Gln Val Phe Leu
65                  70                  75                  80

Lys Leu Asn Ser Leu Gln Thr Asp Asp Thr Ala Thr Tyr Tyr Cys Ala
                85                  90                  95

Lys Gly Gly Tyr Ser Leu Ala His Trp Gly Gln Gly Thr Leu Val Thr
            100                 105                 110

Val Ser Ala
        115


<210> SEQ ID NO 56
<211> LENGTH: 115
<212> TYPE: PRT
<213> ORGANISM: Artificial Sequence
<220> FEATURE:
<223> OTHER INFORMATION: Variable heavy chain amino acid sequences;
      chCD37-3 antibody

<400> SEQUENCE: 56

Gln Val Gln Val Lys Glu Ser Gly Pro Gly Leu Val Ala Pro Ser Gln
1               5                   10                  15

Ser Leu Ser Ile Thr Cys Thr Val Ser Gly Phe Ser Leu Thr Thr Ser
```

-continued

```
            20                  25                  30

Gly Val Ser Trp Val Arg Gln Pro Pro Gly Lys Gly Leu Glu Trp Leu
        35                  40                  45

Gly Val Ile Trp Gly Asp Gly Ser Thr Asn Tyr His Ser Ala Leu Lys
    50                  55                  60

Ser Arg Leu Ser Ile Lys Lys Asp His Ser Lys Ser Gln Val Phe Leu
65                  70                  75                  80

Lys Leu Asn Ser Leu Gln Thr Asp Asp Thr Ala Thr Tyr Tyr Cys Ala
                85                  90                  95

Lys Gly Gly Tyr Ser Leu Ala His Trp Gly Gln Gly Thr Leu Val Thr
            100                 105                 110

Val Ser Ala
        115


<210> SEQ ID NO 57
<211> LENGTH: 115
<212> TYPE: PRT
<213> ORGANISM: Artificial Sequence
<220> FEATURE:
<223> OTHER INFORMATION: Variable heavy chain amino acid sequences;
      huCD37-3v1.0 antibody

<400> SEQUENCE: 57

Gln Val Gln Val Gln Glu Ser Gly Pro Gly Leu Val Ala Pro Ser Gln
1               5                   10                  15

Thr Leu Ser Ile Thr Cys Thr Val Ser Gly Phe Ser Leu Thr Thr Ser
            20                  25                  30

Gly Val Ser Trp Val Arg Gln Pro Pro Gly Lys Gly Leu Glu Trp Leu
        35                  40                  45

Gly Val Ile Trp Gly Asp Gly Ser Thr Asn Tyr His Pro Ser Leu Lys
    50                  55                  60

Ser Arg Leu Ser Ile Lys Lys Asp His Ser Lys Ser Gln Val Phe Leu
65                  70                  75                  80

Lys Leu Asn Ser Leu Thr Ala Ala Asp Thr Ala Thr Tyr Tyr Cys Ala
                85                  90                  95

Lys Gly Gly Tyr Ser Leu Ala His Trp Gly Gln Gly Thr Leu Val Thr
            100                 105                 110

Val Ser Ser
        115


<210> SEQ ID NO 58
<211> LENGTH: 115
<212> TYPE: PRT
<213> ORGANISM: Artificial Sequence
<220> FEATURE:
<223> OTHER INFORMATION: Variable heavy chain amino acid sequences;
      huCD37-3v1.1 antibody

<400> SEQUENCE: 58

Gln Val Gln Val Gln Glu Ser Gly Pro Gly Leu Val Ala Pro Ser Gln
1               5                   10                  15

Thr Leu Ser Ile Thr Cys Thr Val Ser Gly Phe Ser Leu Thr Thr Ser
            20                  25                  30

Gly Val Ser Trp Val Arg Gln Pro Pro Gly Lys Gly Leu Glu Trp Leu
        35                  40                  45

Gly Val Ile Trp Gly Asp Gly Ser Thr Asn Tyr His Ser Ser Leu Lys
    50                  55                  60

Ser Arg Leu Ser Ile Lys Lys Asp His Ser Lys Ser Gln Val Phe Leu
```

```
65                  70                  75                  80

Lys Leu Asn Ser Leu Thr Ala Ala Asp Thr Ala Thr Tyr Tyr Cys Ala
                85                  90                  95

Lys Gly Gly Tyr Ser Leu Ala His Trp Gly Gln Gly Thr Leu Val Thr
            100                 105                 110

Val Ser Ser
        115


<210> SEQ ID NO 59
<211> LENGTH: 115
<212> TYPE: PRT
<213> ORGANISM: Artificial Sequence
<220> FEATURE:
<223> OTHER INFORMATION: Variable heavy chain amino acid sequences;
      muCD37-12 antibody

<400> SEQUENCE: 59

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Lys Tyr
            20                  25                  30

Gly Met Asn Trp Val Lys Gln Ala Gln Gly Lys Gly Leu Lys Trp Met
        35                  40                  45

Gly Trp Ile Asn Thr Asn Thr Gly Glu Ser Arg Asn Ala Glu Glu Phe
    50                  55                  60

Lys Gly Arg Phe Ala Phe Ser Leu Glu Thr Ser Ala Ser Thr Ala Tyr
65                  70                  75                  80

Leu Gln Ile Asn Asn Leu Lys Tyr Glu Asp Thr Ala Thr Tyr Phe Cys
                85                  90                  95

Gly Arg Gly Thr Val Val Ala Asp Trp Gly Gln Gly Thr Thr Leu Thr
            100                 105                 110

Val Ser Ser
        115


<210> SEQ ID NO 60
<211> LENGTH: 115
<212> TYPE: PRT
<213> ORGANISM: Artificial Sequence
<220> FEATURE:
<223> OTHER INFORMATION: Variable heavy chain amino acid sequences;
      chCD37-12 antibody

<400> SEQUENCE: 60

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Lys Tyr
            20                  25                  30

Gly Met Asn Trp Val Lys Gln Ala Gln Gly Lys Gly Leu Lys Trp Met
        35                  40                  45

Gly Trp Ile Asn Thr Asn Thr Gly Glu Ser Arg Asn Ala Glu Glu Phe
    50                  55                  60

Lys Gly Arg Phe Ala Phe Ser Leu Glu Thr Ser Ala Ser Thr Ala Tyr
65                  70                  75                  80

Leu Gln Ile Asn Asn Leu Lys Tyr Glu Asp Thr Ala Thr Tyr Phe Cys
                85                  90                  95

Gly Arg Gly Thr Val Val Ala Asp Trp Gly Gln Gly Thr Thr Leu Thr
            100                 105                 110

Val Ser Ser
```

115

<210> SEQ ID NO 61
<211> LENGTH: 120
<212> TYPE: PRT
<213> ORGANISM: Artificial Sequence
<220> FEATURE:
<223> OTHER INFORMATION: Variable heavy chain amino acid sequences; muCD37-38 antibody

<400> SEQUENCE: 61

```
Asp Val Gln Leu Gln Glu Ser Gly Pro Asp Leu Val Lys Pro Ser Gln
1               5                   10                  15

Ser Leu Ser Leu Thr Cys Thr Val Thr Gly Tyr Ser Ile Thr Ser Gly
            20                  25                  30

Phe Gly Trp His Trp Ile Arg Gln Phe Pro Gly Asn Lys Leu Glu Trp
        35                  40                  45

Met Ala Tyr Ile Leu Tyr Ser Gly Gly Thr Asp Tyr Asn Pro Ser Leu
    50                  55                  60

Lys Ser Arg Ile Ser Ile Thr Arg Asp Thr Ser Lys Asn Gln Phe Phe
65                  70                  75                  80

Leu Arg Leu Ser Ser Val Thr Thr Glu Asp Thr Ala Thr Tyr Tyr Cys
                85                  90                  95

Ala Arg Gly Tyr Tyr Gly Tyr Gly Ala Trp Phe Val Tyr Trp Gly Gln
            100                 105                 110

Gly Thr Leu Val Thr Val Ser Ala
        115                 120
```

<210> SEQ ID NO 62
<211> LENGTH: 120
<212> TYPE: PRT
<213> ORGANISM: Artificial Sequence
<220> FEATURE:
<223> OTHER INFORMATION: Variable heavy chain amino acid sequences; chCD37-38 antibody

<400> SEQUENCE: 62

```
Gln Val Gln Leu Gln Glu Ser Gly Pro Asp Leu Val Lys Pro Ser Gln
1               5                   10                  15

Ser Leu Ser Leu Thr Cys Thr Val Thr Gly Tyr Ser Ile Thr Ser Gly
            20                  25                  30

Phe Gly Trp His Trp Ile Arg Gln Phe Pro Gly Asn Lys Leu Glu Trp
        35                  40                  45

Met Ala Tyr Ile Leu Tyr Ser Gly Gly Thr Asp Tyr Asn Pro Ser Leu
    50                  55                  60

Lys Ser Arg Ile Ser Ile Thr Arg Asp Thr Ser Lys Asn Gln Phe Phe
65                  70                  75                  80

Leu Arg Leu Ser Ser Val Thr Thr Glu Asp Thr Ala Thr Tyr Tyr Cys
                85                  90                  95

Ala Arg Gly Tyr Tyr Gly Tyr Gly Ala Trp Phe Val Tyr Trp Gly Gln
            100                 105                 110

Gly Thr Leu Val Thr Val Ser Ala
        115                 120
```

<210> SEQ ID NO 63
<211> LENGTH: 120
<212> TYPE: PRT
<213> ORGANISM: Artificial Sequence
<220> FEATURE:
<223> OTHER INFORMATION: Variable heavy chain amino acid sequences;

huCD37-38 antibody

<400> SEQUENCE: 63

Gln Val Gln Leu Gln Glu Ser Gly Pro Gly Leu Val Lys Pro Ser Gln
1 5 10 15

Ser Leu Ser Leu Thr Cys Thr Val Ser Gly Tyr Ser Ile Thr Ser Gly
20 25 30

Phe Gly Trp His Trp Ile Arg Gln Phe Pro Gly Lys Gly Leu Glu Trp
35 40 45

Met Ala Tyr Ile Leu Tyr Ser Gly Gly Thr Asp Tyr Asn Pro Ser Leu
50 55 60

Lys Ser Arg Ile Ser Ile Thr Arg Asp Thr Ser Lys Asn Gln Phe Phe
65 70 75 80

Leu Arg Leu Ser Ser Val Thr Ala Ala Asp Thr Ala Thr Tyr Tyr Cys
85 90 95

Ala Arg Gly Tyr Tyr Gly Tyr Gly Ala Trp Phe Val Tyr Trp Gly Gln
100 105 110

Gly Thr Leu Val Thr Val Ser Ser
115 120

<210> SEQ ID NO 64
<211> LENGTH: 120
<212> TYPE: PRT
<213> ORGANISM: Artificial Sequence
<220> FEATURE:
<223> OTHER INFORMATION: Variable heavy chain amino acid sequences;
muCD37-50 antibody

<400> SEQUENCE: 64

Asp Val Gln Leu Gln Glu Ser Gly Pro Asp Leu Leu Lys Pro Ser Gln
1 5 10 15

Ser Leu Ser Leu Thr Cys Thr Val Thr Gly Tyr Ser Ile Thr Ser Gly
20 25 30

Phe Ala Trp His Trp Ile Arg Gln Phe Pro Gly Asn Lys Leu Glu Trp
35 40 45

Met Gly Tyr Ile Leu Tyr Ser Gly Ser Thr Val Tyr Ser Pro Ser Leu
50 55 60

Lys Ser Arg Ile Ser Ile Thr Arg Asp Thr Ser Lys Asn His Phe Phe
65 70 75 80

Leu Gln Leu Asn Ser Val Thr Thr Glu Asp Thr Ala Thr Tyr Tyr Cys
85 90 95

Ala Arg Gly Tyr Tyr Gly Tyr Gly Ala Trp Phe Ala Tyr Trp Gly Gln
100 105 110

Gly Thr Leu Val Thr Val Ser Ala
115 120

<210> SEQ ID NO 65
<211> LENGTH: 120
<212> TYPE: PRT
<213> ORGANISM: Artificial Sequence
<220> FEATURE:
<223> OTHER INFORMATION: Variable heavy chain amino acid sequences;
huCD37-50 antibody

<400> SEQUENCE: 65

Gln Val Gln Leu Gln Glu Ser Gly Pro Gly Leu Leu Lys Pro Ser Gln
1 5 10 15

Ser Leu Ser Leu Thr Cys Thr Val Ser Gly Tyr Ser Ile Thr Ser Gly
20 25 30

```
Phe Ala Trp His Trp Ile Arg Gln His Pro Gly Asn Lys Leu Glu Trp
        35                  40                  45

Met Gly Tyr Ile Leu Tyr Ser Gly Ser Thr Val Tyr Ser Pro Ser Leu
    50                  55                  60

Lys Ser Arg Ile Ser Ile Thr Arg Asp Thr Ser Lys Asn His Phe Phe
65                  70                  75                  80

Leu Gln Leu Asn Ser Val Thr Ala Ala Asp Thr Ala Thr Tyr Tyr Cys
                85                  90                  95

Ala Arg Gly Tyr Tyr Gly Tyr Gly Ala Trp Phe Ala Tyr Trp Gly Gln
            100                 105                 110

Gly Thr Leu Val Thr Val Ser Ala
        115                 120


<210> SEQ ID NO 66
<211> LENGTH: 120
<212> TYPE: PRT
<213> ORGANISM: Artificial Sequence
<220> FEATURE:
<223> OTHER INFORMATION: Variable heavy chain amino acid sequences;
      muCD37-51 antibody

<400> SEQUENCE: 66

Asp Val Gln Leu Gln Glu Ser Gly Pro Asp Leu Leu Lys Pro Ser Gln
1               5                   10                  15

Ser Leu Ser Leu Thr Cys Thr Val Thr Gly Tyr Ser Ile Ser Ser Gly
            20                  25                  30

Phe Ala Trp His Trp Ile Arg Gln Phe Pro Gly Asn Lys Leu Glu Trp
        35                  40                  45

Met Gly Tyr Ile His Tyr Ser Gly Ser Thr Asn Tyr Ser Pro Ser Leu
    50                  55                  60

Lys Ser Arg Ile Ser Ile Thr Arg Asp Ser Ser Lys Asn Gln Phe Phe
65                  70                  75                  80

Leu Gln Leu Asn Ser Val Thr Thr Glu Asp Thr Ala Thr Tyr Tyr Cys
                85                  90                  95

Ala Arg Gly Tyr Tyr Gly Phe Gly Ala Trp Phe Val Tyr Trp Gly Gln
            100                 105                 110

Gly Thr Leu Val Thr Val Ser Ala
        115                 120


<210> SEQ ID NO 67
<211> LENGTH: 120
<212> TYPE: PRT
<213> ORGANISM: Artificial Sequence
<220> FEATURE:
<223> OTHER INFORMATION: Variable heavy chain amino acid sequences;
      huCD37-51 antibody

<400> SEQUENCE: 67

Glu Val Gln Leu Val Glu Ser Gly Pro Glu Val Leu Lys Pro Gly Glu
1               5                   10                  15

Ser Leu Ser Leu Thr Cys Thr Val Ser Gly Tyr Ser Ile Ser Ser Gly
            20                  25                  30

Phe Ala Trp His Trp Ile Arg Gln Phe Pro Gly Lys Gly Leu Glu Trp
        35                  40                  45

Met Gly Tyr Ile His Tyr Ser Gly Ser Thr Asn Tyr Ser Pro Ser Leu
    50                  55                  60

Gln Gly Arg Ile Ser Ile Thr Arg Asp Ser Ser Ile Asn Gln Phe Phe
65                  70                  75                  80
```

```
Leu Gln Leu Asn Ser Val Thr Ala Ser Asp Thr Ala Thr Tyr Tyr Cys
                85                  90                  95

Ala Arg Gly Tyr Tyr Gly Phe Gly Ala Trp Phe Val Tyr Trp Gly Gln
            100                 105                 110

Gly Thr Leu Val Thr Val Ser Ala
        115                 120


<210> SEQ ID NO 68
<211> LENGTH: 120
<212> TYPE: PRT
<213> ORGANISM: Artificial Sequence
<220> FEATURE:
<223> OTHER INFORMATION: Variable heavy chain amino acid sequences;
      muCD37-56 antibody

<400> SEQUENCE: 68

Asp Val Gln Leu Gln Glu Ser Gly Pro Asp Leu Val Lys Pro Ser Gln
1               5                   10                  15

Ser Leu Ser Leu Thr Cys Thr Val Thr Gly Tyr Ser Ile Thr Ser Gly
            20                  25                  30

Phe Ala Trp His Trp Ile Arg Gln Phe Pro Gly Asn Lys Leu Glu Trp
        35                  40                  45

Met Gly Tyr Ile His Tyr Ser Gly Gly Thr Asn Tyr Asn Pro Ser Leu
    50                  55                  60

Lys Ser Arg Val Ser Ile Thr Arg Asp Thr Ser Lys Asn Gln Phe Phe
65                  70                  75                  80

Leu Gln Leu Asn Ser Val Thr Thr Glu Asp Thr Ala Thr Tyr Tyr Cys
                85                  90                  95

Ala Arg Gly Tyr Tyr Gly Phe Gly Ala Trp Phe Ala Tyr Trp Gly Gln
            100                 105                 110

Gly Thr Leu Val Pro Val Ser Ala
        115                 120


<210> SEQ ID NO 69
<211> LENGTH: 120
<212> TYPE: PRT
<213> ORGANISM: Artificial Sequence
<220> FEATURE:
<223> OTHER INFORMATION: Variable heavy chain amino acid sequences;
      huCD37-56 antibody

<400> SEQUENCE: 69

Gln Val Gln Leu Gln Glu Ser Gly Pro Gly Leu Val Lys Pro Ser Gln
1               5                   10                  15

Ser Leu Ser Leu Thr Cys Thr Val Ser Gly Tyr Ser Ile Thr Ser Gly
            20                  25                  30

Phe Ala Trp His Trp Ile Arg Gln Phe Pro Gly Lys Gly Leu Glu Trp
        35                  40                  45

Met Gly Tyr Ile His Tyr Ser Gly Gly Thr Asn Tyr Asn Pro Ser Leu
    50                  55                  60

Lys Ser Arg Val Ser Ile Thr Arg Asp Thr Ser Lys Asn Gln Phe Phe
65                  70                  75                  80

Leu Gln Leu Asn Ser Val Thr Ala Ala Asp Thr Ala Thr Tyr Tyr Cys
                85                  90                  95

Ala Arg Gly Tyr Tyr Gly Phe Gly Ala Trp Phe Ala Tyr Trp Gly Gln
            100                 105                 110

Gly Thr Leu Val Pro Val Ser Ala
        115                 120
```

```
<210> SEQ ID NO 70
<211> LENGTH: 120
<212> TYPE: PRT
<213> ORGANISM: Artificial Sequence
<220> FEATURE:
<223> OTHER INFORMATION: Variable heavy chain amino acid sequences;
      muCD37-57 antibody

<400> SEQUENCE: 70

Asp Val Gln Leu Gln Glu Ser Gly Pro Asp Leu Leu Lys Pro Ser Gln
1               5                   10                  15

Ser Leu Ser Leu Thr Cys Thr Val Thr Gly Tyr Ser Ile Thr Ser Gly
            20                  25                  30

Phe Ala Trp His Trp Ile Arg Gln Phe Pro Gly Asn Lys Leu Glu Trp
        35                  40                  45

Met Gly Tyr Ile Leu Tyr Ser Gly Ser Thr Val Tyr Ser Pro Ser Leu
    50                  55                  60

Lys Ser Arg Ile Ser Ile Thr Arg Asp Thr Ser Lys Asn Gln Phe Phe
65                  70                  75                  80

Leu Gln Leu Asn Ser Val Thr Thr Glu Asp Thr Ala Thr Tyr Tyr Cys
                85                  90                  95

Ala Arg Gly Tyr Tyr Gly Tyr Gly Ala Trp Phe Ala Tyr Trp Gly Gln
            100                 105                 110

Gly Thr Leu Val Thr Val Ser Ala
        115                 120


<210> SEQ ID NO 71
<211> LENGTH: 120
<212> TYPE: PRT
<213> ORGANISM: Artificial Sequence
<220> FEATURE:
<223> OTHER INFORMATION: Variable heavy chain amino acid sequences;
      huCD37-57 antibody

<400> SEQUENCE: 71

Gln Val Gln Leu Gln Glu Ser Gly Pro Gly Leu Leu Lys Pro Ser Gln
1               5                   10                  15

Ser Leu Ser Leu Thr Cys Thr Val Ser Gly Tyr Ser Ile Thr Ser Gly
            20                  25                  30

Phe Ala Trp His Trp Ile Arg Gln Phe Pro Gly Lys Gly Leu Glu Trp
        35                  40                  45

Met Gly Tyr Ile Leu Tyr Ser Gly Ser Thr Val Tyr Ser Pro Ser Leu
    50                  55                  60

Lys Ser Arg Ile Ser Ile Thr Arg Asp Thr Ser Lys Asn Gln Phe Phe
65                  70                  75                  80

Leu Gln Leu Asn Ser Val Thr Ala Ala Asp Thr Ala Thr Tyr Tyr Cys
                85                  90                  95

Ala Arg Gly Tyr Tyr Gly Tyr Gly Ala Trp Phe Ala Tyr Trp Gly Gln
            100                 105                 110

Gly Thr Leu Val Thr Val Ser Ala
        115                 120


<210> SEQ ID NO 72
<211> LENGTH: 108
<212> TYPE: PRT
<213> ORGANISM: Artificial Sequence
<220> FEATURE:
<223> OTHER INFORMATION: Variable light chain amino acid sequences;
      muCD37-3 antibody
```

<400> SEQUENCE: 72

Asp Ile Gln Met Thr Gln Ser Pro Ala Ser Leu Ser Val Ser Val Gly
1 5 10 15

Glu Thr Val Thr Ile Thr Cys Arg Ala Ser Glu Asn Ile Arg Ser Asn
20 25 30

Leu Ala Trp Tyr Gln Gln Lys Gln Gly Lys Ser Pro Gln Leu Leu Val
35 40 45

Asn Val Ala Thr Asn Leu Ala Asp Gly Val Pro Ser Arg Phe Ser Gly
50 55 60

Ser Gly Ser Gly Thr Gln Tyr Ser Leu Lys Ile Asn Ser Leu Gln Ser
65 70 75 80

Glu Asp Phe Gly Thr Tyr Tyr Cys Gln His Tyr Trp Gly Thr Thr Trp
85 90 95

Thr Phe Gly Gly Gly Thr Lys Leu Glu Ile Lys Arg
100 105

<210> SEQ ID NO 73
<211> LENGTH: 108
<212> TYPE: PRT
<213> ORGANISM: Artificial Sequence
<220> FEATURE:
<223> OTHER INFORMATION: Variable light chain amino acid sequences; chCD37-3 antibody

<400> SEQUENCE: 73

Asp Ile Gln Met Thr Gln Ser Pro Ala Ser Leu Ser Val Ser Val Gly
1 5 10 15

Glu Thr Val Thr Ile Thr Cys Arg Ala Ser Glu Asn Ile Arg Ser Asn
20 25 30

Leu Ala Trp Tyr Gln Gln Lys Gln Gly Lys Ser Pro Gln Leu Leu Val
35 40 45

Asn Val Ala Thr Asn Leu Ala Asp Gly Val Pro Ser Arg Phe Ser Gly
50 55 60

Ser Gly Ser Gly Thr Gln Tyr Ser Leu Lys Ile Asn Ser Leu Gln Ser
65 70 75 80

Glu Asp Phe Gly Thr Tyr Tyr Cys Gln His Tyr Trp Gly Thr Thr Trp
85 90 95

Thr Phe Gly Gly Gly Thr Lys Leu Glu Ile Lys Arg
100 105

<210> SEQ ID NO 74
<211> LENGTH: 108
<212> TYPE: PRT
<213> ORGANISM: Artificial Sequence
<220> FEATURE:
<223> OTHER INFORMATION: Variable light chain amino acid sequences; huCD37-3v1.0 and huCD37-3v1.1 antibody

<400> SEQUENCE: 74

Asp Ile Gln Met Thr Gln Ser Pro Ser Ser Leu Ser Val Ser Val Gly
1 5 10 15

Glu Arg Val Thr Ile Thr Cys Arg Ala Ser Glu Asn Ile Arg Ser Asn
20 25 30

Leu Ala Trp Tyr Gln Gln Lys Pro Gly Lys Ser Pro Lys Leu Leu Val
35 40 45

Asn Val Ala Thr Asn Leu Ala Asp Gly Val Pro Ser Arg Phe Ser Gly
50 55 60

```
Ser Gly Ser Gly Thr Asp Tyr Ser Leu Lys Ile Asn Ser Leu Gln Pro
65                  70                  75                  80

Glu Asp Phe Gly Thr Tyr Tyr Cys Gln His Tyr Trp Gly Thr Thr Trp
                85                  90                  95

Thr Phe Gly Gln Gly Thr Lys Leu Glu Ile Lys Arg
            100                 105


<210> SEQ ID NO 75
<211> LENGTH: 112
<212> TYPE: PRT
<213> ORGANISM: Artificial Sequence
<220> FEATURE:
<223> OTHER INFORMATION: Variable light chain amino acid sequences;
      muCD37-12 antibody

<400> SEQUENCE: 75

Asp Ile Val Leu Thr Gln Ser Pro Ala Ser Leu Ala Val Ser Leu Gly
1               5                   10                  15

Gln Arg Ala Thr Ile Ser Cys Arg Ala Ser Gln Ser Val Ser Thr Ser
            20                  25                  30

Ser Tyr Ser Tyr Leu Tyr Trp Phe Gln Gln Lys Pro Gly Gln Pro Pro
        35                  40                  45

Lys Leu Leu Ile Lys Tyr Ala Ser Asn Leu Ala Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Thr Ala Thr Tyr Tyr Cys Gln His Ser Trp
                85                  90                  95

Glu Ile Pro Tyr Thr Phe Gly Gly Gly Thr Lys Leu Glu Ile Lys Arg
            100                 105                 110


<210> SEQ ID NO 76
<211> LENGTH: 112
<212> TYPE: PRT
<213> ORGANISM: Artificial Sequence
<220> FEATURE:
<223> OTHER INFORMATION: Variable light chain amino acid sequences;
      chCD37-12 antibody

<400> SEQUENCE: 76

Asp Ile Val Leu Thr Gln Ser Pro Ala Ser Leu Ala Val Ser Leu Gly
1               5                   10                  15

Gln Arg Ala Thr Ile Ser Cys Arg Ala Ser Gln Ser Val Ser Thr Ser
            20                  25                  30

Ser Tyr Ser Tyr Leu Tyr Trp Phe Gln Gln Lys Pro Gly Gln Pro Pro
        35                  40                  45

Lys Leu Leu Ile Lys Tyr Ala Ser Asn Leu Ala Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Thr Ala Thr Tyr Tyr Cys Gln His Ser Trp
                85                  90                  95

Glu Ile Pro Tyr Thr Phe Gly Gly Gly Thr Lys Leu Glu Ile Lys Arg
            100                 105                 110


<210> SEQ ID NO 77
<211> LENGTH: 107
<212> TYPE: PRT
<213> ORGANISM: Artificial Sequence
<220> FEATURE:
```

<223> OTHER INFORMATION: Variable light chain amino acid sequences;
muCD37-38 antibody

<400> SEQUENCE: 77

Gln Ile Val Leu Thr Gln Ser Pro Ala Ile Met Ser Ala Ser Pro Gly
1 5 10 15

Glu Lys Val Thr Met Thr Cys Ser Ala Ser Ser Ser Val Thr Tyr Met
20 25 30

His Trp Tyr Gln Gln Lys Ser Gly Thr Ser Pro Lys Arg Trp Ile Tyr
35 40 45

Asp Thr Ser Lys Leu Ala Ser Gly Val Pro Ala Arg Phe Ser Gly Gly
50 55 60

Gly Ser Gly Thr Ser Tyr Ser Leu Thr Ile Ser Ser Met Glu Ala Glu
65 70 75 80

Asp Ala Ala Thr Tyr Tyr Cys Gln Gln Trp Ile Ser Asn Pro Pro Thr
85 90 95

Phe Gly Gly Gly Thr Lys Leu Glu Ile Lys Arg
100 105

<210> SEQ ID NO 78
<211> LENGTH: 107
<212> TYPE: PRT
<213> ORGANISM: Artificial Sequence
<220> FEATURE:
<223> OTHER INFORMATION: Variable light chain amino acid sequences;
chCD37-38 antibody

<400> SEQUENCE: 78

Gln Ile Val Leu Thr Gln Ser Pro Ala Ile Met Ser Ala Ser Pro Gly
1 5 10 15

Glu Lys Val Thr Met Thr Cys Ser Ala Ser Ser Ser Val Thr Tyr Met
20 25 30

His Trp Tyr Gln Gln Lys Ser Gly Thr Ser Pro Lys Arg Trp Ile Tyr
35 40 45

Asp Thr Ser Lys Leu Ala Ser Gly Val Pro Ala Arg Phe Ser Gly Gly
50 55 60

Gly Ser Gly Thr Ser Tyr Ser Leu Thr Ile Ser Ser Met Glu Ala Glu
65 70 75 80

Asp Ala Ala Thr Tyr Tyr Cys Gln Gln Trp Ile Ser Asn Pro Pro Thr
85 90 95

Phe Gly Gly Gly Thr Lys Leu Glu Ile Lys Arg
100 105

<210> SEQ ID NO 79
<211> LENGTH: 107
<212> TYPE: PRT
<213> ORGANISM: Artificial Sequence
<220> FEATURE:
<223> OTHER INFORMATION: Variable light chain amino acid sequences;
huCD37-38 antibody

<400> SEQUENCE: 79

Asp Ile Val Leu Thr Gln Ser Pro Ala Ser Met Ser Ala Ser Pro Gly
1 5 10 15

Glu Arg Val Thr Met Thr Cys Ser Ala Ser Ser Ser Val Thr Tyr Met
20 25 30

His Trp Tyr Gln Gln Lys Pro Gly Thr Ser Pro Lys Arg Trp Ile Tyr
35 40 45

Asp Thr Ser Lys Leu Ala Ser Gly Val Pro Ala Arg Phe Ser Gly Ser 50 55 60

Gly Ser Gly Thr Ser Tyr Ser Leu Thr Ile Ser Ser Met Glu Ala Glu
65 70 75 80

Asp Ala Ala Thr Tyr Tyr Cys Gln Gln Trp Ile Ser Asn Pro Pro Thr
85 90 95

Phe Gly Gly Gly Thr Lys Leu Glu Ile Lys Arg
100 105

<210> SEQ ID NO 80
<211> LENGTH: 107
<212> TYPE: PRT
<213> ORGANISM: Artificial Sequence
<220> FEATURE:
<223> OTHER INFORMATION: Variable light chain amino acid sequences; muCD37-50 antibody

<400> SEQUENCE: 80

Gln Ile Val Leu Thr Gln Ser Pro Ala Ile Met Ser Ala Ser Pro Gly
1 5 10 15

Glu Lys Val Thr Met Thr Cys Ser Ala Thr Ser Ser Val Thr Tyr Met
20 25 30

His Trp Tyr Gln Gln Lys Ser Gly Thr Ser Pro Lys Arg Trp Ile Tyr
35 40 45

Asp Thr Ser Lys Leu Pro Tyr Gly Val Pro Gly Arg Phe Ser Gly Ser
50 55 60

Gly Ser Gly Thr Ser Tyr Ser Leu Thr Ile Ser Ser Met Glu Ala Glu
65 70 75 80

Asp Ala Ala Thr Tyr Tyr Cys Gln Gln Trp Ser Asp Asn Pro Pro Thr
85 90 95

Phe Gly Ser Gly Thr Lys Leu Glu Ile Lys Arg
100 105

<210> SEQ ID NO 81
<211> LENGTH: 107
<212> TYPE: PRT
<213> ORGANISM: Artificial Sequence
<220> FEATURE:
<223> OTHER INFORMATION: Variable light chain amino acid sequences; huCD37-50 antibody

<400> SEQUENCE: 81

Glu Ile Val Leu Thr Gln Ser Pro Ala Thr Met Ser Ala Ser Pro Gly
1 5 10 15

Glu Arg Val Thr Met Thr Cys Ser Ala Thr Ser Ser Val Thr Tyr Met
20 25 30

His Trp Tyr Gln Gln Lys Pro Gly Gln Ser Pro Lys Arg Trp Ile Tyr
35 40 45

Asp Thr Ser Asn Leu Pro Tyr Gly Val Pro Ala Arg Phe Ser Gly Ser
50 55 60

Gly Ser Gly Thr Ser Tyr Ser Leu Thr Ile Ser Ser Met Glu Ala Glu
65 70 75 80

Asp Ala Ala Thr Tyr Tyr Cys Gln Gln Trp Ser Asp Asn Pro Pro Thr
85 90 95

Phe Gly Gln Gly Thr Lys Leu Glu Ile Lys Arg
100 105

<210> SEQ ID NO 82
<211> LENGTH: 107
<212> TYPE: PRT

```
<213> ORGANISM: Artificial Sequence
<220> FEATURE:
<223> OTHER INFORMATION: Variable light chain amino acid sequences;
      muCD37-51 antibody

<400> SEQUENCE: 82

Gln Ile Val Leu Thr Gln Ser Pro Ala Ile Met Ser Ala Ser Pro Gly
1               5                   10                  15

Glu Lys Val Thr Met Thr Cys Ser Ala Thr Ser Ser Val Thr Tyr Met
            20                  25                  30

His Trp Tyr Gln Gln Lys Ser Gly Thr Ser Pro Lys Arg Trp Ile Tyr
        35                  40                  45

Asp Thr Ser Lys Leu Ala Ser Gly Val Pro Ala Arg Phe Ser Gly Ser
    50                  55                  60

Gly Ser Gly Thr Ser Tyr Ser Leu Thr Ile Ser Asn Met Glu Ala Glu
65                  70                  75                  80

Asp Ala Ala Thr Tyr Tyr Cys Gln Gln Trp Ser Ser Asn Pro Pro Thr
                85                  90                  95

Phe Gly Ser Gly Thr Lys Leu Glu Ile Lys Arg
            100                 105


<210> SEQ ID NO 83
<211> LENGTH: 107
<212> TYPE: PRT
<213> ORGANISM: Artificial Sequence
<220> FEATURE:
<223> OTHER INFORMATION: Variable light chain amino acid sequences;
      huCD37-51 antibody

<400> SEQUENCE: 83

Glu Ile Val Leu Thr Gln Ser Pro Ala Thr Met Ser Ala Ser Pro Gly
1               5                   10                  15

Glu Arg Val Thr Met Thr Cys Ser Ala Thr Ser Ser Val Thr Tyr Met
            20                  25                  30

His Trp Tyr Gln Gln Lys Pro Gly Gln Ser Pro Lys Arg Trp Ile Tyr
        35                  40                  45

Asp Thr Ser Lys Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Ser Asn Pro Pro Thr
                85                  90                  95

Phe Gly Gln Gly Thr Lys Leu Glu Ile Lys Arg
            100                 105


<210> SEQ ID NO 84
<211> LENGTH: 107
<212> TYPE: PRT
<213> ORGANISM: Artificial Sequence
<220> FEATURE:
<223> OTHER INFORMATION: Variable light chain amino acid sequences;
      muCD37-56 antibody

<400> SEQUENCE: 84

Gln Ile Val Leu Thr Gln Ser Pro Ala Phe Met Ser Ala Ser Pro Gly
1               5                   10                  15

Asp Lys Val Thr Met Thr Cys Ser Ala Ser Ser Ser Val Thr Tyr Met
            20                  25                  30

His Trp Tyr Gln Gln Lys Ser Gly Thr Ser Pro Lys Arg Trp Ile Tyr
        35                  40                  45
```

```
Asp Thr Ser Lys Leu Ala Ser Gly Val Pro Ala Arg Phe Ser Gly Gly
    50                  55                  60

Gly Ser Gly Thr Ser Tyr Ser Leu Thr Ile Ser Thr Met Glu Ala Glu
65                  70                  75                  80

Asp Ala Ala Thr Tyr Tyr Cys Gln Gln Trp Ile Ser Asp Pro Pro Thr
                85                  90                  95

Phe Gly Gly Gly Thr Lys Leu Glu Ile Lys Arg
            100                 105


<210> SEQ ID NO 85
<211> LENGTH: 107
<212> TYPE: PRT
<213> ORGANISM: Artificial Sequence
<220> FEATURE:
<223> OTHER INFORMATION: Variable light chain amino acid sequences;
      huCD37-56 antibody

<400> SEQUENCE: 85

Asp Ile Val Leu Thr Gln Ser Pro Ala Phe Met Ser Ala Ser Pro Gly
1               5                   10                  15

Glu Lys Val Thr Met Thr Cys Ser Ala Ser Ser Ser Val Thr Tyr Met
            20                  25                  30

His Trp Tyr Gln Gln Lys Pro Asp Gln Ser Pro Lys Arg Trp Ile Tyr
        35                  40                  45

Asp Thr Ser Asn Leu Ala Ser Gly Val Pro Ser Arg Phe Ser Gly Gly
    50                  55                  60

Gly Ser Gly Thr Asp Tyr Ser Leu Thr Ile Ser Ser Met Glu Ala Glu
65                  70                  75                  80

Asp Ala Ala Thr Tyr Tyr Cys Gln Gln Trp Ile Ser Asp Pro Pro Thr
                85                  90                  95

Phe Gly Gln Gly Thr Lys Leu Glu Ile Lys Arg
            100                 105


<210> SEQ ID NO 86
<211> LENGTH: 107
<212> TYPE: PRT
<213> ORGANISM: Artificial Sequence
<220> FEATURE:
<223> OTHER INFORMATION: Variable light chain amino acid sequences;
      muCD37-57 antibody

<400> SEQUENCE: 86

Gln Ile Val Leu Thr Gln Ser Pro Ala Ile Met Ser Ala Ser Pro Gly
1               5                   10                  15

Glu Lys Val Thr Met Thr Cys Ser Ala Thr Ser Ser Val Thr Tyr Met
            20                  25                  30

His Trp Tyr Gln Gln Lys Ser Gly Thr Ser Pro Lys Arg Trp Ile Tyr
        35                  40                  45

Asp Thr Ser Lys Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Asp Asn Pro Pro Thr
                85                  90                  95

Phe Gly Ser Gly Thr Lys Leu Glu Ile Lys Arg
            100                 105


<210> SEQ ID NO 87
```

-continued

<211> LENGTH: 107
<212> TYPE: PRT
<213> ORGANISM: Artificial Sequence
<220> FEATURE:
<223> OTHER INFORMATION: Variable light chain amino acid sequences; huCD37-57 antibody

<400> SEQUENCE: 87

Glu Ile Val Leu Thr Gln Ser Pro Ala Thr Met Ser Ala Ser Pro Gly
1 5 10 15

Glu Arg Val Thr Met Thr Cys Ser Ala Thr Ser Ser Val Thr Tyr Met
20 25 30

His Trp Tyr Gln Gln Lys Pro Gly Gln Ser Pro Arg Arg Trp Ile Tyr
35 40 45

Asp Thr Ser Asn Leu Ala Ser Gly Val Pro Ala Arg Phe Ser Gly Ser
50 55 60

Gly Ser Gly Thr Ser Tyr Ser Leu Thr Ile Ser Ser Met Glu Ala Glu
65 70 75 80

Asp Ala Ala Thr Tyr Tyr Cys Gln Gln Trp Ser Asp Asn Pro Pro Thr
85 90 95

Phe Gly Gln Gly Thr Lys Leu Glu Ile Lys Arg
100 105

<210> SEQ ID NO 88
<211> LENGTH: 445
<212> TYPE: PRT
<213> ORGANISM: Artificial Sequence
<220> FEATURE:
<223> OTHER INFORMATION: Full-length heavy chain amino acid sequences; muCD37-3 antibody

<400> SEQUENCE: 88

Gln Val Gln Val Lys Glu Ser Gly Pro Gly Leu Val Ala Pro Ser Gln
1 5 10 15

Ser Leu Ser Ile Thr Cys Thr Val Ser Gly Phe Ser Leu Thr Thr Ser
20 25 30

Gly Val Ser Trp Val Arg Gln Pro Pro Gly Lys Gly Leu Glu Trp Leu
35 40 45

Gly Val Ile Trp Gly Asp Gly Ser Thr Asn Tyr His Ser Ala Leu Lys
50 55 60

Ser Arg Leu Ser Ile Lys Lys Asp His Ser Lys Ser Gln Val Phe Leu
65 70 75 80

Lys Leu Asn Ser Leu Gln Thr Asp Asp Thr Ala Thr Tyr Tyr Cys Ala
85 90 95

Lys Gly Gly Tyr Ser Leu Ala His Trp Gly Gln Gly Thr Leu Val Thr
100 105 110

Val Ser Ala Ala Lys Thr Thr Ala Pro Ser Val Tyr Pro Leu Ala Pro
115 120 125

Val Cys Gly Asp Thr Thr Gly Ser Ser Val Thr Leu Gly Cys Leu Val
130 135 140

Lys Gly Tyr Phe Pro Glu Pro Val Thr Leu Thr Trp Asn Ser Gly Ser
145 150 155 160

Leu Ser Ser Gly Val His Thr Phe Pro Ala Val Leu Gln Ser Asp Leu
165 170 175

Tyr Thr Leu Ser Ser Ser Val Thr Val Thr Ser Ser Thr Trp Pro Ser
180 185 190

Gln Ser Ile Thr Cys Asn Val Ala His Pro Ala Ser Ser Thr Lys Val
195 200 205

```
Asp Lys Lys Ile Glu Pro Arg Gly Pro Thr Ile Lys Pro Cys Pro Pro
    210                 215                 220

Cys Lys Cys Pro Ala Pro Asn Leu Leu Gly Gly Pro Ser Val Phe Ile
225                 230                 235                 240

Phe Pro Pro Lys Ile Lys Asp Val Leu Met Ile Ser Leu Ser Pro Ile
                245                 250                 255

Val Thr Cys Val Val Val Asp Val Ser Glu Asp Asp Pro Asp Val Gln
            260                 265                 270

Ile Ser Trp Phe Val Asn Asn Val Glu Val His Thr Ala Gln Thr Gln
        275                 280                 285

Thr His Arg Glu Asp Tyr Asn Ser Thr Leu Arg Val Val Ser Ala Leu
    290                 295                 300

Pro Ile Gln His Gln Asp Trp Met Ser Gly Lys Glu Phe Lys Cys Lys
305                 310                 315                 320

Val Asn Asn Lys Asp Leu Pro Ala Pro Ile Glu Arg Thr Ile Ser Lys
                325                 330                 335

Pro Lys Gly Ser Val Arg Ala Pro Gln Val Tyr Val Leu Pro Pro Pro
            340                 345                 350

Glu Glu Glu Met Thr Lys Lys Gln Val Thr Leu Thr Cys Met Val Thr
        355                 360                 365

Asp Phe Met Pro Glu Asp Ile Tyr Val Glu Trp Thr Asn Asn Gly Lys
    370                 375                 380

Thr Glu Leu Asn Tyr Lys Asn Thr Glu Pro Val Leu Asp Ser Asp Gly
385                 390                 395                 400

Ser Tyr Phe Met Tyr Ser Lys Leu Arg Val Glu Lys Lys Asn Trp Val
                405                 410                 415

Glu Arg Asn Ser Tyr Ser Cys Ser Val Val His Glu Gly Leu His Asn
            420                 425                 430

His His Thr Thr Lys Ser Phe Ser Arg Thr Pro Gly Lys
        435                 440                 445
```

<210> SEQ ID NO 89
<211> LENGTH: 445
<212> TYPE: PRT
<213> ORGANISM: Artificial Sequence
<220> FEATURE:
<223> OTHER INFORMATION: Full-length heavy chain amino acid sequences; chCD37-3 antibody

<400> SEQUENCE: 89

```
Gln Val Gln Val Lys Glu Ser Gly Pro Gly Leu Val Ala Pro Ser Gln
1               5                   10                  15

Ser Leu Ser Ile Thr Cys Thr Val Ser Gly Phe Ser Leu Thr Thr Ser
            20                  25                  30

Gly Val Ser Trp Val Arg Gln Pro Pro Gly Lys Gly Leu Glu Trp Leu
        35                  40                  45

Gly Val Ile Trp Gly Asp Gly Ser Thr Asn Tyr His Ser Ala Leu Lys
    50                  55                  60

Ser Arg Leu Ser Ile Lys Lys Asp His Ser Lys Ser Gln Val Phe Leu
65                  70                  75                  80

Lys Leu Asn Ser Leu Gln Thr Asp Asp Thr Ala Thr Tyr Tyr Cys Ala
                85                  90                  95

Lys Gly Gly Tyr Ser Leu Ala His Trp Gly Gln Gly Thr Leu Val Thr
            100                 105                 110

Val Ser Ala Ala Ser Thr Lys Gly Pro Ser Val Phe Pro Leu Ala Pro
```

-continued

```
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Asp Glu Leu Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
        435                 440                 445


<210> SEQ ID NO 90
<211> LENGTH: 444
<212> TYPE: PRT
<213> ORGANISM: Artificial Sequence
<220> FEATURE:
<223> OTHER INFORMATION: Full-length heavy chain amino acid sequences;
      huCD37-3v1.0 antibody

<400> SEQUENCE: 90

Gln Val Gln Val Gln Glu Ser Gly Pro Gly Leu Val Ala Pro Ser Gln
1               5                   10                  15

Thr Leu Ser Ile Thr Cys Thr Val Ser Gly Phe Ser Leu Thr Thr Ser
            20                  25                  30
```

-continued

```
Gly Val Ser Trp Val Arg Gln Pro Pro Gly Lys Gly Leu Glu Trp Leu
        35                  40                  45

Gly Val Ile Trp Gly Asp Gly Ser Thr Asn Tyr His Pro Ser Leu Lys
    50                  55                  60

Ser Arg Leu Ser Ile Lys Lys Asp His Ser Lys Ser Gln Val Phe Leu
65                  70                  75                  80

Lys Leu Asn Ser Leu Thr Ala Ala Asp Thr Ala Thr Tyr Tyr Cys Ala
                85                  90                  95

Lys Gly Gly Tyr Ser Leu Ala His Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Asp Glu Leu Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly
        435                 440
```

-continued

<210> SEQ ID NO 91
<211> LENGTH: 444
<212> TYPE: PRT
<213> ORGANISM: Artificial Sequence
<220> FEATURE:
<223> OTHER INFORMATION: Full-length heavy chain amino acid sequences; huCD37-3v1.1 antibody

<400> SEQUENCE: 91

```
Gln Val Gln Val Gln Glu Ser Gly Pro Gly Leu Val Ala Pro Ser Gln
1               5                   10                  15

Thr Leu Ser Ile Thr Cys Thr Val Ser Gly Phe Ser Leu Thr Thr Ser
            20                  25                  30

Gly Val Ser Trp Val Arg Gln Pro Pro Gly Lys Gly Leu Glu Trp Leu
        35                  40                  45

Gly Val Ile Trp Gly Asp Gly Ser Thr Asn Tyr His Ser Ser Leu Lys
    50                  55                  60

Ser Arg Leu Ser Ile Lys Lys Asp His Ser Lys Ser Gln Val Phe Leu
65                  70                  75                  80

Lys Leu Asn Ser Leu Thr Ala Ala Asp Thr Ala Thr Tyr Tyr Cys Ala
                85                  90                  95

Lys Gly Gly Tyr Ser Leu Ala His Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Asp Glu Leu Thr Lys Asn Gln Val Ser Leu Thr Cys Leu Val Lys
        355                 360                 365
```

-continued

```
Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly
        435                 440


<210> SEQ ID NO 92
<211> LENGTH: 445
<212> TYPE: PRT
<213> ORGANISM: Artificial Sequence
<220> FEATURE:
<223> OTHER INFORMATION: Full-length heavy chain amino acid sequences;
      muCD37-12 antibody

<400> SEQUENCE: 92

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Lys Tyr
            20                  25                  30

Gly Met Asn Trp Val Lys Gln Ala Gln Gly Lys Gly Leu Lys Trp Met
        35                  40                  45

Gly Trp Ile Asn Thr Asn Thr Gly Glu Ser Arg Asn Ala Glu Glu Phe
    50                  55                  60

Lys Gly Arg Phe Ala Phe Ser Leu Glu Thr Ser Ala Ser Thr Ala Tyr
65                  70                  75                  80

Leu Gln Ile Asn Asn Leu Lys Tyr Glu Asp Thr Ala Thr Tyr Phe Cys
                85                  90                  95

Gly Arg Gly Thr Val Val Ala Asp Trp Gly Gln Gly Thr Thr Leu Thr
            100                 105                 110

Val Ser Ser Ala Lys Thr Thr Ala Pro Ser Val Tyr Pro Leu Ala Pro
        115                 120                 125

Val Cys Gly Asp Thr Thr Gly Ser Ser Val Thr Leu Gly Cys Leu Val
    130                 135                 140

Lys Gly Tyr Phe Pro Glu Pro Val Thr Leu Thr Trp Asn Ser Gly Ser
145                 150                 155                 160

Leu Ser Ser Gly Val His Thr Phe Pro Ala Val Leu Gln Ser Asp Leu
                165                 170                 175

Tyr Thr Leu Ser Ser Ser Val Thr Val Thr Ser Ser Thr Trp Pro Ser
            180                 185                 190

Gln Ser Ile Thr Cys Asn Val Ala His Pro Ala Ser Ser Thr Lys Val
        195                 200                 205

Asp Lys Lys Ile Glu Pro Arg Gly Pro Thr Ile Lys Pro Cys Pro Pro
    210                 215                 220

Cys Lys Cys Pro Ala Pro Asn Leu Leu Gly Gly Pro Ser Val Phe Ile
225                 230                 235                 240

Phe Pro Pro Lys Ile Lys Asp Val Leu Met Ile Ser Leu Ser Pro Ile
                245                 250                 255

Val Thr Cys Val Val Val Asp Val Ser Glu Asp Asp Pro Asp Val Gln
            260                 265                 270

Ile Ser Trp Phe Val Asn Asn Val Glu Val His Thr Ala Gln Thr Gln
        275                 280                 285
```

Thr His Arg Glu Asp Tyr Asn Ser Thr Leu Arg Val Val Ser Ala Leu
290 295 300

Pro Ile Gln His Gln Asp Trp Met Ser Gly Lys Glu Phe Lys Cys Lys
305 310 315 320

Val Asn Asn Lys Asp Leu Pro Ala Pro Ile Glu Arg Thr Ile Ser Lys
325 330 335

Pro Lys Gly Ser Val Arg Ala Pro Gln Val Tyr Val Leu Pro Pro Pro
340 345 350

Glu Glu Glu Met Thr Lys Lys Gln Val Thr Leu Thr Cys Met Val Thr
355 360 365

Asp Phe Met Pro Glu Asp Ile Tyr Val Glu Trp Thr Asn Asn Gly Lys
370 375 380

Thr Glu Leu Asn Tyr Lys Asn Thr Glu Pro Val Leu Asp Ser Asp Gly
385 390 395 400

Ser Tyr Phe Met Tyr Ser Lys Leu Arg Val Glu Lys Lys Asn Trp Val
405 410 415

Glu Arg Asn Ser Tyr Ser Cys Ser Val Val His Glu Gly Leu His Asn
420 425 430

His His Thr Thr Lys Ser Phe Ser Arg Thr Pro Gly Lys
435 440 445

<210> SEQ ID NO 93
<211> LENGTH: 445
<212> TYPE: PRT
<213> ORGANISM: Artificial Sequence
<220> FEATURE:
<223> OTHER INFORMATION: Full-length heavy chain amino acid sequences; chCD37-12 antibody

<400> SEQUENCE: 93

Gln Ile Gln Leu Val Gln Ser Gly Pro Glu Leu Lys Lys Pro Gly Glu
1 5 10 15

Thr Val Lys Ile Ser Cys Lys Ala Ser Gly Tyr Thr Phe Thr Lys Tyr
20 25 30

Gly Met Asn Trp Val Lys Gln Ala Gln Gly Lys Gly Leu Lys Trp Met
35 40 45

Gly Trp Ile Asn Thr Asn Thr Gly Glu Ser Arg Asn Ala Glu Glu Phe
50 55 60

Lys Gly Arg Phe Ala Phe Ser Leu Glu Thr Ser Ala Ser Thr Ala Tyr
65 70 75 80

Leu Gln Ile Asn Asn Leu Lys Tyr Glu Asp Thr Ala Thr Tyr Phe Cys
85 90 95

Gly Arg Gly Thr Val Val Ala Asp Trp Gly Gln Gly Thr Thr Leu Thr
100 105 110

Val Ser Ser Ala Ser Thr Lys Gly Pro Ser Val Phe Pro Leu Ala Pro
115 120 125

Ser Ser Lys Ser Thr Ser Gly Gly Thr Ala Ala Leu Gly Cys Leu Val
130 135 140

Lys Asp Tyr Phe Pro Glu Pro Val Thr Val Ser Trp Asn Ser Gly Ala
145 150 155 160

Leu Thr Ser Gly Val His Thr Phe Pro Ala Val Leu Gln Ser Ser Gly
165 170 175

Leu Tyr Ser Leu Ser Ser Val Val Thr Val Pro Ser Ser Ser Leu Gly
180 185 190

Thr Gln Thr Tyr Ile Cys Asn Val Asn His Lys Pro Ser Asn Thr Lys

```
        195                 200                 205

Val Asp Lys Lys Val Glu Pro Lys Ser Cys Asp Lys Thr His Thr Cys
    210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Asp Glu Leu Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
        435                 440                 445


<210> SEQ ID NO 94
<211> LENGTH: 444
<212> TYPE: PRT
<213> ORGANISM: Artificial Sequence
<220> FEATURE:
<223> OTHER INFORMATION: Full-length heavy chain amino acid sequences;
      muCD37-38 antibody

<400> SEQUENCE: 94

Asp Val Gln Leu Gln Glu Ser Gly Pro Asp Leu Val Lys Pro Ser Gln
1               5                   10                  15

Ser Leu Ser Leu Thr Cys Thr Val Thr Gly Tyr Ser Ile Thr Ser Gly
            20                  25                  30

Phe Gly Trp His Trp Ile Arg Gln Phe Pro Gly Asn Lys Leu Glu Trp
        35                  40                  45

Met Ala Tyr Ile Leu Tyr Ser Gly Gly Thr Asp Tyr Asn Pro Ser Leu
    50                  55                  60

Lys Ser Arg Ile Ser Ile Thr Arg Asp Thr Ser Lys Asn Gln Phe Phe
65                  70                  75                  80

Leu Arg Leu Ser Ser Val Thr Thr Glu Asp Thr Ala Thr Tyr Tyr Cys
                85                  90                  95

Ala Arg Gly Tyr Tyr Gly Tyr Gly Ala Trp Phe Val Tyr Trp Gly Gln
            100                 105                 110
```

-continued

```
Gly Thr Leu Val Thr Val Ser Ala Ala Lys Thr Thr Pro Pro Ser Val
        115                 120                 125

Tyr Pro Leu Ala Pro Gly Ser Ala Ala Gln Thr Asn Ser Met Val Thr
    130                 135                 140

Leu Gly Cys Leu Val Lys Gly Tyr Phe Pro Glu Pro Val Thr Val Thr
145                 150                 155                 160

Trp Asn Ser Gly Ser Leu Ser Ser Gly Val His Thr Phe Pro Ala Val
                165                 170                 175

Leu Glu Ser Asp Leu Tyr Thr Leu Ser Ser Ser Val Thr Val Pro Ser
            180                 185                 190

Ser Met Arg Pro Ser Glu Thr Val Thr Cys Asn Val Ala His Pro Ala
        195                 200                 205

Ser Ser Thr Lys Val Asp Lys Lys Ile Val Pro Arg Asp Cys Gly Cys
    210                 215                 220

Lys Pro Cys Ile Cys Thr Val Pro Glu Val Ser Ser Val Phe Ile Phe
225                 230                 235                 240

Pro Pro Lys Pro Lys Asp Val Leu Thr Ile Thr Leu Thr Pro Lys Val
                245                 250                 255

Thr Cys Val Val Val Asp Ile Ser Lys Asp Asp Pro Glu Val Gln Phe
            260                 265                 270

Ser Trp Phe Val Asp Asp Val Glu Val His Thr Ala Gln Thr Gln Pro
        275                 280                 285

Arg Glu Glu Gln Phe Asn Ser Thr Phe Arg Ser Val Ser Glu Leu Pro
    290                 295                 300

Ile Met His Gln Asp Trp Leu Asn Gly Lys Glu Phe Lys Cys Arg Val
305                 310                 315                 320

Asn Ser Ala Ala Phe Pro Ala Pro Ile Glu Lys Thr Ile Ser Lys Thr
                325                 330                 335

Lys Gly Arg Pro Lys Ala Pro Gln Val Tyr Thr Ile Pro Pro Pro Lys
            340                 345                 350

Glu Gln Met Ala Lys Asp Lys Val Ser Leu Thr Cys Met Ile Thr Asp
        355                 360                 365

Phe Phe Pro Glu Asp Ile Thr Val Glu Trp Gln Trp Asn Gly Gln Pro
    370                 375                 380

Ala Glu Asn Tyr Lys Asn Thr Gln Pro Ile Met Asn Thr Asn Gly Ser
385                 390                 395                 400

Tyr Phe Val Tyr Ser Lys Leu Asn Val Gln Lys Ser Asn Trp Glu Ala
                405                 410                 415

Gly Asn Thr Phe Thr Cys Ser Val Leu His Glu Gly Leu His Asn His
            420                 425                 430

His Thr Glu Lys Ser Leu Ser His Ser Pro Gly Lys
        435                 440


<210> SEQ ID NO 95
<211> LENGTH: 449
<212> TYPE: PRT
<213> ORGANISM: Artificial Sequence
<220> FEATURE:
<223> OTHER INFORMATION: Full-length heavy chain amino acid sequences;
      chCD37-38 antibody

<400> SEQUENCE: 95

Gln Val Gln Leu Gln Glu Ser Gly Pro Asp Leu Val Lys Pro Ser Gln
1               5                   10                  15

Ser Leu Ser Leu Thr Cys Thr Val Thr Gly Tyr Ser Ile Thr Ser Gly
            20                  25                  30
```

-continued

```
Phe Gly Trp His Trp Ile Arg Gln Phe Pro Gly Asn Lys Leu Glu Trp
        35                  40                  45

Met Ala Tyr Ile Leu Tyr Ser Gly Gly Thr Asp Tyr Asn Pro Ser Leu
    50                  55                  60

Lys Ser Arg Ile Ser Ile Thr Arg Asp Thr Ser Lys Asn Gln Phe Phe
65                  70                  75                  80

Leu Arg Leu Ser Ser Val Thr Thr Glu Asp Thr Ala Thr Tyr Tyr Cys
                85                  90                  95

Ala Arg Gly Tyr Tyr Gly Tyr Gly Ala Trp Phe Val Tyr Trp Gly Gln
            100                 105                 110

Gly Thr Leu Val Thr Val Ser Ala Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445
```

Gly

<210> SEQ ID NO 96
<211> LENGTH: 449
<212> TYPE: PRT
<213> ORGANISM: Artificial Sequence
<220> FEATURE:
<223> OTHER INFORMATION: Full-length heavy chain amino acid sequences; huCD37-38 antibody

<400> SEQUENCE: 96

Gln Val Gln Leu Gln Glu Ser Gly Pro Gly Leu Val Lys Pro Ser Gln
1 5 10 15

Ser Leu Ser Leu Thr Cys Thr Val Ser Gly Tyr Ser Ile Thr Ser Gly
20 25 30

Phe Gly Trp His Trp Ile Arg Gln Phe Pro Gly Lys Gly Leu Glu Trp
35 40 45

Met Ala Tyr Ile Leu Tyr Ser Gly Gly Thr Asp Tyr Asn Pro Ser Leu
50 55 60

Lys Ser Arg Ile Ser Ile Thr Arg Asp Thr Ser Lys Asn Gln Phe Phe
65 70 75 80

Leu Arg Leu Ser Ser Val Thr Ala Ala Asp Thr Ala Thr Tyr Tyr Cys
85 90 95

Ala Arg Gly Tyr Tyr Gly Tyr Gly Ala Trp Phe Val Tyr Trp Gly Gln
100 105 110

Gly Thr Leu Val Thr Val Ser Ser Ala Ser Thr Lys Gly Pro Ser Val
115 120 125

Phe Pro Leu Ala Pro Ser Ser Lys Ser Thr Ser Gly Gly Thr Ala Ala
130 135 140

Leu Gly Cys Leu Val Lys Asp Tyr Phe Pro Glu Pro Val Thr Val Ser
145 150 155 160

Trp Asn Ser Gly Ala Leu Thr Ser Gly Val His Thr Phe Pro Ala Val
165 170 175

Leu Gln Ser Ser Gly Leu Tyr Ser Leu Ser Ser Val Val Thr Val Pro
180 185 190

Ser Ser Ser Leu Gly Thr Gln Thr Tyr Ile Cys Asn Val Asn His Lys
195 200 205

Pro Ser Asn Thr Lys Val Asp Lys Lys Val Glu Pro Lys Ser Cys Asp
210 215 220

Lys Thr His Thr Cys Pro Pro Cys Pro Ala Pro Glu Leu Leu Gly Gly
225 230 235 240

Pro Ser Val Phe Leu Phe Pro Pro Lys Pro Lys Asp Thr Leu Met Ile
245 250 255

Ser Arg Thr Pro Glu Val Thr Cys Val Val Val Asp Val Ser His Glu
260 265 270

Asp Pro Glu Val Lys Phe Asn Trp Tyr Val Asp Gly Val Glu Val His
275 280 285

Asn Ala Lys Thr Lys Pro Arg Glu Glu Gln Tyr Asn Ser Thr Tyr Arg
290 295 300

Val Val Ser Val Leu Thr Val Leu His Gln Asp Trp Leu Asn Gly Lys
305 310 315 320

Glu Tyr Lys Cys Lys Val Ser Asn Lys Ala Leu Pro Ala Pro Ile Glu
325 330 335

Lys Thr Ile Ser Lys Ala Lys Gly Gln Pro Arg Glu Pro Gln Val Tyr
340 345 350

```
Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly


<210> SEQ ID NO 97
<211> LENGTH: 450
<212> TYPE: PRT
<213> ORGANISM: Artificial Sequence
<220> FEATURE:
<223> OTHER INFORMATION: Full-length heavy chain amino acid sequences;
      muCD37-50 antibody

<400> SEQUENCE: 97

Asp Val Gln Leu Gln Glu Ser Gly Pro Asp Leu Leu Lys Pro Ser Gln
1               5                   10                  15

Ser Leu Ser Leu Thr Cys Thr Val Thr Gly Tyr Ser Ile Thr Ser Gly
            20                  25                  30

Phe Ala Trp His Trp Ile Arg Gln Phe Pro Gly Asn Lys Leu Glu Trp
        35                  40                  45

Met Gly Tyr Ile Leu Tyr Ser Gly Ser Thr Val Tyr Ser Pro Ser Leu
    50                  55                  60

Lys Ser Arg Ile Ser Ile Thr Arg Asp Thr Ser Lys Asn His Phe Phe
65                  70                  75                  80

Leu Gln Leu Asn Ser Val Thr Thr Glu Asp Thr Ala Thr Tyr Tyr Cys
                85                  90                  95

Ala Arg Gly Tyr Tyr Gly Tyr Gly Ala Trp Phe Ala Tyr Trp Gly Gln
            100                 105                 110

Gly Thr Leu Val Thr Val Ser Ala Ala Lys Thr Thr Ala Pro Ser Val
        115                 120                 125

Tyr Pro Leu Ala Pro Val Cys Gly Asp Thr Thr Gly Ser Ser Val Thr
    130                 135                 140

Leu Gly Cys Leu Val Lys Gly Tyr Phe Pro Glu Pro Val Thr Leu Thr
145                 150                 155                 160

Trp Asn Ser Gly Ser Leu Ser Ser Gly Val His Thr Phe Pro Ala Val
                165                 170                 175

Leu Gln Ser Asp Leu Tyr Thr Leu Ser Ser Ser Val Thr Val Thr Ser
            180                 185                 190

Ser Thr Trp Pro Ser Gln Ser Ile Thr Cys Asn Val Ala His Pro Ala
        195                 200                 205

Ser Ser Thr Lys Val Asp Lys Lys Ile Glu Pro Arg Gly Pro Thr Ile
    210                 215                 220

Lys Pro Cys Pro Pro Cys Lys Cys Pro Ala Pro Asn Leu Leu Gly Gly
225                 230                 235                 240

Pro Ser Val Phe Ile Phe Pro Pro Lys Ile Lys Asp Val Leu Met Ile
                245                 250                 255
```

```
Ser Leu Ser Pro Ile Val Thr Cys Val Val Val Asp Val Ser Glu Asp
            260                 265                 270

Asp Pro Asp Val Gln Ile Ser Trp Phe Val Asn Asn Val Glu Val His
        275                 280                 285

Thr Ala Gln Thr Gln Thr His Arg Glu Asp Tyr Asn Ser Thr Leu Arg
    290                 295                 300

Val Val Ser Ala Leu Pro Ile Gln His Gln Asp Trp Met Ser Gly Lys
305                 310                 315                 320

Glu Phe Lys Cys Lys Val Asn Asn Lys Asp Leu Pro Ala Pro Ile Glu
                325                 330                 335

Arg Thr Ile Ser Lys Pro Lys Gly Ser Val Arg Ala Pro Gln Val Tyr
            340                 345                 350

Val Leu Pro Pro Pro Glu Glu Glu Met Thr Lys Lys Gln Val Thr Leu
        355                 360                 365

Thr Cys Met Val Thr Asp Phe Met Pro Glu Asp Ile Tyr Val Glu Trp
    370                 375                 380

Thr Asn Asn Gly Lys Thr Glu Leu Asn Tyr Lys Asn Thr Glu Pro Val
385                 390                 395                 400

Leu Asp Ser Asp Gly Ser Tyr Phe Met Tyr Ser Lys Leu Arg Val Glu
                405                 410                 415

Lys Lys Asn Trp Val Glu Arg Asn Ser Tyr Ser Cys Ser Val Val His
            420                 425                 430

Glu Gly Leu His Asn His His Thr Thr Lys Ser Phe Ser Arg Thr Pro
        435                 440                 445

Gly Lys
    450


<210> SEQ ID NO 98
<211> LENGTH: 449
<212> TYPE: PRT
<213> ORGANISM: Artificial Sequence
<220> FEATURE:
<223> OTHER INFORMATION: Full-length heavy chain amino acid sequences;
      huCD37-50 antibody

<400> SEQUENCE: 98

Gln Val Gln Leu Gln Glu Ser Gly Pro Gly Leu Leu Lys Pro Ser Gln
1               5                   10                  15

Ser Leu Ser Leu Thr Cys Thr Val Ser Gly Tyr Ser Ile Thr Ser Gly
            20                  25                  30

Phe Ala Trp His Trp Ile Arg Gln His Pro Gly Asn Lys Leu Glu Trp
        35                  40                  45

Met Gly Tyr Ile Leu Tyr Ser Gly Ser Thr Val Tyr Ser Pro Ser Leu
    50                  55                  60

Lys Ser Arg Ile Ser Ile Thr Arg Asp Thr Ser Lys Asn His Phe Phe
65                  70                  75                  80

Leu Gln Leu Asn Ser Val Thr Ala Ala Asp Thr Ala Thr Tyr Tyr Cys
                85                  90                  95

Ala Arg Gly Tyr Tyr Gly Tyr Gly Ala Trp Phe Ala Tyr Trp Gly Gln
            100                 105                 110

Gly Thr Leu Val Thr Val Ser Ala Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160
```

Trp Asn Ser Gly Ala Leu Thr Ser Gly Val His Thr Phe Pro Ala Val
165 170 175

Leu Gln Ser Ser Gly Leu Tyr Ser Leu Ser Ser Val Val Thr Val Pro
180 185 190

Ser Ser Ser Leu Gly Thr Gln Thr Tyr Ile Cys Asn Val Asn His Lys
195 200 205

Pro Ser Asn Thr Lys Val Asp Lys Lys Val Glu Pro Lys Ser Cys Asp
210 215 220

Lys Thr His Thr Cys Pro Pro Cys Pro Ala Pro Glu Leu Leu Gly Gly
225 230 235 240

Pro Ser Val Phe Leu Phe Pro Pro Lys Pro Lys Asp Thr Leu Met Ile
245 250 255

Ser Arg Thr Pro Glu Val Thr Cys Val Val Val Asp Val Ser His Glu
260 265 270

Asp Pro Glu Val Lys Phe Asn Trp Tyr Val Asp Gly Val Glu Val His
275 280 285

Asn Ala Lys Thr Lys Pro Arg Glu Glu Gln Tyr Asn Ser Thr Tyr Arg
290 295 300

Val Val Ser Val Leu Thr Val Leu His Gln Asp Trp Leu Asn Gly Lys
305 310 315 320

Glu Tyr Lys Cys Lys Val Ser Asn Lys Ala Leu Pro Ala Pro Ile Glu
325 330 335

Lys Thr Ile Ser Lys Ala Lys Gly Gln Pro Arg Glu Pro Gln Val Tyr
340 345 350

Thr Leu Pro Pro Ser Arg Asp Glu Leu Thr Lys Asn Gln Val Ser Leu
355 360 365

Thr Cys Leu Val Lys Gly Phe Tyr Pro Ser Asp Ile Ala Val Glu Trp
370 375 380

Glu Ser Asn Gly Gln Pro Glu Asn Asn Tyr Lys Thr Thr Pro Pro Val
385 390 395 400

Leu Asp Ser Asp Gly Ser Phe Phe Leu Tyr Ser Lys Leu Thr Val Asp
405 410 415

Lys Ser Arg Trp Gln Gln Gly Asn Val Phe Ser Cys Ser Val Met His
420 425 430

Glu Ala Leu His Asn His Tyr Thr Gln Lys Ser Leu Ser Leu Ser Pro
435 440 445

Gly

<210> SEQ ID NO 99
<211> LENGTH: 450
<212> TYPE: PRT
<213> ORGANISM: Artificial Sequence
<220> FEATURE:
<223> OTHER INFORMATION: Full-length heavy chain amino acid sequences; muCD37-51 antibody

<400> SEQUENCE: 99

Asp Val Gln Leu Gln Glu Ser Gly Pro Asp Leu Leu Lys Pro Ser Gln
1 5 10 15

Ser Leu Ser Leu Thr Cys Thr Val Thr Gly Tyr Ser Ile Ser Ser Gly
20 25 30

Phe Ala Trp His Trp Ile Arg Gln Phe Pro Gly Asn Lys Leu Glu Trp
35 40 45

Met Gly Tyr Ile His Tyr Ser Gly Ser Thr Asn Tyr Ser Pro Ser Leu
50 55 60

```
Lys Ser Arg Ile Ser Ile Thr Arg Asp Ser Ser Lys Asn Gln Phe Phe
65                  70                  75                  80

Leu Gln Leu Asn Ser Val Thr Thr Glu Asp Thr Ala Thr Tyr Tyr Cys
                85                  90                  95

Ala Arg Gly Tyr Tyr Gly Phe Gly Ala Trp Phe Val Tyr Trp Gly Gln
            100                 105                 110

Gly Thr Leu Val Thr Val Ser Ala Ala Lys Thr Thr Ala Pro Ser Val
        115                 120                 125

Tyr Pro Leu Ala Pro Val Cys Gly Asp Thr Thr Gly Ser Ser Val Thr
    130                 135                 140

Leu Gly Cys Leu Val Lys Gly Tyr Phe Pro Glu Pro Val Thr Leu Thr
145                 150                 155                 160

Trp Asn Ser Gly Ser Leu Ser Ser Gly Val His Thr Phe Pro Ala Val
                165                 170                 175

Leu Gln Ser Asp Leu Tyr Thr Leu Ser Ser Ser Val Thr Val Thr Ser
            180                 185                 190

Ser Thr Trp Pro Ser Gln Ser Ile Thr Cys Asn Val Ala His Pro Ala
        195                 200                 205

Ser Ser Thr Lys Val Asp Lys Lys Ile Glu Pro Arg Gly Pro Thr Ile
    210                 215                 220

Lys Pro Cys Pro Pro Cys Lys Cys Pro Ala Pro Asn Leu Leu Gly Gly
225                 230                 235                 240

Pro Ser Val Phe Ile Phe Pro Pro Lys Ile Lys Asp Val Leu Met Ile
                245                 250                 255

Ser Leu Ser Pro Ile Val Thr Cys Val Val Val Asp Val Ser Glu Asp
            260                 265                 270

Asp Pro Asp Val Gln Ile Ser Trp Phe Val Asn Asn Val Glu Val His
        275                 280                 285

Thr Ala Gln Thr Gln Thr His Arg Glu Asp Tyr Asn Ser Thr Leu Arg
    290                 295                 300

Val Val Ser Ala Leu Pro Ile Gln His Gln Asp Trp Met Ser Gly Lys
305                 310                 315                 320

Glu Phe Lys Cys Lys Val Asn Asn Lys Asp Leu Pro Ala Pro Ile Glu
                325                 330                 335

Arg Thr Ile Ser Lys Pro Lys Gly Ser Val Arg Ala Pro Gln Val Tyr
            340                 345                 350

Val Leu Pro Pro Pro Glu Glu Glu Met Thr Lys Lys Gln Val Thr Leu
        355                 360                 365

Thr Cys Met Val Thr Asp Phe Met Pro Glu Asp Ile Tyr Val Glu Trp
    370                 375                 380

Thr Asn Asn Gly Lys Thr Glu Leu Asn Tyr Lys Asn Thr Glu Pro Val
385                 390                 395                 400

Leu Asp Ser Asp Gly Ser Tyr Phe Met Tyr Ser Lys Leu Arg Val Glu
                405                 410                 415

Lys Lys Asn Trp Val Glu Arg Asn Ser Tyr Ser Cys Ser Val Val His
            420                 425                 430

Glu Gly Leu His Asn His His Thr Thr Lys Ser Phe Ser Arg Thr Pro
        435                 440                 445

Gly Lys
    450
```

<210> SEQ ID NO 100
<211> LENGTH: 449

```
<212> TYPE: PRT
<213> ORGANISM: Artificial Sequence
<220> FEATURE:
<223> OTHER INFORMATION: Full-length heavy chain amino acid sequences;
      huCD37-51 antibody

<400> SEQUENCE: 100

Glu Val Gln Leu Val Glu Ser Gly Pro Glu Val Leu Lys Pro Gly Glu
1               5                   10                  15

Ser Leu Ser Leu Thr Cys Thr Val Ser Gly Tyr Ser Ile Ser Ser Gly
            20                  25                  30

Phe Ala Trp His Trp Ile Arg Gln Phe Pro Gly Lys Gly Leu Glu Trp
        35                  40                  45

Met Gly Tyr Ile His Tyr Ser Gly Ser Thr Asn Tyr Ser Pro Ser Leu
    50                  55                  60

Gln Gly Arg Ile Ser Ile Thr Arg Asp Ser Ser Ile Asn Gln Phe Phe
65                  70                  75                  80

Leu Gln Leu Asn Ser Val Thr Ala Ser Asp Thr Ala Thr Tyr Tyr Cys
                85                  90                  95

Ala Arg Gly Tyr Tyr Gly Phe Gly Ala Trp Phe Val Tyr Trp Gly Gln
            100                 105                 110

Gly Thr Leu Val Thr Val Ser Ala Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380
```

-continued

```
Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly
```

<210> SEQ ID NO 101
<211> LENGTH: 444
<212> TYPE: PRT
<213> ORGANISM: Artificial Sequence
<220> FEATURE:
<223> OTHER INFORMATION: Full-length heavy chain amino acid sequences; muCD37-56 antibody

<400> SEQUENCE: 101

```
Asp Val Gln Leu Gln Glu Ser Gly Pro Asp Leu Val Lys Pro Ser Gln
1               5                   10                  15

Ser Leu Ser Leu Thr Cys Thr Val Thr Gly Tyr Ser Ile Thr Ser Gly
            20                  25                  30

Phe Ala Trp His Trp Ile Arg Gln Phe Pro Gly Asn Lys Leu Glu Trp
        35                  40                  45

Met Gly Tyr Ile His Tyr Ser Gly Gly Thr Asn Tyr Asn Pro Ser Leu
    50                  55                  60

Lys Ser Arg Val Ser Ile Thr Arg Asp Thr Ser Lys Asn Gln Phe Phe
65                  70                  75                  80

Leu Gln Leu Asn Ser Val Thr Thr Glu Asp Thr Ala Thr Tyr Tyr Cys
                85                  90                  95

Ala Arg Gly Tyr Tyr Gly Phe Gly Ala Trp Phe Ala Tyr Trp Gly Gln
            100                 105                 110

Gly Thr Leu Val Pro Val Ser Ala Ala Lys Thr Thr Pro Pro Ser Val
        115                 120                 125

Tyr Pro Leu Ala Pro Gly Ser Ala Ala Gln Thr Asn Ser Met Val Thr
    130                 135                 140

Leu Gly Cys Leu Val Lys Gly Tyr Phe Pro Glu Pro Val Thr Val Thr
145                 150                 155                 160

Trp Asn Ser Gly Ser Leu Ser Ser Gly Val His Thr Phe Pro Ala Val
                165                 170                 175

Leu Glu Ser Asp Leu Tyr Thr Leu Ser Ser Ser Val Thr Val Pro Ser
            180                 185                 190

Ser Met Arg Pro Ser Glu Thr Val Thr Cys Asn Val Ala His Pro Ala
        195                 200                 205

Ser Ser Thr Lys Val Asp Lys Lys Ile Val Pro Arg Asp Cys Gly Cys
    210                 215                 220

Lys Pro Cys Ile Cys Thr Val Pro Glu Val Ser Ser Val Phe Ile Phe
225                 230                 235                 240

Pro Pro Lys Pro Lys Asp Val Leu Thr Ile Thr Leu Thr Pro Lys Val
                245                 250                 255

Thr Cys Val Val Val Asp Ile Ser Lys Asp Asp Pro Glu Val Gln Phe
            260                 265                 270

Ser Trp Phe Val Asp Asp Val Glu Val His Thr Ala Gln Thr Gln Pro
        275                 280                 285
```

```
Arg Glu Glu Gln Phe Asn Ser Thr Phe Arg Ser Val Ser Glu Leu Pro
    290                 295                 300

Ile Met His Gln Asp Trp Leu Asn Gly Lys Glu Phe Lys Cys Arg Val
305                 310                 315                 320

Asn Ser Ala Ala Phe Pro Ala Pro Ile Glu Lys Thr Ile Ser Lys Thr
                325                 330                 335

Lys Gly Arg Pro Lys Ala Pro Gln Val Tyr Thr Ile Pro Pro Pro Lys
            340                 345                 350

Glu Gln Met Ala Lys Asp Lys Val Ser Leu Thr Cys Met Ile Thr Asp
        355                 360                 365

Phe Phe Pro Glu Asp Ile Thr Val Glu Trp Gln Trp Asn Gly Gln Pro
    370                 375                 380

Ala Glu Asn Tyr Lys Asn Thr Gln Pro Ile Met Asn Thr Asn Gly Ser
385                 390                 395                 400

Tyr Phe Val Tyr Ser Lys Leu Asn Val Gln Lys Ser Asn Trp Glu Ala
                405                 410                 415

Gly Asn Thr Phe Thr Cys Ser Val Leu His Glu Gly Leu His Asn His
            420                 425                 430

His Thr Glu Lys Ser Leu Ser His Ser Pro Gly Lys
        435                 440


<210> SEQ ID NO 102
<211> LENGTH: 449
<212> TYPE: PRT
<213> ORGANISM: Artificial Sequence
<220> FEATURE:
<223> OTHER INFORMATION: Full-length heavy chain amino acid sequences;
      huCD37-56 antibody

<400> SEQUENCE: 102

Gln Val Gln Leu Gln Glu Ser Gly Pro Gly Leu Val Lys Pro Ser Gln
1               5                   10                  15

Ser Leu Ser Leu Thr Cys Thr Val Ser Gly Tyr Ser Ile Thr Ser Gly
            20                  25                  30

Phe Ala Trp His Trp Ile Arg Gln Phe Pro Gly Lys Gly Leu Glu Trp
        35                  40                  45

Met Gly Tyr Ile His Tyr Ser Gly Gly Thr Asn Tyr Asn Pro Ser Leu
    50                  55                  60

Lys Ser Arg Val Ser Ile Thr Arg Asp Thr Ser Lys Asn Gln Phe Phe
65                  70                  75                  80

Leu Gln Leu Asn Ser Val Thr Ala Ala Asp Thr Ala Thr Tyr Tyr Cys
                85                  90                  95

Ala Arg Gly Tyr Tyr Gly Phe Gly Ala Trp Phe Ala Tyr Trp Gly Gln
            100                 105                 110

Gly Thr Leu Val Pro Val Ser Ala Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
```

-continued

```
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly


<210> SEQ ID NO 103
<211> LENGTH: 450
<212> TYPE: PRT
<213> ORGANISM: Artificial Sequence
<220> FEATURE:
<223> OTHER INFORMATION: Full-length heavy chain amino acid sequences;
      muCD37-57 antibody

<400> SEQUENCE: 103

Asp Val Gln Leu Gln Glu Ser Gly Pro Asp Leu Leu Lys Pro Ser Gln
1               5                   10                  15

Ser Leu Ser Leu Thr Cys Thr Val Thr Gly Tyr Ser Ile Thr Ser Gly
            20                  25                  30

Phe Ala Trp His Trp Ile Arg Gln Phe Pro Gly Asn Lys Leu Glu Trp
        35                  40                  45

Met Gly Tyr Ile Leu Tyr Ser Gly Ser Thr Val Tyr Ser Pro Ser Leu
    50                  55                  60

Lys Ser Arg Ile Ser Ile Thr Arg Asp Thr Ser Lys Asn Gln Phe Phe
65                  70                  75                  80

Leu Gln Leu Asn Ser Val Thr Thr Glu Asp Thr Ala Thr Tyr Tyr Cys
                85                  90                  95

Ala Arg Gly Tyr Tyr Gly Tyr Gly Ala Trp Phe Ala Tyr Trp Gly Gln
```

-continued

```
            100                 105                 110

Gly Thr Leu Val Thr Val Ser Ala Ala Lys Thr Thr Ala Pro Ser Val
        115                 120                 125

Tyr Pro Leu Ala Pro Val Cys Gly Asp Thr Thr Gly Ser Ser Val Thr
    130                 135                 140

Leu Gly Cys Leu Val Lys Gly Tyr Phe Pro Glu Pro Val Thr Leu Thr
145                 150                 155                 160

Trp Asn Ser Gly Ser Leu Ser Ser Gly Val His Thr Phe Pro Ala Val
                165                 170                 175

Leu Gln Ser Asp Leu Tyr Thr Leu Ser Ser Ser Val Thr Val Thr Ser
            180                 185                 190

Ser Thr Trp Pro Ser Gln Ser Ile Thr Cys Asn Val Ala His Pro Ala
        195                 200                 205

Ser Ser Thr Lys Val Asp Lys Lys Ile Glu Pro Arg Gly Pro Thr Ile
    210                 215                 220

Lys Pro Cys Pro Pro Cys Lys Cys Pro Ala Pro Asn Leu Leu Gly Gly
225                 230                 235                 240

Pro Ser Val Phe Ile Phe Pro Pro Lys Ile Lys Asp Val Leu Met Ile
                245                 250                 255

Ser Leu Ser Pro Ile Val Thr Cys Val Val Val Asp Val Ser Glu Asp
            260                 265                 270

Asp Pro Asp Val Gln Ile Ser Trp Phe Val Asn Asn Val Glu Val His
        275                 280                 285

Thr Ala Gln Thr Gln Thr His Arg Glu Asp Tyr Asn Ser Thr Leu Arg
    290                 295                 300

Val Val Ser Ala Leu Pro Ile Gln His Gln Asp Trp Met Ser Gly Lys
305                 310                 315                 320

Glu Phe Lys Cys Lys Val Asn Asn Lys Asp Leu Pro Ala Pro Ile Glu
                325                 330                 335

Arg Thr Ile Ser Lys Pro Lys Gly Ser Val Arg Ala Pro Gln Val Tyr
            340                 345                 350

Val Leu Pro Pro Pro Glu Glu Glu Met Thr Lys Lys Gln Val Thr Leu
        355                 360                 365

Thr Cys Met Val Thr Asp Phe Met Pro Glu Asp Ile Tyr Val Glu Trp
    370                 375                 380

Thr Asn Asn Gly Lys Thr Glu Leu Asn Tyr Lys Asn Thr Glu Pro Val
385                 390                 395                 400

Leu Asp Ser Asp Gly Ser Tyr Phe Met Tyr Ser Lys Leu Arg Val Glu
                405                 410                 415

Lys Lys Asn Trp Val Glu Arg Asn Ser Tyr Ser Cys Ser Val Val His
            420                 425                 430

Glu Gly Leu His Asn His His Thr Thr Lys Ser Phe Ser Arg Thr Pro
        435                 440                 445

Gly Lys
    450
```

<210> SEQ ID NO 104
<211> LENGTH: 449
<212> TYPE: PRT
<213> ORGANISM: Artificial Sequence
<220> FEATURE:
<223> OTHER INFORMATION: Full-length heavy chain amino acid sequences; huCD37-57 antibody

<400> SEQUENCE: 104

-continued

```
Gln Val Gln Leu Gln Glu Ser Gly Pro Gly Leu Leu Lys Pro Ser Gln
1               5                   10                  15

Ser Leu Ser Leu Thr Cys Thr Val Ser Gly Tyr Ser Ile Thr Ser Gly
            20                  25                  30

Phe Ala Trp His Trp Ile Arg Gln Phe Pro Gly Lys Gly Leu Glu Trp
        35                  40                  45

Met Gly Tyr Ile Leu Tyr Ser Gly Ser Thr Val Tyr Ser Pro Ser Leu
    50                  55                  60

Lys Ser Arg Ile Ser Ile Thr Arg Asp Thr Ser Lys Asn Gln Phe Phe
65                  70                  75                  80

Leu Gln Leu Asn Ser Val Thr Ala Ala Asp Thr Ala Thr Tyr Tyr Cys
                85                  90                  95

Ala Arg Gly Tyr Tyr Gly Tyr Gly Ala Trp Phe Ala Tyr Trp Gly Gln
            100                 105                 110

Gly Thr Leu Val Thr Val Ser Ala Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
```

```
            420                 425                 430

Glu Ala Leu His Asn His Tyr Thr Gln Lys Ser Leu Ser Leu Ser Pro
        435                 440                 445

Gly
```

<210> SEQ ID NO 105
<211> LENGTH: 214
<212> TYPE: PRT
<213> ORGANISM: Artificial Sequence
<220> FEATURE:
<223> OTHER INFORMATION: Full-length light chain amino acid sequences; muCD37-3 antibody

<400> SEQUENCE: 105

```
Asp Ile Gln Met Thr Gln Ser Pro Ala Ser Leu Ser Val Ser Val Gly
1               5                   10                  15

Glu Thr Val Thr Ile Thr Cys Arg Ala Ser Glu Asn Ile Arg Ser Asn
            20                  25                  30

Leu Ala Trp Tyr Gln Gln Lys Gln Gly Lys Ser Pro Gln Leu Leu Val
        35                  40                  45

Asn Val Ala Thr Asn Leu Ala Asp Gly Val Pro Ser Arg Phe Ser Gly
    50                  55                  60

Ser Gly Ser Gly Thr Gln Tyr Ser Leu Lys Ile Asn Ser Leu Gln Ser
65                  70                  75                  80

Glu Asp Phe Gly Thr Tyr Tyr Cys Gln His Tyr Trp Gly Thr Thr Trp
                85                  90                  95

Thr Phe Gly Gly Gly Thr Lys Leu Glu Ile Lys Arg Ala Asp Ala Ala
            100                 105                 110

Pro Thr Val Ser Ile Phe Pro Pro Ser Ser Glu Gln Leu Thr Ser Gly
        115                 120                 125

Gly Ala Ser Val Val Cys Phe Leu Asn Asn Phe Tyr Pro Lys Asp Ile
    130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
        195                 200                 205

Phe Asn Arg Asn Glu Cys
    210
```

<210> SEQ ID NO 106
<211> LENGTH: 214
<212> TYPE: PRT
<213> ORGANISM: Artificial Sequence
<220> FEATURE:
<223> OTHER INFORMATION: Full-length light chain amino acid sequences; chCD37-3 antibody

<400> SEQUENCE: 106

```
Asp Ile Gln Met Thr Gln Ser Pro Ala Ser Leu Ser Val Ser Val Gly
1               5                   10                  15

Glu Thr Val Thr Ile Thr Cys Arg Ala Ser Glu Asn Ile Arg Ser Asn
            20                  25                  30

Leu Ala Trp Tyr Gln Gln Lys Gln Gly Lys Ser Pro Gln Leu Leu Val
        35                  40                  45
```

```
Asn Val Ala Thr Asn Leu Ala Asp Gly Val Pro Ser Arg Phe Ser Gly
    50                  55                  60

Ser Gly Ser Gly Thr Gln Tyr Ser Leu Lys Ile Asn Ser Leu Gln Ser
65                  70                  75                  80

Glu Asp Phe Gly Thr Tyr Tyr Cys Gln His Tyr Trp Gly Thr Thr Trp
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 107
<211> LENGTH: 214
<212> TYPE: PRT
<213> ORGANISM: Artificial Sequence
<220> FEATURE:
<223> OTHER INFORMATION: Full-length light chain amino acid sequences;
      huCD37-3v1.0 and huCD37-3v1.1 antibody

<400> SEQUENCE: 107

Asp Ile Gln Met Thr Gln Ser Pro Ser Ser Leu Ser Val Ser Val Gly
1               5                   10                  15

Glu Arg Val Thr Ile Thr Cys Arg Ala Ser Glu Asn Ile Arg Ser Asn
            20                  25                  30

Leu Ala Trp Tyr Gln Gln Lys Pro Gly Lys Ser Pro Lys Leu Leu Val
        35                  40                  45

Asn Val Ala Thr Asn Leu Ala Asp Gly Val Pro Ser Arg Phe Ser Gly
    50                  55                  60

Ser Gly Ser Gly Thr Asp Tyr Ser Leu Lys Ile Asn Ser Leu Gln Pro
65                  70                  75                  80

Glu Asp Phe Gly Thr Tyr Tyr Cys Gln His Tyr Trp Gly Thr Thr Trp
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
```

```
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 108
<211> LENGTH: 218
<212> TYPE: PRT
<213> ORGANISM: Artificial Sequence
<220> FEATURE:
<223> OTHER INFORMATION: Full-length light chain amino acid sequences;
      muCD37-12 antibody

<400> SEQUENCE: 108

Asp Ile Val Leu Thr Gln Ser Pro Ala Ser Leu Ala Val Ser Leu Gly
1               5                   10                  15

Gln Arg Ala Thr Ile Ser Cys Arg Ala Ser Gln Ser Val Ser Thr Ser
            20                  25                  30

Ser Tyr Ser Tyr Leu Tyr Trp Phe Gln Gln Lys Pro Gly Gln Pro Pro
        35                  40                  45

Lys Leu Leu Ile Lys Tyr Ala Ser Asn Leu Ala Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Thr Ala Thr Tyr Tyr Cys Gln His Ser Trp
                85                  90                  95

Glu Ile Pro Tyr Thr Phe Gly Gly Gly Thr Lys Leu Glu Ile Lys Arg
            100                 105                 110

Ala Asp Ala Ala Pro Thr Val Ser Ile Phe Pro Pro Ser Ser Glu Gln
        115                 120                 125

Leu Thr Ser Gly Gly Ala Ser Val Val Cys Phe Leu Asn Asn Phe Tyr
    130                 135                 140

Pro Lys Asp Ile Asn Val Lys Trp Lys Ile Asp Gly Ser Glu Arg Gln
145                 150                 155                 160

Asn Gly Val Leu Asn Ser Trp Thr Asp Gln Asp Ser Lys Asp Ser Thr
                165                 170                 175

Tyr Ser Met Ser Ser Thr Leu Thr Leu Thr Lys Asp Glu Tyr Glu Arg
            180                 185                 190

His Asn Ser Tyr Thr Cys Glu Ala Thr His Lys Thr Ser Thr Ser Pro
        195                 200                 205

Ile Val Lys Ser Phe Asn Arg Asn Glu Cys
    210                 215


<210> SEQ ID NO 109
<211> LENGTH: 218
<212> TYPE: PRT
<213> ORGANISM: Artificial Sequence
<220> FEATURE:
<223> OTHER INFORMATION: Full-length light chain amino acid sequences;
      chCD37-12 antibody

<400> SEQUENCE: 109

Asp Ile Val Leu Thr Gln Ser Pro Ala Ser Leu Ala Val Ser Leu Gly
1               5                   10                  15

Gln Arg Ala Thr Ile Ser Cys Arg Ala Ser Gln Ser Val Ser Thr Ser
            20                  25                  30

Ser Tyr Ser Tyr Leu Tyr Trp Phe Gln Gln Lys Pro Gly Gln Pro Pro
```

```
        35                  40                  45

Lys Leu Leu Ile Lys Tyr Ala Ser Asn Leu Ala Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Thr Ala Thr Tyr Tyr Cys Gln His Ser Trp
                85                  90                  95

Glu Ile Pro Tyr Thr Phe Gly Gly Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215


<210> SEQ ID NO 110
<211> LENGTH: 213
<212> TYPE: PRT
<213> ORGANISM: Artificial Sequence
<220> FEATURE:
<223> OTHER INFORMATION: Full-length light chain amino acid sequences;
      muCD37-38 antibody

<400> SEQUENCE: 110

Gln Ile Val Leu Thr Gln Ser Pro Ala Ile Met Ser Ala Ser Pro Gly
1               5                   10                  15

Glu Lys Val Thr Met Thr Cys Ser Ala Ser Ser Ser Val Thr Tyr Met
            20                  25                  30

His Trp Tyr Gln Gln Lys Ser Gly Thr Ser Pro Lys Arg Trp Ile Tyr
        35                  40                  45

Asp Thr Ser Lys Leu Ala Ser Gly Val Pro Ala Arg Phe Ser Gly Gly
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ile Ser Asn Pro Pro Thr
                85                  90                  95

Phe Gly Gly Gly Thr Lys Leu Glu Ile Lys Arg Ala Asp Ala Ala Pro
            100                 105                 110

Thr Val Ser Ile Phe Pro Pro Ser Ser Glu Gln Leu Thr Ser Gly Gly
        115                 120                 125

Ala Ser Val Val Cys Phe Leu Asn Asn Phe Tyr Pro Lys Asp Ile Asn
    130                 135                 140

Val Lys Trp Lys Ile Asp Gly Ser Glu Arg Gln Asn Gly Val Leu Asn
145                 150                 155                 160

Ser Trp Thr Asp Gln Asp Ser Lys Asp Ser Thr Tyr Ser Met Ser Ser
                165                 170                 175
```

```
Thr Leu Thr Leu Thr Lys Asp Glu Tyr Glu Arg His Asn Ser Tyr Thr
            180                 185                 190

Cys Glu Ala Thr His Lys Thr Ser Thr Ser Pro Ile Val Lys Ser Phe
        195                 200                 205

Asn Arg Asn Glu Cys
    210


<210> SEQ ID NO 111
<211> LENGTH: 213
<212> TYPE: PRT
<213> ORGANISM: Artificial Sequence
<220> FEATURE:
<223> OTHER INFORMATION: Full-length light chain amino acid sequences;
      chCD37-38 antibody

<400> SEQUENCE: 111

Gln Ile Val Leu Thr Gln Ser Pro Ala Ile Met Ser Ala Ser Pro Gly
1               5                   10                  15

Glu Lys Val Thr Met Thr Cys Ser Ala Ser Ser Ser Val Thr Tyr Met
            20                  25                  30

His Trp Tyr Gln Gln Lys Ser Gly Thr Ser Pro Lys Arg Trp Ile Tyr
        35                  40                  45

Asp Thr Ser Lys Leu Ala Ser Gly Val Pro Ala Arg Phe Ser Gly Gly
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ile Ser Asn Pro Pro Thr
                85                  90                  95

Phe Gly Gly Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210


<210> SEQ ID NO 112
<211> LENGTH: 213
<212> TYPE: PRT
<213> ORGANISM: Artificial Sequence
<220> FEATURE:
<223> OTHER INFORMATION: Full-length light chain amino acid sequences;
      huCD37-38 antibody

<400> SEQUENCE: 112

Asp Ile Val Leu Thr Gln Ser Pro Ala Ser Met Ser Ala Ser Pro Gly
1               5                   10                  15

Glu Arg Val Thr Met Thr Cys Ser Ala Ser Ser Ser Val Thr Tyr Met
            20                  25                  30
```

```
His Trp Tyr Gln Gln Lys Pro Gly Thr Ser Pro Lys Arg Trp Ile Tyr
        35                  40                  45

Asp Thr Ser Lys Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ile Ser Asn Pro Pro Thr
                85                  90                  95

Phe Gly Gly Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210


<210> SEQ ID NO 113
<211> LENGTH: 213
<212> TYPE: PRT
<213> ORGANISM: Artificial Sequence
<220> FEATURE:
<223> OTHER INFORMATION: Full-length light chain amino acid sequences;
      muCD37-50 antibody

<400> SEQUENCE: 113

Gln Ile Val Leu Thr Gln Ser Pro Ala Ile Met Ser Ala Ser Pro Gly
1               5                   10                  15

Glu Lys Val Thr Met Thr Cys Ser Ala Thr Ser Ser Val Thr Tyr Met
            20                  25                  30

His Trp Tyr Gln Gln Lys Ser Gly Thr Ser Pro Lys Arg Trp Ile Tyr
        35                  40                  45

Asp Thr Ser Lys Leu Pro Tyr Gly Val Pro Gly Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Asp Asn Pro Pro Thr
                85                  90                  95

Phe Gly Ser Gly Thr Lys Leu Glu Ile Lys Arg Ala Asp Ala Ala Pro
            100                 105                 110

Thr Val Ser Ile Phe Pro Pro Ser Ser Glu Gln Leu Thr Ser Gly Gly
        115                 120                 125

Ala Ser Val Val Cys Phe Leu Asn Asn Phe Tyr Pro Lys Asp Ile Asn
    130                 135                 140

Val Lys Trp Lys Ile Asp Gly Ser Glu Arg Gln Asn Gly Val Leu Asn
145                 150                 155                 160

Ser Trp Thr Asp Gln Asp Ser Lys Asp Ser Thr Tyr Ser Met Ser Ser
                165                 170                 175
```

```
Thr Leu Thr Leu Thr Lys Asp Glu Tyr Glu Arg His Asn Ser Tyr Thr
            180                 185                 190

Cys Glu Ala Thr His Lys Thr Ser Thr Ser Pro Ile Val Lys Ser Phe
        195                 200                 205

Asn Arg Asn Glu Cys
    210


<210> SEQ ID NO 114
<211> LENGTH: 213
<212> TYPE: PRT
<213> ORGANISM: Artificial Sequence
<220> FEATURE:
<223> OTHER INFORMATION: Full-length light chain amino acid sequences;
      huCD37-50 antibody

<400> SEQUENCE: 114

Glu Ile Val Leu Thr Gln Ser Pro Ala Thr Met Ser Ala Ser Pro Gly
1               5                   10                  15

Glu Arg Val Thr Met Thr Cys Ser Ala Thr Ser Ser Val Thr Tyr Met
            20                  25                  30

His Trp Tyr Gln Gln Lys Pro Gly Gln Ser Pro Lys Arg Trp Ile Tyr
        35                  40                  45

Asp Thr Ser Asn Leu Pro Tyr Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Asp Asn Pro Pro Thr
                85                  90                  95

Phe Gly Gln Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210


<210> SEQ ID NO 115
<211> LENGTH: 213
<212> TYPE: PRT
<213> ORGANISM: Artificial Sequence
<220> FEATURE:
<223> OTHER INFORMATION: Full-length light chain amino acid sequences;
      muCD37-51 antibody

<400> SEQUENCE: 115

Gln Ile Val Leu Thr Gln Ser Pro Ala Ile Met Ser Ala Ser Pro Gly
1               5                   10                  15

Glu Lys Val Thr Met Thr Cys Ser Ala Thr Ser Ser Val Thr Tyr Met
            20                  25                  30
```

```
His Trp Tyr Gln Gln Lys Ser Gly Thr Ser Pro Lys Arg Trp Ile Tyr
        35                  40                  45

Asp Thr Ser Lys Leu Ala Ser Gly Val Pro Ala Arg Phe Ser Gly Ser
    50                  55                  60

Gly Ser Gly Thr Ser Tyr Ser Leu Thr Ile Ser Asn Met Glu Ala Glu
65                  70                  75                  80

Asp Ala Ala Thr Tyr Tyr Cys Gln Gln Trp Ser Ser Asn Pro Pro Thr
                85                  90                  95

Phe Gly Ser Gly Thr Lys Leu Glu Ile Lys Arg Ala Asp Ala Ala Pro
            100                 105                 110

Thr Val Ser Ile Phe Pro Pro Ser Ser Glu Gln Leu Thr Ser Gly Gly
        115                 120                 125

Ala Ser Val Val Cys Phe Leu Asn Asn Phe Tyr Pro Lys Asp Ile Asn
    130                 135                 140

Val Lys Trp Lys Ile Asp Gly Ser Glu Arg Gln Asn Gly Val Leu Asn
145                 150                 155                 160

Ser Trp Thr Asp Gln Asp Ser Lys Asp Ser Thr Tyr Ser Met Ser Ser
                165                 170                 175

Thr Leu Thr Leu Thr Lys Asp Glu Tyr Glu Arg His Asn Ser Tyr Thr
            180                 185                 190

Cys Glu Ala Thr His Lys Thr Ser Thr Ser Pro Ile Val Lys Ser Phe
        195                 200                 205

Asn Arg Asn Glu Cys
    210


<210> SEQ ID NO 116
<211> LENGTH: 213
<212> TYPE: PRT
<213> ORGANISM: Artificial Sequence
<220> FEATURE:
<223> OTHER INFORMATION: Full-length light chain amino acid sequences;
      huCD37-51 antibody

<400> SEQUENCE: 116

Glu Ile Val Leu Thr Gln Ser Pro Ala Thr Met Ser Ala Ser Pro Gly
1               5                   10                  15

Glu Arg Val Thr Met Thr Cys Ser Ala Thr Ser Ser Val Thr Tyr Met
            20                  25                  30

His Trp Tyr Gln Gln Lys Pro Gly Gln Ser Pro Lys Arg Trp Ile Tyr
        35                  40                  45

Asp Thr Ser Lys Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Ser Asn Pro Pro Thr
                85                  90                  95

Phe Gly Gln Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
```

```
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210


<210> SEQ ID NO 117
<211> LENGTH: 213
<212> TYPE: PRT
<213> ORGANISM: Artificial Sequence
<220> FEATURE:
<223> OTHER INFORMATION: Full-length light chain amino acid sequences;
      muCD37-56 antibody

<400> SEQUENCE: 117

Gln Ile Val Leu Thr Gln Ser Pro Ala Phe Met Ser Ala Ser Pro Gly
1               5                   10                  15

Asp Lys Val Thr Met Thr Cys Ser Ala Ser Ser Ser Val Thr Tyr Met
            20                  25                  30

His Trp Tyr Gln Gln Lys Ser Gly Thr Ser Pro Lys Arg Trp Ile Tyr
        35                  40                  45

Asp Thr Ser Lys Leu Ala Ser Gly Val Pro Ala Arg Phe Ser Gly Gly
    50                  55                  60

Gly Ser Gly Thr Ser Tyr Ser Leu Thr Ile Ser Thr Met Glu Ala Glu
65                  70                  75                  80

Asp Ala Ala Thr Tyr Tyr Cys Gln Gln Trp Ile Ser Asp Pro Pro Thr
                85                  90                  95

Phe Gly Gly Gly Thr Lys Leu Glu Ile Lys Arg Ala Asp Ala Ala Pro
            100                 105                 110

Thr Val Ser Ile Phe Pro Pro Ser Ser Glu Gln Leu Thr Ser Gly Gly
        115                 120                 125

Ala Ser Val Val Cys Phe Leu Asn Asn Phe Tyr Pro Lys Asp Ile Asn
    130                 135                 140

Val Lys Trp Lys Ile Asp Gly Ser Glu Arg Gln Asn Gly Val Leu Asn
145                 150                 155                 160

Ser Trp Thr Asp Gln Asp Ser Lys Asp Ser Thr Tyr Ser Met Ser Ser
                165                 170                 175

Thr Leu Thr Leu Thr Lys Asp Glu Tyr Glu Arg His Asn Ser Tyr Thr
            180                 185                 190

Cys Glu Ala Thr His Lys Thr Ser Thr Ser Pro Ile Val Lys Ser Phe
        195                 200                 205

Asn Arg Asn Glu Cys
    210


<210> SEQ ID NO 118
<211> LENGTH: 213
<212> TYPE: PRT
<213> ORGANISM: Artificial Sequence
<220> FEATURE:
<223> OTHER INFORMATION: Full-length light chain amino acid sequences;
      huCD37-56 antibody

<400> SEQUENCE: 118

Asp Ile Val Leu Thr Gln Ser Pro Ala Phe Met Ser Ala Ser Pro Gly
1               5                   10                  15

Glu Lys Val Thr Met Thr Cys Ser Ala Ser Ser Ser Val Thr Tyr Met
```

```
            20                  25                  30

His Trp Tyr Gln Gln Lys Pro Asp Gln Ser Pro Lys Arg Trp Ile Tyr
        35                  40                  45

Asp Thr Ser Asn Leu Ala Ser Gly Val Pro Ser Arg Phe Ser Gly Gly
    50                  55                  60

Gly Ser Gly Thr Asp Tyr Ser Leu Thr Ile Ser Ser Met Glu Ala Glu
65                  70                  75                  80

Asp Ala Ala Thr Tyr Tyr Cys Gln Gln Trp Ile Ser Asp Pro Pro Thr
                85                  90                  95

Phe Gly Gln Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210


<210> SEQ ID NO 119
<211> LENGTH: 213
<212> TYPE: PRT
<213> ORGANISM: Artificial Sequence
<220> FEATURE:
<223> OTHER INFORMATION: Full-length light chain amino acid sequences;
      muCD37-57 antibody

<400> SEQUENCE: 119

Gln Ile Val Leu Thr Gln Ser Pro Ala Ile Met Ser Ala Ser Pro Gly
1               5                   10                  15

Glu Lys Val Thr Met Thr Cys Ser Ala Thr Ser Ser Val Thr Tyr Met
            20                  25                  30

His Trp Tyr Gln Gln Lys Ser Gly Thr Ser Pro Lys Arg Trp Ile Tyr
        35                  40                  45

Asp Thr Ser Lys Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Asp Asn Pro Pro Thr
                85                  90                  95

Phe Gly Ser Gly Thr Lys Leu Glu Ile Lys Arg Ala Asp Ala Ala Pro
            100                 105                 110

Thr Val Ser Ile Phe Pro Pro Ser Ser Glu Gln Leu Thr Ser Gly Gly
        115                 120                 125

Ala Ser Val Val Cys Phe Leu Asn Asn Phe Tyr Pro Lys Asp Ile Asn
    130                 135                 140

Val Lys Trp Lys Ile Asp Gly Ser Glu Arg Gln Asn Gly Val Leu Asn
145                 150                 155                 160
```

Ser Trp Thr Asp Gln Asp Ser Lys Asp Ser Thr Tyr Ser Met Ser Ser
165 170 175

Thr Leu Thr Leu Thr Lys Asp Glu Tyr Glu Arg His Asn Ser Tyr Thr
180 185 190

Cys Glu Ala Thr His Lys Thr Ser Thr Ser Pro Ile Val Lys Ser Phe
195 200 205

Asn Arg Asn Glu Cys
210

<210> SEQ ID NO 120
<211> LENGTH: 213
<212> TYPE: PRT
<213> ORGANISM: Artificial Sequence
<220> FEATURE:
<223> OTHER INFORMATION: Full-length light chain amino acid sequences; huCD37-57 antibody

<400> SEQUENCE: 120

Glu Ile Val Leu Thr Gln Ser Pro Ala Thr Met Ser Ala Ser Pro Gly
1 5 10 15

Glu Arg Val Thr Met Thr Cys Ser Ala Thr Ser Ser Val Thr Tyr Met
20 25 30

His Trp Tyr Gln Gln Lys Pro Gly Gln Ser Pro Arg Arg Trp Ile Tyr
35 40 45

Asp Thr Ser Asn Leu Ala Ser Gly Val Pro Ala Arg Phe Ser Gly Ser
50 55 60

Gly Ser Gly Thr Ser Tyr Ser Leu Thr Ile Ser Ser Met Glu Ala Glu
65 70 75 80

Asp Ala Ala Thr Tyr Tyr Cys Gln Gln Trp Ser Asp Asn Pro Pro Thr
85 90 95

Phe Gly Gln Gly Thr Lys Leu Glu Ile Lys Arg Thr Val Ala Ala Pro
100 105 110

Ser Val Phe Ile Phe Pro Pro Ser Asp Glu Gln Leu Lys Ser Gly Thr
115 120 125

Ala Ser Val Val Cys Leu Leu Asn Asn Phe Tyr Pro Arg Glu Ala Lys
130 135 140

Val Gln Trp Lys Val Asp Asn Ala Leu Gln Ser Gly Asn Ser Gln Glu
145 150 155 160

Ser Val Thr Glu Gln Asp Ser Lys Asp Ser Thr Tyr Ser Leu Ser Ser
165 170 175

Thr Leu Thr Leu Ser Lys Ala Asp Tyr Glu Lys His Lys Val Tyr Ala
180 185 190

Cys Glu Val Thr His Gln Gly Leu Ser Ser Pro Val Thr Lys Ser Phe
195 200 205

Asn Arg Gly Glu Cys
210

<210> SEQ ID NO 121
<211> LENGTH: 345
<212> TYPE: DNA
<213> ORGANISM: Artificial Sequence
<220> FEATURE:
<223> OTHER INFORMATION: Variable heavy chain polynucleotide sequences; muCD37-3 antibody

<400> SEQUENCE: 121
caggtgcagg tgaaggagtc aggacctggc ctggtggcgc cctcacagag cctgtccatt 60
acatgcactg tctcagggtt ctcattaacc acctctggtg taagctgggt tcgccagcct 120
ccaggaaagg gtctggagtg gctgggagta atatggggtg acgggagcac aaactatcat 180
tcagctctca aatccagact gagcatcaag aaggatcact ccaagagcca agttttctta 240
aaactgaaca gtctgcaaac tgatgacaca gccacgtact actgtgccaa aggaggctac 300
tcgttggctc actggggcca agggactctg gtcacagtct ctgca 345

<210> SEQ ID NO 122
<211> LENGTH: 431
<212> TYPE: DNA
<213> ORGANISM: Artificial Sequence
<220> FEATURE:
<223> OTHER INFORMATION: Variable heavy chain polynucleotide sequences;
chCD37-3 antibody

<400> SEQUENCE: 122
aagcttgcca ccatggctgt cctggcactg ctcctctgcc tggtgacata cccaagctgt 60
gtcctatcac aggtgcaggt gaaggagtca ggacctggcc tggtggcgcc ctcacagagc 120
ctgtccatta catgcactgt ctcagggttc tcattaacca cctctggtgt aagctgggtt 180
cgccagcctc caggaaaggg tctggagtgg ctgggagtaa tatggggtga cgggagcaca 240
aactatcatt cagctctcaa atccagactg agcatcaaga aggatcactc caagagccaa 300
gttttcttaa aactgaacag tctgcaaact gatgacacag ccacgtacta ctgtgccaaa 360
ggaggctact cgttggctca ctggggccaa gggactctgg tcacagtctc tgcagcctct 420
acgaagggcc c 431

<210> SEQ ID NO 123
<211> LENGTH: 431
<212> TYPE: DNA
<213> ORGANISM: Artificial Sequence
<220> FEATURE:
<223> OTHER INFORMATION: Variable heavy chain polynucleotide sequences;
huCD37-3v1.0 antibody

<400> SEQUENCE: 123
aagcttgcca ccatgggttg gagctgcatt attctgtttc tggtggccac cgccaccggt 60
gtgcactcac aagtccaagt ccaagaatct ggtccaggtc tggtggcccc ttcccaaact 120
ctgagcatca cctgtaccgt ttctggtttt agccttacca cctctggtgt gagttgggta 180
cgccaaccac ccggtaaggg tctcgaatgg ctgggtgtaa tctggggtga tggttccaca 240
aattaccatc cttccctcaa gtcccgcctt agcatcaaaa aggatcacag caaaagtcaa 300
gttttcctga aactgaatag tctgacagca gccgatacag ccacctacta ttgcgccaag 360
ggtggttata gtcttgcaca ctggggtcaa ggtaccctcg ttaccgtctc ctcagctagt 420
accaagggcc c 431

<210> SEQ ID NO 124
<211> LENGTH: 431
<212> TYPE: DNA
<213> ORGANISM: Artificial Sequence
<220> FEATURE:
<223> OTHER INFORMATION: Variable heavy chain polynucleotide sequences;
huCD37-3v1.1 antibody

<400> SEQUENCE: 124
aagcttgcca ccatgggctg gagctgtatc attctgtttc tggtggcgac agctactggg 60
gtccactccc aagtgcaggt acaagagtcc gggcctggat tggtcgcacc aagccagacc 120
ctctctatca cttgtaccgt tagcgggttc tctctgacaa ccagtggagt gagttgggtg 180
aggcagccac caggaaaggg actggagtgg ctgggggtga tttggggcga cggcagcaca 240
aactatcatt ccagtcttaa atctcggttg tccattaaaa aagaccatag taaatctcaa 300
gttttcctga aactcaatag cctgacagcc gcagacactg ctacgtatta ctgcgccaaa 360
ggaggataca gtctggctca ctggggacag ggaccctgg tgaccgtgtc atccgcatca 420
acaaagggcc c 431

<210> SEQ ID NO 125
<211> LENGTH: 345
<212> TYPE: DNA
<213> ORGANISM: Artificial Sequence
<220> FEATURE:
<223> OTHER INFORMATION: Variable heavy chain polynucleotide sequences; muCD37-12 antibody

<400> SEQUENCE: 125
cagatccagt tggtgcagtc tggacctgag ctgaagaagc ctggagagac agtcaagatc 60
tcctgcaagg cttctgggta taccttcaca aagtatggaa tgaactgggt gaagcaggct 120
caaggaaagg gtttaaagtg gatgggctgg ataaacacca acactggaga gtcaagaaat 180
gctgaagaat tcaagggacg gtttgccttc tctttggaaa cctctgccag cactgcctat 240
ttgcagatca acaacctcaa atatgaggac acggctacat atttctgtgg aaggggcacg 300
gtagtagcgg actggggcca aggcaccact ctcacagtct cctca 345

<210> SEQ ID NO 126
<211> LENGTH: 431
<212> TYPE: DNA
<213> ORGANISM: Artificial Sequence
<220> FEATURE:
<223> OTHER INFORMATION: Variable heavy chain polynucleotide sequences; chCD37-12 antibody

<400> SEQUENCE: 126
aagcttgcca ccatggggtg gtcatgcata atcctctttc tggtcgctac tgctaccggt 60
gtgcactcac agattcagct ggttcaaagt ggcccagagc tgaaaaagcc aggggaaaca 120
gtgaaaataa gttgcaaggc atccggttac actttcacaa agtacggcat gaactgggtc 180
aagcaggccc agggcaaggg gctcaaatgg atgggttgga tcaataccaa cactggcgag 240
tctaggaatg ctgaggagtt taagggccgg tttgccttca gcctggagac aagtgccagc 300
acagcttacc tgcaaatcaa caatctgaag tatgaggata cagcaaccta tttctgcggc 360
cgcggcactg tcgttgcaga ctggggacaa ggtaccacct tgactgtatc cagtgccagc 420
actaagggcc c 431

<210> SEQ ID NO 127
<211> LENGTH: 360
<212> TYPE: DNA
<213> ORGANISM: Artificial Sequence
<220> FEATURE:
<223> OTHER INFORMATION: Variable heavy chain polynucleotide sequences; muCD37-38 antibody

<400> SEQUENCE: 127
gatgtgcagc ttcaggagtc aggacctgac ctggtgaaac cttctcagtc actttcactc 60
acctgcactg tcactggcta ctccatcacc agtggttttg gctggcactg gatccggcag 120
tttccaggaa acaagctgga atggatggcc tacatactct acagtggtgg cactgactac 180
aacccatctc tcaaaagtcg aatctctatc actcgagaca cttccaagaa ccagttcttc 240
ctgcggttga gttctgtgac tactgaggac acagccacat attactgtgc aagaggctac 300
tatggttacg gggcctggtt tgtttactgg ggccaaggga ctctggtcac tgtctctgca 360

<210> SEQ ID NO 128
<211> LENGTH: 446
<212> TYPE: DNA
<213> ORGANISM: Artificial Sequence
<220> FEATURE:
<223> OTHER INFORMATION: Variable heavy chain polynucleotide sequences; chCD37-38 antibody

<400> SEQUENCE: 128
aagcttgcca ccatgggctg gagttgtatc attctgtttt tggtggccac cgccactgga 60
gtccattccc aagtgcaact ccaggaatct ggccctgacc tggttaagcc atctcagagc 120
ctctccctga cctgcactgt tacaggatac tcaatcacat caggctttgg ctggcactgg 180
atcagacaat ttcccgggaa caagttggaa tggatggctt acattctgta tagcgggggt 240
accgattaca atccttccct caagagccga atctctatca ccagggatac aagcaagaac 300 caatttttc tccgcctcag ctctgtgact accgaagata ccgctactta ctattgtgcc 360
aggggctact atggatatgg tgcatggttc gtctattggg gccagggaac cctggtgact 420
gtgagcgctg cctctaccaa gggccc 446

<210> SEQ ID NO 129
<211> LENGTH: 446
<212> TYPE: DNA
<213> ORGANISM: Artificial Sequence
<220> FEATURE:
<223> OTHER INFORMATION: Variable heavy chain polynucleotide sequences; huCD37-38 antibody

<400> SEQUENCE: 129
aagcttgcca ccatgggttg gagctgcatc attcttttcc tggtcgctac tgcaactgga 60
gtccactcac aggtccagct gcaagagtcc ggtcctgggc ttgtgaaacc cagccagtcc 120
ctcagtctca cctgtactgt ctctggctac tctattacca gtgggttcgg ctggcattgg 180
attaggcagt ttcccggtaa ggggctggag tggatggcat atatcctgta cagcggagga 240
accgattaca acccaagtct gaagagcagg atcagcatta cccgggacac aagcaaaaac 300
cagtttttcc ttcggctgtc tagtgttaca gctgcagaca ccgctactta ctattgtgct 360
cggggttact atggctatgg ggcttggttt gtgtattggg gacaaggcac tcttgtgacc 420
gtgagcagcg cctcaacaaa gggccc 446

<210> SEQ ID NO 130
<211> LENGTH: 360
<212> TYPE: DNA
<213> ORGANISM: Artificial Sequence
<220> FEATURE:
<223> OTHER INFORMATION: Variable heavy chain polynucleotide sequences; muCD37-50 antibody

<400> SEQUENCE: 130
gatgtgcagc ttcaggagtc aggacctgac ctgttgaaac cttctcagtc actttcactc 60
acctgcactg tcactggcta ctccatcacc agtggtttg cctggcactg gatccggcag 120
tttccaggaa acaaactgga atggatgggc tacatactct acagtggtag cactgtctac 180
agcccatctc tcaaaagtcg aatctctatc actcgagaca catccaagaa ccacttcttc 240
ctgcagttga attctgtgac tactgaggac acagccacat attactgtgc aagagggtac 300
tatggttacg gcgcctggtt tgcttactgg ggccaaggga ctctggtcac tgtctctgca 360

<210> SEQ ID NO 131
<211> LENGTH: 360
<212> TYPE: DNA
<213> ORGANISM: Artificial Sequence
<220> FEATURE:
<223> OTHER INFORMATION: Variable heavy chain polynucleotide sequences; muCD37-51 antibody

<400> SEQUENCE: 131
gatgtgcagc ttcaggagtc aggacctgac ctgttgaaac cttctcagtc actttcactc 60
acctgcactg tcactggcta ctccatctcc agtggttttg cctggcactg gatccggcag 120
tttccaggaa acaaactgga atggatgggc tacatacact acagtggtag cactaactac 180
agcccatctc tcaaaagtcg aatctctatc actcgagact catccaagaa ccagttcttc 240
ctgcagttga attctgtgac tactgaggac acagccacat attactgtgc aagaggatac 300
tatggtttcg gcgcctggtt tgtttactgg ggccaaggga ctctggtcac tgtctctgca 360

<210> SEQ ID NO 132
<211> LENGTH: 360
<212> TYPE: DNA
<213> ORGANISM: Artificial Sequence
<220> FEATURE:
<223> OTHER INFORMATION: Variable heavy chain polynucleotide sequences; muCD37-56 antibody

<400> SEQUENCE: 132
gatgtgcagc ttcaggagtc aggacctgac ctggtgaaac cttctcagtc actttcactc 60
acctgcactg tcactggcta ctccatcacc agtggttttg cctggcactg gatccggcag 120
tttccaggaa acaaactgga atggatgggc tacatacact acagtggtgg cactaactac 180
aacccatctc tcaaaagtcg agtctctatc actcgagaca catccaagaa ccagttcttc 240
ctgcagttga attctgtgac tactgaggac acagccacat attactgtgc aagaggctac 300
tatggtttcg gggcctggtt tgcttactgg ggccaaggga ctctggtccc tgtctctgca 360

<210> SEQ ID NO 133
<211> LENGTH: 446
<212> TYPE: DNA
<213> ORGANISM: Artificial Sequence
<220> FEATURE:
<223> OTHER INFORMATION: Variable heavy chain polynucleotide sequences; huCD37-56 antibody

<400> SEQUENCE: 133
aagcttgcca ccatggggtg gagctgcatt atcctgttcc tcgtcgccac cgcaaccggc 60
gtccactccc aggtgcagct gcaagaaagc gggccaggat tggtaaaacc ttcccagtct 120
ctgagtctta cttgtaccgt atctggatac agtatcacat ctggcttcgc ctggcattgg 180
attcgccagt ttcccggcaa ggggcttgag tggatggggt atattcatta ttctggaggt 240
accaactaca acccttccct gaagagtcga gtctcaatta ccagggacac ttccaagaac 300
caattctttt tgcagcttaa ttcagtgacc gctgccgaca ccgctactta ctactgcgcc 360
cggggctact atgggtttgg tgcctggttc gcctactggg gccaggggac cctggtgccc 420
gtgtctgctg cctccacaaa gggccc 446

<210> SEQ ID NO 134
<211> LENGTH: 360

-continued

<212> TYPE: DNA
<213> ORGANISM: Artificial Sequence
<220> FEATURE:
<223> OTHER INFORMATION: Variable heavy chain polynucleotide sequences; muCD37-57 antibody

<400> SEQUENCE: 134
gatgtgcagc ttcaggagtc aggacctgac ctgttgaaac cttctcagtc actttcactc 60
acctgcactg tcactggcta ctccatcacc agtggttttg cctggcactg gatccggcag 120
tttccaggaa acaaactgga atggatgggc tacatactct acagtggtag cactgtctac 180
agcccatctc tcaaaagtcg aatctctatc actcgagaca catccaagaa ccagttcttc 240
ctgcagttga attctgtgac tactgaggac acagccacat attactgtgc aagagggtac 300
tatggttacg gcgcctggtt tgcttactgg ggccaaggga ctctggtcac tgtctctgca 360

<210> SEQ ID NO 135
<211> LENGTH: 446
<212> TYPE: DNA
<213> ORGANISM: Artificial Sequence
<220> FEATURE:
<223> OTHER INFORMATION: Variable heavy chain polynucleotide sequences; huCD37-57 antibody

<400> SEQUENCE: 135
aagcttgcca ccatgggctg gagctgcatc attctgtttc tggtggccac agcaactggc 60
gttcacagtc aagtccaact gcaggagagc ggccccggac tcctgaaacc atctcagtca 120
ctcagtctga catgtactgt gagcggctac agcattacct caggcttcgc ttggcattgg 180
atcaggcagt tccccggaaa aggtctggag tggatggggt acattctgta cagcggcagt 240
acagtgtatt caccctcctt gaaatctagg atatcaatca cacgtgatac aagcaaaaat 300
cagttcttcc tccagctgaa ctccgtcacc gccgcagaca cagcaaccta ttattgtgct 360
cgcggatact acggatatgg cgcatggttc gcctattggg gccaggggac actcgtgacc 420
gtttccgccg cctccacaaa gggccc 446

<210> SEQ ID NO 136
<211> LENGTH: 324
<212> TYPE: DNA
<213> ORGANISM: Artificial Sequence
<220> FEATURE:
<223> OTHER INFORMATION: Variable light chain polynucleotide sequences; muCD37-3 antibody

<400> SEQUENCE: 136
gacatccaga tgactcagtc tccagcctcc ctttctgtat ctgtgggaga aactgtcacc 60
atcacatgtc gagcaagtga gaatattcgc agtaatttag catggtatca gcagaaacag 120
ggaaaatctc ctcagctcct ggtcaatgtt gcaacaaact tagcagatgg tgtgccatca 180
aggttcagtg gcagtggatc aggcacacag tattccctca agatcaacag cctgcagtct 240
gaagattttg ggacttatta ctgtcaacat tattggggta ctacgtggac gttcggtgga 300
ggcaccaagc tggaaatcaa acgt 324

<210> SEQ ID NO 137
<211> LENGTH: 399
<212> TYPE: DNA
<213> ORGANISM: Artificial Sequence
<220> FEATURE:
<223> OTHER INFORMATION: Variable light chain polynucleotide sequences; chCD37-3 antibody

<400> SEQUENCE: 137

```
gaattcgcca ccatgagtgt gcccactcag gtcctggggt tgctgctgct gtggcttaca     60

gatgccagat gtgacatcca gatgactcag tctccagcct ccctttctgt atctgtggga    120

gaaactgtca ccatcacatg tcgagcaagt gagaatattc gcagtaattt agcatggtat    180

cagcagaaac agggaaaatc tcctcagctc ctggtcaatg ttgcaacaaa cttagcagat    240

ggtgtgccat caaggttcag tggcagtgga tcaggcacac agtattccct caagatcaac    300

agcctgcagt ctgaagattt tgggacttat tactgtcaac attattgggg tactacgtgg    360

acgttcggtg gaggcaccaa gctggaaatc aaacgtacg                           399
```

<210> SEQ ID NO 138
<211> LENGTH: 396
<212> TYPE: DNA
<213> ORGANISM: Artificial Sequence
<220> FEATURE:
<223> OTHER INFORMATION: Variable light chain polynucleotide sequences; huCD37-3v1.0 and huCD37-3v1.1 antibody

<400> SEQUENCE: 138

```
gaattcgcca ccatgggttg gtcctgcatc atcttgtttc tcgtggccac agccaccggt     60

gttcactctg atatacaaat gactcaaagc ccttccagtt tgagcgtaag tgtgggtgaa    120

cgcgtaacaa tcacctgtag agctagtgaa aacatccgca gtaatctcgc atggtaccaa    180

caaaagccag gtaagtcacc taagctcctc gtgaatgttg ctaccaacct cgctgatggt    240

gtgccttcac gattctctgg ttcaggttcc ggtaccgatt attcacttaa gatcaactca    300

ctccaaccag aagatttcgg tacatattac tgtcaacact actggggtac gacctggaca    360

ttcggtcaag gtactaagct ggaaatcaag cgtacg                              396
```

<210> SEQ ID NO 139
<211> LENGTH: 336
<212> TYPE: DNA
<213> ORGANISM: Artificial Sequence
<220> FEATURE:
<223> OTHER INFORMATION: Variable light chain polynucleotide sequences; muCD37-12 antibody

<400> SEQUENCE: 139

```
gacattgtgc taacacagtc tcctgcttcc ttagctgtat ctctggggca gagggccacc     60

atctcatgca gggccagcca aagtgtcagt acatctagct atagttattt gtactggttc    120

cagcagaaac caggacagcc acccaaactc ctcatcaagt atgcatccaa cctagcatct    180

ggggtccctg ccaggttcag tggcagtggg tctgggacag acttcaccct caacatccat    240

cctgtggagg aggaggatac tgcaacatat tactgtcaac acagttggga gattccgtac    300

acgttcggag gggggaccaa actggaaata aaacgg                              336
```

<210> SEQ ID NO 140
<211> LENGTH: 408
<212> TYPE: DNA
<213> ORGANISM: Artificial Sequence
<220> FEATURE:
<223> OTHER INFORMATION: Variable light chain polynucleotide sequences; chCD37-12 antibody

<400> SEQUENCE: 140

```
gaattcgcca ccatgggttg gtcctgtata atcctgttct tggtggccac cgctactggc     60

gttcatagtg atattgtact cactcagtca ccagccagtc tggcagtgtc cctgggccag    120
```

-continued

```
cgtgccacca tctcctgccg ggcctcacag tccgtgagca ctagctctta ttcctatctc    180

tactggtttc aacagaagcc aggacagccc cctaagctgc tgatcaagta cgcctccaac    240

ctcgccagcg gcgttcccgc tagattctct ggttccggta gcggaactga tttcactttg    300

aacatccacc ccgttgagga agaggatacc gccacttact attgtcaaca ctcttgggag    360

attccttaca cctttggagg aggaacaaag ctcgaaatta agcgtacg                408


<210> SEQ ID NO 141
<211> LENGTH: 321
<212> TYPE: DNA
<213> ORGANISM: Artificial Sequence
<220> FEATURE:
<223> OTHER INFORMATION: Variable light chain polynucleotide sequences;
      muCD37-38 antibody

<400> SEQUENCE: 141

caaattgttc tcacccagtc tccagcaatc atgtctgcat ctccagggga gaaggtcacc     60

atgacctgca gtgccagctc aagtgtaact tacatgcact ggtaccagca gaagtcaggc    120

acctccccca aaagatggat ttatgacaca tccaaactgg cttctggagt ccctgctcgc    180

ttcagtggcg gtgggtctgg gacctcttac tctctcacaa tcagcagcat ggaggctgaa    240

gatgctgcca cttattactg ccagcagtgg attagtaacc cacccacgtt cggagggggg    300

accaagctgg aaattaaacg g                                              321


<210> SEQ ID NO 142
<211> LENGTH: 393
<212> TYPE: DNA
<213> ORGANISM: Artificial Sequence
<220> FEATURE:
<223> OTHER INFORMATION: Variable light chain polynucleotide sequences;
      chCD37-38 antibody

<400> SEQUENCE: 142

gaattcgcca ccatgggctg gtcctgtatc atcctgtttc tcgtggccac agctacaggt     60

gttcattctc agattgtgct gacccaatca ccagctatta tgtccgctag ccccggcgag    120

aaagtgacaa tgacatgtag cgctagctct tctgtgactt acatgcattg gtatcaacag    180

aagtcaggta ccagtcccaa gcgttggatc tacgacacat ccaaactggc ctccggagtc    240

cctgccaggt tcagcggagg tgggtccggc accagttatt cactgaccat atcctctatg    300

gaagctgaag atgctgctac ttattattgt caacaatgga tttctaaccc ccccaccttt    360

ggtggcggaa caaagctgga gatcaagcgt acg                                393


<210> SEQ ID NO 143
<211> LENGTH: 393
<212> TYPE: DNA
<213> ORGANISM: Artificial Sequence
<220> FEATURE:
<223> OTHER INFORMATION: Variable light chain polynucleotide sequences;
      huCD37-38 antibody

<400> SEQUENCE: 143

gaattcgcca ccatgggatg gtcctgcatt attctgttct tggtcgccac tgctactggc     60

gttcactctg acattgtgct cacacagtct ccagcctcaa tgtctgcttc ccccggtgag    120

cgggtgacca tgacatgctc tgccagttcc tccgtgacat atatgcattg gtatcagcaa    180

aaacccggta cctctccaaa aagatggatc tacgacactt caaagcttgc atcaggcgtt    240

cctgccagat tttccgggtc tgggtctggc acttcataca gtctgaccat tagttccatg    300
```

```
gaagctgaag atgcagccac ctattactgt cagcagtgga tttcaaatcc tcctaccttc    360

ggcggcggaa ccaaactgga gataaagcgt acg                                 393


<210> SEQ ID NO 144
<211> LENGTH: 321
<212> TYPE: DNA
<213> ORGANISM: Artificial Sequence
<220> FEATURE:
<223> OTHER INFORMATION: Variable light chain polynucleotide sequences;
      muCD37-50 antibody

<400> SEQUENCE: 144

caaattgttc tcacccagtc tccagcaatc atgtctgcat ctccagggga gaaggtcacc     60

atgacctgca gtgccacctc aagtgtgact tacatgcact ggtaccagca gaagtcaggc    120

acctccccca aaagatggat ttatgacaca tccaaactgc cttatggagt ccctggtcgt    180

ttcagtggta gtgggtctgg gacctcttac tctctcacaa tcagcagcat ggaggctgaa    240

gatgctgcca cttattactg ccagcagtgg agtgataacc cacccacgtt cggctcgggg    300

acaaagttgg aaataaagcg g                                              321


<210> SEQ ID NO 145
<211> LENGTH: 393
<212> TYPE: DNA
<213> ORGANISM: Artificial Sequence
<220> FEATURE:
<223> OTHER INFORMATION: Variable light chain polynucleotide sequences;
      huCD37-50 antibody

<400> SEQUENCE: 145

gaattcgcca ccatgggttg gtcatgcatt attctgttcc tggttgctac cgcaacagga     60

gtacatagtg agatagtcct cacccaaagt cctgctacta tgtctgccag cccaggagag    120

cgtgtgacca tgacttgctc tgcaacctca agtgtgacat acatgcattg gtatcagcaa    180

aagcctggcc aatcccctaa aaggtggatc tacgatactt ctaatctgcc atacggtgtg    240

cccgcaaggt tctccgggag tggcagtggc accagttata gtctgaccat cagttcaatg    300

gaagcagagg atgcagcaac ctattattgt cagcagtggt ccgataatcc ccctactttt    360

ggtcagggta caaagctgga gattaagcgt acg                                 393


<210> SEQ ID NO 146
<211> LENGTH: 321
<212> TYPE: DNA
<213> ORGANISM: Artificial Sequence
<220> FEATURE:
<223> OTHER INFORMATION: Variable light chain polynucleotide sequences;
      muCD37-51 antibody

<400> SEQUENCE: 146

caaattgttc tcacccagtc tccagcaatc atgtctgcat ctccagggga gaaggtcacc     60

atgacctgca gtgccacctc aagtgtgact tacatgcact ggtaccagca gaagtcaggc    120

acctccccca aaagatggat ttatgacaca tccaaactgg cttctggagt ccctgctcgc    180

ttcagtggca gtgggtctgg gacctcttac tctctcacaa tcagcaacat ggaggctgaa    240

gatgctgcca cttattactg ccagcagtgg agtagtaacc cacccacgtt cggctcgggg    300

acaaagttgg aaataaagcg g                                              321


<210> SEQ ID NO 147
<211> LENGTH: 393
<212> TYPE: DNA
```

<213> ORGANISM: Artificial Sequence
<220> FEATURE:
<223> OTHER INFORMATION: Variable light chain polynucleotide sequences; huCD37-51 antibody

<400> SEQUENCE: 147
gaattcgcca ccatgggatg gagctgtatt attctgttcc tggttgctac tgctactggc 60
gtccattccg agatagtcct cacccagagc cccgcaacca tgagtgcctc ccctggggag 120
cgagtgacta tgacttgttc cgccacttct tcagttacct atatgcattg gtatcagcag 180
aaacctggac agtctccaaa gcgttggatt tacgacacct ccaacctggc ttcaggagtt 240
cctgctaggt tcagcggatc tgggtctggc acaagttatt cactcaccat tagttccatg 300
gaggccgaag atgccgctac ttactactgt cagcagtgga gcagcaaccc ccctacattc 360
gggcagggaa ctaagctgga gatcaaacgt acg 393

<210> SEQ ID NO 148
<211> LENGTH: 321
<212> TYPE: DNA
<213> ORGANISM: Artificial Sequence
<220> FEATURE:
<223> OTHER INFORMATION: Variable light chain polynucleotide sequences; muCD37-56 antibody

<400> SEQUENCE: 148
caaattgttc tcacccagtc tccagcattc atgtctgcat ctccagggga taaggtcacc 60
atgacctgca gtgccagttc aagtgttact tacatgcact ggtatcagca gaagtcaggc 120
acctccccca aaagatggat ttatgacaca tccaaactgg cttctggagt ccctgctcgc 180
ttcagtggcg gtgggtctgg gacctcttac tctctcacaa tcagcaccat ggaggctgaa 240
gatgctgcca cttattactg ccagcagtgg attagtgacc cacccacgtt cggagggggg 300
accaagctgg aaataaaacg g 321

<210> SEQ ID NO 149
<211> LENGTH: 393
<212> TYPE: DNA
<213> ORGANISM: Artificial Sequence
<220> FEATURE:
<223> OTHER INFORMATION: Variable light chain polynucleotide sequences; huCD37-56 antibody

<400> SEQUENCE: 149
gaattcgcca ccatgggctg gtcctgtatc atcctgtttc tggtggcaac cgctactggg 60
gttcactctg atattgtcct gacacagagt ccagccttca tgagtgcttc tcccggagaa 120
aaggtcacaa tgacttgttc agcttcctcc tccgtcacat acatgcattg gtaccagcag 180
aagcctgacc agagtcctaa gaggtggatc tatgatacaa gcaatctggc ttccggtgtc 240
ccctcccgct tttcaggcgg cggaagcgga actgactata gccttaccat ctcctcaatg 300
gaagccgagg acgctgctac atattactgc cagcaatgga tcagcgaccc tcctactttc 360
ggacagggaa caaaattgga aattaagcgt acg 393

<210> SEQ ID NO 150
<211> LENGTH: 321
<212> TYPE: DNA
<213> ORGANISM: Artificial Sequence
<220> FEATURE:
<223> OTHER INFORMATION: Variable light chain polynucleotide sequences; muCD37-57 antibody

<400> SEQUENCE: 150

```
caaattgttc tcacccagtc tccagcaatc atgtctgcat ctccagggga gaaggtcacc     60

atgacctgca gtgccacctc aagtgtgact tacatgcact ggtaccagca gaagtcaggc    120

acctccccca aaagatggat ttatgacaca tccaaactgg cttctggagt ccctgctcgc    180

ttcagtggca gtgggtctgg gacctcttac tctctcacaa tcagcagcat ggaggctgaa    240

gatgctgcca cttattactg ccagcagtgg agtgataacc cacccacgtt cggctcgggg    300

acaaagttgg aaataaagcg g                                              321
```

<210> SEQ ID NO 151
<211> LENGTH: 393
<212> TYPE: DNA
<213> ORGANISM: Artificial Sequence
<220> FEATURE:
<223> OTHER INFORMATION: Variable light chain polynucleotide sequences; huCD37-57 antibody

<400> SEQUENCE: 151

```
gaattcgcca ccatggggtg gtcctgtatt atcctgttcc tggtcgcaac cgccacaggc     60

gttcactccg agatcgtgtt gactcagagc ccagccacca tgtccgcttc ccccggggag    120

agagtgacaa tgacttgttc cgccacaagt tctgtaacct acatgcattg gtaccagcaa    180

aaaccaggac agagtccccg tcgttggatt tatgatacct ctaacctggc ttcaggcgtt    240

cctgcccgct tttctggtag tggatctggg acttcctata gccttaccat aagctctatg    300

gaagccgagg acgccgctac atactactgc cagcagtgga gtgataaccc ccccaccttc    360

gggcagggaa ccaaattgga gatcaaacgt acg                                 393
```

<210> SEQ ID NO 152
<211> LENGTH: 1410
<212> TYPE: DNA
<213> ORGANISM: Artificial Sequence
<220> FEATURE:
<223> OTHER INFORMATION: Full-length heavy chain polynucleotide sequences; chCD37-3 antibody

<400> SEQUENCE: 152

```
aagcttgcca ccatggctgt cctggcactg ctcctctgcc tggtgacata cccaagctgt     60

gtcctatcac aggtgcaggt gaaggagtca ggacctggcc tggtggcgcc ctcacagagc    120

ctgtccatta catgcactgt ctcagggttc tcattaacca cctctggtgt aagctgggtt    180

cgccagcctc caggaaaggg tctggagtgg ctgggagtaa tatggggtga cgggagcaca    240

aactatcatt cagctctcaa atccagactg agcatcaaga aggatcactc caagagccaa    300

gttttcttaa aactgaacag tctgcaaact gatgacacag ccacgtacta ctgtgccaaa    360

ggaggctact cgttggctca ctggggccaa gggactctgg tcacagtctc tgcagcctct    420

acgaagggcc catcagtttt ccccttggct ccaagttcta aatccacaag cggtggaaca    480

gctgcactgg gatgcctcgt taaagattat ttccctgagc ctgtgacagt gagctggaat    540

agcggagcat tgacttcagg tgtgcacact tttcccgctg tgttgcagtc ctccggtctg    600

tactcactgt ccagtgtcgt aaccgtccct tctagcagct tgggaaccca gacctacatc    660

tgtaacgtca accataaacc atccaacaca aaggtggata agaaggttga accaaagagc    720

tgtgataaga cacatacatg ccctccttgt cctgcaccag agctcctcgg aggtccatct    780

gtgttcctgt ttccccccaa acccaaggac actcttatga tctctcgtac tccagaggtc    840

acctgtgttg ttgtcgacgt gagccatgaa gatcccgagg ttaaattcaa ctggtacgtg    900
```

gatggagtcg aggttcacaa tgccaagacc aagcccaggg aggagcaata taattctaca 960
tatcgggtag tgagcgttct gaccgtgctc caccaagatt ggctcaatgg aaaagagtac 1020
aagtgcaagg tgtccaacaa ggctcttccc gctcccattg agaaaactat ctccaaagcc 1080
aaggggcagc cacgggaacc ccaggtgtat acattgcccc catctagaga cgagctgacc 1140
aagaaccagg tgagtctcac ttgtctggtc aaggggtttt acccttctga cattgctgta 1200
gagtgggagt ctaacggaca gccagaaaac aactacaaga caactccccc agtgctggac 1260
agcgacggga gcttcttcct ctactccaag ttgactgtag acaagtctag atggcagcaa 1320
ggaaacgttt tctcctgctc agtaatgcat gaggctctgc acaatcacta tacccagaaa 1380
tcactgtccc ttagcccagg gtgactcgag 1410

<210> SEQ ID NO 153
<211> LENGTH: 1410
<212> TYPE: DNA
<213> ORGANISM: Artificial Sequence
<220> FEATURE:
<223> OTHER INFORMATION: Full-length heavy chain polynucleotide
sequences; huCD37-3v1.0 antibody

<400> SEQUENCE: 153
aagcttgcca ccatgggttg gagctgcatt attctgtttc tggtggccac cgccaccggt 60
gtgcactcac aagtccaagt ccaagaatct ggtccaggtc tggtggcccc ttcccaaact 120
ctgagcatca cctgtaccgt ttctggtttt agccttacca cctctggtgt gagttgggta 180
cgccaaccac ccggtaaggg tctcgaatgg ctgggtgtaa tctggggtga tggttccaca 240
aattaccatc cttccctcaa gtcccgcctt agcatcaaaa aggatcacag caaaagtcaa 300
gttttcctga aactgaatag tctgacagca gccgatacag ccacctacta ttgcgccaag 360
ggtggttata gtcttgcaca ctggggtcaa ggtaccctcg ttaccgtctc ctcagctagt 420
accaagggcc catcagtttt ccccttggct ccaagttcta aatccacaag cggtggaaca 480
gctgcactgg gatgcctcgt taaagattat ttccctgagc ctgtgacagt gagctggaat 540
agcggagcat tgacttcagg tgtgcacact tttcccgctg tgttgcagtc ctccggtctg 600
tactcactgt ccagtgtcgt aaccgtccct tctagcagct tgggaaccca gacctacatc 660
tgtaacgtca accataaacc atccaacaca aaggtggata agaaggttga accaaagagc 720
tgtgataaga cacatacatg ccctccttgt cctgcaccag agctcctcgg aggtccatct 780
gtgttcctgt ttcccccaa acccaaggac actcttatga tctctcgtac tccagaggtc 840
acctgtgttg ttgtcgacgt gagccatgaa gatcccgagg ttaaattcaa ctggtacgtg 900
gatggagtcg aggttcacaa tgccaagacc aagcccaggg aggagcaata taattctaca 960
tatcgggtag tgagcgttct gaccgtgctc caccaagatt ggctcaatgg aaaagagtac 1020
aagtgcaagg tgtccaacaa ggctcttccc gctcccattg agaaaactat ctccaaagcc 1080
aaggggcagc cacgggaacc ccaggtgtat acattgcccc catctagaga cgagctgacc 1140
aagaaccagg tgagtctcac ttgtctggtc aaggggtttt acccttctga cattgctgta 1200
gagtgggagt ctaacggaca gccagaaaac aactacaaga caactccccc agtgctggac 1260
agcgacggga gcttcttcct ctactccaag ttgactgtag acaagtctag atggcagcaa 1320
ggaaacgttt tctcctgctc agtaatgcat gaggctctgc acaatcacta tacccagaaa 1380
tcactgtccc ttagcccagg gtgactcgag 1410

<210> SEQ ID NO 154

<211> LENGTH: 1410
<212> TYPE: DNA
<213> ORGANISM: Artificial Sequence
<220> FEATURE:
<223> OTHER INFORMATION: Full-length heavy chain polynucleotide sequences; huCD37-3v1.1 antibody

<400> SEQUENCE: 154

```
aagcttgcca ccatgggctg gagctgtatc attctgtttc tggtggcgac agctactggg     60
gtccactccc aagtgcaggt acaagagtcc gggcctggat tggtcgcacc aagccagacc    120
ctctctatca cttgtaccgt tagcgggttc tctctgacaa ccagtggagt gagttgggtg    180
aggcagccac caggaaaggg actggagtgg ctgggggtga tttggggcga cggcagcaca    240
aactatcatt ccagtcttaa atctcggttg tccattaaaa aagaccatag taaatctcaa    300
gttttcctga aactcaatag cctgacagcc gcagacactg ctacgtatta ctgcgccaaa    360
ggaggataca gtctggctca ctggggacag ggaccctgg tgaccgtgtc atccgcatca    420
acaaagggcc catcagtttt ccccttggct ccaagttcta aatccacaag cggtggaaca    480
gctgcactgg gatgcctcgt taaagattat ttccctgagc ctgtgacagt gagctggaat    540
agcggagcat tgacttcagg tgtgcacact tttcccgctg tgttgcagtc ctccggtctg    600
tactcactgt ccagtgtcgt aaccgtccct tctagcagct tgggaaccca gacctacatc    660
tgtaacgtca accataaacc atccaacaca aaggtggata agaaggttga accaaagagc    720
tgtgataaga cacatacatg ccctccttgt cctgcaccag agctcctcgg aggtccatct    780
gtgttcctgt ttcccccaa acccaaggac actcttatga tctctcgtac tccagaggtc    840
acctgtgttg ttgtcgacgt gagccatgaa gatcccgagg ttaaattcaa ctggtacgtg    900
gatggagtcg aggttcacaa tgccaagacc aagcccaggg aggagcaata taattctaca    960
tatcgggtag tgagcgttct gaccgtgctc caccaagatt ggctcaatgg aaaagagtac   1020
aagtgcaagg tgtccaacaa ggctcttccc gctcccattg agaaaactat ctccaaagcc   1080
aaggggcagc cacgggaacc ccaggtgtat acattgcccc catctagaga cgagctgacc   1140
aagaaccagg tgagtctcac ttgtctggtc aaggggtttt acccttctga cattgctgta   1200
gagtgggagt ctaacggaca gccagaaaac aactacaaga caactccccc agtgctggac   1260
agcgacggga gcttcttcct ctactccaag ttgactgtag acaagtctag atggcagcaa   1320
ggaaacgttt tctcctgctc agtaatgcat gaggctctgc acaatcacta tacccagaaa   1380
tcactgtccc ttagcccagg gtgactcgag                                    1410
```

<210> SEQ ID NO 155
<211> LENGTH: 1410
<212> TYPE: DNA
<213> ORGANISM: Artificial Sequence
<220> FEATURE:
<223> OTHER INFORMATION: Full-length heavy chain polynucleotide sequences; chCD37-12 antibody

<400> SEQUENCE: 155

```
aagcttgcca ccatggggtg gtcatgcata atcctctttc tggtcgctac tgctaccggt     60
gtgcactcac agattcagct ggttcaaagt ggcccagagc tgaaaaagcc aggggaaaca    120
gtgaaaataa gttgcaaggc atccggttac actttcacaa agtacggcat gaactgggtc    180
aagcaggccc agggcaaggg gctcaaatgg atgggttgga tcaataccaa cactggcgag    240
tctaggaatg ctgaggagtt taagggccgg tttgccttca gcctggagac aagtgccagc    300
acagcttacc tgcaaatcaa caatctgaag tatgaggata cagcaaccta tttctgcggc    360
```

```
cgcggcactg tcgttgcaga ctggggacaa ggtaccacct tgactgtatc cagtgccagc    420
actaagggcc catcagtttt ccccttggct ccaagttcta aatccacaag cggtggaaca    480
gctgcactgg gatgcctcgt taaagattat ttccctgagc ctgtgacagt gagctggaat    540
agcggagcat tgacttcagg tgtgcacact tttcccgctg tgttgcagtc ctccggtctg    600
tactcactgt ccagtgtcgt aaccgtccct tctagcagct tgggaaccca gacctacatc    660
tgtaacgtca accataaacc atccaacaca aaggtggata agaaggttga accaaagagc    720
tgtgataaga cacatacatg ccctccttgt cctgcaccag agctcctcgg aggtccatct    780
gtgttcctgt ttcccccaa acccaaggac actcttatga tctctcgtac tccagaggtc    840
acctgtgttg ttgtcgacgt gagccatgaa gatcccgagg ttaaattcaa ctggtacgtg    900
gatggagtcg aggttcacaa tgccaagacc aagcccaggg aggagcaata taattctaca    960
tatcgggtag tgagcgttct gaccgtgctc caccaagatt ggctcaatgg aaaagagtac   1020
aagtgcaagg tgtccaacaa ggctcttccc gctcccattg agaaaactat ctccaaagcc   1080
aaggggcagc cacgggaacc ccaggtgtat acattgcccc catctagaga cgagctgacc   1140
aagaaccagg tgagtctcac ttgtctggtc aaggggtttt acccttctga cattgctgta   1200
gagtgggagt ctaacggaca gccagaaaac aactacaaga caactccccc agtgctggac   1260
agcgacggga gcttcttcct ctactccaag ttgactgtag acaagtctag atggcagcaa   1320
ggaaacgttt tctcctgctc agtaatgcat gaggctctgc acaatcacta tacccagaaa   1380
tcactgtccc ttagcccagg gtgactcgag                                    1410
```

```
<210> SEQ ID NO 156
<211> LENGTH: 1425
<212> TYPE: DNA
<213> ORGANISM: Artificial Sequence
<220> FEATURE:
<223> OTHER INFORMATION: Full-length heavy chain polynucleotide
      sequences; chCD37-38 antibody

<400> SEQUENCE: 156
```

```
aagcttgcca ccatgggctg gagttgtatc attctgtttt tggtggccac cgccactgga     60
gtccattccc aagtgcaact ccaggaatct ggccctgacc tggttaagcc atctcagagc    120
ctctccctga cctgcactgt tacaggatac tcaatcacat caggctttgg ctggcactgg    180
atcagacaat ttcccgggaa caagttggaa tggatggctt acattctgta tagcgggggt    240
accgattaca atccttccct caagagccga atctctatca ccagggatac aagcaagaac    300
caattttttc tccgcctcag ctctgtgact accgaagata ccgctactta ctattgtgcc    360
aggggctact atggatatgg tgcatggttc gtctattggg gccagggaac cctggtgact    420
gtgagcgctg cctctaccaa gggcccatca gttttcccct tggctccaag ttctaaatcc    480
acaagcggtg gaacagctgc actgggatgc ctcgttaaag attatttccc tgagcctgtg    540
acagtgagct ggaatagcgg agcattgact tcaggtgtgc acacttttcc cgctgtgttg    600
cagtcctccg gtctgtactc actgtccagt gtcgtaaccg tcccttctag cagcttggga    660
acccagacct acatctgtaa cgtcaaccat aaaccatcca acacaaaggt ggataagaag    720
gttgaaccaa agagctgtga taagacacat acatgccctc cttgtcctgc accagagctc    780
ctcggaggtc catctgtgtt cctgtttccc cccaaaccca aggacactct tatgatctct    840
cgtactccag aggtcacctg tgttgttgtc gacgtgagcc atgaagatcc cgaggttaaa    900
ttcaactggt acgtggatgg agtcgaggtt cacaatgcca agaccaagcc cagggaggag    960
```

```
caatataatt ctacatatcg ggtagtgagc gttctgaccg tgctccacca agattggctc   1020

aatggaaaag agtacaagtg caaggtgtcc aacaaggctc ttcccgctcc cattgagaaa   1080

actatctcca aagccaaggg gcagccacgg gaaccccagg tgtatacatt gcccccatct   1140

agagacgagc tgaccaagaa ccaggtgagt ctcacttgtc tggtcaaggg gttttaccct   1200

tctgacattg ctgtagagtg ggagtctaac ggacagccag aaaacaacta caagacaact   1260

cccccagtgc tggacagcga cgggagcttc ttcctctact ccaagttgac tgtagacaag   1320

tctagatggc agcaaggaaa cgttttctcc tgctcagtaa tgcatgaggc tctgcacaat   1380

cactataccc agaaatcact gtcccttagc ccagggtgac tcgag                    1425
```

<210> SEQ ID NO 157
<211> LENGTH: 1425
<212> TYPE: DNA
<213> ORGANISM: Artificial Sequence
<220> FEATURE:
<223> OTHER INFORMATION: Full-length heavy chain polynucleotide sequences; huCD37-38 antibody

<400> SEQUENCE: 157

```
aagcttgcca ccatgggttg gagctgcatc attcttttcc tggtcgctac tgcaactgga     60

gtccactcac aggtccagct gcaagagtcc ggtcctgggc ttgtgaaacc cagccagtcc    120

ctcagtctca cctgtactgt ctctggctac tctattacca gtgggttcgg ctggcattgg    180

attaggcagt ttcccggtaa ggggctggag tggatggcat atatcctgta cagcggagga    240

accgattaca acccaagtct gaagagcagg atcagcatta cccgggacac aagcaaaaac    300

cagtttttcc ttcggctgtc tagtgttaca gctgcagaca ccgctactta ctattgtgct    360

cggggttact atggctatgg ggcttggttt gtgtattggg gacaaggcac tcttgtgacc    420

gtgagcagcg cctcaacaaa gggcccatca gttttcccct tggctccaag ttctaaatcc    480

acaagcggtg gaacagctgc actgggatgc ctcgttaaag attatttccc tgagcctgtg    540

acagtgagct ggaatagcgg agcattgact tcaggtgtgc acacttttcc cgctgtgttg    600

cagtcctccg gtctgtactc actgtccagt gtcgtaaccg tcccttctag cagcttggga    660

acccagacct acatctgtaa cgtcaaccat aaaccatcca acacaaaggt ggataagaag    720

gttgaaccaa agagctgtga taagacacat acatgccctc cttgtcctgc accagagctc    780

ctcggaggtc catctgtgtt cctgtttccc cccaaaccca aggacactct tatgatctct    840

cgtactccag aggtcacctg tgttgttgtc gacgtgagcc atgaagatcc cgaggttaaa    900

ttcaactggt acgtggatgg agtcgaggtt cacaatgcca agaccaagcc cagggaggag    960

caatataatt ctacatatcg ggtagtgagc gttctgaccg tgctccacca agattggctc   1020

aatggaaaag agtacaagtg caaggtgtcc aacaaggctc ttcccgctcc cattgagaaa   1080

actatctcca aagccaaggg gcagccacgg gaaccccagg tgtatacatt gcccccatct   1140

agagacgagc tgaccaagaa ccaggtgagt ctcacttgtc tggtcaaggg gttttaccct   1200

tctgacattg ctgtagagtg ggagtctaac ggacagccag aaaacaacta caagacaact   1260

cccccagtgc tggacagcga cgggagcttc ttcctctact ccaagttgac tgtagacaag   1320

tctagatggc agcaaggaaa cgttttctcc tgctcagtaa tgcatgaggc tctgcacaat   1380

cactataccc agaaatcact gtcccttagc ccagggtgac tcgag                    1425
```

<210> SEQ ID NO 158
<211> LENGTH: 1425

<212> TYPE: DNA
<213> ORGANISM: Artificial Sequence
<220> FEATURE:
<223> OTHER INFORMATION: Full-length heavy chain polynucleotide
      sequences; huCD37-50 antibody

<400> SEQUENCE: 158
aagcttgcca ccatggggtg gtcctgcata atccttttcc tggttgctac tgctaccgga 60
gtccattcac aggtgcagct gcaggagtcc ggccccggcc tgctcaagcc ttctcagagt 120
ctgagtctga cttgtactgt ttctggctac agcataacca gcggtttcgc ttggcactgg 180
atcagacagc atcccggcaa caaactggag tggatgggat acatactgta ctcaggctca 240
actgtctatt ccccctccct gaaatcccgg atcagtatta cccgtgacac ttctaagaac 300 cattttttc tgcagctgaa cagcgttacc gcagctgaca ctgcaaccta ctactgtgcc 360
cggggatatt atggatacgg agcttggttc gcttactggg gccaaggcac cctcgtaact 420
gtgagtgctg cttccaccaa gggcccatca gttttcccct tggctccaag ttctaaatcc 480
acaagcggtg gaacagctgc actgggatgc ctcgttaaag attatttccc tgagcctgtg 540
acagtgagct ggaatagcgg agcattgact tcaggtgtgc acacttttcc cgctgtgttg 600
cagtcctccg gtctgtactc actgtccagt gtcgtaaccg tcccttctag cagcttggga 660
acccagacct acatctgtaa cgtcaaccat aaaccatcca acacaaaggt ggataagaag 720
gttgaaccaa agagctgtga taagacacat acatgccctc cttgtcctgc accagagctc 780
ctcggaggtc catctgtgtt cctgtttccc cccaaaccca aggacactct tatgatctct 840
cgtactccag aggtcacctg tgttgttgtc gacgtgagcc atgaagatcc cgaggttaaa 900
ttcaactggt acgtggatgg agtcgaggtt cacaatgcca agaccaagcc cagggaggag 960
caatataatt ctacatatcg ggtagtgagc gttctgaccg tgctccacca agattggctc 1020
aatggaaaag agtacaagtg caaggtgtcc aacaaggctc ttcccgctcc cattgagaaa 1080
actatctcca aagccaaggg gcagccacgg gaaccccagg tgtatacatt gcccccatct 1140
agagacgagc tgaccaagaa ccaggtgagt ctcacttgtc tggtcaaggg gttttaccct 1200
tctgacattg ctgtagagtg ggagtctaac ggacagccag aaaacaacta caagacaact 1260
cccccagtgc tggacagcga cgggagcttc ttcctctact ccaagttgac tgtagacaag 1320
tctagatggc agcaaggaaa cgttttctcc tgctcagtaa tgcatgaggc tctgcacaat 1380
cactataccc agaaatcact gtcccttagc ccagggtgac tcgag 1425

<210> SEQ ID NO 159
<211> LENGTH: 1425
<212> TYPE: DNA
<213> ORGANISM: Artificial Sequence
<220> FEATURE:
<223> OTHER INFORMATION: Full-length heavy chain polynucleotide
      sequences; huCD37-51 antibody

<400> SEQUENCE: 159
aagcttgcca ccatgggttg gtcttgcatc atcctgttcc tggtggccac tgccactggc 60
gtgcattcag aagttcagtt ggtggagtcc ggcccagaag tgctgaaacc cggcgaatca 120
ctgtccctga cttgtaccgt gtcaggttat agcatcagca gcggctttgc ttggcactgg 180
attcggcagt ttccaggcaa gggactggaa tggatgggct acatccatta cagtggctca 240
accaattaca gccctagcct gcagggccga atctctatta ccagggatag ttctattaac 300
cagtttttcc tgcagcttaa ttccgtgact gcctctgaca cagcaactta ctattgcgcc 360
cgtggctact acgggttcgg agcctggttt gtatactggg gtcagggcac cctggtcact 420
gtctcagccg cctctaccaa gggcccatca gttttcccct tggctccaag ttctaaatcc 480
acaagcggtg gaacagctgc actgggatgc ctcgttaaag attatttccc tgagcctgtg 540
acagtgagct ggaatagcgg agcattgact tcaggtgtgc acacttttcc cgctgtgttg 600
cagtcctccg gtctgtactc actgtccagt gtcgtaaccg tcccttctag cagcttggga 660
acccagacct acatctgtaa cgtcaaccat aaaccatcca acacaaaggt ggataagaag 720
gttgaaccaa agagctgtga taagacacat acatgccctc cttgtcctgc accagagctc 780
ctcggaggtc catctgtgtt cctgtttccc cccaaaccca aggacactct tatgatctct 840
cgtactccag aggtcacctg tgttgttgtc gacgtgagcc atgaagatcc cgaggttaaa 900
ttcaactggt acgtggatgg agtcgaggtt cacaatgcca agaccaagcc cagggaggag 960
caatataatt ctacatatcg ggtagtgagc gttctgaccg tgctccacca agattggctc 1020
aatggaaaag agtacaagtg caaggtgtcc aacaaggctc ttcccgctcc cattgagaaa 1080
actatctcca aagccaaggg gcagccacgg gaaccccagg tgtatacatt gcccccatct 1140
agagacgagc tgaccaagaa ccaggtgagt ctcacttgtc tggtcaaggg gttttaccct 1200
tctgacattg ctgtagagtg ggagtctaac ggacagccag aaaacaacta caagacaact 1260
cccccagtgc tggacagcga cgggagcttc ttcctctact ccaagttgac tgtagacaag 1320
tctagatggc agcaaggaaa cgttttctcc tgctcagtaa tgcatgaggc tctgcacaat 1380
cactataccc agaaatcact gtcccttagc ccagggtgac tcgag 1425

<210> SEQ ID NO 160
<211> LENGTH: 1425
<212> TYPE: DNA
<213> ORGANISM: Artificial Sequence
<220> FEATURE:
<223> OTHER INFORMATION: Full-length heavy chain polynucleotide sequences; huCD37-56 antibody

<400> SEQUENCE: 160
aagcttgcca ccatggggtg gagctgcatt atcctgttcc tcgtcgccac cgcaaccggc 60
gtccactccc aggtgcagct gcaagaaagc gggccaggat tggtaaaacc ttcccagtct 120
ctgagtctta cttgtaccgt atctggatac agtatcacat ctggcttcgc ctggcattgg 180
attcgccagt ttcccggcaa ggggcttgag tggatggggt atattcatta ttctggaggt 240
accaactaca acccttccct gaagagtcga gtctcaatta ccagggacac ttccaagaac 300
caattctttt tgcagcttaa ttcagtgacc gctgccgaca ccgctactta ctactgcgcc 360
cggggctact atgggtttgg tgcctggttc gcctactggg gccaggggac cctggtgccc 420
gtgtctgctg cctccacaaa gggcccatca gttttcccct tggctccaag ttctaaatcc 480
acaagcggtg gaacagctgc actgggatgc ctcgttaaag attatttccc tgagcctgtg 540
acagtgagct ggaatagcgg agcattgact tcaggtgtgc acacttttcc cgctgtgttg 600
cagtcctccg gtctgtactc actgtccagt gtcgtaaccg tcccttctag cagcttggga 660
acccagacct acatctgtaa cgtcaaccat aaaccatcca acacaaaggt ggataagaag 720
gttgaaccaa agagctgtga taagacacat acatgccctc cttgtcctgc accagagctc 780
ctcggaggtc catctgtgtt cctgtttccc cccaaaccca aggacactct tatgatctct 840
cgtactccag aggtcacctg tgttgttgtc gacgtgagcc atgaagatcc cgaggttaaa 900
ttcaactggt acgtggatgg agtcgaggtt cacaatgcca agaccaagcc cagggaggag 960
caatataatt ctacatatcg ggtagtgagc gttctgaccg tgctccacca agattggctc 1020
aatggaaaag agtacaagtg caaggtgtcc aacaaggctc ttcccgctcc cattgagaaa 1080
actatctcca aagccaaggg gcagccacgg gaaccccagg tgtatacatt gcccccatct 1140
agagacgagc tgaccaagaa ccaggtgagt ctcacttgtc tggtcaaggg gttttaccct 1200
tctgacattg ctgtagagtg ggagtctaac ggacagccag aaaacaacta caagacaact 1260
cccccagtgc tggacagcga cgggagcttc ttcctctact ccaagttgac tgtagacaag 1320
tctagatggc agcaaggaaa cgttttctcc tgctcagtaa tgcatgaggc tctgcacaat 1380
cactataccc agaaatcact gtcccttagc ccagggtgac tcgag 1425

<210> SEQ ID NO 161
<211> LENGTH: 1425
<212> TYPE: DNA
<213> ORGANISM: Artificial Sequence
<220> FEATURE:
<223> OTHER INFORMATION: Full-length heavy chain polynucleotide sequences; huCD37-57 antibody

<400> SEQUENCE: 161
aagcttgcca ccatgggctg gagctgcatc attctgtttc tggtggccac agcaactggc 60
gttcacagtc aagtccaact gcaggagagc ggccccggac tcctgaaacc atctcagtca 120
ctcagtctga catgtactgt gagcggctac agcattacct caggcttcgc ttggcattgg 180
atcaggcagt tccccggaaa aggtctggag tggatggggt acattctgta cagcggcagt 240
acagtgtatt caccctcctt gaaatctagg atatcaatca cacgtgatac aagcaaaaat 300
cagttcttcc tccagctgaa ctccgtcacc gccgcagaca cagcaaccta ttattgtgct 360
cgcggatact acggatatgg cgcatggttc gcctattggg gccaggggac actcgtgacc 420
gtttccgccg cctccacaaa gggcccatca gttttcccct tggctccaag ttctaaatcc 480
acaagcggtg gaacagctgc actgggatgc ctcgttaaag attatttccc tgagcctgtg 540
acagtgagct ggaatagcgg agcattgact tcaggtgtgc acacttttcc cgctgtgttg 600
cagtcctccg gtctgtactc actgtccagt gtcgtaaccg tcccttctag cagcttggga 660
acccagacct acatctgtaa cgtcaaccat aaaccatcca acacaaaggt ggataagaag 720
gttgaaccaa agagctgtga taagacacat acatgccctc cttgtcctgc accagagctc 780
ctcggaggtc catctgtgtt cctgtttccc cccaaaccca aggacactct tatgatctct 840
cgtactccag aggtcacctg tgttgttgtc gacgtgagcc atgaagatcc cgaggttaaa 900
ttcaactggt acgtggatgg agtcgaggtt cacaatgcca agaccaagcc cagggaggag 960
caatataatt ctacatatcg ggtagtgagc gttctgaccg tgctccacca agattggctc 1020
aatggaaaag agtacaagtg caaggtgtcc aacaaggctc ttcccgctcc cattgagaaa 1080
actatctcca aagccaaggg gcagccacgg gaaccccagg tgtatacatt gcccccatct 1140
agagacgagc tgaccaagaa ccaggtgagt ctcacttgtc tggtcaaggg gttttaccct 1200
tctgacattg ctgtagagtg ggagtctaac ggacagccag aaaacaacta caagacaact 1260
cccccagtgc tggacagcga cgggagcttc ttcctctact ccaagttgac tgtagacaag 1320
tctagatggc agcaaggaaa cgttttctcc tgctcagtaa tgcatgaggc tctgcacaat 1380
cactataccc agaaatcact gtcccttagc ccagggtgac tcgag 1425

<210> SEQ ID NO 162
<211> LENGTH: 717
<212> TYPE: DNA

<213> ORGANISM: Artificial Sequence
<220> FEATURE:
<223> OTHER INFORMATION: Full-length light chain polynucleotide
sequences; chCD37-3 antibody

<400> SEQUENCE: 162
gaattcgcca ccatgagtgt gcccactcag gtcctggggt tgctgctgct gtggcttaca 60
gatgccagat gtgacatcca gatgactcag tctccagcct ccctttctgt atctgtggga 120
gaaactgtca ccatcacatg tcgagcaagt gagaatattc gcagtaattt agcatggtat 180
cagcagaaac agggaaaatc tcctcagctc ctggtcaatg ttgcaacaaa cttagcagat 240
ggtgtgccat caaggttcag tggcagtgga tcaggcacac agtattccct caagatcaac 300
agcctgcagt ctgaagattt tgggacttat tactgtcaac attattgggg tactacgtgg 360
acgttcggtg gaggcaccaa gctggaaatc aaacgtacgg tggctgcacc atctgtcttc 420
atcttcccgc catctgatga gcagttgaaa tctggaactg cctctgttgt gtgcctgctg 480
aataacttct atcccagaga ggccaaagta cagtggaagg tggataacgc cctccaatcg 540
ggtaactccc aggagagtgt cacagagcag gacagcaagg acagcaccta cagcctcagc 600
agcaccctga cgctgagcaa agcagactac gagaaacaca aagtctacgc ctgcgaagtc 660
acccatcagg gcctgagctc gcccgtcaca aagagcttca acaggggaga gtgttag 717

<210> SEQ ID NO 163
<211> LENGTH: 714
<212> TYPE: DNA
<213> ORGANISM: Artificial Sequence
<220> FEATURE:
<223> OTHER INFORMATION: Full-length light chain polynucleotide
sequences; huCD37-3v1.0 and huCD37-3v1.1 antibody

<400> SEQUENCE: 163
gaattcgcca ccatgggttg gtcctgcatc atcttgtttc tcgtggccac agccaccggt 60
gttcactctg atatacaaat gactcaaagc ccttccagtt tgagcgtaag tgtgggtgaa 120
cgcgtaacaa tcacctgtag agctagtgaa aacatccgca gtaatctcgc atggtaccaa 180
caaaagccag gtaagtcacc taagctcctc gtgaatgttg ctaccaacct cgctgatggt 240
gtgccttcac gattctctgg ttcaggttcc ggtaccgatt attcacttaa gatcaactca 300
ctccaaccag aagatttcgg tacatattac tgtcaacact actggggtac gacctggaca 360
ttcggtcaag gtactaagct ggaaatcaag cgtacggtgg ctgcaccatc tgtcttcatc 420
ttcccgccat ctgatgagca gttgaaatct ggaactgcct ctgttgtgtg cctgctgaat 480
aacttctatc ccagagaggc caaagtacag tggaaggtgg ataacgccct ccaatcgggt 540
aactcccagg agagtgtcac agagcaggac agcaaggaca gcacctacag cctcagcagc 600
accctgacgc tgagcaaagc agactacgag aaacacaaag tctacgcctg cgaagtcacc 660
catcagggcc tgagctcgcc cgtcacaaag agcttcaaca ggggagagtg ttag 714

<210> SEQ ID NO 164
<211> LENGTH: 726
<212> TYPE: DNA
<213> ORGANISM: Artificial Sequence
<220> FEATURE:
<223> OTHER INFORMATION: Full-length light chain polynucleotide
sequences; chCD37-12 antibody

<400> SEQUENCE: 164
gaattcgcca ccatgggttg gtcctgtata atcctgttct tggtggccac cgctactggc 60

```
gttcatagtg atattgtact cactcagtca ccagccagtc tggcagtgtc cctgggccag    120

cgtgccacca tctcctgccg ggcctcacag tccgtgagca ctagctctta ttcctatctc    180

tactggtttc aacagaagcc aggacagccc cctaagctgc tgatcaagta cgcctccaac    240

ctcgccagcg gcgttcccgc tagattctct ggttccggta gcggaactga tttcactttg    300

aacatccacc ccgttgagga agaggatacc gccacttact attgtcaaca ctcttgggag    360

attccttaca cctttggagg aggaacaaag ctcgaaatta agcgtacggt ggctgcacca    420

tctgtcttca tcttcccgcc atctgatgag cagttgaaat ctggaactgc ctctgttgtg    480

tgcctgctga ataacttcta tcccagagag gccaaagtac agtggaaggt ggataacgcc    540

ctccaatcgg gtaactccca ggagagtgtc acagagcagg acagcaagga cagcacctac    600

agcctcagca gcaccctgac gctgagcaaa gcagactacg agaaacacaa agtctacgcc    660

tgcgaagtca cccatcaggg cctgagctcg cccgtcacaa agagcttcaa caggggagag    720

tgttag                                                                726
```

<210> SEQ ID NO 165
<211> LENGTH: 711
<212> TYPE: DNA
<213> ORGANISM: Artificial Sequence
<220> FEATURE:
<223> OTHER INFORMATION: Full-length light chain polynucleotide sequences; chCD37-38 antibody

<400> SEQUENCE: 165

```
gaattcgcca ccatgggctg gtcctgtatc atcctgtttc tcgtggccac agctacaggt     60

gttcattctc agattgtgct gacccaatca ccagctatta tgtccgctag ccccggcgag    120

aaagtgacaa tgacatgtag cgctagctct tctgtgactt acatgcattg gtatcaacag    180

aagtcaggta ccagtcccaa gcgttggatc tacgacacat ccaaactggc ctccggagtc    240

cctgccaggt tcagcggagg tgggtccggc accagttatt cactgaccat atcctctatg    300

gaagctgaag atgctgctac ttattattgt caacaatgga tttctaaccc ccccaccttt    360

ggtggcggaa caaagctgga gatcaagcgt acggtggctg caccatctgt cttcatcttc    420

ccgccatctg atgagcagtt gaaatctgga actgcctctg ttgtgtgcct gctgaataac    480

ttctatccca gagaggccaa agtacagtgg aaggtggata acgccctcca atcgggtaac    540

tcccaggaga gtgtcacaga gcaggacagc aaggacagca cctacagcct cagcagcacc    600

ctgacgctga gcaaagcaga ctacgagaaa cacaaagtct acgcctgcga agtcacccat    660

cagggcctga gctcgcccgt cacaaagagc ttcaacaggg gagagtgtta g             711
```

<210> SEQ ID NO 166
<211> LENGTH: 711
<212> TYPE: DNA
<213> ORGANISM: Artificial Sequence
<220> FEATURE:
<223> OTHER INFORMATION: Full-length light chain polynucleotide sequences; huCD37-38 antibody

<400> SEQUENCE: 166

```
gaattcgcca ccatgggatg gtcctgcatt attctgttct tggtcgccac tgctactggc     60

gttcactctg acattgtgct cacacagtct ccagcctcaa tgtctgcttc ccccggtgag    120

cgggtgacca tgacatgctc tgccagttcc tccgtgacat atatgcattg gtatcagcaa    180

aaacccggta cctctccaaa aagatggatc tacgacactt caaagcttgc atcaggcgtt    240

cctgccagat tttccgggtc tgggtctggc acttcataca gtctgaccat tagttccatg    300
```

gaagctgaag atgcagccac ctattactgt cagcagtgga tttcaaatcc tcctaccttc 360
ggcggcggaa ccaaactgga gataaagcgt acggtggctg caccatctgt cttcatcttc 420
ccgccatctg atgagcagtt gaaatctgga actgcctctg ttgtgtgcct gctgaataac 480
ttctatccca gagaggccaa agtacagtgg aaggtggata acgccctcca atcgggtaac 540
tcccaggaga gtgtcacaga gcaggacagc aaggacagca cctacagcct cagcagcacc 600
ctgacgctga gcaaagcaga ctacgagaaa cacaaagtct acgcctgcga agtcacccat 660
cagggcctga gctcgcccgt cacaaagagc ttcaacaggg gagagtgtta g 711

<210> SEQ ID NO 167
<211> LENGTH: 711
<212> TYPE: DNA
<213> ORGANISM: Artificial Sequence
<220> FEATURE:
<223> OTHER INFORMATION: Full-length light chain polynucleotide sequences; huCD37-50 antibody

<400> SEQUENCE: 167
gaattcgcca ccatgggttg gtcatgcatt attctgttcc tggttgctac cgcaacagga 60
gtacatagtg agatagtcct cacccaaagt cctgctacta tgtctgccag cccaggagag 120
cgtgtgacca tgacttgctc tgcaacctca agtgtgacat acatgcattg gtatcagcaa 180
aagcctggcc aatcccctaa aaggtggatc tacgatactt ctaatctgcc atacggtgtg 240
cccgcaaggt tctccgggag tggcagtggc accagttata gtctgaccat cagttcaatg 300
gaagcagagg atgcagcaac ctattattgt cagcagtggt ccgataatcc ccctactttt 360
ggtcagggta caaagctgga gattaagcgt acggtggctg caccatctgt cttcatcttc 420
ccgccatctg atgagcagtt gaaatctgga actgcctctg ttgtgtgcct gctgaataac 480
ttctatccca gagaggccaa agtacagtgg aaggtggata acgccctcca atcgggtaac 540
tcccaggaga gtgtcacaga gcaggacagc aaggacagca cctacagcct cagcagcacc 600
ctgacgctga gcaaagcaga ctacgagaaa cacaaagtct acgcctgcga agtcacccat 660
cagggcctga gctcgcccgt cacaaagagc ttcaacaggg gagagtgtta g 711

<210> SEQ ID NO 168
<211> LENGTH: 711
<212> TYPE: DNA
<213> ORGANISM: Artificial Sequence
<220> FEATURE:
<223> OTHER INFORMATION: Full-length light chain polynucleotide sequences; huCD37-51 antibody

<400> SEQUENCE: 168
gaattcgcca ccatgggatg gagctgtatt attctgttcc tggttgctac tgctactggc 60
gtccattccg agatagtcct cacccagagc cccgcaacca tgagtgcctc ccctggggag 120
cgagtgacta tgacttgttc cgccacttct tcagttacct atatgcattg gtatcagcag 180
aaacctggac agtctccaaa gcgttggatt tacgacacct ccaacctggc ttcaggagtt 240
cctgctaggt tcagcggatc tgggtctggc acaagttatt cactcaccat tagttccatg 300
gaggccgaag atgccgctac ttactactgt cagcagtgga gcagcaaccc ccctacattc 360
gggcagggaa ctaagctgga gatcaaacgt acggtggctg caccatctgt cttcatcttc 420
ccgccatctg atgagcagtt gaaatctgga actgcctctg ttgtgtgcct gctgaataac 480
ttctatccca gagaggccaa agtacagtgg aaggtggata acgccctcca atcgggtaac 540

```
tcccaggaga gtgtcacaga gcaggacagc aaggacagca cctacagcct cagcagcacc    600

ctgacgctga gcaaagcaga ctacgagaaa cacaaagtct acgcctgcga agtcacccat    660

cagggcctga gctcgcccgt cacaaagagc ttcaacaggg gagagtgtta g             711

<210> SEQ ID NO 169
<211> LENGTH: 711
<212> TYPE: DNA
<213> ORGANISM: Artificial Sequence
<220> FEATURE:
<223> OTHER INFORMATION: Full-length light chain polynucleotide
      sequences; huCD37-56 antibody

<400> SEQUENCE: 169

gaattcgcca ccatgggctg gtcctgtatc atcctgtttc tggtggcaac cgctactggg     60

gttcactctg atattgtcct gacacagagt ccagccttca tgagtgcttc tcccggagaa    120

aaggtcacaa tgacttgttc agcttcctcc tccgtcacat acatgcattg gtaccagcag    180

aagcctgacc agagtcctaa gaggtggatc tatgatacaa gcaatctggc ttccggtgtc    240

ccctcccgct tttcaggcgg cggaagcgga actgactata gccttaccat ctcctcaatg    300

gaagccgagg acgctgctac atattactgc cagcaatgga tcagcgaccc tcctactttc    360

ggacagggaa caaaattgga aattaagcgt acggtggctg caccatctgt cttcatcttc    420

ccgccatctg atgagcagtt gaaatctgga actgcctctg ttgtgtgcct gctgaataac    480

ttctatccca gagaggccaa agtacagtgg aaggtggata acgccctcca atcgggtaac    540

tcccaggaga gtgtcacaga gcaggacagc aaggacagca cctacagcct cagcagcacc    600

ctgacgctga gcaaagcaga ctacgagaaa cacaaagtct acgcctgcga agtcacccat    660

cagggcctga gctcgcccgt cacaaagagc ttcaacaggg gagagtgtta g             711

<210> SEQ ID NO 170
<211> LENGTH: 711
<212> TYPE: DNA
<213> ORGANISM: Artificial Sequence
<220> FEATURE:
<223> OTHER INFORMATION: Full-length light chain polynucleotide
      sequences; huCD37-57 antibody

<400> SEQUENCE: 170

gaattcgcca ccatggggtg gtcctgtatt atcctgttcc tggtcgcaac cgccacaggc     60

gttcactccg agatcgtgtt gactcagagc ccagccacca tgtccgcttc ccccggggag    120

agagtgacaa tgacttgttc cgccacaagt tctgtaacct acatgcattg gtaccagcaa    180

aaaccaggac agagtccccg tcgttggatt tatgatacct ctaacctggc ttcaggcgtt    240

cctgcccgct tttctggtag tggatctggg acttcctata gccttaccat aagctctatg    300

gaagccgagg acgccgctac atactactgc cagcagtgga gtgataaccc ccccaccttc    360

gggcagggaa ccaaattgga gatcaaacgt acggtggctg caccatctgt cttcatcttc    420

ccgccatctg atgagcagtt gaaatctgga actgcctctg ttgtgtgcct gctgaataac    480

ttctatccca gagaggccaa agtacagtgg aaggtggata acgccctcca atcgggtaac    540

tcccaggaga gtgtcacaga gcaggacagc aaggacagca cctacagcct cagcagcacc    600

ctgacgctga gcaaagcaga ctacgagaaa cacaaagtct acgcctgcga agtcacccat    660

cagggcctga gctcgcccgt cacaaagagc ttcaacaggg gagagtgtta g             711

<210> SEQ ID NO 171
<211> LENGTH: 32
```

<212> TYPE: DNA
<213> ORGANISM: Artificial Sequence
<220> FEATURE:
<223> OTHER INFORMATION: Degenerate primer EcoMH1
<220> FEATURE:
<221> NAME/KEY: misc_feature
<222> LOCATION: (13)..(13)
<223> OTHER INFORMATION: s is g or c
<220> FEATURE:
<221> NAME/KEY: misc_feature
<222> LOCATION: (15)..(15)
<223> OTHER INFORMATION: r is a or g
<220> FEATURE:
<221> NAME/KEY: misc_feature
<222> LOCATION: (18)..(18)
<223> OTHER INFORMATION: n is g, a, t or c
<220> FEATURE:
<221> NAME/KEY: misc_feature
<222> LOCATION: (19)..(19)
<223> OTHER INFORMATION: m is a or c
<220> FEATURE:
<221> NAME/KEY: misc_feature
<222> LOCATION: (25)..(25)
<223> OTHER INFORMATION: s is g or c
<220> FEATURE:
<221> NAME/KEY: misc_feature
<222> LOCATION: (28)..(28)
<223> OTHER INFORMATION: s is g or c

<400> SEQUENCE: 171
cttccggaat tcsargtnma gctgsagsag tc 32

<210> SEQ ID NO 172
<211> LENGTH: 35
<212> TYPE: DNA
<213> ORGANISM: Artificial Sequence
<220> FEATURE:
<223> OTHER INFORMATION: Degenerate primer EcoMH2
<220> FEATURE:
<221> NAME/KEY: misc_feature
<222> LOCATION: (13)..(13)
<223> OTHER INFORMATION: s is g or c
<220> FEATURE:
<221> NAME/KEY: misc_feature
<222> LOCATION: (15)..(15)
<223> OTHER INFORMATION: r is a or g
<220> FEATURE:
<221> NAME/KEY: misc_feature
<222> LOCATION: (18)..(18)
<223> OTHER INFORMATION: n is g, a, t or c
<220> FEATURE:
<221> NAME/KEY: misc_feature
<222> LOCATION: (19)..(19)
<223> OTHER INFORMATION: m is a or c
<220> FEATURE:
<221> NAME/KEY: misc_feature
<222> LOCATION: (25)..(25)
<223> OTHER INFORMATION: s is g or c
<220> FEATURE:
<221> NAME/KEY: misc_feature
<222> LOCATION: (28)..(28)
<223> OTHER INFORMATION: s is g or c
<220> FEATURE:
<221> NAME/KEY: misc_feature
<222> LOCATION: (33)..(33)
<223> OTHER INFORMATION: w is a or t

<400> SEQUENCE: 172
cttccggaat tcsargtnma gctgsagsag tcwgg 35

<210> SEQ ID NO 173
<211> LENGTH: 36
<212> TYPE: DNA
<213> ORGANISM: Artificial Sequence
<220> FEATURE:

<223> OTHER INFORMATION: Degenerate primer BamIgG1

<400> SEQUENCE: 173
ggaggatcca tagacagatg ggggtgtcgt tttggc 36

<210> SEQ ID NO 174
<211> LENGTH: 31
<212> TYPE: DNA
<213> ORGANISM: Artificial Sequence
<220> FEATURE:
<223> OTHER INFORMATION: Degenerate primer SacIMK
<220> FEATURE:
<221> NAME/KEY: misc_feature
<222> LOCATION: (10)..(10)
<223> OTHER INFORMATION: y is c or t
<220> FEATURE:
<221> NAME/KEY: misc_feature
<222> LOCATION: (17)..(17)
<223> OTHER INFORMATION: m is a or c
<220> FEATURE:
<221> NAME/KEY: misc_feature
<222> LOCATION: (19)..(19)
<223> OTHER INFORMATION: s is g or c
<220> FEATURE:
<221> NAME/KEY: misc_feature
<222> LOCATION: (22)..(22)
<223> OTHER INFORMATION: m is a or c
<220> FEATURE:
<221> NAME/KEY: misc_feature
<222> LOCATION: (25)..(25)
<223> OTHER INFORMATION: r is a or g
<220> FEATURE:
<221> NAME/KEY: misc_feature
<222> LOCATION: (26)..(26)
<223> OTHER INFORMATION: w is a or t
<220> FEATURE:
<221> NAME/KEY: misc_feature
<222> LOCATION: (28)..(28)
<223> OTHER INFORMATION: m is a or c

<400> SEQUENCE: 174
ggagctcgay attgtgmtsa cmcarwctmc a 31

<210> SEQ ID NO 175
<211> LENGTH: 46
<212> TYPE: DNA
<213> ORGANISM: Artificial Sequence
<220> FEATURE:
<223> OTHER INFORMATION: Degenerate primer HindKL

<400> SEQUENCE: 175
tatagagctc aagcttggat ggtgggaaga tggatacagt tggtgc 46

<210> SEQ ID NO 176
<211> LENGTH: 16
<212> TYPE: PRT
<213> ORGANISM: Artificial Sequence
<220> FEATURE:
<223> OTHER INFORMATION: Kabat Defined CD37-3 HC CDR2 for Murine
<220> FEATURE:
<221> NAME/KEY: MISC_FEATURE
<222> LOCATION: (10)..(16)
<223> OTHER INFORMATION: Portion of the Kabat heavy chain CDR2 not
considered a CDR for resurfacing

<400> SEQUENCE: 176

Val Ile Trp Gly Asp Gly Ser Thr Asn Tyr His Ser Ala Leu Lys Ser
1 5 10 15

<210> SEQ ID NO 177
<211> LENGTH: 16

<212> TYPE: PRT
<213> ORGANISM: Artificial Sequence
<220> FEATURE:
<223> OTHER INFORMATION: Kabat Defined CD37-3 HC CDR2 for Human
<220> FEATURE:
<221> NAME/KEY: MISC_FEATURE
<222> LOCATION: (10)..(16)
<223> OTHER INFORMATION: Portion of the Kabat heavy chain CDR2 not considered a CDR for resurfacing

<400> SEQUENCE: 177

Val Ile Trp Gly Asp Gly Ser Thr Asn Tyr His Pro Ser Leu Lys Ser
1 5 10 15

<210> SEQ ID NO 178
<211> LENGTH: 16
<212> TYPE: PRT
<213> ORGANISM: Artificial Sequence
<220> FEATURE:
<223> OTHER INFORMATION: Kabat Defined CD37-50 HC CDR2 for Murine
<220> FEATURE:
<221> NAME/KEY: MISC_FEATURE
<222> LOCATION: (10)..(16)
<223> OTHER INFORMATION: Portion of the Kabat heavy chain CDR2 not considered a CDR for resurfacing

<400> SEQUENCE: 178

Tyr Ile Leu Tyr Ser Gly Ser Thr Val Tyr Ser Pro Ser Leu Lys Ser
1 5 10 15

<210> SEQ ID NO 179
<211> LENGTH: 16
<212> TYPE: PRT
<213> ORGANISM: Artificial Sequence
<220> FEATURE:
<223> OTHER INFORMATION: Kabat Defined CD37-50 HC CDR2 for Human
<220> FEATURE:
<221> NAME/KEY: MISC_FEATURE
<222> LOCATION: (10)..(16)
<223> OTHER INFORMATION: Portion of the Kabat heavy chain CDR2 not considered a CDR for resurfacing

<400> SEQUENCE: 179

Tyr Ile Leu Tyr Ser Gly Ser Thr Val Tyr Ser Pro Ser Leu Lys Ser
1 5 10 15

<210> SEQ ID NO 180
<211> LENGTH: 281
<212> TYPE: PRT
<213> ORGANISM: Artificial Sequence
<220> FEATURE:
<223> OTHER INFORMATION: hCD37-M1

<400> SEQUENCE: 180

Met Ser Ala Gln Glu Ser Cys Leu Ser Leu Ile Lys Tyr Phe Leu Phe
1 5 10 15

Val Phe Asn Leu Phe Phe Phe Val Leu Gly Ser Leu Ile Phe Cys Phe
20 25 30

Gly Ile Trp Ile Leu Ile Asp Lys Thr Ser Phe Val Ser Phe Val Gly
35 40 45

Leu Ala Phe Val Pro Leu Gln Ile Trp Ser Lys Val Leu Ala Ile Ser
50 55 60

Gly Ile Phe Thr Met Gly Ile Ala Leu Leu Gly Cys Val Gly Ala Leu
65 70 75 80

Lys Glu Leu Arg Cys Leu Leu Gly Leu Tyr Phe Gly Met Leu Leu Leu
85 90 95

```
Leu Phe Ala Thr Gln Ile Thr Leu Gly Ile Leu Ile Ser Thr Gln Arg
            100                 105                 110

Val Arg Leu Glu Arg Arg Val Gln Glu Leu Val Leu Arg Thr Ile Gln
        115                 120                 125

Ser Tyr Arg Thr Asn Pro Asp Glu Thr Ala Ala Glu Glu Ser Trp Asp
    130                 135                 140

Tyr Val Gln Phe Gln Leu Arg Cys Cys Gly Trp His Tyr Pro Gln Asp
145                 150                 155                 160

Trp Phe Gln Val Leu Ile Leu Arg Gly Asn Gly Ser Glu Ala His Arg
                165                 170                 175

Val Pro Cys Ser Cys Tyr Asn Leu Ser Ala Thr Asn Asp Ser Thr Ile
            180                 185                 190

Leu Asp Lys Val Ile Leu Pro Gln Leu Ser Arg Leu Gly His Leu Ala
        195                 200                 205

Arg Ser Arg His Ser Ala Asp Ile Cys Ala Val Pro Ala Glu Ser His
    210                 215                 220

Ile Tyr Arg Glu Gly Cys Ala Gln Gly Leu Gln Lys Trp Leu His Asn
225                 230                 235                 240

Asn Leu Ile Ser Ile Val Gly Ile Cys Leu Gly Val Gly Leu Leu Glu
                245                 250                 255

Leu Gly Phe Met Thr Leu Ser Ile Phe Leu Cys Arg Asn Leu Asp His
            260                 265                 270

Val Tyr Asn Arg Leu Ala Arg Tyr Arg
        275                 280


<210> SEQ ID NO 181
<211> LENGTH: 281
<212> TYPE: PRT
<213> ORGANISM: Artificial Sequence
<220> FEATURE:
<223> OTHER INFORMATION: hCD37-M2

<400> SEQUENCE: 181

Met Ser Ala Gln Glu Ser Cys Leu Ser Leu Ile Lys Tyr Phe Leu Phe
1               5                   10                  15

Val Phe Asn Leu Phe Phe Phe Val Leu Gly Ser Leu Ile Phe Cys Phe
            20                  25                  30

Gly Ile Trp Ile Leu Ile Asp Lys Thr Ser Phe Val Ser Phe Val Gly
        35                  40                  45

Leu Ala Phe Val Pro Leu Gln Ile Trp Ser Lys Val Leu Ala Ile Ser
    50                  55                  60

Gly Ile Phe Thr Met Gly Ile Ala Leu Leu Gly Cys Val Gly Ala Leu
65                  70                  75                  80

Lys Glu Leu Arg Cys Leu Leu Gly Leu Tyr Phe Gly Met Leu Leu Leu
                85                  90                  95

Leu Phe Ala Thr Gln Ile Thr Leu Gly Ile Leu Ile Ser Thr Gln Arg
            100                 105                 110

Ala Gln Leu Glu Arg Ser Leu Arg Asp Val Val Glu Lys Thr Ile Gln
        115                 120                 125

Lys Tyr Gly Thr Asn Pro Glu Glu Thr Ala Ala Glu Glu Ser Trp Asp
    130                 135                 140

Tyr Ala Gln Phe Gln Leu Arg Cys Cys Gly Trp Gln Ser Pro Arg Asp
145                 150                 155                 160

Trp Asn Lys Ala Gln Met Leu Lys Ala Asn Glu Ser Glu Glu Pro Arg
                165                 170                 175
```

```
Val Pro Cys Ser Cys Tyr Asn Leu Ser Ala Thr Asn Asp Ser Thr Ile
            180                 185                 190

Leu Asp Lys Val Ile Leu Pro Gln Leu Ser Arg Leu Gly His Leu Ala
        195                 200                 205

Arg Ser Arg His Ser Ala Asp Ile Cys Ala Val Pro Ala Glu Ser His
    210                 215                 220

Ile Tyr Arg Glu Gly Cys Ala Gln Gly Leu Gln Lys Trp Leu His Asn
225                 230                 235                 240

Asn Leu Ile Ser Ile Val Gly Ile Cys Leu Gly Val Gly Leu Leu Glu
                245                 250                 255

Leu Gly Phe Met Thr Leu Ser Ile Phe Leu Cys Arg Asn Leu Asp His
            260                 265                 270

Val Tyr Asn Arg Leu Ala Arg Tyr Arg
        275                 280


<210> SEQ ID NO 182
<211> LENGTH: 281
<212> TYPE: PRT
<213> ORGANISM: Artificial Sequence
<220> FEATURE:
<223> OTHER INFORMATION: hCD37-M3

<400> SEQUENCE: 182

Met Ser Ala Gln Glu Ser Cys Leu Ser Leu Ile Lys Tyr Phe Leu Phe
1               5                   10                  15

Val Phe Asn Leu Phe Phe Phe Val Leu Gly Ser Leu Ile Phe Cys Phe
            20                  25                  30

Gly Ile Trp Ile Leu Ile Asp Lys Thr Ser Phe Val Ser Phe Val Gly
        35                  40                  45

Leu Ala Phe Val Pro Leu Gln Ile Trp Ser Lys Val Leu Ala Ile Ser
    50                  55                  60

Gly Ile Phe Thr Met Gly Ile Ala Leu Leu Gly Cys Val Gly Ala Leu
65                  70                  75                  80

Lys Glu Leu Arg Cys Leu Leu Gly Leu Tyr Phe Gly Met Leu Leu Leu
                85                  90                  95

Leu Phe Ala Thr Gln Ile Thr Leu Gly Ile Leu Ile Ser Thr Gln Arg
            100                 105                 110

Ala Gln Leu Glu Arg Ser Leu Arg Asp Val Val Glu Lys Thr Ile Gln
        115                 120                 125

Lys Tyr Gly Thr Asn Pro Glu Glu Thr Ala Ala Glu Glu Ser Trp Asp
    130                 135                 140

Tyr Val Gln Phe Gln Leu Arg Cys Cys Gly Trp His Tyr Pro Gln Asp
145                 150                 155                 160

Trp Phe Gln Val Leu Ile Leu Arg Gly Asn Gly Ser Glu Ala His Arg
                165                 170                 175

Val Pro Cys Ser Cys Tyr Asn Ser Thr Ala Thr Asn Asp Ser Thr Val
            180                 185                 190

Phe Asp Lys Leu Phe Phe Ser Gln Leu Ser Arg Leu Gly His Leu Ala
        195                 200                 205

Arg Ser Arg His Ser Ala Asp Ile Cys Ala Val Pro Ala Glu Ser His
    210                 215                 220

Ile Tyr Arg Glu Gly Cys Ala Gln Gly Leu Gln Lys Trp Leu His Asn
225                 230                 235                 240

Asn Leu Ile Ser Ile Val Gly Ile Cys Leu Gly Val Gly Leu Leu Glu
                245                 250                 255
```

```
Leu Gly Phe Met Thr Leu Ser Ile Phe Leu Cys Arg Asn Leu Asp His
            260                 265                 270

Val Tyr Asn Arg Leu Ala Arg Tyr Arg
        275                 280
```

<210> SEQ ID NO 183
<211> LENGTH: 281
<212> TYPE: PRT
<213> ORGANISM: Artificial Sequence
<220> FEATURE:
<223> OTHER INFORMATION: hCD37-M45

<400> SEQUENCE: 183

```
Met Ser Ala Gln Glu Ser Cys Leu Ser Leu Ile Lys Tyr Phe Leu Phe
1               5                   10                  15

Val Phe Asn Leu Phe Phe Phe Val Leu Gly Ser Leu Ile Phe Cys Phe
            20                  25                  30

Gly Ile Trp Ile Leu Ile Asp Lys Thr Ser Phe Val Ser Phe Val Gly
        35                  40                  45

Leu Ala Phe Val Pro Leu Gln Ile Trp Ser Lys Val Leu Ala Ile Ser
    50                  55                  60

Gly Ile Phe Thr Met Gly Ile Ala Leu Leu Gly Cys Val Gly Ala Leu
65                  70                  75                  80

Lys Glu Leu Arg Cys Leu Leu Gly Leu Tyr Phe Gly Met Leu Leu Leu
                85                  90                  95

Leu Phe Ala Thr Gln Ile Thr Leu Gly Ile Leu Ile Ser Thr Gln Arg
            100                 105                 110

Ala Gln Leu Glu Arg Ser Leu Arg Asp Val Val Glu Lys Thr Ile Gln
        115                 120                 125

Lys Tyr Gly Thr Asn Pro Glu Glu Thr Ala Ala Glu Glu Ser Trp Asp
    130                 135                 140

Tyr Val Gln Phe Gln Leu Arg Cys Cys Gly Trp His Tyr Pro Gln Asp
145                 150                 155                 160

Trp Phe Gln Val Leu Ile Leu Arg Gly Asn Gly Ser Glu Ala His Arg
                165                 170                 175

Val Pro Cys Ser Cys Tyr Asn Leu Ser Ala Thr Asn Asp Ser Thr Ile
            180                 185                 190

Leu Asp Lys Val Ile Leu Pro Gln Leu Ser Arg Leu Gly Pro Arg Ala
        195                 200                 205

Lys Leu Arg Gln Thr Ala Asp Ile Cys Ala Leu Pro Ala Lys Ala His
    210                 215                 220

Ile Tyr Arg Glu Gly Cys Ala Gln Ser Leu Gln Lys Trp Leu His Asn
225                 230                 235                 240

Asn Leu Ile Ser Ile Val Gly Ile Cys Leu Gly Val Gly Leu Leu Glu
                245                 250                 255

Leu Gly Phe Met Thr Leu Ser Ile Phe Leu Cys Arg Asn Leu Asp His
            260                 265                 270

Val Tyr Asn Arg Leu Ala Arg Tyr Arg
        275                 280
```

<210> SEQ ID NO 184
<211> LENGTH: 128
<212> TYPE: PRT
<213> ORGANISM: Artificial Sequence
<220> FEATURE:
<223> OTHER INFORMATION: muCD37-R176

<400> SEQUENCE: 184

```
Ile Ser Thr Gln Arg Val Arg Leu Glu Arg Arg Val Gln Glu Leu Val
1               5                   10                  15

Leu Arg Thr Ile Gln Ser Tyr Arg Thr Asn Pro Asp Glu Thr Ala Ala
            20                  25                  30

Glu Glu Ser Trp Asp Tyr Ala Gln Phe Gln Leu Arg Cys Cys Gly Trp
        35                  40                  45

Gln Ser Pro Arg Asp Trp Asn Lys Ala Gln Met Leu Lys Ala Asn Glu
    50                  55                  60

Ser Glu Glu Pro Arg Val Pro Cys Ser Cys Tyr Asn Ser Thr Ala Thr
65                  70                  75                  80

Asn Asp Ser Thr Val Phe Asp Lys Leu Phe Phe Ser Gln Leu Ser Arg
                85                  90                  95

Leu Gly Pro Arg Ala Lys Leu Arg Gln Thr Ala Asp Ile Cys Ala Leu
            100                 105                 110

Pro Ala Lys Ala His Ile Tyr Arg Glu Gly Cys Ala Gln Ser Leu Gln
        115                 120                 125
```

<210> SEQ ID NO 185
<211> LENGTH: 280
<212> TYPE: PRT
<213> ORGANISM: Artificial Sequence
<220> FEATURE:
<223> OTHER INFORMATION: hCD37mECD-H1

<400> SEQUENCE: 185

```
Met Ser Ala Gln Glu Ser Cys Leu Ser Leu Ile Lys Tyr Phe Leu Phe
1               5                   10                  15

Val Phe Asn Leu Phe Phe Phe Val Leu Gly Ser Leu Ile Phe Cys Phe
            20                  25                  30

Gly Ile Trp Ile Leu Ile Asp Lys Thr Ser Phe Val Ser Phe Val Gly
        35                  40                  45

Leu Ala Phe Val Pro Leu Gln Ile Trp Ser Lys Val Leu Ala Ile Ser
    50                  55                  60

Gly Ile Phe Thr Met Gly Ile Ala Leu Leu Gly Cys Val Gly Ala Leu
65                  70                  75                  80

Lys Glu Leu Arg Cys Leu Leu Gly Leu Tyr Phe Gly Met Leu Leu Leu
                85                  90                  95

Leu Phe Ala Thr Gln Ile Thr Leu Gly Ile Leu Ile Ser Thr Gln Arg
            100                 105                 110

Ala Gln Leu Glu Arg Ser Leu Arg Asp Val Val Glu Lys Thr Ile Gln
        115                 120                 125

Lys Tyr Gly Thr Asn Pro Glu Glu Thr Ala Ala Glu Glu Ser Trp Asp
    130                 135                 140

Tyr Ala Gln Phe Gln Leu Arg Cys Cys Gly Trp Gln Ser Pro Arg Asp
145                 150                 155                 160

Trp Asn Lys Ala Gln Met Leu Lys Ala Asn Glu Ser Glu Glu Pro Arg
                165                 170                 175

Val Pro Cys Ser Cys Tyr Asn Ser Thr Ala Thr Asn Asp Ser Thr Val
            180                 185                 190

Phe Asp Lys Leu Phe Phe Ser Gln Leu Ser Arg Leu Gly Pro Arg Ala
        195                 200                 205

Lys Leu Arg Gln Thr Ala Asp Ile Cys Ala Leu Pro Ala Lys Ala His
    210                 215                 220

Ile Tyr Arg Glu Gly Cys Ala Gln Ser Leu Gln Lys Trp Leu His Asn
225                 230                 235                 240
```

```
Asn Leu Ile Ser Ile Val Gly Ile Cys Leu Gly Val Gly Leu Leu Glu
                245                 250                 255

Leu Gly Phe Met Thr Leu Ser Ile Phe Leu Cys Arg Asn Leu Asp His
            260                 265                 270

Val Tyr Asn Arg Leu Ala Arg Tyr
        275                 280
```

<210> SEQ ID NO 186
<211> LENGTH: 281
<212> TYPE: PRT
<213> ORGANISM: Artificial Sequence
<220> FEATURE:
<223> OTHER INFORMATION: hCD37mECD-H2

<400> SEQUENCE: 186

```
Met Ser Ala Gln Glu Ser Cys Leu Ser Leu Ile Lys Tyr Phe Leu Phe
1               5                   10                  15

Val Phe Asn Leu Phe Phe Phe Val Leu Gly Ser Leu Ile Phe Cys Phe
            20                  25                  30

Gly Ile Trp Ile Leu Ile Asp Lys Thr Ser Phe Val Ser Phe Val Gly
        35                  40                  45

Leu Ala Phe Val Pro Leu Gln Ile Trp Ser Lys Val Leu Ala Ile Ser
    50                  55                  60

Gly Ile Phe Thr Met Gly Ile Ala Leu Leu Gly Cys Val Gly Ala Leu
65                  70                  75                  80

Lys Glu Leu Arg Cys Leu Leu Gly Leu Tyr Phe Gly Met Leu Leu Leu
                85                  90                  95

Leu Phe Ala Thr Gln Ile Thr Leu Gly Ile Leu Ile Ser Thr Gln Arg
            100                 105                 110

Val Arg Leu Glu Arg Arg Val Gln Glu Leu Val Leu Arg Thr Ile Gln
        115                 120                 125

Ser Tyr Arg Thr Asn Pro Asp Glu Thr Ala Ala Glu Glu Ser Trp Asp
    130                 135                 140

Tyr Val Gln Phe Gln Leu Arg Cys Cys Gly Trp His Tyr Pro Gln Asp
145                 150                 155                 160

Trp Phe Gln Val Leu Ile Leu Arg Gly Asn Gly Ser Glu Ala His Arg
                165                 170                 175

Val Pro Cys Ser Cys Tyr Asn Ser Thr Ala Thr Asn Asp Ser Thr Val
            180                 185                 190

Phe Asp Lys Leu Phe Phe Ser Gln Leu Ser Arg Leu Gly Pro Arg Ala
        195                 200                 205

Lys Leu Arg Gln Thr Ala Asp Ile Cys Ala Leu Pro Ala Lys Ala His
    210                 215                 220

Ile Tyr Arg Glu Gly Cys Ala Gln Ser Leu Gln Lys Trp Leu His Asn
225                 230                 235                 240

Asn Leu Ile Ser Ile Val Gly Ile Cys Leu Gly Val Gly Leu Leu Glu
                245                 250                 255

Leu Gly Phe Met Thr Leu Ser Ile Phe Leu Cys Arg Asn Leu Asp His
            260                 265                 270

Val Tyr Asn Arg Leu Ala Arg Tyr Arg
        275                 280
```

<210> SEQ ID NO 187
<211> LENGTH: 281
<212> TYPE: PRT
<213> ORGANISM: Artificial Sequence
<220> FEATURE:
<223> OTHER INFORMATION: hCD37mECD-H3

<400> SEQUENCE: 187

Met Ser Ala Gln Glu Ser Cys Leu Ser Leu Ile Lys Tyr Phe Leu Phe
1 5 10 15

Val Phe Asn Leu Phe Phe Phe Val Leu Gly Ser Leu Ile Phe Cys Phe
20 25 30

Gly Ile Trp Ile Leu Ile Asp Lys Thr Ser Phe Val Ser Phe Val Gly
35 40 45

Leu Ala Phe Val Pro Leu Gln Ile Trp Ser Lys Val Leu Ala Ile Ser
50 55 60

Gly Ile Phe Thr Met Gly Ile Ala Leu Leu Gly Cys Val Gly Ala Leu
65 70 75 80

Lys Glu Leu Arg Cys Leu Leu Gly Leu Tyr Phe Gly Met Leu Leu Leu
85 90 95

Leu Phe Ala Thr Gln Ile Thr Leu Gly Ile Leu Ile Ser Thr Gln Arg
100 105 110

Val Arg Leu Glu Arg Arg Val Gln Glu Leu Val Leu Arg Thr Ile Gln
115 120 125

Ser Tyr Arg Thr Asn Pro Asp Glu Thr Ala Ala Glu Glu Ser Trp Asp
130 135 140

Tyr Ala Gln Phe Gln Leu Arg Cys Cys Gly Trp Gln Ser Pro Arg Asp
145 150 155 160

Trp Asn Lys Ala Gln Met Leu Lys Ala Asn Glu Ser Glu Glu Pro Arg
165 170 175

Val Pro Cys Ser Cys Tyr Asn Leu Ser Ala Thr Asn Asp Ser Thr Ile
180 185 190

Leu Asp Lys Val Ile Leu Pro Gln Leu Ser Arg Leu Gly Pro Arg Ala
195 200 205

Lys Leu Arg Gln Thr Ala Asp Ile Cys Ala Leu Pro Ala Lys Ala His
210 215 220

Ile Tyr Arg Glu Gly Cys Ala Gln Ser Leu Gln Lys Trp Leu His Asn
225 230 235 240

Asn Leu Ile Ser Ile Val Gly Ile Cys Leu Gly Val Gly Leu Leu Glu
245 250 255

Leu Gly Phe Met Thr Leu Ser Ile Phe Leu Cys Arg Asn Leu Asp His
260 265 270

Val Tyr Asn Arg Leu Ala Arg Tyr Arg
275 280

<210> SEQ ID NO 188
<211> LENGTH: 281
<212> TYPE: PRT
<213> ORGANISM: Artificial Sequence
<220> FEATURE:
<223> OTHER INFORMATION: hCD37mECD-H4

<400> SEQUENCE: 188

Met Ser Ala Gln Glu Ser Cys Leu Ser Leu Ile Lys Tyr Phe Leu Phe
1 5 10 15

Val Phe Asn Leu Phe Phe Phe Val Leu Gly Ser Leu Ile Phe Cys Phe
20 25 30

Gly Ile Trp Ile Leu Ile Asp Lys Thr Ser Phe Val Ser Phe Val Gly
35 40 45

Leu Ala Phe Val Pro Leu Gln Ile Trp Ser Lys Val Leu Ala Ile Ser

```
    50                  55                  60

Gly Ile Phe Thr Met Gly Ile Ala Leu Leu Gly Cys Val Gly Ala Leu
65                  70                  75                  80

Lys Glu Leu Arg Cys Leu Leu Gly Leu Tyr Phe Gly Met Leu Leu Leu
                85                  90                  95

Leu Phe Ala Thr Gln Ile Thr Leu Gly Ile Leu Ile Ser Thr Gln Arg
            100                 105                 110

Val Arg Leu Glu Arg Arg Val Gln Glu Leu Val Leu Arg Thr Ile Gln
        115                 120                 125

Ser Tyr Arg Thr Asn Pro Asp Glu Thr Ala Ala Glu Glu Ser Trp Asp
    130                 135                 140

Tyr Ala Gln Phe Gln Leu Arg Cys Cys Gly Trp Gln Ser Pro Arg Asp
145                 150                 155                 160

Trp Asn Lys Ala Gln Met Leu Lys Ala Asn Glu Ser Glu Glu Pro Arg
                165                 170                 175

Val Pro Cys Ser Cys Tyr Asn Ser Thr Ala Thr Asn Asp Ser Thr Val
            180                 185                 190

Phe Asp Lys Leu Phe Phe Ser Gln Leu Ser Arg Leu Gly His Leu Ala
        195                 200                 205

Arg Ser Arg His Ser Ala Asp Ile Cys Ala Leu Pro Ala Lys Ala His
    210                 215                 220

Ile Tyr Arg Glu Gly Cys Ala Gln Ser Leu Gln Lys Trp Leu His Asn
225                 230                 235                 240

Asn Leu Ile Ser Ile Val Gly Ile Cys Leu Gly Val Gly Leu Leu Glu
                245                 250                 255

Leu Gly Phe Met Thr Leu Ser Ile Phe Leu Cys Arg Asn Leu Asp His
            260                 265                 270

Val Tyr Asn Arg Leu Ala Arg Tyr Arg
        275                 280
```

<210> SEQ ID NO 189
<211> LENGTH: 281
<212> TYPE: PRT
<213> ORGANISM: Artificial Sequence
<220> FEATURE:
<223> OTHER INFORMATION: hCD37mECD-H5

<400> SEQUENCE: 189

```
Met Ser Ala Gln Glu Ser Cys Leu Ser Leu Ile Lys Tyr Phe Leu Phe
1               5                   10                  15

Val Phe Asn Leu Phe Phe Phe Val Leu Gly Ser Leu Ile Phe Cys Phe
            20                  25                  30

Gly Ile Trp Ile Leu Ile Asp Lys Thr Ser Phe Val Ser Phe Val Gly
        35                  40                  45

Leu Ala Phe Val Pro Leu Gln Ile Trp Ser Lys Val Leu Ala Ile Ser
    50                  55                  60

Gly Ile Phe Thr Met Gly Ile Ala Leu Leu Gly Cys Val Gly Ala Leu
65                  70                  75                  80

Lys Glu Leu Arg Cys Leu Leu Gly Leu Tyr Phe Gly Met Leu Leu Leu
                85                  90                  95

Leu Phe Ala Thr Gln Ile Thr Leu Gly Ile Leu Ile Ser Thr Gln Arg
            100                 105                 110

Val Arg Leu Glu Arg Arg Val Gln Glu Leu Val Leu Arg Thr Ile Gln
        115                 120                 125

Ser Tyr Arg Thr Asn Pro Asp Glu Thr Ala Ala Glu Glu Ser Trp Asp
```

```
    130                 135                 140

Tyr Ala Gln Phe Gln Leu Arg Cys Cys Gly Trp Gln Ser Pro Arg Asp
145                 150                 155                 160

Trp Asn Lys Ala Gln Met Leu Lys Ala Asn Glu Ser Glu Glu Pro Arg
                165                 170                 175

Val Pro Cys Ser Cys Tyr Asn Ser Thr Ala Thr Asn Asp Ser Thr Val
            180                 185                 190

Phe Asp Lys Leu Phe Phe Ser Gln Leu Ser Arg Leu Gly Pro Arg Ala
        195                 200                 205

Lys Leu Arg Gln Thr Ala Asp Ile Cys Ala Val Pro Ala Glu Ser His
    210                 215                 220

Ile Tyr Arg Glu Gly Cys Ala Gln Gly Leu Gln Lys Trp Leu His Asn
225                 230                 235                 240

Asn Leu Ile Ser Ile Val Gly Ile Cys Leu Gly Val Gly Leu Leu Glu
                245                 250                 255

Leu Gly Phe Met Thr Leu Ser Ile Phe Leu Cys Arg Asn Leu Asp His
            260                 265                 270

Val Tyr Asn Arg Leu Ala Arg Tyr Arg
        275                 280
```

<210> SEQ ID NO 190
<211> LENGTH: 281
<212> TYPE: PRT
<213> ORGANISM: Artificial Sequence
<220> FEATURE:
<223> OTHER INFORMATION: hCD37mECD-H45

<400> SEQUENCE: 190

```
Met Ser Ala Gln Glu Ser Cys Leu Ser Leu Ile Lys Tyr Phe Leu Phe
1               5                   10                  15

Val Phe Asn Leu Phe Phe Phe Val Leu Gly Ser Leu Ile Phe Cys Phe
            20                  25                  30

Gly Ile Trp Ile Leu Ile Asp Lys Thr Ser Phe Val Ser Phe Val Gly
        35                  40                  45

Leu Ala Phe Val Pro Leu Gln Ile Trp Ser Lys Val Leu Ala Ile Ser
    50                  55                  60

Gly Ile Phe Thr Met Gly Ile Ala Leu Leu Gly Cys Val Gly Ala Leu
65                  70                  75                  80

Lys Glu Leu Arg Cys Leu Leu Gly Leu Tyr Phe Gly Met Leu Leu Leu
                85                  90                  95

Leu Phe Ala Thr Gln Ile Thr Leu Gly Ile Leu Ile Ser Thr Gln Arg
            100                 105                 110

Val Arg Leu Glu Arg Arg Val Gln Glu Leu Val Leu Arg Thr Ile Gln
        115                 120                 125

Ser Tyr Arg Thr Asn Pro Asp Glu Thr Ala Ala Glu Glu Ser Trp Asp
    130                 135                 140

Tyr Ala Gln Phe Gln Leu Arg Cys Cys Gly Trp Gln Ser Pro Arg Asp
145                 150                 155                 160

Trp Asn Lys Ala Gln Met Leu Lys Ala Asn Glu Ser Glu Glu Pro Arg
                165                 170                 175

Val Pro Cys Ser Cys Tyr Asn Ser Thr Ala Thr Asn Asp Ser Thr Val
            180                 185                 190

Phe Asp Lys Leu Phe Phe Ser Gln Leu Ser Arg Leu Gly His Leu Ala
        195                 200                 205

Arg Ser Arg His Ser Ala Asp Ile Cys Ala Val Pro Ala Glu Ser His
```

```
    210                 215                 220

Ile Tyr Arg Glu Gly Cys Ala Gln Gly Leu Gln Lys Trp Leu His Asn
225                 230                 235                 240

Asn Leu Ile Ser Ile Val Gly Ile Cys Leu Gly Val Gly Leu Leu Glu
                245                 250                 255

Leu Gly Phe Met Thr Leu Ser Ile Phe Leu Cys Arg Asn Leu Asp His
            260                 265                 270

Val Tyr Asn Arg Leu Ala Arg Tyr Arg
        275                 280


<210> SEQ ID NO 191
<211> LENGTH: 281
<212> TYPE: PRT
<213> ORGANISM: Artificial Sequence
<220> FEATURE:
<223> OTHER INFORMATION: hCD37-Mac12

<400> SEQUENCE: 191

Met Ser Ala Gln Glu Ser Cys Leu Ser Leu Ile Lys Tyr Phe Leu Phe
1               5                   10                  15

Val Phe Asn Leu Phe Phe Phe Val Leu Gly Ser Leu Ile Phe Cys Phe
            20                  25                  30

Gly Ile Trp Ile Leu Ile Asp Lys Thr Ser Phe Val Ser Phe Val Gly
        35                  40                  45

Leu Ala Phe Val Pro Leu Gln Ile Trp Ser Lys Val Leu Ala Ile Ser
    50                  55                  60

Gly Ile Phe Thr Met Gly Ile Ala Leu Leu Gly Cys Val Gly Ala Leu
65                  70                  75                  80

Lys Glu Leu Arg Cys Leu Leu Gly Leu Tyr Phe Gly Met Leu Leu Leu
                85                  90                  95

Leu Phe Ala Thr Gln Ile Thr Leu Gly Ile Leu Ile Ser Thr Gln Arg
            100                 105                 110

Ala Gln Leu Glu Arg Ser Leu Gln Asp Ile Val Glu Lys Thr Ile Gln
        115                 120                 125

Arg Tyr His Thr Asn Pro Glu Glu Thr Ala Ala Glu Glu Ser Trp Asp
    130                 135                 140

Tyr Val Gln Phe Gln Leu Arg Cys Cys Gly Trp His Ser Pro Gln Asp
145                 150                 155                 160

Trp Phe Gln Val Leu Thr Leu Arg Gly Asn Gly Ser Glu Ala His Arg
                165                 170                 175

Val Pro Cys Ser Cys Tyr Asn Leu Ser Ala Thr Asn Asp Ser Thr Ile
            180                 185                 190

Leu Asp Lys Val Ile Leu Pro Gln Leu Ser Arg Leu Gly His Leu Ala
        195                 200                 205

Arg Ser Arg His Ser Ala Asp Ile Cys Ala Val Pro Ala Glu Ser His
    210                 215                 220

Ile Tyr Arg Glu Gly Cys Ala Gln Gly Leu Gln Lys Trp Leu His Asn
225                 230                 235                 240

Asn Leu Ile Ser Ile Val Gly Ile Cys Leu Gly Val Gly Leu Leu Glu
                245                 250                 255

Leu Gly Phe Met Thr Leu Ser Ile Phe Leu Cys Arg Asn Leu Asp His
            260                 265                 270

Val Tyr Asn Arg Leu Ala Arg Tyr Arg
        275                 280
```

<210> SEQ ID NO 192
<211> LENGTH: 281
<212> TYPE: PRT
<213> ORGANISM: Artificial Sequence
<220> FEATURE:
<223> OTHER INFORMATION: hCD37-Mac4

<400> SEQUENCE: 192

```
Met Ser Ala Gln Glu Ser Cys Leu Ser Leu Ile Lys Tyr Phe Leu Phe
1               5                   10                  15

Val Phe Asn Leu Phe Phe Phe Val Leu Gly Ser Leu Ile Phe Cys Phe
            20                  25                  30

Gly Ile Trp Ile Leu Ile Asp Lys Thr Ser Phe Val Ser Phe Val Gly
        35                  40                  45

Leu Ala Phe Val Pro Leu Gln Ile Trp Ser Lys Val Leu Ala Ile Ser
    50                  55                  60

Gly Ile Phe Thr Met Gly Ile Ala Leu Leu Gly Cys Val Gly Ala Leu
65                  70                  75                  80

Lys Glu Leu Arg Cys Leu Leu Gly Leu Tyr Phe Gly Met Leu Leu Leu
                85                  90                  95

Leu Phe Ala Thr Gln Ile Thr Leu Gly Ile Leu Ile Ser Thr Gln Arg
            100                 105                 110

Ala Gln Leu Glu Arg Ser Leu Arg Asp Val Val Glu Lys Thr Ile Gln
        115                 120                 125

Lys Tyr Gly Thr Asn Pro Glu Glu Thr Ala Ala Glu Glu Ser Trp Asp
    130                 135                 140

Tyr Val Gln Phe Gln Leu Arg Cys Cys Gly Trp His Tyr Pro Gln Asp
145                 150                 155                 160

Trp Phe Gln Val Leu Ile Leu Arg Gly Asn Gly Ser Glu Ala His Arg
                165                 170                 175

Val Pro Cys Ser Cys Tyr Asn Leu Ser Ala Thr Asn Asp Ser Thr Ile
            180                 185                 190

Leu Asp Lys Val Ile Leu Pro Gln Leu Ser Arg Leu Gly Gln Leu Ala
        195                 200                 205

Arg Ser Arg His Ser Thr Asp Ile Cys Ala Val Pro Ala Glu Ser His
    210                 215                 220

Ile Tyr Arg Glu Gly Cys Ala Gln Gly Leu Gln Lys Trp Leu His Asn
225                 230                 235                 240

Asn Leu Ile Ser Ile Val Gly Ile Cys Leu Gly Val Gly Leu Leu Glu
                245                 250                 255

Leu Gly Phe Met Thr Leu Ser Ile Phe Leu Cys Arg Asn Leu Asp His
            260                 265                 270

Val Tyr Asn Arg Leu Ala Arg Tyr Arg
        275                 280
```

<210> SEQ ID NO 193
<211> LENGTH: 281
<212> TYPE: PRT
<213> ORGANISM: Artificial Sequence
<220> FEATURE:
<223> OTHER INFORMATION: hCD37-Mac5

<400> SEQUENCE: 193

```
Met Ser Ala Gln Glu Ser Cys Leu Ser Leu Ile Lys Tyr Phe Leu Phe
1               5                   10                  15

Val Phe Asn Leu Phe Phe Phe Val Leu Gly Ser Leu Ile Phe Cys Phe
            20                  25                  30
```

```
Gly Ile Trp Ile Leu Ile Asp Lys Thr Ser Phe Val Ser Phe Val Gly
        35                  40                  45

Leu Ala Phe Val Pro Leu Gln Ile Trp Ser Lys Val Leu Ala Ile Ser
    50                  55                  60

Gly Ile Phe Thr Met Gly Ile Ala Leu Leu Gly Cys Val Gly Ala Leu
65                  70                  75                  80

Lys Glu Leu Arg Cys Leu Leu Gly Leu Tyr Phe Gly Met Leu Leu Leu
                85                  90                  95

Leu Phe Ala Thr Gln Ile Thr Leu Gly Ile Leu Ile Ser Thr Gln Arg
            100                 105                 110

Ala Gln Leu Glu Arg Ser Leu Arg Asp Val Val Glu Lys Thr Ile Gln
        115                 120                 125

Lys Tyr Gly Thr Asn Pro Glu Glu Thr Ala Ala Glu Glu Ser Trp Asp
    130                 135                 140

Tyr Val Gln Phe Gln Leu Arg Cys Cys Gly Trp His Tyr Pro Gln Asp
145                 150                 155                 160

Trp Phe Gln Val Leu Ile Leu Arg Gly Asn Gly Ser Glu Ala His Arg
                165                 170                 175

Val Pro Cys Ser Cys Tyr Asn Leu Ser Ala Thr Asn Asp Ser Thr Ile
            180                 185                 190

Leu Asp Lys Val Ile Leu Pro Gln Leu Ser Arg Leu Gly His Leu Ala
        195                 200                 205

Arg Ser Arg His Ser Ala Asp Ile Cys Ala Val Pro Ala Asn Ser His
    210                 215                 220

Ile Tyr Arg Glu Gly Cys Ala Arg Ser Leu Gln Lys Trp Leu His Asn
225                 230                 235                 240

Asn Leu Ile Ser Ile Val Gly Ile Cys Leu Gly Val Gly Leu Leu Glu
                245                 250                 255

Leu Gly Phe Met Thr Leu Ser Ile Phe Leu Cys Arg Asn Leu Asp His
            260                 265                 270

Val Tyr Asn Arg Leu Ala Arg Tyr Arg
        275                 280


<210> SEQ ID NO 194
<211> LENGTH: 280
<212> TYPE: PRT
<213> ORGANISM: Artificial Sequence
<220> FEATURE:
<223> OTHER INFORMATION: hCD37-Mac45

<400> SEQUENCE: 194

Met Ser Ala Gln Glu Ser Cys Leu Ser Leu Ile Lys Tyr Phe Leu Phe
1               5                   10                  15

Val Phe Asn Leu Phe Phe Phe Val Leu Gly Ser Leu Ile Phe Cys Phe
            20                  25                  30

Gly Ile Trp Ile Leu Ile Asp Lys Thr Ser Phe Val Ser Phe Val Gly
        35                  40                  45

Leu Ala Phe Val Pro Leu Gln Ile Trp Ser Lys Val Leu Ala Ile Ser
    50                  55                  60

Gly Ile Phe Thr Met Gly Ile Ala Leu Leu Gly Cys Val Gly Ala Leu
65                  70                  75                  80

Lys Glu Leu Arg Cys Leu Leu Gly Leu Tyr Phe Gly Met Leu Leu Leu
                85                  90                  95

Leu Phe Ala Thr Gln Ile Thr Leu Gly Ile Leu Ile Ser Thr Gln Arg
            100                 105                 110
```

-continued

```
Ala Gln Leu Glu Arg Ser Leu Arg Asp Val Val Glu Lys Thr Ile Gln
        115                 120                 125

Lys Tyr Gly Thr Asn Pro Glu Glu Thr Ala Ala Glu Glu Ser Trp Asp
    130                 135                 140

Tyr Val Gln Phe Gln Leu Arg Cys Cys Gly Trp His Tyr Pro Gln Asp
145                 150                 155                 160

Trp Phe Gln Val Leu Ile Leu Arg Gly Asn Gly Ser Glu Ala His Arg
                165                 170                 175

Val Pro Cys Ser Cys Tyr Asn Leu Ser Ala Thr Asn Asp Ser Thr Ile
            180                 185                 190

Leu Asp Lys Val Ile Leu Pro Gln Leu Ser Arg Leu Gly Gln Leu Ala
        195                 200                 205

Arg Ser Arg His Ser Thr Asp Ile Cys Ala Val Pro Ala Asn Ser His
    210                 215                 220

Ile Tyr Arg Glu Gly Cys Ala Arg Ser Leu Gln Lys Trp Leu His Asn
225                 230                 235                 240

Asn Leu Ile Ser Ile Val Gly Ile Cys Leu Gly Val Gly Leu Leu Glu
                245                 250                 255

Leu Gly Phe Met Thr Leu Ser Ile Phe Leu Cys Arg Asn Leu Asp His
            260                 265                 270

Val Tyr Asn Arg Leu Ala Arg Tyr
        275                 280


<210> SEQ ID NO 195
<211> LENGTH: 446
<212> TYPE: DNA
<213> ORGANISM: Artificial Sequence
<220> FEATURE:
<223> OTHER INFORMATION: Variable heavy chain polynucleotide sequences;
      huCD37-50 antibody

<400> SEQUENCE: 195

aagcttgcca ccatggggtg gtcctgcata atccttttcc tggttgctac tgctaccgga      60

gtccattcac aggtgcagct gcaggagtcc ggccccggcc tgctcaagcc ttctcagagt     120

ctgagtctga cttgtactgt ttctggctac agcataacca gcggtttcgc ttggcactgg     180

atcagacagc atcccggcaa caaactggag tggatgggat acatactgta ctcaggctca     240

actgtctatt ccccctccct gaaatcccgg atcagtatta cccgtgacac ttctaagaac     300

catttttttc tgcagctgaa cagcgttacc gcagctgaca ctgcaaccta ctactgtgcc     360

cggggatatt atggatacgg agcttggttc gcttactggg gccaaggcac cctcgtaact     420

gtgagtgctg cttccaccaa gggccc                                          446


<210> SEQ ID NO 196
<211> LENGTH: 446
<212> TYPE: DNA
<213> ORGANISM: Artificial Sequence
<220> FEATURE:
<223> OTHER INFORMATION: Variable heavy chain polynucleotide sequences;
      huCD37-51 antibody

<400> SEQUENCE: 196

aagcttgcca ccatgggttg gtcttgcatc atcctgttcc tggtggccac tgccactggc      60

gtgcattcag aagttcagtt ggtggagtcc ggcccagaag tgctgaaacc cggcgaatca     120

ctgtccctga cttgtaccgt gtcaggttat agcatcagca gcggctttgc ttggcactgg     180

attcggcagt ttccaggcaa gggactggaa tggatgggct acatccatta cagtggctca     240
```

-continued

```
accaattaca gccctagcct gcagggccga atctctatta ccagggatag ttctattaac    300

cagtttttcc tgcagcttaa ttccgtgact gcctctgaca cagcaactta ctattgcgcc    360

cgtggctact acgggttcgg agcctggttt gtatactggg gtcagggcac cctggtcact    420

gtctcagccg cctctaccaa gggccc                                         446
```